US008071650B2

(12) United States Patent
Suh et al.

(10) Patent No.: US 8,071,650 B2
(45) Date of Patent: Dec. 6, 2011

(54) THIOUREA DERIVATIVES AND THE PHARMACEUTICAL COMPOSITIONS CONTAINING THE SAME

(75) Inventors: Young Ger Suh, Kyunggi-do (KR); Uh Taek Oh, Kyunggi-do (KR); Hee Doo Kim, Seoul (KR); Jee Woo Lee, Seoul (KR); Hyeung Geun Park, Seoul (KR); Ok Hui Park, Chungchongnam-do (KR); Yong Sil Lee, Seoul (KR); Young Ho Park, Seoul (KR); Yung Hyup Joo, Seoul (KR); Jin Kyu Choi, Kyunggi-do (KR); Kyung Min Lim, Kyunggi-do (KR); Sun Young Kim, Kyunggi-do (KR); Jin Kwan Kim, Seoul (KR); Hyun Ju Koh, Seoul (KR); Joo Hyun Moh, Kyunggi-do (KR); Yeon Su Jeong, Kyunggi-do (KR); Jung Bum Yi, Kyunggi-do (KR); Young Im Oh, Kyunggi-do (KR)

(73) Assignee: Pacific Corporation, Seoul (KR)

(*) Notice: Subject to any disclaimer, the term of this patent is extended or adjusted under 35 U.S.C. 154(b) by 1096 days.

(21) Appl. No.: 11/727,413

(22) Filed: Mar. 26, 2007

(65) Prior Publication Data
US 2008/0064687 A1    Mar. 13, 2008

Related U.S. Application Data

(63) Continuation of application No. 10/169,805, filed as application No. PCT/KR01/01407 on Aug. 20, 2001, now abandoned.

(30) Foreign Application Priority Data

Aug. 21, 2000  (KR) ................. 2000-48385
Aug. 21, 2000  (KR) ................. 2000-48388
Dec. 29, 2000  (KR) ................. 2000-85126

(51) Int. Cl.
*A61K 31/24*    (2006.01)
*A61K 31/17*    (2006.01)
*A61K 31/16*    (2006.01)
*C07C 335/20*   (2006.01)
*C07C 279/28*   (2006.01)
*C07C 311/13*   (2006.01)

(52) U.S. Cl. .......... 514/586; 514/535; 514/609; 564/27; 564/104; 560/13

(58) Field of Classification Search .......... 560/13; 564/104, 27; 514/535, 609, 586
See application file for complete search history.

(56) References Cited

U.S. PATENT DOCUMENTS

| 3,117,994 A * | 1/1964 | McKay et al. ........... 564/237 |
| 3,546,344 A | 12/1970 | Martin et al. ........... 424/322 |
| 4,460,602 A | 7/1984 | Buckwalter et al. ........... 424/322 |
| 5,403,868 A * | 4/1995 | Reid et al. ........... 514/586 |
| 5,780,483 A * | 7/1998 | Widdowson et al. ........... 514/311 |
| 6,057,451 A | 5/2000 | Crute et al. ........... 548/194 |
| 6,288,091 B1 | 9/2001 | Crute et al. ........... 514/346 |
| 2003/0203944 A1 | 10/2003 | Suh et al. |
| 2003/0212140 A1 | 11/2003 | Suh et al. |

FOREIGN PATENT DOCUMENTS

| EP | 0 405 233 B1 | 10/1993 |
| EP | 0 462 933 B1 | 6/1994 |
| EP | 0 528 146 B1 | 2/1996 |
| GB | 1031165 | 5/1966 |
| GB | 2 168 975 A | 7/1986 |
| GB | 2 206 347 A | 1/1989 |
| JP | 11-35545 | 2/1999 |
| WO | WO 95/13387 | 5/1995 |
| WO | WO 95/21886 | 8/1995 |
| WO | WO 98/05779 | 2/1998 |
| WO | WO 98/18914 | 5/1998 |
| WO | WO 99/00115 | 1/1999 |
| WO | WO 99/37676 | 7/1999 |
| WO | WO 99/43801 | 9/1999 |
| WO | WO 00/50387 | 8/2000 |
| WO | WO 02/08221 A2 | 1/2002 |
| WO | WO 02/072536 A1 | 9/2002 |
| WO | WO 02/076946 A2 | 10/2002 |
| WO | WO 02/090326 A1 | 11/2002 |
| WO | WO 03/014064 A1 | 2/2003 |

OTHER PUBLICATIONS

Domenico Spina et al., Pharmacology of airway irritability, pp. 264-272.
Jeewoo Lee et al., *Bioorganic & Medicinal Chemistry*, 9 (2001) 19-32.
Yun Wang et al., *Molecular Pharmacology*, vol. 62. No. 4, pp. 947-956 (2002).
Jung Wha Yoon et al., *Bioorganic & Medicinal Chemistry Letters*, 4 pp (Article in Press).
Hyeung-geun Park et al., *Bioorganic & Medicinal Chemistry Letters* 13 (2003) pp. 601-604.
Hyeung-geun Park et al., *Bioorganic & Medicinal Chemistry Letters* 13 (2003) pp. 197-200.

(Continued)

*Primary Examiner* — Peter O Sullivan
(74) *Attorney, Agent, or Firm* — Rothwell, Figg, Ernst & Manbeck, P.C.

(57) ABSTRACT

The present invention relates to novel thiourea derivatives as a modulator for vanilloid receptor (VR) and the pharmaceutical compositions containing the same. As diseases associated with the activity of vanilloid receptor, pain acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fervescence, stomach-duodenal ulcer, inflammatory bowel disease and inflammatory diseases can be enumerated. The present invention provides a pharmaceutical composition for prevention or treatment of these diseases.

27 Claims, No Drawings

OTHER PUBLICATIONS

Oh et al., 1996, J. Neurosci. 16 pp. 1659-1667.

Wrigglesworth et al., "Analogues of Capsaicin with Agonist Activity as Novel Analgesic Agents: Structure-Activity Studies. 4. Potent, Orally Active Analgesics," J. Med Chem. 1996, 39 4942-4951.

McKay et al., "Bacteriostats. VI.[1a] Bacteriostatic Activities of Some Substituted Guanidines[1b]," Bacteriostats. VI, Sep. 1963, 587-595.

"Controlling Pain in the 21st Century," Report on the Society for Medicines Research Meeting Held at Charing Cross and Westminster Medical School, London, Jul. 10, 1997.

Modulation of Capsaicin-Induced Calcium Uptake into Primary Cultured Rat Dorsal Root Ganglion Sensory Neurons and Characterization of Capsaicin-Hydrolyzing Enzyme Purified from Rat Liver, Feb. 1996.

Christopher S. J. Walpole et al., "The Discovery of Capsazepine, the First Competitive Antagonist of the Sensory Neuron Excitants Capsaicin and Resiniferatoxin," J. Med. Chem., vol. 37, No. 13, Jun. 24, 1994, pp. 1942-1954.

Gilles Klopman et al., "Quantitative structure-agonist activity relationship of capsaicin analogues," Journal of Computer-Aided Molecular Design, vol. 9, No. 3, (1995) pp. 283-294.

M. Hosseini et al., "Using Artificial Neural Networks to Classify the Activity of Capsaicin and its Analogues," J. Chem. Inf. Comput. Sci., vol. 37, No. 6, Nov. 1997, pp. 1129-1137.

Edward K. Dziadulewicz et al., "1-(2-Nitrophenyl)thiosemicarbazides: A Novel Class of Potent, Orally Active Non-Peptide Antagonist for the Bradykinin $B_2$ Receptor," J. Med. Chem. vol. 43, No. 5, 3/9/200 pp. 769-771.

John F. Olin et al., "The Action of the Halogen Hydrins and of Ethylene Oxide on the Thioureas," Journal of the American Chemical Society, vol. 52, No. 8, Aug. 1930, pp. 3323-3327.

Charles Larsen et al., "Thermal Fragmentations VI. The Preparation of Aryl N-Monoalkyldithiocarbamates and Their Behaviour upon Heating," ACTA Chemica Scandinavica, vol. 27, No. 6, Jun. 1973, pp. 2001-2012.

Zhen-Chu Chen et al., "Polyvalent Iodine in Synthesis. 2. A New Method for the Preparation of Aryl Esters of Dithiocarbamic Acids," Journal of Organic Chemistry, vol. 52, No. 18, Sep. 4, 1987, pp. 4117-4118.

Eugene Lieber et al., "Reaction of 5-Amino-1,2,3,4-Thiatriazole with Benzylamine," Journal of Organic Chemistry, vol. 22. No. 930, Sep. 1957, pp. 1054-1056.

J. Bourdais et al., "Polycyclic Azines. Ill. Synthesis of 3-Aminoimidazol[1,5-α]pyridine Derivatives by Cyclodesulphurization of N'-Substituted -N-(2-Pyridylmethyl)thioureas with Dicyclohexylcarbodiimide (2,3)," Journal of Heterocyclic Chemistry, vol. 17, No. 5, May 1980, pp. 555-558.

Walter Ried et al., "2-Imino-1,3-thiezetidine aus Thioharnstoffen mit intramolekularer Wasserstoffbrücke," Chemische Berichte, vol. 111, No. 1, Jan. 1978, pp. 143-154.

Szallasi and Blumberg, 1999, Pharm. Rev. 51, pp. 159-211.

Wrigglesworth and Walpole, 1998, Drugs of the Future 23, pp. 531-538.

Wood et al., 1998, J. Neurosci. 8 pp. 3208-3220.

Caterina et al., 1997, Nature 389, pp. 816-824.

Tominaga et al., 1998, Neuron 21, pp. 531-543.

Caterina et al., 2000, Science 288, pp. 306-313.

Davis et al., 2000, Nature 405, pp. 183-187.

Hwang et al., 2000, PNAS 97, pp. 6155-6160.

Zygmunt et al, 2000, Trends Pharmacol. Sci, 21, pp. 43-44.

Ren et al., 2000, Dig. Dis. Sci. 45, pp. 830-836.

Perkins and Campbell, 1992, Br. J. Pharmacol. 107, pp. 329-333.

Kwak et al., 1998, Neurosci. 86, pp. 619-626.

Santos and Calixto, 1997, Neurosci. Lett 235, pp. 73-76.

McDonnell et al., 2002, Bioorg. Med. Chem. Lett. 12, pp. 1189-1192.

Lee et al., 2002, Bioorg. Med. Chem. Lett. 10, pp. 1171-1179.

Lee et al., 2001, Bioorg. Med. Chem. Lett. 9, pp. 1713-1720.

Wahl et al., 2001, Mol. Pharmacol. 59, pp. 9-15.

Chem Abstract Online printout of JP 11-35545, 1999, m=221070-38-3.

Jeewoo Lee et al., "3-Acyloxy-2-phenalkylpropyl Amides and Esters of Homovanillic Acid as Novel Vanilloid Receptor Agonists," Bioorganic & Medicinal Chemistry Letters 9 (1999) 2909-2914.

K. D. Janda et al., "Antibody Catalysis of Bimolecular Amide Formation," J. Am. Chem. Soc. 1988, 110, 4835-4837.

Accession No. (AN) 2004:429173 CHEMCATS, Jan. 1, 2004.

Accession No. (AN) 2003:2480724 CHEMCATS, Nov. 12, 2004.

* cited by examiner

THIOUREA DERIVATIVES AND THE PHARMACEUTICAL COMPOSITIONS CONTAINING THE SAME

RELATED APPLICATIONS

This application is a continuation of application Ser. No. 10/169,805, filed Jul. 9, 2002 now abandoned, which is a §371 of International Application No. PCT/KR01/01407, filed August 20, 2001 and claims priority of Korean Applications Nos. 2000/48385 and 2000/48388, both filed Aug. 21, 2000 and 2000/85126 filed Dec. 29, 2000, all of which are incorporated herein by reference.

TECHNICAL FIELD

The present invention relates to novel thiourea derivatives and the pharmaceutical compositions containing the same, and particularly, to novel thiourea compounds as a modulator for vanilloid receptor (VR) and the pharmaceutical compositions thereof. Here, the modulator means the thing that can be bonded to the receptor to act as an antagonist or an agonist.

BACKGROUND ART

As diseases associated with the activity of vanilloid receptor, pain, acute pain, chronic pain, neuropathic pain, postoperative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fervescence, stomach-duodenal ulcer, inflammatory bowel disease and inflammatory diseases can be enumerated. The present invention provides pharmaceutical compositions for prevention or treatment of these diseases. Yet, the diseases described above are only for enumeration, not to limit the scope of clinical application of vanilloid receptor modulator.

Capsaicin (8-methyl-N-vanillyl-6-nonenamide) is a main pungent component in hot peppers. Hot peppers have been used, for a long time, not only as a spice but also as traditional medicine in the treatment of gastric disorders and when applied locally, for the relief of pain and inflammation (Szallasi and Blumberg, 1999, Pharm, Rev. 51, pp 159-211). Capsaicin has a wide spectrum of biological actions, and not only exhibits effects on the cardiovascular and respiratory systems but also induces pain and irritancy on local application. Capsaicin, however, after such induction of pain, induces desensitization, both to capsaicin itself and also to other noxious stimuli to make the pain stopped. Based on this property, capsaicin and its analogues such as olvanil, nuvanil, DA-5018, SDZ-249482, resiniferatoxin are either used as analgesic agent, therapeutic agent for incontinentia urinae or skin disorder, or under development (Wriggleworth and Walpole, 1998, Drugs of the Future 23, pp 531-538).

Transmissions of mechanical, thermal and chemical noxious stimuli are mainly occurred by primary afferent nerve fibers of fine unmyelinated nerve (C-fiber) and thin myelinated nerve (A-fiber), and main reaction site of capsaicin and its analog called vanilloid is present at the nerve fiber transmitting the noxious stimuli. Capsaicin acts at the receptor existing on these neurons to induce potent stimuli by causing potent inflow of mono-and di-valent cations such as calcium and sodium, then exhibits potent analgesic effect by blocking the nervous function (Wood et al., 1988, J. Neurosci, 8, pp 3208-3220). Vanilloid receptor (VR-1) has been recently cloned and its existence becomes clear(Caterina et al., 1997, Nature 389, pp 816-824). It was clarified that this receptor transmits not only stimuli by capsaicin anlogues(vanilloid) but also various noxious stimuli such as proton and thermal stimuli (Tominaga et al., 1998, Neuron 21, pp 531-543). Based on this, it is considered that vanilloid receptor functions as a integrative modulator against various noxious stimuli and carries out critical role in transmissions of pain and noxious stimuli. Recently, knock-out mouse in which gene encoding for vanilloid receptor was deleted was prepared (Caterina et al., 2000, Science 288, pp 306-313; Davis et al., 2000, Nature 405, pp 183-187). Compared to normal mice, the mouse was found out to exhibit much reduced reaction to thermal stimuli and thermal pain, while exhibiting no difference in general behavior, reconfirming the importance of the receptor in transmission of noxious signal. However, except proton, no other endogenous ligand, not exogenous ligand such as capsaicin, actually involved in transmission of noxious stimuli at vanilloid receptor was known. It is considered that leucotriene metabolite represented by 12-hydroperoxyeicosatetraenoic acid (12-HPETE) (Hwang et al., 2000, PNAS 11, pp 6155-6160) and arachidonic acid derivatives such as anandamide (Zygmunt et al., 2000, Trends Pharmacol. Sci. 21, pp 43-44) act as the most likely endogenous ligand for the receptor and proton acts as a cofactor with receptor-stimulating activity, rather than as a direct ligand.

As such, a capsaicin-sensitive sensory nerve cell and a vanilloid receptor existing in the cell are distributed over the entire body and play basic function in transmission of noxious stimuli and pain, further act as crucial factor in expression of neurogenic inflammation, thereby to have close relation with the cause of neuropathies, nerve injury, stroke, asthma, chronic obstructive pulmonary diseases, urinary bladder hypersensitiveness, irritable bowel syndrome, inflammatory bowel disease, fervescence, skin disorder and inflammatory disease. Lately, their correlation even with neuropathic disease is suggested (WO 99/00125). Recently, attention has focused to the role of afferent sensory nerve responding to capsaicin in gastrointestinal injury, and it was proposed that the afferent nerve might have a dual character that it exhibits protective action against gastric damage by improving gastric microcirculation through releasing peripheral neuropeptide such as CGRP (calcitonin gene-related peptide), while inducing gastric injury by stimulating sympathetic nervous system (Ren et al., 2000, Dig. Dis. Sci. 45, pp 830-836). It is determined that vanilloid receptor modulator has very high potential to be used for prevention or treatment of the said various diseases by modulating the activity of the vanilloid receptor conducting such varied functions.

As described above, there has been widely studied for clinical application of vanilloid receptor agonist, and it is understood that there is a possibility that the agonist derived from the present studies will be developed for clinical application. Though it may be, theoretically, anticipated that antagonist for this receptor would exhibit substantial degree of inhibitory action against pain and neurogenic inflammation, it was found out that the competitive antagonist for this receptor, capsazepine, almost the only one known until now, failed to exhibit significant analgesic and anti-inflammatory effects (Perkins and Campbell, 1992, Br. J. Pharmacol. 107, pp 329-333). Therefore, not much progress was made on this field. However, recently, there has been a report on significant results for analgesic action of capsazepine in animal studies (Kwak et al., 1998, Neurosci. 86, pp 619-626; Santos and calixto, 1997, Neurosci. Lett. 235, pp 73-76), in particular, the inventors of the present invention clearly demonstrated through animal studies the analgesic and anti-inflammatory effects of the strong vanilloid receptor antagonists which were identified through experiments in our laboratory, and based on this, strongly suggest the development potential of vanilloid receptor antagonist as an analgesic, anti-inflammatory and anti-ulcerous agent. Yet, though the vanilloid receptor antagonist or agonist derived from the present studies will mainly act based on the antagonistic or agonistic activity of itself, even a possibility that it could exhibit the pharmacological activity through transformation into agonist or antagonist via metabolism after absorption into body is not to be excluded.

The present invention is to provide novel compounds which are acted as a modulator for vanilloid receptor and exhibit excellent analgesic, anti-inflammatory and anti-ulcer effects, and pharmaceutical compositions containing the same.

DISCLOSURE OF THE INVENTION

In order to attain the above objects, the present invention provides a novel compound of the following formula (I):

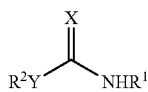

wherein,
X represents S, O or —NCN;
Y represents single bond, NR$^3$, O or S;
R$^1$ represents

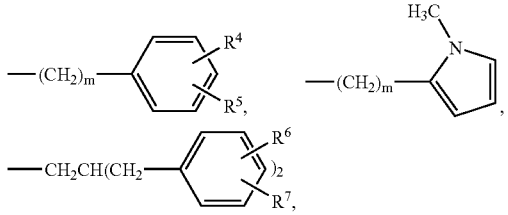

pyridinylmethyl, pyrrolylmethyl, oxazolylmethyl, pyrazolylmethyl, imidazolylmethyl, anthracenylmethyl, naphthylmethyl, quinolinylmethyl, alkoxycarbonyl or alkylcarbonyloxy (wherein, m is 0, 1, 2, 3 or 4; R$^4$ and R$^5$ are independentyl hydrogen, lower alkyl having 1 to 5 carbon atoms, hydroxy, methanesulfonylamino, lower alkoxy having 1 to 5 carbon atoms, methoxyalkoxy, methoxyalkoxyalkyl, alkoxycarbonyloxy, benzyloxy, acetoxymethyl, propinoyloxymethyl, butoxyalkyl, trimethylacetoxy, trimethylacetoxymethyl or halogen; and R$^6$ and R$^7$ are independently hydrogen, lower alkyl having 1 to 5 carbon atoms);

R$^2$ represents R$^8$—(CH$_2$)$_n$—

{wherein, n is 0, 1, 2, 3 or 4; R$^8$ is benzoyl, imidazolyl, indolyl, indazolyl thiazolyl, pyrazolyl, oxazolyl isoxazolyl, benzimidazolyl, chromonyl or benzothiazolyl substituted or unsubstituted with lower alkyl having 1 to 5 carbon atoms, nitro, amino, cyano, methanesulfonylamino, formyl or halogen, or

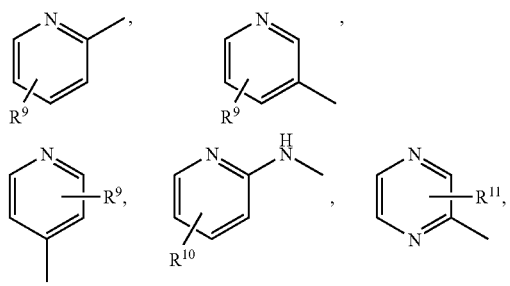

(wherein, R$^9$ is hydrogen, halogen, lower alkyl having 1 to 5 carbon atoms, lower alkoxy having 1 to 5 carbon atoms, hydroxy, nitro, cyano, —NHSO$_2$R$^{12}$, —S(O)$_p$R$^{12}$, —NR$^{13}$R$^{14}$, carboxyl; R$^{10}$ is hydrogen, nitro, NHSO$_2$R$^{12}$, S(O)$_p$R$^{12}$ or NR$^{13}$R$^{14}$; R$^{11}$ is hydrogen or cyano; R$^{12}$ is lower alkyl having 1 to 5 carbon atoms, methylphenyl, NR$^{13}$R$^{14}$, trifluoromethyl or alkenyl; R$^{13}$ and R$^{14}$ are independently hydrogen or lower alkyl having 1 to 5 carbon atoms; and p is 0 or 2.); or

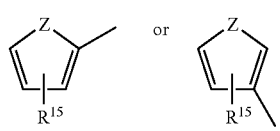

(wherein, Z is O, S, NH or —NCH$_3$; R$^{15}$ is hydrogen, halogen, lower alkyl having 1 to 5 carbon atoms, nitro, cyano, —NHSO$_2$R$^{12}$, —S(O)$_p$R$^{12}$, N,N-dimethylaminomethyl or alkoxycarbonylamino; and p and R$^{12}$ have the same meanings as defined in R$^9$);

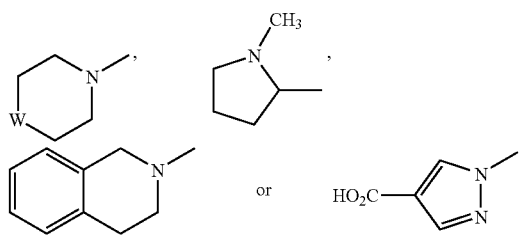

(wherein, W is O, S, NH, NR$^{16}$, —N(SO$_2$CH$_3$)— or —CH$_2$—; and R$^{16}$ is pyridinyl or pyrimidinyl substituted or unsubstituted with lower alkyl having 1 to 5 carbon atoms, nitro, methanesulfonylamino or halogen; or benzyl or phenethyl substituted or unsubstitued with lower alkyl having 1 to 5 carbon atoms, alkoxy, hydroxy, nitro, methanesulfonylamino or halogen);
or

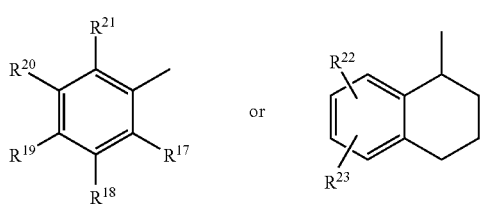

(wherein, $R^{17}$, $R^{18}$, $R^{19}$, $R^{20}$ and $R^{21}$ are independently hydrogen, halogen, lower alkyl having 1 to 5 carbon atoms, alkoxy, methylenedioxy, methanesulfonylaminomethyl, alkoxycarbonyl, hydroxy, sulfamoyl, aminoalkoxy, alkoxycarbonylamino, —NHCH$_2$CO$_2$H, alkoxyalkylcarbonylamino, alkoxycarbonylalkylamino, nitro, formyl, acetyl, formylamino, acetoxyamino, cyano, —OSO$_2$CH$_3$, —NHSO$_2$R$^{12}$, —N(SO$_2$R$^{12}$)CH$_3$, —N(SO$_2$R$^{12}$)$_2$, —S(O)$_p$R$^2$, —NR$^{13}$R$^{14}$, thiocarbamoyl, —C(=O)NHNH$_2$, —C(=O)NHOH, —C(=O)NHOCH$_3$, —PO(=O)(OCH$_3$)$_2$, carboxyl, NHBoc, —NHC(=O)SCH$_3$ or guanidine; $R^{22}$ and $R^{23}$ are independently hydrogen, halogen, alkoxy or hydroxy, and p, $R^{12}$, $R^{13}$ and $R^{14}$ have the same meanings as defined in $R^9$);

or hydroxyphenylaLkyl or (methanesulfonylaminophenyl)alkyl}; and $R^3$ represents hydrogen, alkyl or cycloalkyl having 1 to 8 carbon atoms, lower alkylphenyl having 1 to 5 carbon atoms, pyridinylethyl, bisphenylmethyl; or phenylalkyl substituted with lower alkyl having 1 to 5 carbon atoms, halogen or methanesulfonylamino.

Preferably, in the above formula (I),

X represents S, O or —NCN;

Y represents NR$^3$ or O;

$R^1$ represents

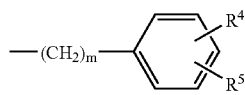

(wherein, m is 0, 1 or 2; and $R^4$ and $R^5$ are independently hydrogen, lower alkyl having 1 to 4 carbon atoms, hydroxy, methanesulfonylamino, lower alkoxy having 1 to 5 carbon atoms, methoxyalkoxy, methoxyalkoxyalkyl, benzyloxy, acetoxymethyl, trimethylacetoxymethyl or halogen);

$R^2$ represents $R^8$—(CH$_2$)$_n$—

{wherein, n is 0, 1, 2 or 3; and 10 is benzoyl, imidazolyl, indolyl, indazolyl, thiazolyl, pyrazolyl, oxazolyl, benzimidazolyl or chromonyl substituted or unsubstituted with lower alkyl having 1 to 5 carbon atoms, nitro, amino, cyano, methanesulfonylamino, formyl or halogen, or

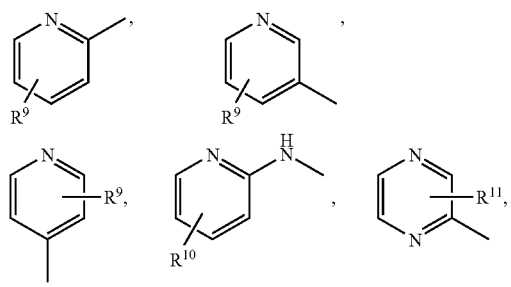

(wherein, $R^9$ is hydrogen, halogen, lower alkyl having 1 to 4 carbon atoms, lower alkoxy having 1 to 4 carbon atoms, nitro, cyano, —NHSO$_2$R$^{12}$, —NR$^{13}$R$^{14}$ or carboxyl; $R^{10}$ is hydrogen, nitro, NHSO$_2$R$^{12}$ or —NR$^{13}$R$^{14}$; $R^{11}$ is hydrogen or cyano; $R^{12}$ is lower alkyl having 1 to 4 carbon atoms, methylphenyl, —NR$^{13}$R$^{14}$ or trifluoromethyl; $R^{13}$ and $R^{14}$ are independently hydrogen or lower alkyl having 1 to 4 carbon atoms; and p is 0 or 2);

or

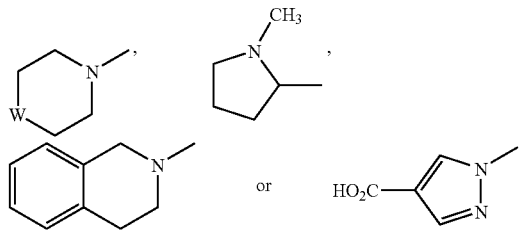

(wherein, Z is O, S, NH or —NCH$_3$; $R^{15}$ is hydrogen, lower alkyl having 1 to 4 carbon atoms, nitro, cyano or NHSO$_2$R$^{12}$; and $R^{12}$ has the same meanings as defined in $R^9$); or

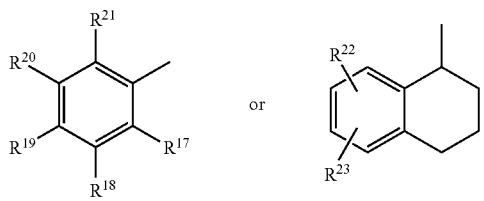

(wherein, W is O, S, NH, NR$^{16}$ or —CH$_2$—; and $R^{16}$ is pyridinyl or pyrimidinyl substituted or unsubstituted with lower alkyl having 1 to 4 carbon atoms, nitro or methanesulfonylamino; or benzyl or phenethyl substituted or unsubstituted with lower alkyl having 1 to 4 carbon atoms, alkoxy, hydroxy or methanesulfonylamino);

or (wherein, $R^{17}$, $R^{18}$, $R^{19}$, $R^{20}$ and $R^{21}$ are independently hydrogen, halogen, lower alkyl having 1 to 5 carbon atoms, alkoxy, methylenedioxy, methanesulfonylaminomethyl, alkoxycarbonyl, hydroxy, sulfamoyl, alkoxycarbonylamino, —NHCH$_2$CO$_2$H, alkoxyalkylcarbonylamino, alkoxycarbonylalkylamino, nitro, formyl, acetyl, formylamino, acetoxyamino, cyano, —OSO$_2$CH$_3$, —NHSO$_2$R$^{12}$, —N(SO$_2$R$^{12}$)CH$_3$, —N(SO$_2$R$^{12}$)$_2$, —S(O)$_p$R$^{12}$, NR$^{13}$R$^{14}$, thiocarbamoyl, —C(=O)NHNH$_2$, —C(=O)NHOH, —C(=O)NHOCH$_3$, carboxyl, NHBoc, —NHC(=O)SCH$_3$, guanidine; $R^{22}$ and $R^{23}$ are independently hydrogen, alkoxy or hydroxy; and p, $R^{12}$, $R^{13}$ and $R^{14}$ have the same meanings as defined in $R^9$);

or hydroxyphenylalkyl or (methanesulfonylaminophenyl)alkyl}; and $R^3$ represents hydrogen, alkyl having 1 to 4 carbon atoms, lower alkylphenyl having 1 to 3 carbon atoms, pyridinylethyl or bisphenylmethyl; or phenylalkyl substituted with lower alkyl having 1 to 4 carbon atoms, halogen or methanesulfonylamino.

More preferably, in the above formula (I),

X represents S, O or —NCN;

Y represents NR$^3$ or O;

R¹ represents

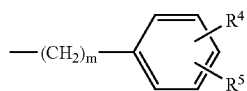

(wherein, m is 1 or 2; and $R^4$ and $R^5$ are independently hydrogen, t-butyl, hydroxy, methanesulfonylamino, lower alkoxy having 1 to 5 carbon atoms, methoxymethoxy, methoxyethoxy, benzyloxy, acetoxymethyl, trimethylacetoxymethyl or halogen);

$R^2$ represents $R^8$—$(CH_2)_n$—

{wherein, n is 1, 2 or 3; $R^8$ is benzoyl, imidazolyl, indolyl indazolyl, thiazolyl, pyrazolyl or benzimidazolyl substituted or unsubstituted with methyl, nitro or halogen;

or

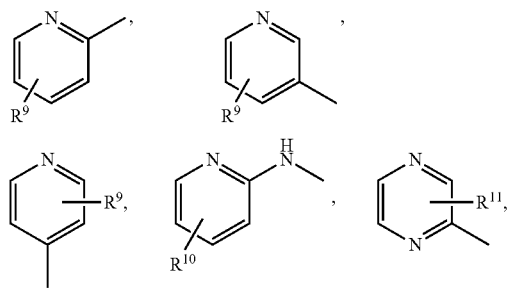

(wherein, $R^9$ is hydrogen, halogen, methyl, nitro or methanesulfonylamino; $R^{10}$ is hydrogen or nitro; and $R^{11}$ is hydrogen or cyano);

or

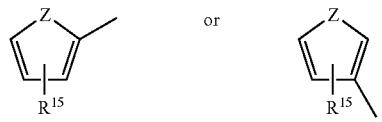

(wherein, Z is O, S, NH or —$NCH_3$; and $R^{15}$ is hydrogen, methyl, nitro, cyano or methanesulfonylamino);

or

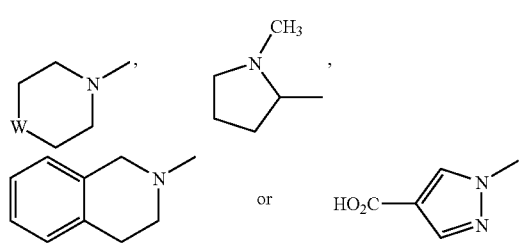

(wherein, W is O, S, NH, $NR^{16}$ or —$CH_2$—; and $R^{16}$ is pyridinyl, pyrimidinyl; or benzyl or phenethyl substituted or unsubstituted with methyl, methoxy or hydroxy);

or

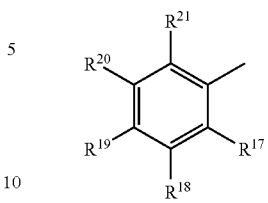 or 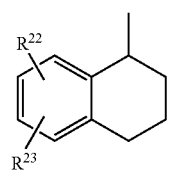

(wherein, $R^{17}$, $R^{18}$, $R^{19}$, $R^{20}$ and $R^{21}$ are independently hydrogen, halogen, lower alkyl having 1 to 4 carbon atoms, methoxy, methylenedioxy, methanesulfonylaminomethyl, methoxycarbonyl, hydroxy, sulfamoyl, alkoxycarbonylamino, —$NHCH_2CO_2H$, methoxymethylcarbonylamino, alkoxycarbonylalkylamino, nitro, acetyl, formylamino, acetoxyamino, cyano, —$OSO_2CH_3$, —$NHSO_2R^{12}$, —$N(SO_2R^{12})CH_3$, —$N(SO_2R^{12})_2$, —$S(O)_pR^{12}$, $NR^{13}R^{14}$, thiocarbamoyl, —C(=O)$NHNH_2$, —C(=O)NHOH, —C(=O)$NHOCH_3$, carboxyl, NHBoc, —NHC(=O)$SCH_3$, guanidine; $R^{22}$ and $R^{23}$ are independently hydrogen, methoxy or hydroxy; and p, $R^{12}$, $R^{13}$ and $R^{14}$ have the same meanings as defined in $R^9$);

or hydroxyphenylalkyl or (methanesulfonylaminophenyl) alkyl}; and $R^3$ represents hydrogen, methyl, isopropyl, isobutyl, cyclohexyl, benzyl, phenethyl or bisphenylmethyl; or phenylalkyl substituted with t-butyl, halogen or methanesulfonylamino.

Preferable examples of the compounds of formula (I) according to the present invention are as follows:

1-(4-t-butylbenzyl)-3-[2-(1-methyl-1H-pyrrol-2-yl)ethyl] thiourea;

1-(4-t-butylbenzyl)-3-(4-amino-2,5-difluorobenzyl)thiourea;

1-(4-t-butylbenzyl)-3-(4-sulfamoylbenzyl)thiourea;

1-(4-t-butylbenzyl)-3-(3-fluoro-4-methanesulfonylaminobenzyl)thiourea;

1-phenethyl-3-(3-fluoro-4-methanesulfonylaminobenzyl) thiourea;

1-(4-t-butylbenzyl)-3-(3-chloro-4-methanesulfonylaminobenzyl)thiourea;

1-(4-t-butylbenzyl)-3-(3-methoxycarboxyl-4-methanesulfonylaminobenzyl)thiourea;

1-(4-t-butylbenzyl)-3-(3-carboxyl-4-methanesulfonylaminobenzyl)thiourea;

1-(4-t-butylbenzyl)-3-((3-N-hydroxyaminocarbonyl-4-methanesulfonylamino)benzyl)thiourea;

1-(4-t-butylbenzyl)-3-(3-methoxycarboxylbenzyl)thiourea;

1-(4-t-butylbenzyl)-3-(3-carboxylbenzyl)thiourea;

1-(4-t-butylbenzyl)-3-(2,3,5,6-tetrafluoro-4-methanesulfonylaminobenzyl)thiourea;

1-(4-t-butylbenzyl)-3-(2,5-difluoro-4-methanesulfonylaminobenzyl)thiourea;

1-(4-t-butylbenzyl)-3-[(3-methanesulfonylamino-6-pyridinyl)methyl]thiourea;

1-(4-t-butylbenzyl)-3-(2,6-dichloro-5-methanesulfonylaminobenzyl)thiourea;

1-(4-t-butylbenzyl)-3-(4-methanesulfonylaminophenethyl)thiourea;

1-(4-t-butylbenzyl)3-(4-methanesulfonylaminobenzyl) thiourea;

1-(4-t-butylbenzyl)-3-[2,6-difluoro-3-(N-methanesulfonylamino)benzyl]thiourea;

1-(4-t-butylbenzyl)-3-[3-(N-methanesulfonylamino)benzyl]thiourea;

1-(4-t-butyl-2-methoxybenzyl)-3-(4-methanesulfonylaminobenzyl)thiourea;

1-(4-t-butyl-2-ethoxybenzyl)-3-4-methanesulfonylaminobenzyl)thiourea 1-(4-t-butyl-2-propoxybenzyl)-3-(4-methanesulfonylaminobenzyl)thiourea;

1-(4-t-butyl-2-butoxybenzyl)-3-(4-methanesulfonylaminobenzyl)thiourea;

1-(4-t-butyl-2-isopropoxybenzyl)-3-(4-methanesulfonylaminobenzyl)thiourea;

1-(4-t-butyl-2-isobutoxybenzyl)-3-(4-methanesulfonylaminobenzyl)thiourea;

1-(4-t-butyl-2-neopentoxybenzyl)-3-(4-methanesulfonylaminobenzyl)thiourea;

1-(4-t-butyl-2-methoxymethoxybenzyl)-3-(4-methanesulfonylaminobenzyl)thiourea;

1-(4-t-butyl-2-methoxyethoxybenzyl)-3-(4-methanesulfonylaminobenzyl)thiourea;

1-(4-t-butyl-2-benzyloxybenzyl)-3-(4-methanesulfonylaminobenzyl)thiourea;

1-(2-acetoxymethyl-4-t-butylbenzyl)-3-(4-methanesulfonylaminobenzyl)thiourea;

1-(4-t-butylbenzyl)-3-[2-(4-methylthiazol-5-yl)ethyl]thiourea;

1-(4-t-butylbenzyl)-3-((2-chloro-5-pyridinyl)methyl)thiourea;

1-(4-t-butylbenzyl)-3-(2-pyridin-2-ylethyl)thiourea;

1-(4-t-butylbenzyl)-3-(2,5-difluorobenzyl)thiourea;

1-(4t-butylbenzyl)-3-(3-fluorophenethyl)thiourea;

1-(4-t-butylbenzyl)-3-(4-sulfamoylphenethyl)thiourea;

1-(4-t-butylbenzyl)-3-(4-morpholinylethyl)thiourea;

1-(4-t-butylbenzyl)-3-[2-(1H-imidazol-4-yl)ethyl]thiourea;

1-(4-t-butylbenzyl)-3-[2-thiophen-2-ethyl]thiourea;

1-(4-t-butylbenzyl)-3-(4-methanesulfonylamino-1-methyl-1H-pyrrol-2-yl)thiourea;

1-benzyl-1-(3-(4-hydroxy-3-methoxyphenyl)propyl)-3-phenethylthiourea;

1-(3-(4-hydroxy-3-methoxyphenyl)propyl)-1-phenethyl-3-phenethylthiourea;

1-bisphenylmethyl-1-(3-(4-hydroxy-3-methoxyphenyl)propyl)-3-phenethylthiourea; or N″-cyano-N-(4-t-butylbenzyl)-N-(4-methanesulfonylaminobenzyl)guanidine.

More preferable examples of the compounds of formula (I) according to the present invention are follows:

1-(4-t-butylbenzyl)-3-(3-fluoro-4-methanesulfonylaminobenzyl)thiourea;

1-(4-t-butylbenzyl)-3-(3-chloro-4-methanesulfonylaminobenzyl)thiourea;

1-(4-t-butylbenzyl)-3-(3-methoxycarboxylmethanesulfonylaminobenzyl)thiourea;

1-(4-t-butylbenzyl)-3-(4-methanesulfonylaminobenzyl)thiourea; or 1-(4-t-butyl-2-isobutoxybenzyl)-3-(4-methanesulfonylamino)thiourea.

The compounds according to the present invention can chemically be synthesized by the following reaction schemes. However, these are given only for illusion of the invention and not intended to limit them.

[SCHEME 1]

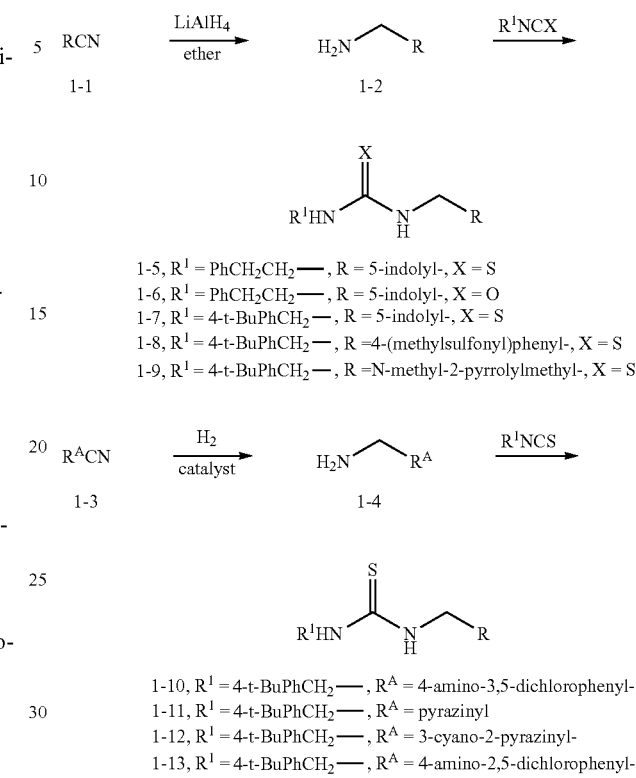

As depicted in the above Scheme 1, the nitrile compound 1-1 or 1-3 is reduced with lithium aluminium hydride or hydrogen to afford an amine 1-2 or 1-4, and then suitable isothiocyanate or isocyanate is reacted therewith to prepare thiourea or urea compound 1-5~1-13.

[SCHEME 2]

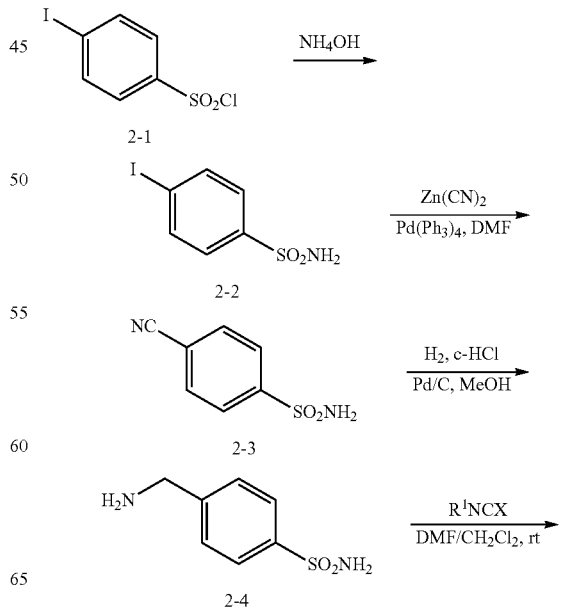

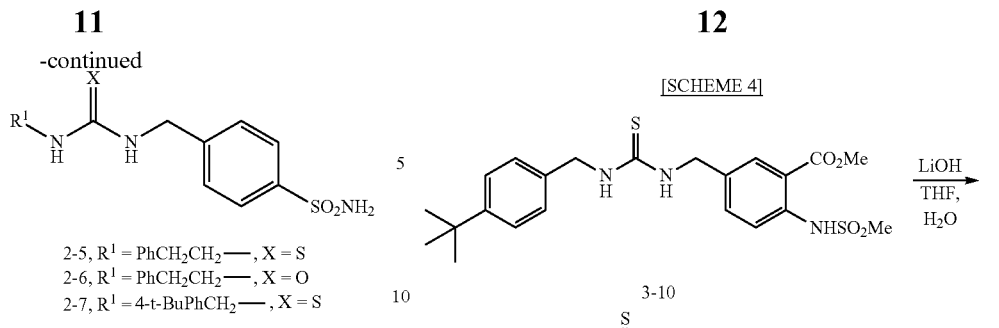

2-5, R¹ = PhCH₂CH₂—, X = S
2-6, R¹ = PhCH₂CH₂—, X = O
2-7, R¹ = 4-t-BuPhCH₂—, X = S

As depicted in the above Scheme 2, pipsyl chloride is treated with ammonia solution to afford compound 2-2 and the nitrile compound 2-3 is obtained therefrom using palladium catalyst. The compound 2-3 is subjected to catalytic reduction using palladium and concentrated hydrochloric acid to prepare amine compound 2-4, and compounds 2-5, 2-6 and 2-7 are synthesized therefrom according to the procedure as described in Scheme 1.

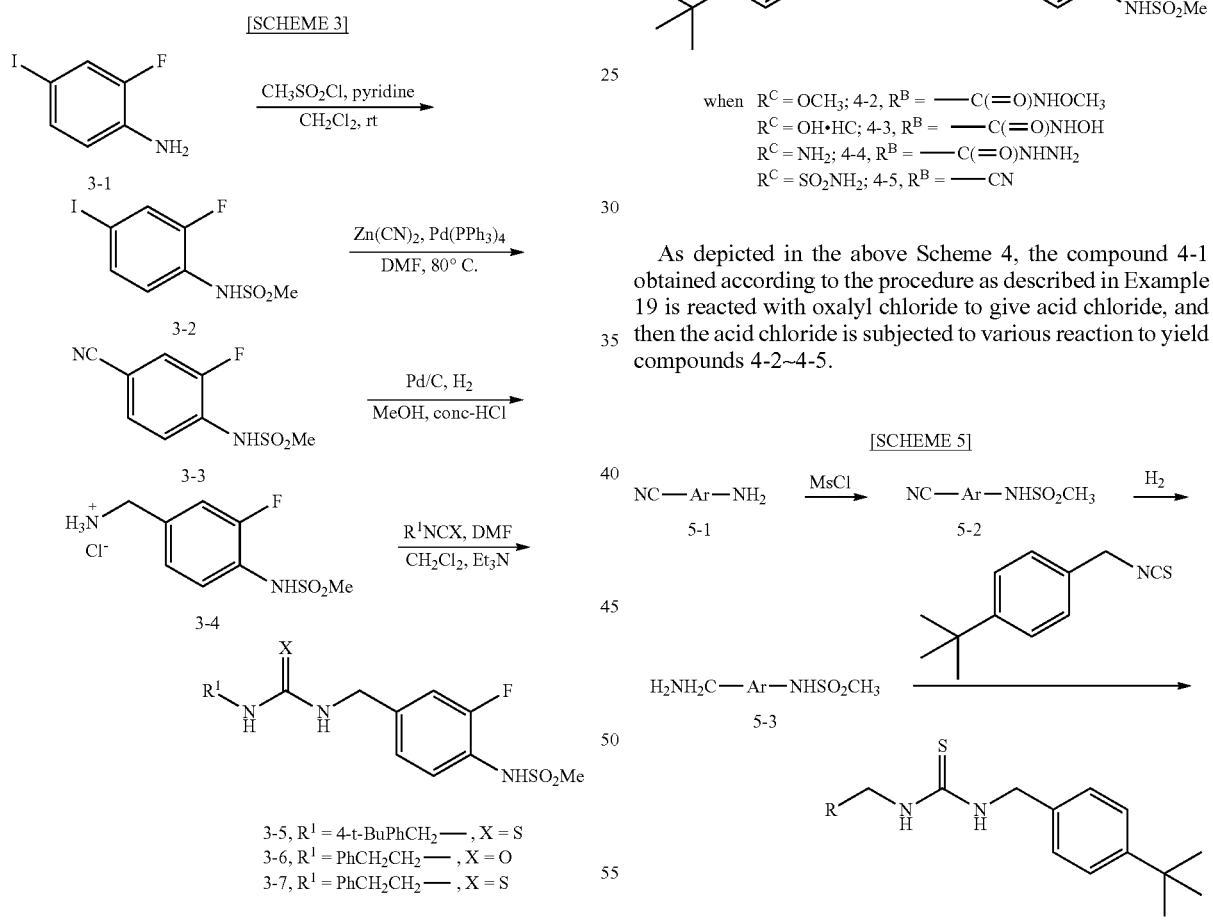

3-5, R¹ = 4-t-BuPhCH₂—, X = S
3-6, R¹ = PhCH₂CH₂—, X = O
3-7, R¹ = PhCH₂CH₂—, X = S

As depicted in the above Scheme 3, 2-fluoroiodo phenylamine compound 3-1 is mesylated, and cyano group is introduced thereinto in the presence of palladium catalyst. And the compound 3-3 is reduced to afford primary amine compound 3-4. The obtained intermediate is reacted with isocyanate or isothiocyanate to synthesize compounds 3-5~3-7. And their derivatives such as compound 3-8~3-10 (Example 16~18) and 4-6~4-13 (Example 24~31) are synthesized according to the similar procedure as the synthetic method of the compounds 3-5~3-7.

[SCHEME 4]

when R^C = OCH₃; 4-2, R^B = —C(=O)NHOCH₃
R^C = OH·HC; 4-3, R^B = —C(=O)NHOH
R^C = NH₂; 4-4, R^B = —C(=O)NHNH₂
R^C = SO₂NH₂; 4-5, R^B = —CN As depicted in the above Scheme 4, the compound 4-1 obtained according to the procedure as described in Example 19 is reacted with oxalyl chloride to give acid chloride, and then the acid chloride is subjected to various reaction to yield compounds 4-2~4-5.

[SCHEME 5]

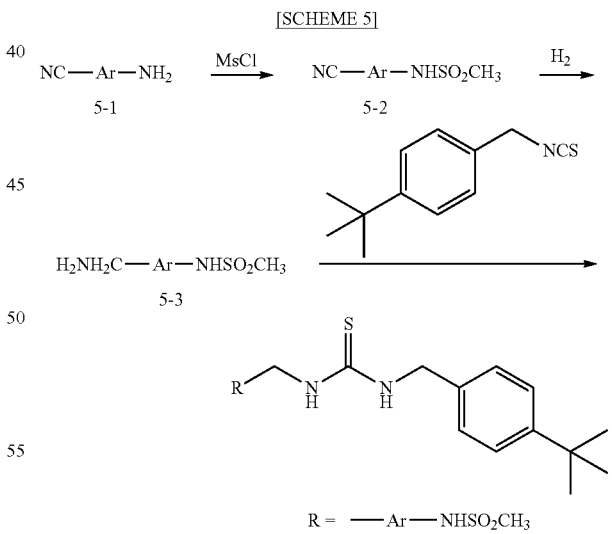

R = —Ar—NHSO₂CH₃

5-4 R = 4-methanesulfonylamino-2,3,5,6-tetrafluorophenyl-
5-5 R = 4-methanesulfonylamino-2,5-difluorophenyl-
5-6 R = 5-methanesulfonylaminopyridin-2-yl-
5-7 R = 4-methanesulfonylamino-3,5-dichlorophenyl-
5-8 R = 4-methanesulfonylaminophenylmethyl-
5-9 R = 2-methanesulfonylaminophenylmethyl- As depicted in the above Scheme 5, amine compound 5-1 is mesylated and the obtained compound 5-2 is hydrogenated to afford amine compound 5-3, and then 4-t-butylbenzyl-isothiocyanate is reacted therewith to synthesize compound 5-4~5-9.

[SCHEME 6]

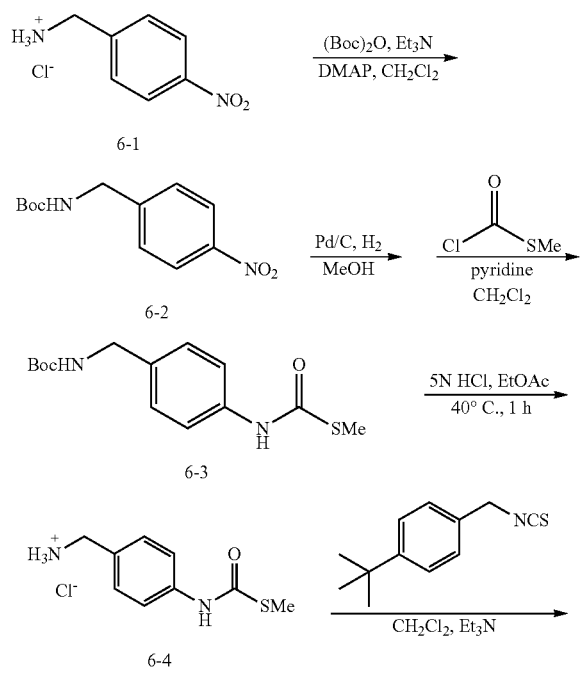

As depicted in the above Scheme 6, the amine group of 4-nitrobenzylamine hydrochloride compound 6-1 is protected. Nitro group thereof is reduced to give amino group and then methylchlorothiol formate is reacted therewith to prepare compound 6-3, followed by reacting 4-t-butylbenzyl-isothiocyanate therewith to obtain compound 6-5.

[SCHEME 7]

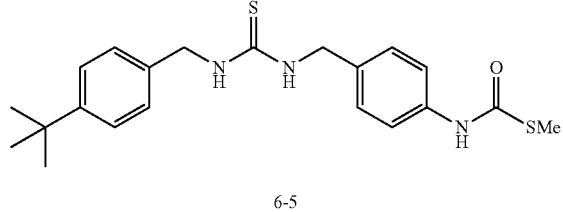

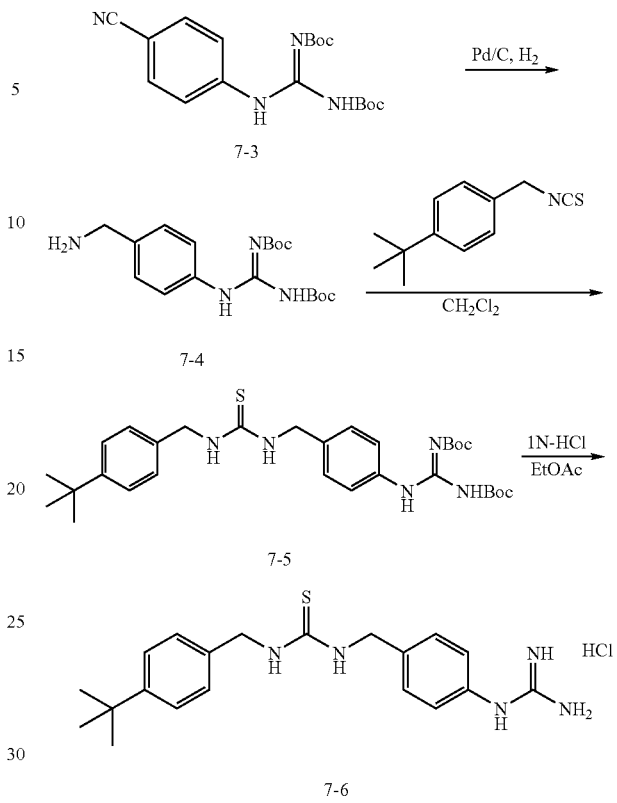

As depicted in the above Scheme 7, guanidine group and cyano group are introduced into 4-iodoaniline 7-1 to prepare compound 7-3, and the compound 7-3 is reduced in the presence of palladium catalyst to give amine compound 7-4. The compound 7-4 is reacted with 4-t-butylbenzylisothiocyanate, followed by deprotection to synthesize compound 7-6.

[SCHEME 8]

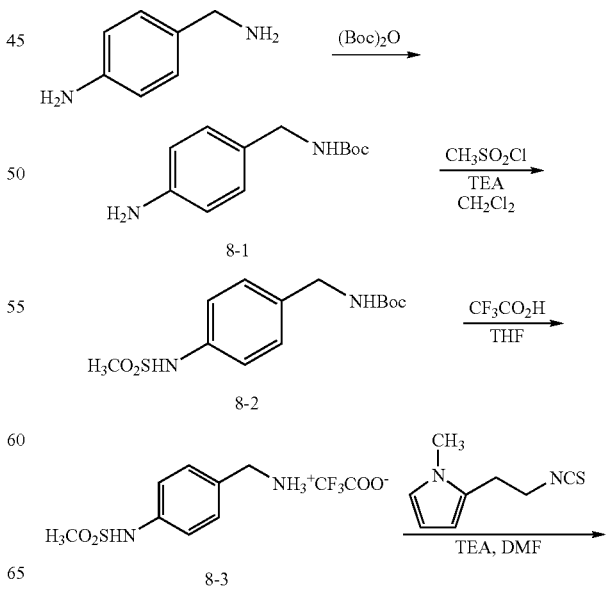

-continued

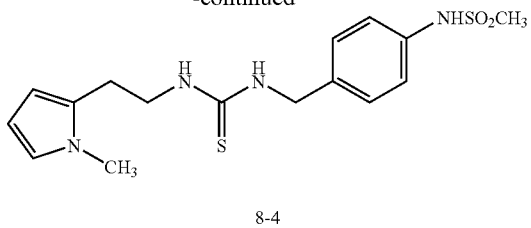

8-4

As depicted in the above Scheme 8, 4-aminobenzylamine is selectively protected with t-butoxycarbonyl group (Boc) to prepare compound 8-1 and methanesulfonyl chloride is reacted with NH₂ group thereof to yield compound 8-2. Boc group is removed therefrom in acidic condition, and then 2-(1-methyl-1H-pyrrol-2-yl)ethylisocyanate is reacted therewith to yield compound 8-4.

[SCHEME 9]

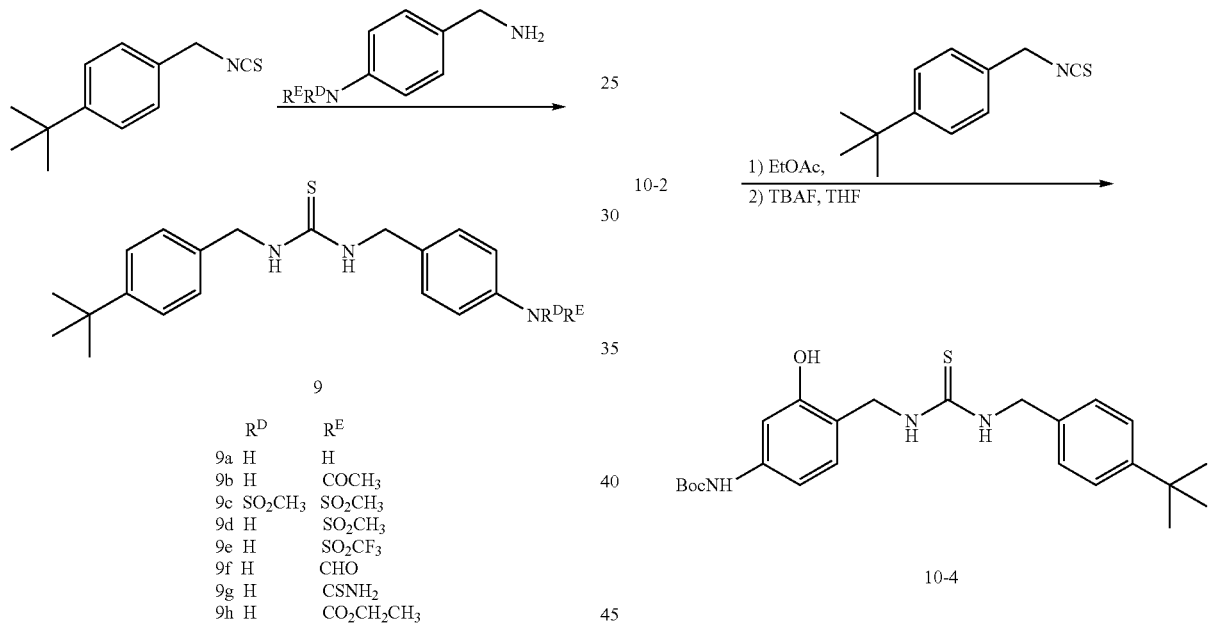

|    | $R^D$ | $R^E$ |
|----|-------|-------|
| 9a | H | H |
| 9b | H | COCH₃ |
| 9c | SO₂CH₃ | SO₂CH₃ |
| 9d | H | SO₂CH₃ |
| 9e | H | SO₂CF₃ |
| 9f | H | CHO |
| 9g | H | CSNH₂ |
| 9h | H | CO₂CH₂CH₃ |

Compounds 9a~9h are synthesized by reacting 4t-butyl-benzylisothiocyanate with corresponding benzylamine derivatives, respectively.

[SCHEME 10]

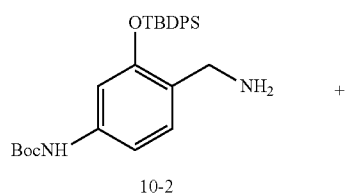

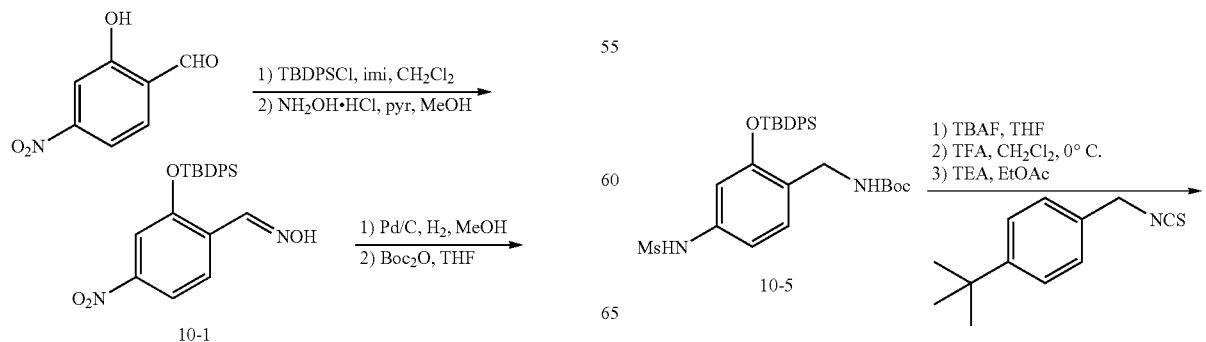

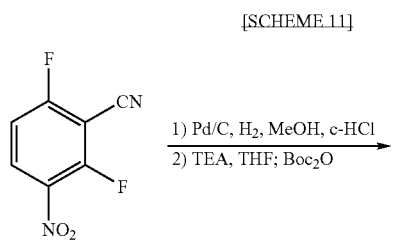

10-6

As depicted in the above Scheme 10, hydroxy group of 2-hydroxy-4-nitrobenzaldehyde is protected with TBDPS, and then oxime 10-1 is prepared therefrom. The compound 10-1 is reduced with hydrogen in the presence of palladium catalyst and protected with Boc group to afford compounds 10-2 and 10-3. The compound 10-2 is reacted with t-butylbenzylisothiocyanate, and then TBDPS is removed therefrom to synthesize compound 10-4. Two protecting groups of compound 10-3 are removed using trifluoroacetic acid and the deprotected compound is protected with Boc group in the presence of triethylamine to synthesize compound 10-5. TBDPS and Boc group are removed from the compound 10-5 and t-butylbenzylisothiocyanate is reacted therewith in the presence of triethylamine to give compound 10-6.

[SCHEME 11]

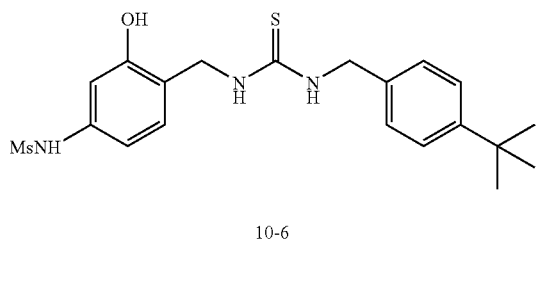

11-1

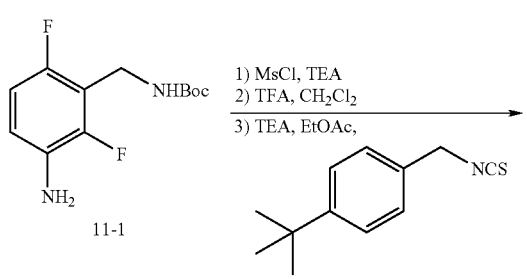

11-2

As depicted in the above Scheme 11, 2,6-difluoro-3-nitrobenzonitrile is reduced and then protected with Boc group to prepare compound 11-1. The amino group of the compound 11-1 is mesylated, and after removing of the Boc group therefrom, the mesylated compound is reacted with 4-t-butylbenzylisothiocyanate to give compound 11-2.

[SCHEME 12]

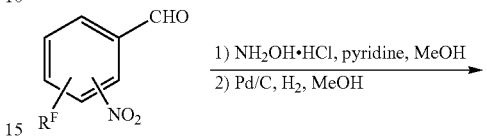

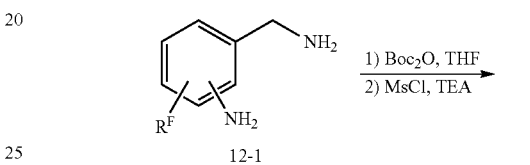

12-1

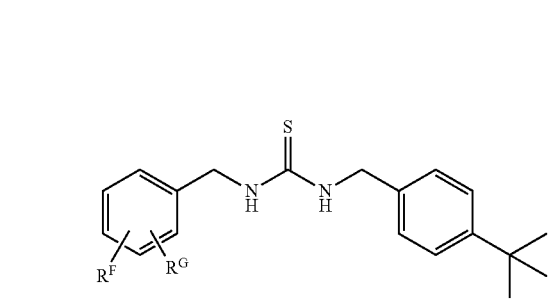

12-2

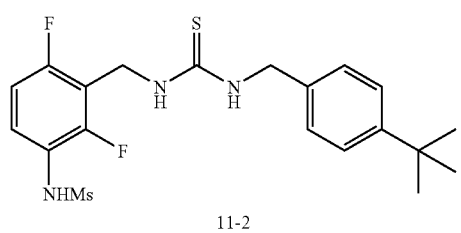

12-3

$R^F$ = H or F
$R^G$ = NHMs or NMs$_2$

As depicted in the above Scheme 12, the carbonyl group of nitrobenzaldehyde is converted into oxime group, and the oxime group and nitro group are reduced with hydrogen in the presence of Pd/C catalyst to prepare amine compound 12-1. The amine compound 12-1 is selectively protected and mesylated to afford compound 12-2. Boc group is removed from compound 12-2, and, in the presence of triethylamine, t-butylbenzylisothiocyanate compound is reacted therewith to synthesize compound 12-3a~12-3g.

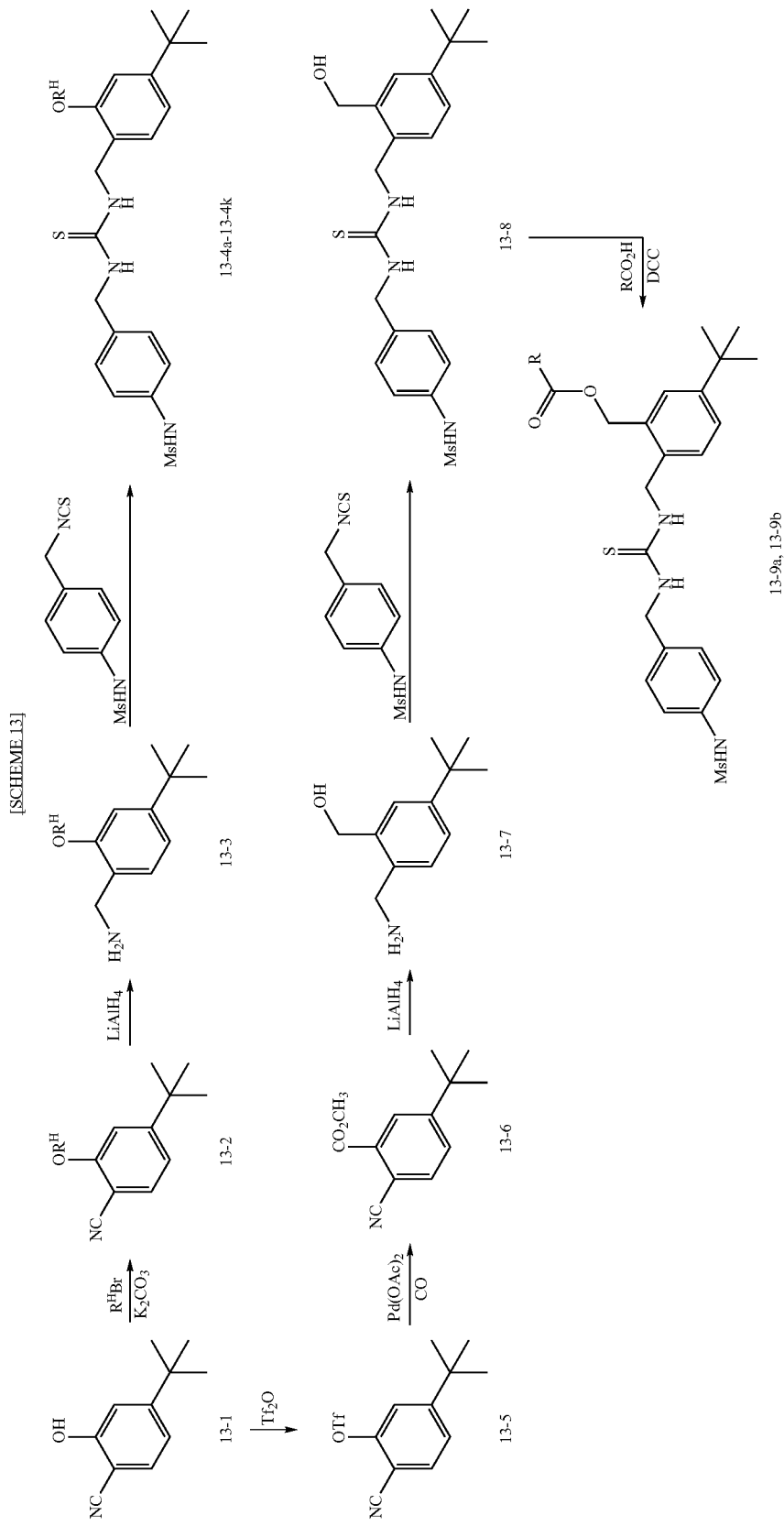

As depicted in the above Scheme 13, 4-t-butyl-2-hydroxybenzonitrile 13-1 as a starting material is O-alkylated and reduced to prepare amine compound 13-3. 4-Methanesulfonaminobenzylisothiocyanate is reacted therewith to yield thiourea compound 13-4a~13-4k. And compound 13-1 is reacted with O-triflate, and subsequently with carbon monoxide in the presence of palladium acetate catalyst to yield ester 13-6. The ester 13-6 is reduced, and then reacted with 4-methanesulfonaminobenzylisothiocyanate to prepare alcohol compound 13-8. The prepared compound 13-8 is subjected to condensation reaction with acid to yield the corresponding thiourea compound 13-9a and 13-9b.

[SCHEME 14]

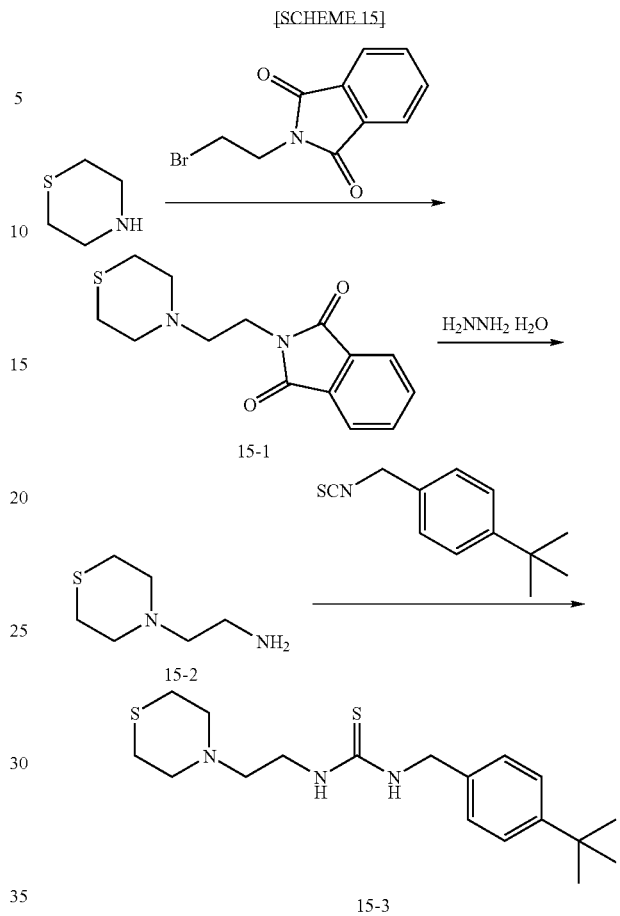

[SCHEME 15]

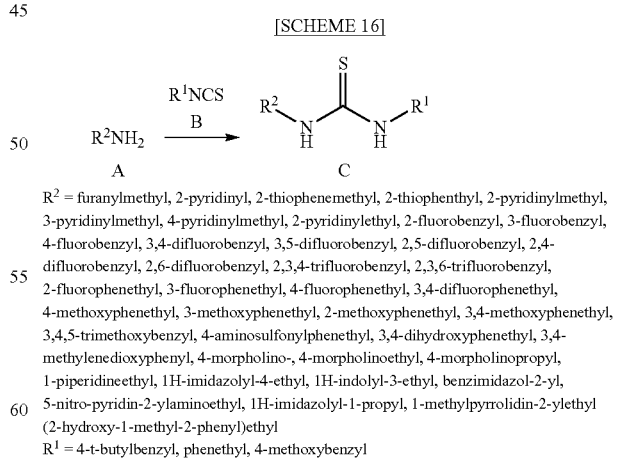

Thiomorpholine is reacted with 2-(bromoethyl)phthalimide in the presence of base to yield compound 15-1. Phthaloyl group of the compound 15-1 is treated with hydrazine to prepare amine compound 15-2 and 4-t-butylbenzylisothiocyanate is reacted therewith to afford the objective compound 15-3.

As depicted in the above Scheme 14, respective compounds 14-1 and 14-4 are obtained from 4-(methylthio)benzylalcohol and 4-methylthiazol-5-ethanol, respectively, under Mitsunobu condition, or obtained by introducing mesyl group into 4-(methylthio)benzylalcohol and 4-methylthiazol-5-ethanol, respectively, followed by reacting potassium phthalimide therewith. Phthalimide group is removed from compounds 14-1 and 14-4 with hydrazine to give amine compounds 14-2 and 14-5, respectively. The obtained amine compounds 14-2 and 14-5 are separately reacted with one equivalent of 4-t-butylbenzylisothiocyanate to the objective thiourea compounds 14-3 and 14-6, respectively. 2-Chloro-5-chloromethylpyridine is reacted with potassium phthalimide to yield compound 14-7, and then compound 14-9 is synthesized according to the same procedure as the synthetic method of the compounds 14-3 and 14-6.

[SCHEME 16]

$R^2$ = furanylmethyl, 2-pyridinyl, 2-thiophenemethyl, 2-thiophenthyl, 2-pyridinylmethyl, 3-pyridinylmethyl, 4-pyridinylmethyl, 2-pyridinylethyl, 2-fluorobenzyl, 3-fluorobenzyl, 4-fluorobenzyl, 3,4-difluorobenzyl, 3,5-difluorobenzyl, 2,5-difluorobenzyl, 2,4-difluorobenzyl, 2,6-difluorobenzyl, 2,3,4-trifluorobenzyl, 2,3,6-trifluorobenzyl, 2-fluorophenethyl, 3-fluorophenethyl, 4-fluorophenethyl, 3,4-difluorophenethyl, 4-methoxyphenethyl, 3-methoxyphenethyl, 2-methoxyphenethyl, 3,4-methoxyphenethyl, 3,4,5-trimethoxybenzyl, 4-aminosulfonylphenethyl, 3,4-dihydroxyphenethyl, 3,4-methylenedioxyphenyl, 4-morpholino-, 4-morpholinoethyl, 4-morpholinopropyl, 1-piperidineethyl, 1H-imidazolyl-4-ethyl, 1H-indolyl-3-ethyl, benzimidazol-2-yl, 5-nitro-pyridin-2-ylaminoethyl, 1H-imidazolyl-1-propyl, 1-methylpyrrolidin-2-ylethyl (2-hydroxy-1-methyl-2-phenyl)ethyl
$R^1$ = 4-t-butylbenzyl, phenethyl, 4-methoxybenzyl As depicted in the above Scheme 16, compound A and isothiocyanate compound B of the above formula are reacted with each other in the presence of suitable solvent (dichloromethane, acetonitrile, ethylacetate, dimethylformamide)

using suitable condition (triethylamine) to yield thiourea compound C (Example 76~122).

[SCHEME 17]

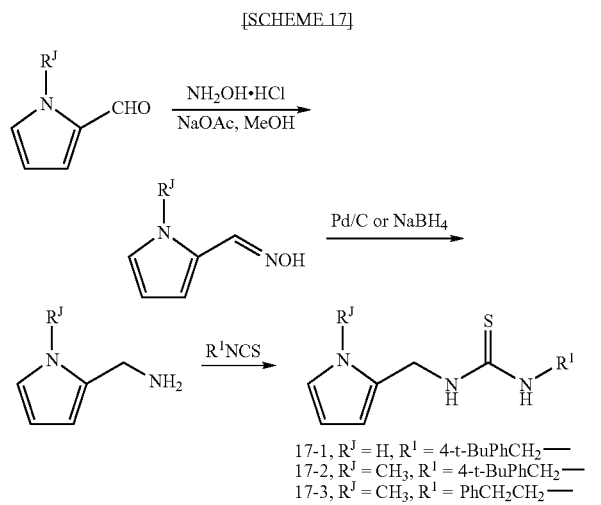

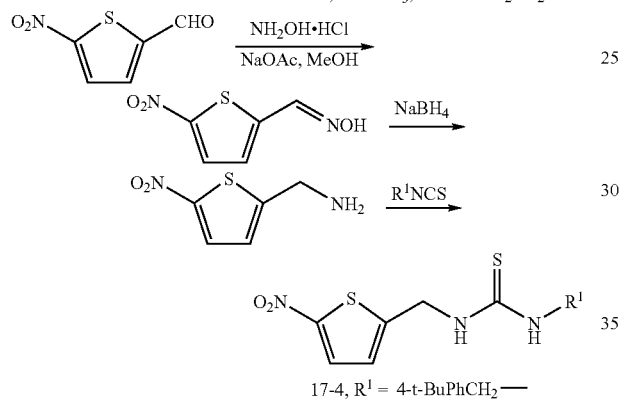

As depicted in the above Scheme 17, pyrrolecarboxaldehyde and 5-nitro-2-thiophenaldehyde are respectively converted to oximes, and the oximes are reduced to prepare primary amine hydrochloride. The prepared intermediates are reacted with isothiocyanates to give compounds 17-1~17-4, respectively.

[SCHEME 18]

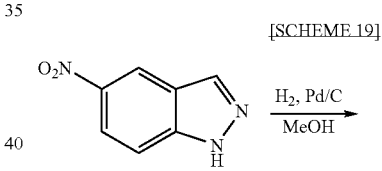

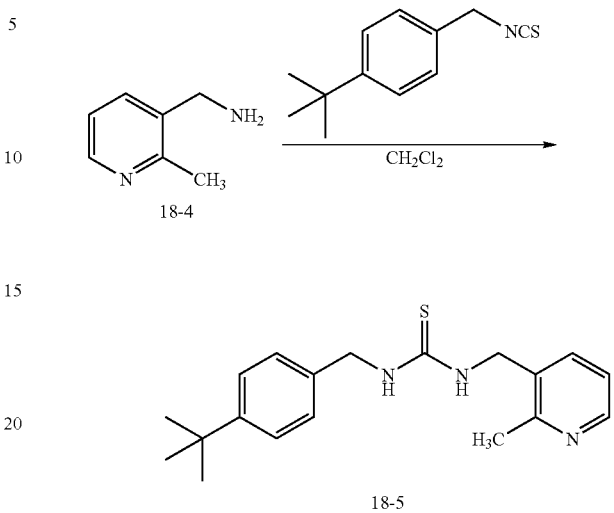

As depicted in the above Scheme 18, ethyl-2-methyl nicotinate 18-1 is reduced to prepare alcohol, and then amine is introduced thereinto. The prepared intermediate is reacted with 4t-butylbenzylisothiocyanate to yield compound 18-5.

[SCHEME 19]

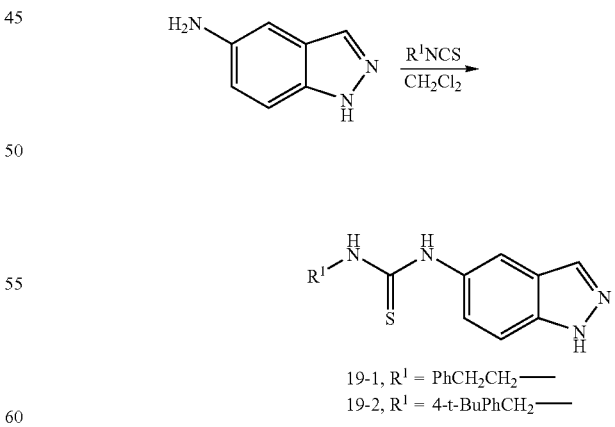

As depicted in the above Scheme 19, 5-nitro-1H-indazole is reduced to prepare amine, and then isothiocyanate is reacted therewith to afford compounds 19-1 and 19-2.

[SCHEME 20]

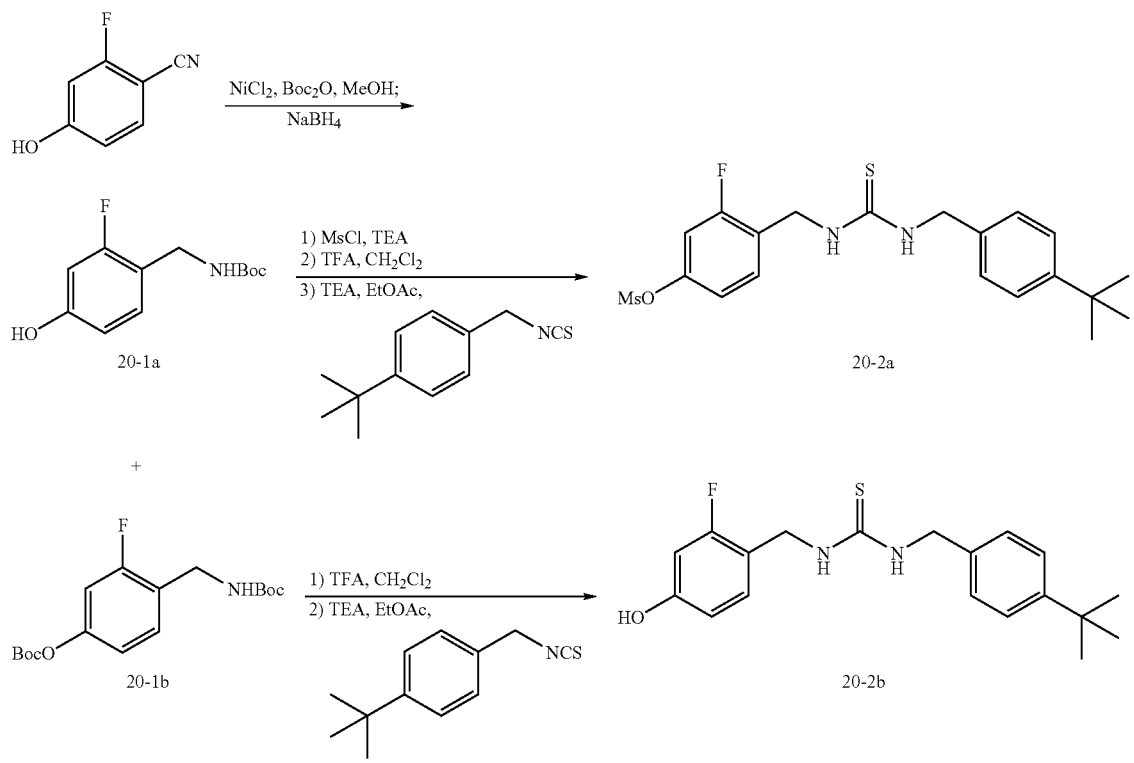

As depicted in the above Scheme 20, 2-fluorohydroxybenzonitrile is reduced with sodium borohydride in the presence of nickel catalyst, and procteted with Boc group to prepare protected amine compounds 20-1a and 20-1b. Phenol group of compound 20-1a is mesylated, and Boc group is removed therefrom, followed by reacting with t-butylbenzylisothiocyanate to give compound 20-2a. And compound 20-2b is obtained from compound 20-1b, according to the similar procedure as the synthetic method of compound 2-2a.

[SCHEME 21]

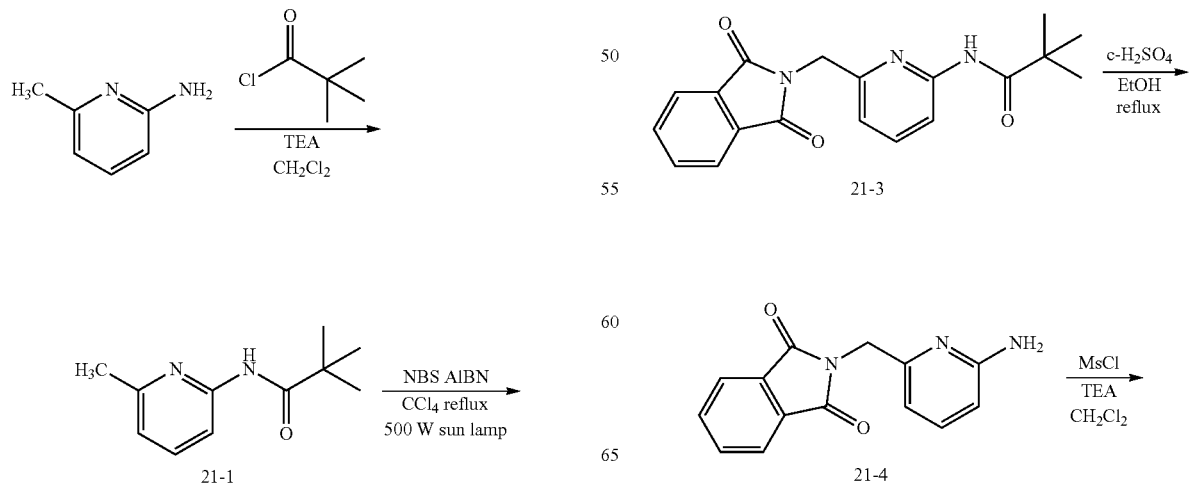

-continued

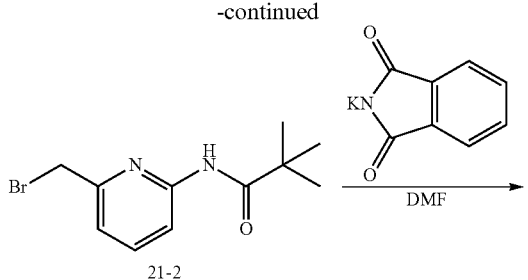

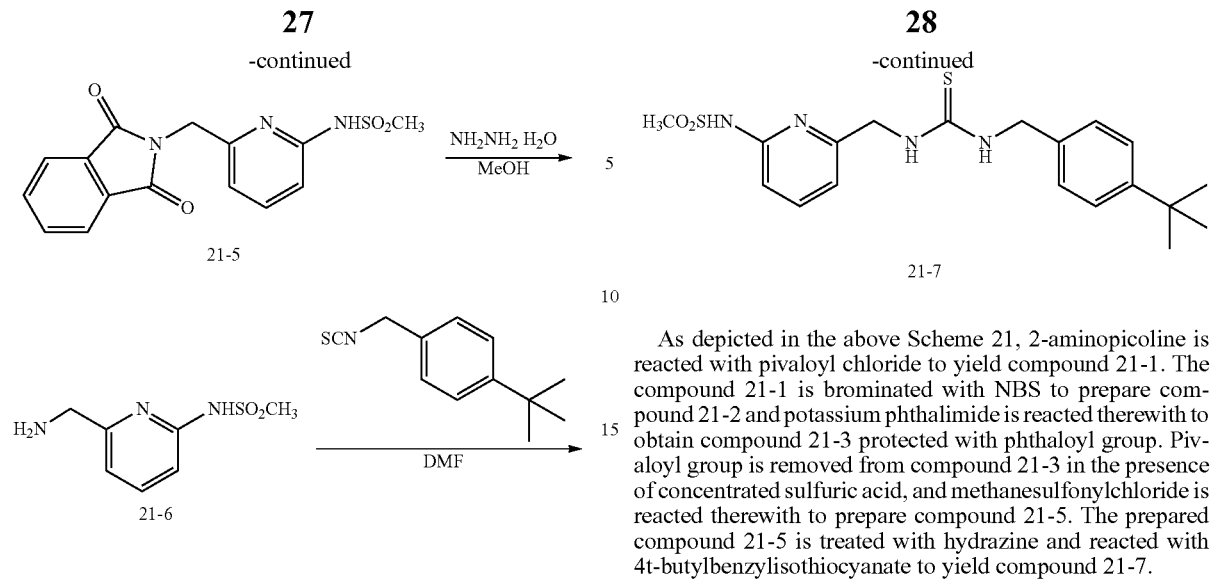

As depicted in the above Scheme 21, 2-aminopicoline is reacted with pivaloyl chloride to yield compound 21-1. The compound 21-1 is brominated with NBS to prepare compound 21-2 and potassium phthalimide is reacted therewith to obtain compound 21-3 protected with phthaloyl group. Pivaloyl group is removed from compound 21-3 in the presence of concentrated sulfuric acid, and methanesulfonylchloride is reacted therewith to prepare compound 21-5. The prepared compound 21-5 is treated with hydrazine and reacted with 4t-butylbenzylisothiocyanate to yield compound 21-7.

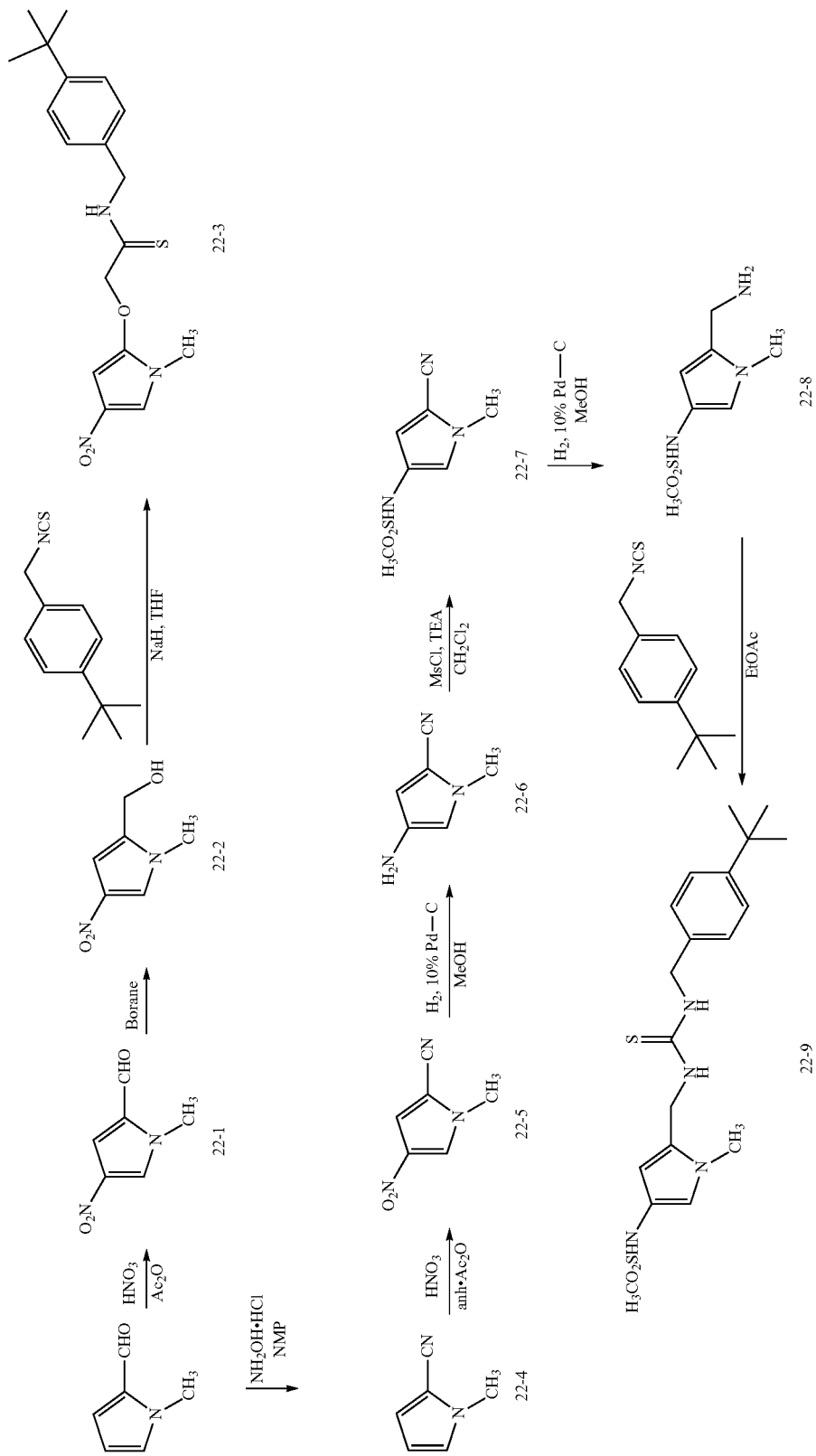

Nitro group is selectively introduced into pyrrolecarboxaldehyde under nitric acid/acetic anhydride condition and the compound 22-1 was reduced with borane to prepare alcohol 22-2. The prepared compound 22-2 is reacted with 4-t-butylbenzylisothiocyanate in the presence of sodium hydride to yield compound 22-3. And pyrrolecarboxaldehyde is reacted with hydroxylamine hydrochloride in the presence of 1-methyl-2-pyrrolidinone (NMP) as a solvent to produce nitrile compound 22-4 and nitro group is introduced thereinto under the similar condition as above. The nitro group is reduced and mesylated to give compound 22-7. The nitrile group of the compound 22-7 is reduced in the presence of palladium/carbon and 4-t-butylbenzylisothiocyanate is reacted therewith to synthesize compound 22-9.

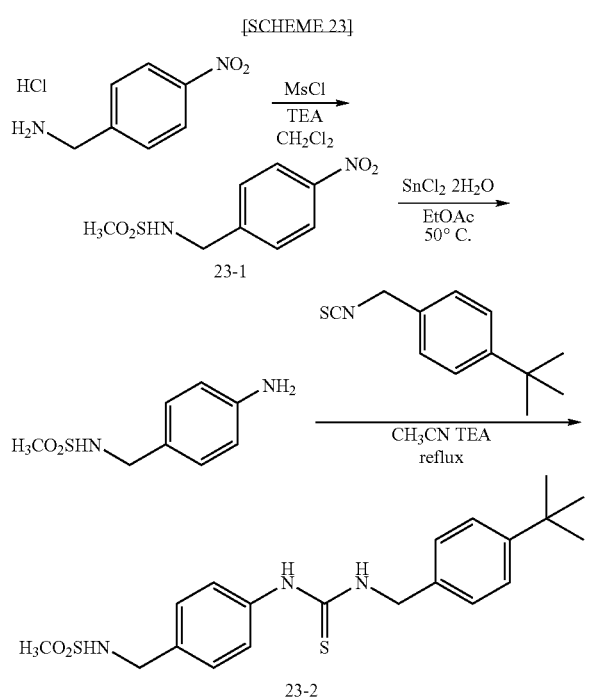

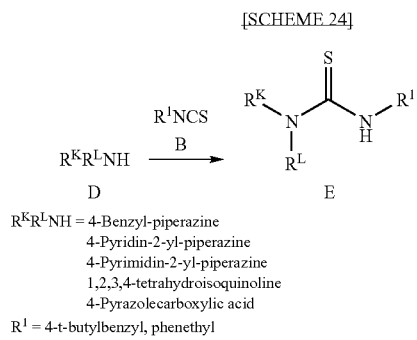

As depicted in the above Scheme 23, 4-nitrobenzylamine hydrochloride is converted to methanesulfonyl derivatives 23-1. Nitro group of the compound 23-1 is reduced with tin (II) chloride and 4-t-butylbenzylisothiocyanate is reacted therewith to give compound 23-2.

As depicted in the above Scheme 24, amine compound D is reacted with isothiocyanate compound B in suitable solvent to yield thiourea compound E (example 136~141).

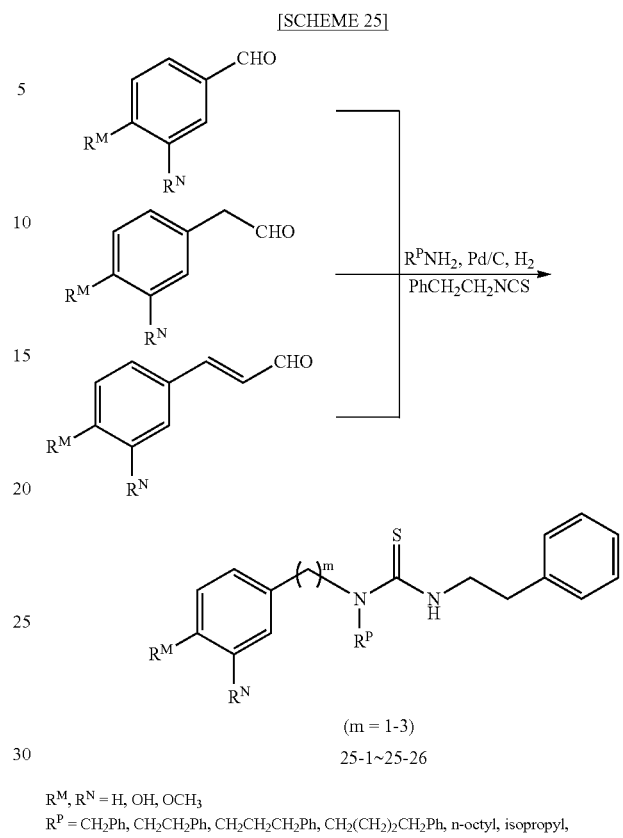

As depicted in the above Scheme 25, benzaldehyde, phenylacetaldehyde and cinnamaldehyde derivatives are subjected to reductive amination with alkylamine to prepare the corresponding secondary amines, respectively, and phenethylisothiocyanates are reacted therewith to obtain compounds 25-1~25-26 (Example 142~167, respectively).

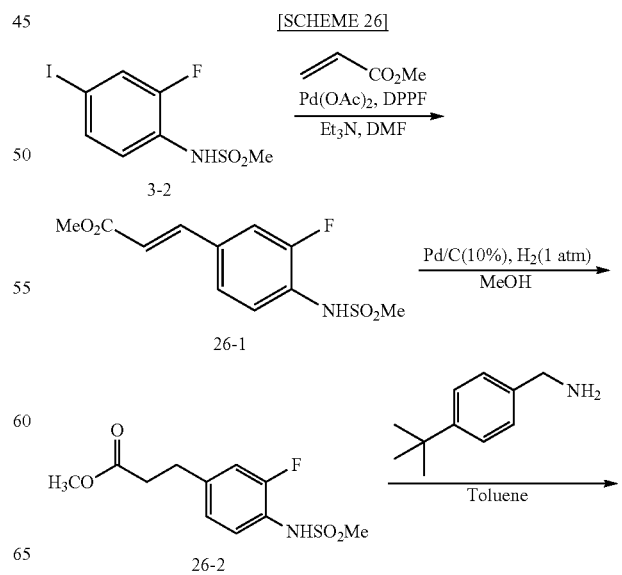

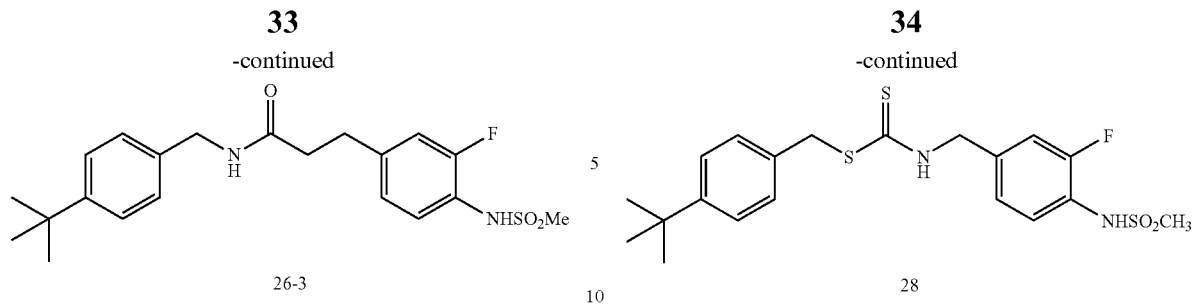

As depicted in the above Scheme 26, 2-fluoro-4-iodo methanesulfonylbenzylamine 3-2 is subjected to cross coupling using palladium to prepare compound 26-1 and the compound 26-1 is hydrogenated in the presence of palladium/carbon to give compound 26-2. The compound 26-2 is reacted with 4-t-butylbenzylamine to synthesize amide compound 26-3.

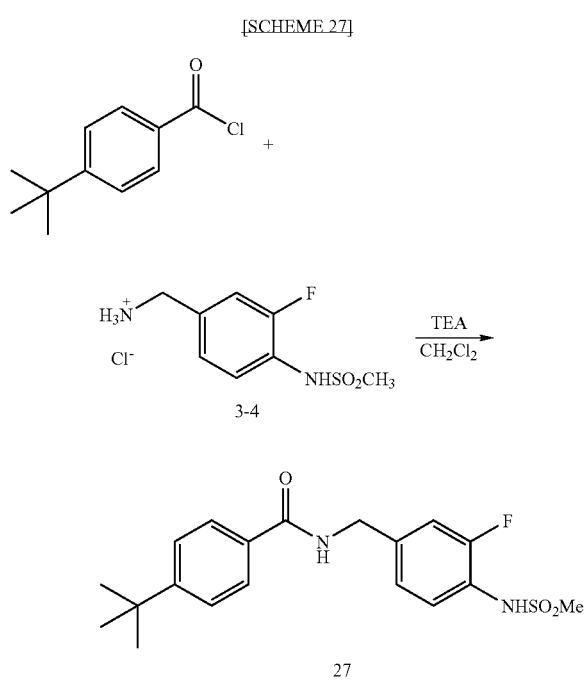

4-t-butylbenzoylchloride is reacted with 3-fluoro-4-methanesulfonylaminobenzylamine hydrochloride (3-4) to yield amide compound 27.

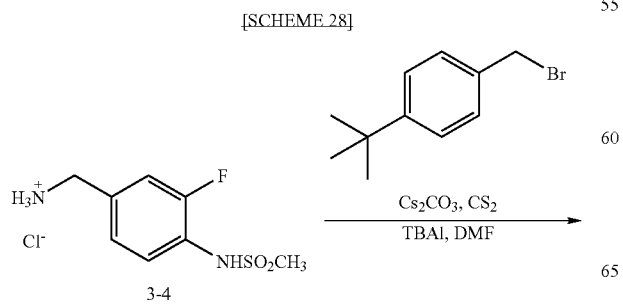

As depicted in the above Scheme 28, 3-fluoro-4-methanesulfonylaminobenzyl amine hydrochloride 3-4 is reacted with 4-t-butylbenzyl bromide and carbon disulfide in the presence of cesium carbonate to yield compound 28.

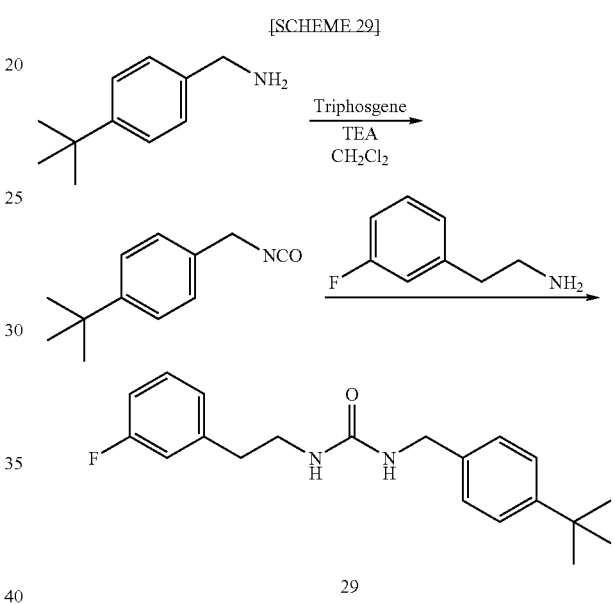

As depicted in the above Scheme 29, 4-t-butylbenzylamine is reacted with triphosgene to prepare isocyanate, and 3-fluorophenethylamine is reacted therewith to afford compound 29.

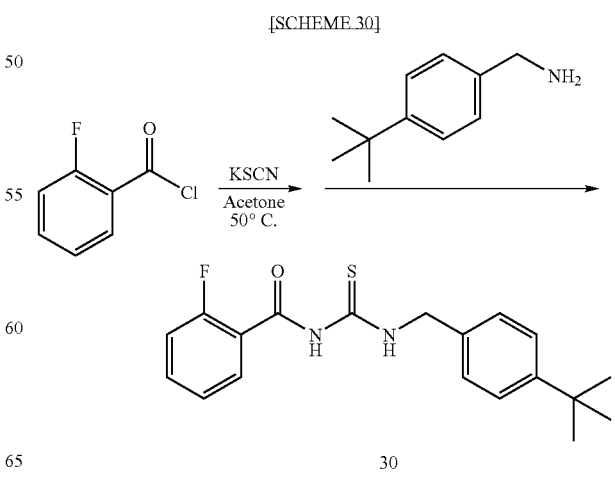

As depicted in the above Scheme 30, 2-fluorobenzoyl chloride is reacted successively with KSCN and 4t-butylbenzylamine to obtain final compound 30.

[Scheme 31]

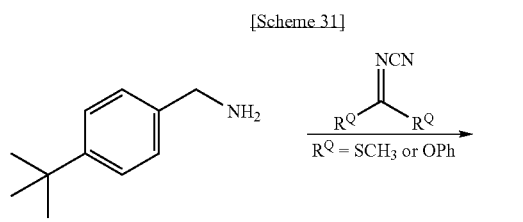

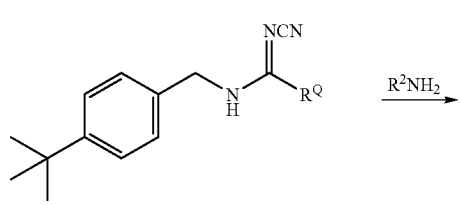

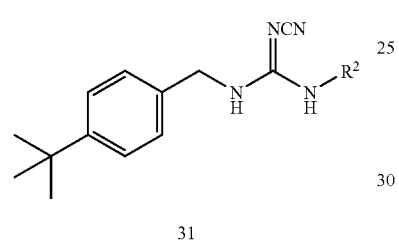

31

31-1 R² = 2-Pyridinylethyl
31-2 R² = 3-Fluorophenethyl
31-3 R² = 3,4-Difluorophenethyl
31-4 R² = 2-Fluorobenzyl
31-5 R² = 2,3,4-Trifluorobenzyl
31-6 R² = 4-Methanesulfonylaminobenzyl-

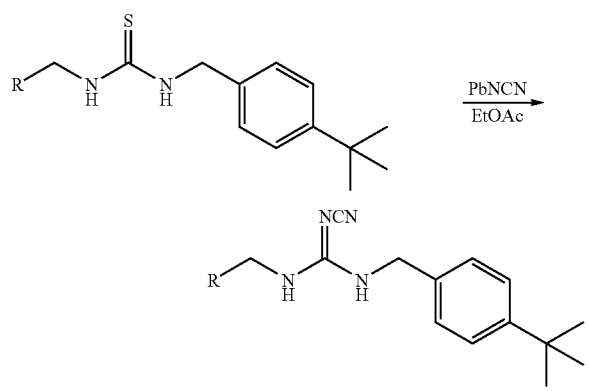

31-7, R = 2,6-difluoro-3-methanesulfonylaminophenyl-
31-8, R = 2-fluoro-5-methanesulfonylaminophenyl-
31-9, R = R = 1-methyl-1H-pyrrol-2-ylmethyl- As depicted in the above Scheme 31, cyanoguanidine compounds are synthesized by two methods. As one method, 4-t-butylbenzylamine is reacted with dimethyl N-cyanodithioiminocarbonate or diphenyl cyanocarbonimidate, and then amine is reacted therewith to yield final compounds 31-1~31-6 (Example 173~178). And thiourea compound is reacted with lead cyanamide to give compounds 31-7~31-9 (Example 179~181).

[Scheme 32]

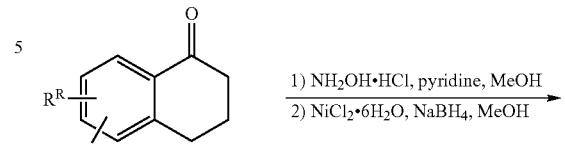

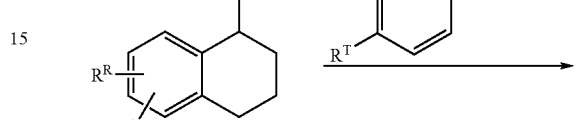

32-1, R^R = 6-OMe, R^S = H
32-3, R^R = 5-OMe, R^S = H
32-5, R^R = 7-OMe, R^S = H

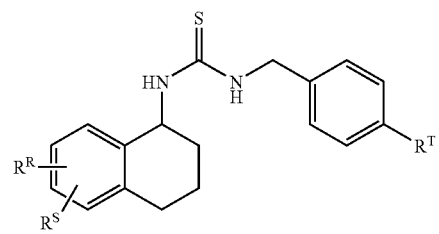

32-2, R^R = 6-OMe, R^S = H, R^T = Cl
32-4, R^R = 5-OMe, R^S = H, R^T = Cl
32-6, R^R = 7-OMe, R^S = H, R^T = Cl
32-7, R^R = 5-OMe, R^S = H, R^T = t-Bu
32-8, R^R = 8-OMe, R^S = H, R^T = t-Bu
32-9, R^R = 7-OMe, R^S = H, R^T = t-Bu
32-10, R^R = 5-OMe, R^S = 7-OMe, R^T = t-Bu
32-11, R^R = 5-OH, R^S = H, R^T = t-Bu
32-12, R^R = 7-OH, R^S = H, R^T = Cl

As depicted in the above Scheme 32, tetralone is converted to oxime and the oxime is reduced with nickel catalyst and sodium borohydride to prepare amine compounds 32-1, 32-3 and 32-5. These compounds are reacted with various benzylisothiocyanates to give compounds 32-2, 32-4 and 32-6~32-10. And methoxy group of compounds 32-3 and 32-5 are treated with hydrobromic acid to form hydroxy group and the resulting compound are reacted with various benzylisothiocyanates in the presence of triethylamine to yield compounds 32-11 and 32-12.

[Scheme 33]

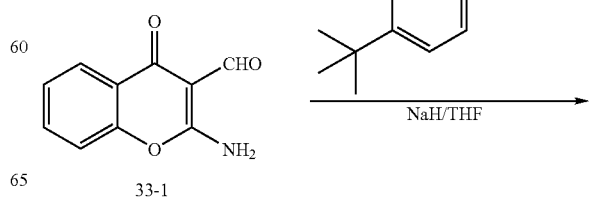

33-1

37

-continued

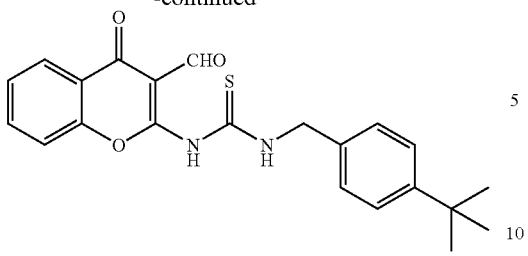

33-2

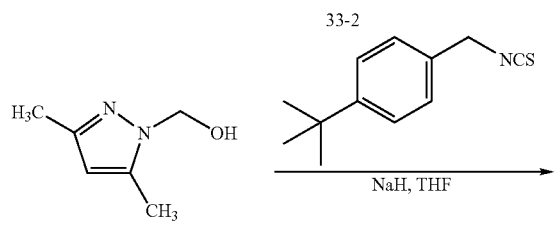

33-3

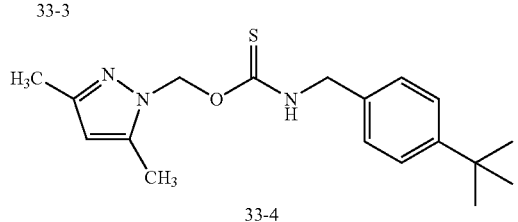

33-4

As depicted in the above Scheme 33, 2-amino-3-formyl-chromone 33-1 or 3,5-dimethylpyrazole-1-methanol 33-3 is, respectively, reacted with 4-t-butylbenzylisothiocyanate in the presence of base to give compounds 33-2 or 33-4.

[Scheme 34]

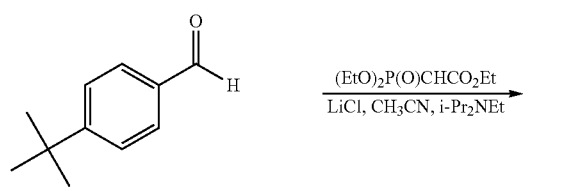

34-1

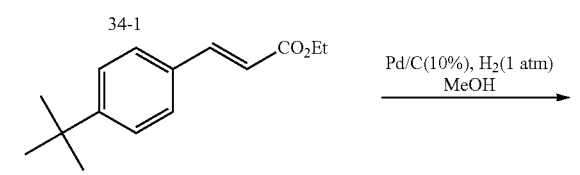

34-2

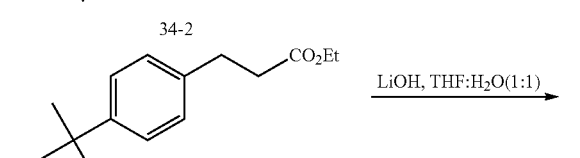

34-3

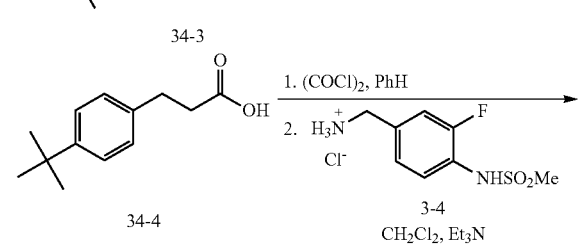

34-4

38

-continued

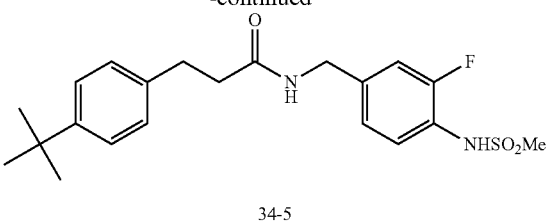

34-5

As depicted in the above Scheme 34, 4-t-butylbenzaldehyde is reacted with phosphonate to prepare compound 34-2, and the compound 34-2 is reduced and hydrolyzed to give 4-t-butylhydrocinnamic acid 34-4. The obtained compound is reacted with compound 3-4 which is prepared according to the procedure as described in Example 13, to synthesize final compound 34-5.

[Scheme 35]

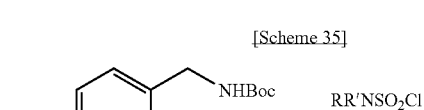

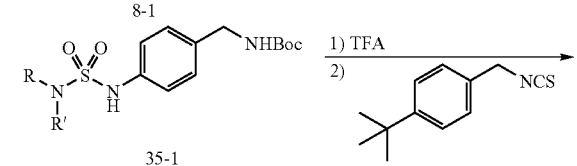

35-2

As depicted in the above Scheme 35, N-t-butyloxycarbonyl-p-aminobenzylamine 8-1 is reacted with sulfamoyl chloride in basic condition to prepare compound 35-1. The prepared compound 35-1 is deprotected with trifluoroacetic acid to afford amine, and 4-t-butylbenzylisothiocyanate is subjected to condensation reaction therewith to yield thiourea compounds 35-2a, 35-2b and 35-2c. 3-Nitro-4-aminobenzonitrile is mesylated to give compound 35-4, and then nitrile group of the compound 35-4 is reduced with borane to afford amine. 4t-Butylbenzylisothiocyanate is subjected to condensation reaction therewith to synthesize thiourea compound 35-5.

The pharmaceutical composition containing the compound of the present invention as an active ingredient can be used for preventing or treating pain, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fervescence, stomach-duodenal ulcer, inflammatory bowel disease and inflammatory diseases.

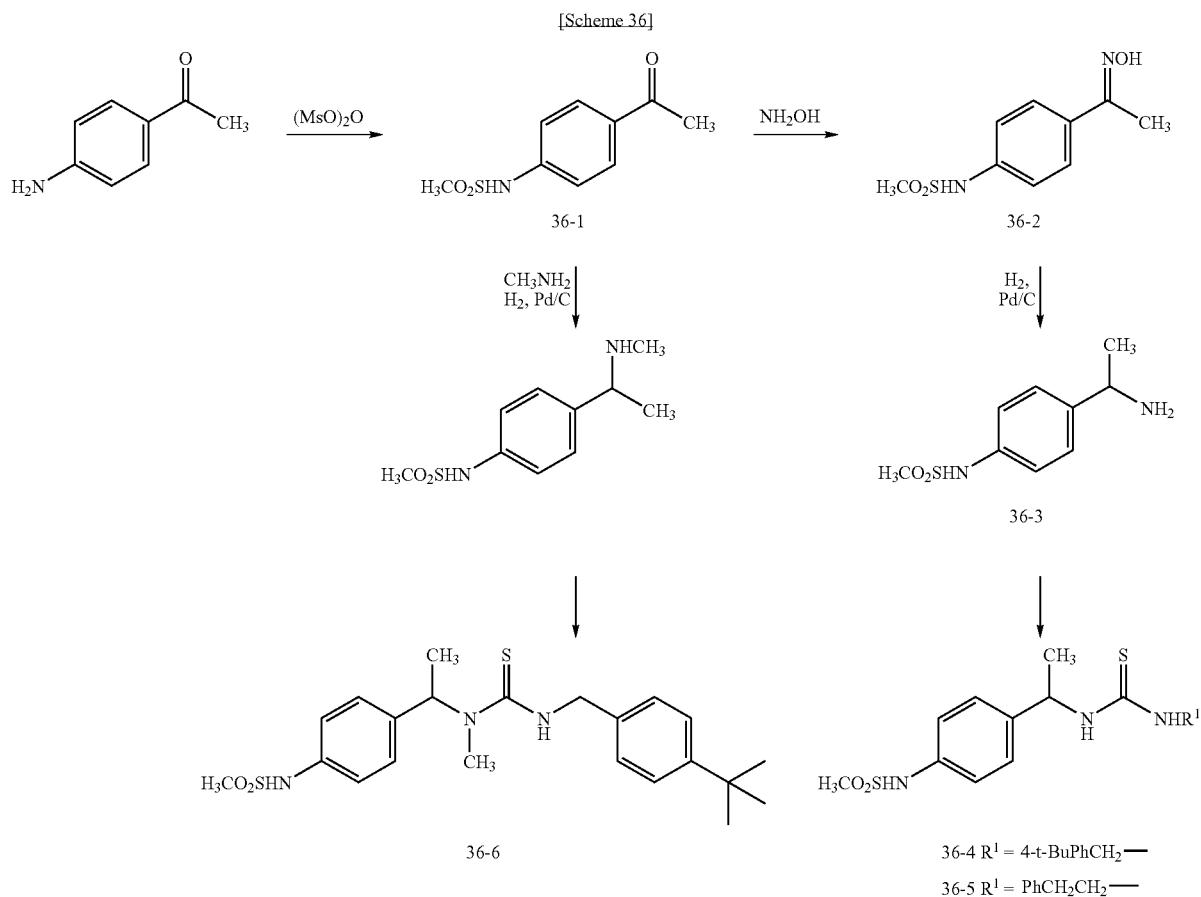

As depicted in the above Scheme 36, oxime 36-2, prepared from 4-aminoacetophenone as a starting material, is reduced to yield compound 36-3. Isothiocyanates are reacted therewith to give compounds 36-4 and 36-5. And compound 36-1 is reduced with methylamine to afford benzylamine derivatives, and 4-t-butylbenzylisothiocyanate is reacted therewith to synthesize compound 36-6.

The compound of formula (I) according to the present invention can be provided as a pharmaceutical composition containing pharmaceutically acceptable carriers, adjuvants, or diluents. For instance, the compounds of the present invention can be dissolved in oils, propylene glycol or other solvents which are commonly used to produce an injection Suitable examples of the carriers include physiological saline, polyethylene glycol, ethanol, vegetable oils, isopropyl myristate, etc., but are not limited to them. For topical administration, the compounds of the present invention can be formulated in the form of ointment or cream.

Hereinafter, the formulating methods and kinds of excipients will be described, but the present invention is not limited to them.

The compound according to the present invention may also be used in the forms of pharmaceutically acceptable salts thereof, for example, alkali metals salts such as sodium salts, potassium salts and the like; alkali earth metals salts such as calcium salts, magnesium salts and the like; amines such as triethanolamine or ammonium salts, and may be used either alone or in combination or in admixture with other pharmaceutically active compounds.

The compounds of the present invention may be formulated into injections by dissolving, suspending or emulsifying in water-soluble solvent such as saline and 5% dextrose, or in water-insoluble solvents such as vegetable oils, synthetic fatty acid glyceride, higher fatty acid esters and propylene glycol. The formulations of the invention may include any of conventional additives such as dissolving agents, isotonic agents, suspending agents, emulsifiers, stabilizers and preservatives.

The preferable dose level of the compounds according to the present invention depends upon a variety of factors including the condition and body weight of the patient, severity of the particular disease, dosage form, and route and period of administration, but may appropriately be chosen by those skilled in the art. The compounds of the present invention are preferably administered in an amount ranging from 0.001 to 100 mg/kg of body weight per day, and more preferably from 0.01 to 30 mg/kg of body weight per day. Doses may be administered once a day, or several times a day with each divided portions. The compounds of the present invention are used in a pharmaceutical composition in an amount of 0.0001~10% by weight, and preferably 0.001~1% by weight, based on the total amount of the composition.

The pharmaceutical composition of the present invention can be administered to a mammalian subject such as rat, mouse, domestic animals, human being and the like via various routes. The methods of administration which may easily be expected include oral and rectal administration; intravenous, intramuscular, subcutaneous, intrauterine, duramatral and intracerebroventricular injections.

BEST MODE FOR CARRYING OUT THE INVENTION

The present invention is more specifically explained by the following examples. However, it should be understood that the present invention is not limited to these examples in any manner.

EXAMPLE 1

Synthesis of 1-(1H-indol-5-ylmethyl)-3-phenethylthiourea (1-5)

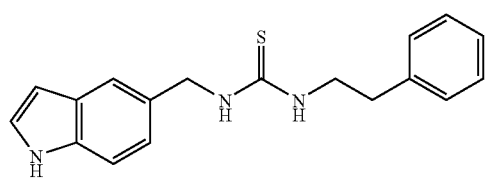

1-5

Step 1: synthesis of (1H-indol-5-yl)methylamine

To an ice cold suspension of aluminium chloride (126 mg) in ether (1.5 ml) was added a suspension of lithium aluminium hydride (55 mg) in ether (1.5 ml), followed by stirring for 5 min. A solution of 5-cyanoindole (103 mg) in ether (5 ml) was added dropwise thereto. The mixture was stirred at room temperature for 6 hours, followed by adding aqueous Rochel solution thereto and then stirring for 5 hours. The resulting mixture was basified with 1M aqueous sodium hydroxide solution, extracted twice with ethyl acetate (50 ml), washed with saturated aqueous sodium chloride solution, dried over magnesium sulfate and then filtered to yield (1H-indol-5-yl)methylamine (93 mg, 88%).

$^1$H NMR(300 MHz, CD$_3$OD): δ 7.46(d, 1H, J=1.0 Hz), 7.29(d, 1H, J=8.3 Hz), 7.14(d, 1H, J=3.2 Hz), 7.02(dd, 1H, J=1.7, 8.3 Hz), 6.34(dd, 1H, J=0.7, 3.2 Hz), 3.89(s, 2H)

Step 2: synthesis of 1-(1H-indol-5-ylmethyl)-3-phenethylthiourea (1-5)

(1H-indol-5-yl)methylamine (8.5 mg) prepared in Step 1 was dissolved in dimethylformamide (100 μl) and the solution was diluted with dichloromethane (1 ml). To the diluted solution was added phenethylisothiocyanate (40 μl) and the mixture was stirred at room temperature for 2 hours. The resulting mixture was concentrated under reduced pressure and the obtained residue was chromatographed on a silica gel column eluting with ethyl acetate/hexane (2/3) to yield 1-(1H-indol-5-ylmethyl)-3-phenethylthiourea (15 mg, 83%).

$^1$H NMR(300 MHz, CDCl$_3$): δ 8.17(s, 1H), 7.53(s, 1H), 7.28(d, 1H, J=8.3 Hz), 7.11-7.19(m, 5H), 6.98-7.04(m, 2H), 6.46(t, 1H, J=2.2 Hz), 6.03(s, 1H), 5.59(s, 1H), 4.44(s, 2H), 3.66(m, 2H), 2.77(t, 2H, J=6.8 Hz)

EXAMPLE 2

Synthesis of 1-(1H-indol-5-ylmethyl)-3-phenethylurea (1-6)

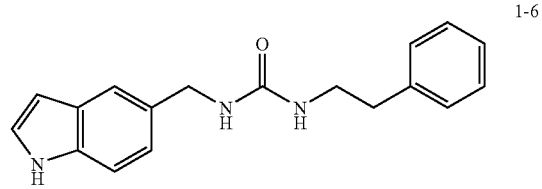

1-6

(1H-indol-5-yl)methylamine (12.5 mg) was reacted with phenethylisocyanate (30 μl) according to the similar procedure as described in step 2 of Example 1, to give 1-(1H-indol-5-ylmethyl)-3-phenethylurea (1-6) (19 mg, 76%).

$^1$H NMR(300 MHz, CDCl$_3$): δ 8.16(s, 1H), 7.44(s, 1H), 7.27(d, 1H, J=8.3 Hz), 7.02-7.21(m, 7H), 6.43-6.45(m, 1H), 4.48(t, 1H), 4.31(d, 2H, J=5.6 Hz), 4.22(m, 1H), 3.37(q, 2H, J=6.8 Hz), 2.71(t, 2H, J=6.8 Hz)

EXAMPLE 3

Synthesis of 1-(4-t-butylbenzyl)-3-(1H-indol-5-ylmethyl)thiourea (1-7)

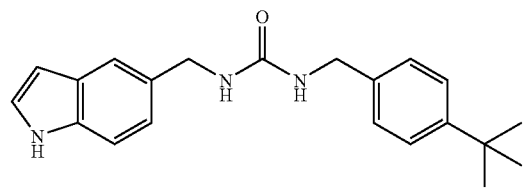

1-7

Step 1: synthesis of 4-t-butylbenzylisothiocyanate

Di-2-pyridyl thionocarbonate (45 mg) was dissolved in methylenechloride (2 ml) and to the solution were added 4-t-butylbenzylamine (29 mg) and triethylamine (20 μl), followed by stirring at room temperature for 2 hours. The reaction solution was concentrated under reduced pressure and the obtained residue was chromatographed on a silica gel column eluting with ethyl acetate/hexane (1/10) to yield 4-t-butylbenzylisothiocyanate (26 mg, 71%).

¹H NMR(300 MHz, CDCl₃): δ 7.39(d, 2H, J=8.5 Hz), 7.23(d, 2H, J=8.3 Hz), 4.65(s, 2H), 1.30(s, 9H)

Step 2: Synthesis of 1-(4-t-butylbenzyl)-3-(1H-indol-5-ylmethyl)thiourea (1-7)

(1H-indol-5-yl)methylamine (15 mg) was reacted with 4-t-butylbenzylisothiocyanate (20 mg) according to the similar procedure as described in Step 2 of Example 1, to synthesize 1-(4-t-butylbenzyl)-3-(1H-indol-5-ylmethyl)thiourea (1-7) (21 mg, 70%).

¹H NMR(300 MHz, CDCl₃): δ 8.33(s, 1H), 7.48(s, 1H), 7.19-7.33(m, 4H), 7.03-7.10(m, 4H), 6.47(t, 1H), 6.18(s, 1H), 6.06(s, 1H), 4.58(d, 2H, J=13 Hz), 1.26(s, 9H)

EXAMPLE 4

Synthesis of 1-(4-t-butylbenzyl)-3-(4-methanesulfonylbenzyl)thiourea (1-8)

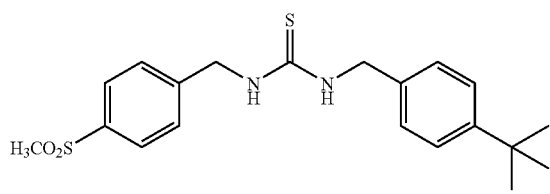

1-8

Lithium aluminum hydride (0.38 g) was dissolved in anhydrous ether (20 ml). The solution was cooled to 0° C. and 4-(methylsulfonyl)benzonitrile (1.81 g) was slowly added dropwise thereto. The mixture was stirred for 3 hours while allowed to slowly warm up to room temperature and the reaction was quenched with 20% aqueous sodium hydroxide solution and water. The water layer was washed with ether, and then the ether layer was mixed with the organic layer. The combined organic layer was dried over anhydrous magnesium sulfate and concentrated. The residue was purified by column-chromatography (acetone) to yield a liquid (0.3 g).

The obtained liquid was dissolved in dichloromethane (10 ml) and 4-t-butylbenzylisothiocyanate (0.33 g) was added thereto, followed by stirring at room temperature for 19 hours. The reaction mixture was concentrated and then purified by column-chromatography (hexane/ethyl acetate=1/1) to yield compound 1-8 (0.02 g) as a white solid.

¹H NMR(300 MHz, CDCl₃): δ 7.85-7.81(m, 2H), 7.41-7.30(m, 4H), 7.27-7.23(m, 2H), 6.25(brs, 1H), 6.05(brs, 1H), 4.88(d, 2H, J=6 Hz), 4.60-4.55(m, 2H), 3.01(s, 3H), 1.31(s, 9H)

EXAMPLE 5

Synthesis of 1-(4-t-butylbenzyl)-3-[2-(1-methyl-1H-pyrrol-2-yl)ethyl]thiourea (1-9)

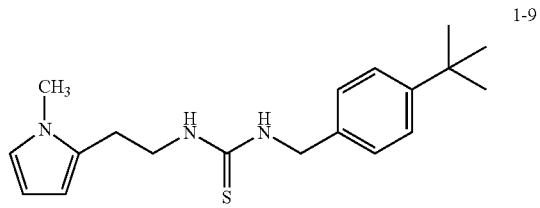

1-9

Step 1: Synthesis of (1-methyl-1H-pyrrol-2-yl)ethylamine 1-methyl-2-pyrroleacetonitrile (2 g) was slowly added dropwise to a suspension of lithium aluminium hydride (695 mg) in ether (100 ml) while the temperature was adjusted to −78° C. The mixture was stirred for 1 hour, and then stirred for 3 hours at room temperature. After confirming the completion of the reaction using TLC, 15% aqueous sodium hydroxide solution (10 ml) and water (20 ml) were added dropwise and the resulting mixture was stirred for 1 hour. The reaction mixture was extracted three times with ether. The organic layer was washed with saturated aqueous sodium chloride solution and concentrated under reduced pressure to yield amine compound. The amine compound, which was not purified, was used in the following reaction.

Step 2: Synthesis of 1-(4-t-butylbenzyl)-3-[2-(1-methyl-1H-pyrrol-2-yl)ethyl]thiourea (1-9)

Amine (250 mg) prepared in Step 1 and 4-t-butylbenzylisothiocyanate (420 mg) were dissolved in ethyl acetate (20 ml) and the solution was stirred at room temperature for 12 hours. The resulting mixture was concentrated under reduced pressure to remove the solvent and the residue was purified by column-chromatography (ethyl acetate/hexane=1/3) to yield compound 1-9 (498 mg, 75%) as a liquid.

¹H NMR (300 MHz, CDCl₃) δ 7.37(d, 2H), 7.19(d, 2H), 6.54(m, 1H), 6.01(m, 1H), 5.83(s, 1H), 4.46(brs, 2H), 3.72 (brs, 2H), 2.841(t, 2H, J=6.9 Hz), 1.31(s, 9H)

EXAMPLE 6

Synthesis of 1-(4-amino-3,5-dichlorobenzyl)-3-(4-t-butylbenzyl)thiourea (1-10)

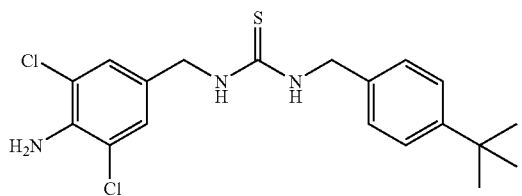

1-10

4-amino-3,5-dichlorobenzonitrile (260 mg) was dissolved in methanol (20 ml) and a small amount of concentrated hydrochloric acid and 5% palladium/carbon catalyst was added thereto. After the mixture was stirred for 15 hours, the reaction mixture was filtered through celite and concentrated. The obtained mixture was dissolved in dichloromethane (10 ml), and 4-t-butylbenzylisothiocyanate (200 mg) and triethylamine (2 ml) was added thereto, followed by stirring at room temperature for 15 hours. The resulting mixture was extracted with water and dichloromethane, and the residue was purified by column-chromatography (hexane/ethyl acetate=1/1) to yield compound 1-10 (72 mg, 13%) as a liquid.

$^1$H NMR (300 MHz, CDCl$_3$) δ 7.40-7.00(m, 6H), 5.92(brs, 2H), 4.58(m, 2H), 4.45(m, 2H), 3.71(brs, 2H), 1.31(s, 9H)

EXAMPLE 7

Synthesis of 1-(4-t-butylbenzyl)-3-(pyrazin-2-yl-methyl)thiourea (1-11)

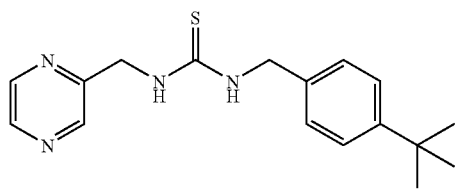

1-11

Pyrazinecarbonitrile (500 mg) and 10% palladium/carbon (450 mg) were dissolved in anhydrous methanol (30 ml) and the mixture was stirred under hydrogen atmosphere for 12 hours.

The resulting mixture was filtered, and then the filtrate was concentrated under reduced pressure. The obtained compound (200 mg) and 4-t-butylbenzylisothiocyanate (330 mg) were dissolved in ethyl acetate (30 ml). The solution was stirred for 12 hours and then concentrated. The resulting residue was purified by column-chromatography (ethyl acetate/hexne=3/1) to yield the compound 1-11 (271 mg, 53%).

$^1$H NMR (300 MHz, CDCl$_3$) δ 8.51(s, 1H), 8.41(s, 1H), 8.16(s, 1H), 7.38(m, 2H), 7.29(m, 2H), 5.10(s, 2H), 4.86(d, 2H, J=2.25 Hz), 1.33(s, 9H)

EXAMPLE 8

Synthesis of 1-(4-t-butylbenzyl)-3-(3-cyanopyrazin-2-ylmethyl)thiourea (1-12)

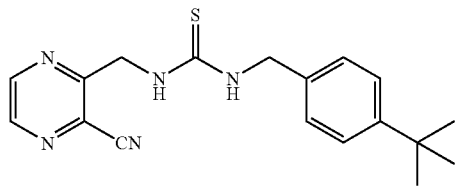

1-12

2,3-pyrazinedicarbonitrile (200 mg) and 10% palladium/carbon (200 mg) were dissolved in anhydrous methanol (30 ml) and the mixture was stirred under hydrogen atmosphere for 12 hours. The resulting mixture was filtered, and then the filtrate was dried under reduced pressure to give an amine. The obtained amine (150 mg) and 4-t-butylbenzylisothiocyanate (180 mg) were dissolved in ethyl acetate (30 ml). The solution was stirred for 12 hours to complete the reaction and purified by column-chromatography (ethyl acetate/hexane=3/1) to yield the compound 1-12 (77 mg, 25%) as a white solid.

$^1$H NMR (300 MHz, CDCl$_3$) δ 8.76(m, 1H), 8.67(m, 1H), 7.38(m, 4H), 5.38(s, 2H), 4.98(d, 2H, J=2.7 Hz), 1.32(s, 9H)

EXAMPLE 9

Synthesis of 1-(4-amino-2,5-difluorobenzyl)-3-(4-t-butylbenzyl)thiourea (1-13)

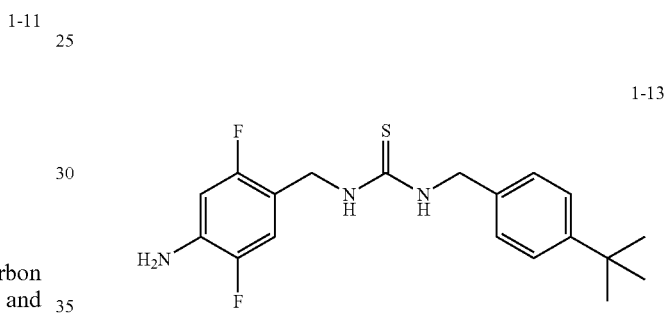

1-13

Step 1: Synthesis of 4-amino-2,5-difluorobenzylamine 4-amino-2,5-difluorobenzonitrile (400 mg) and Raney nickel Catalyst were added to methanol (20 ml) and the mixture was stirred under hydrogen atmosphere at room temperature for 18 hours. After confirming the completion of the reaction, the resulting mixture was filtered through celite and the filtrate was concentrated under reduced pressure. The following procedure was carried out, using the concentrate which was not purified.

Step 2: Synthesis of 1-(4-amino-2,5-difluorobenzyl)-3-(4-t-butylbenzyl)thiourea (1-13)

The compound (330 mg) obtained in Step 1 and 4-t-butylbenzylisothiocyanate (428 mg) were dissolved in ethyl acetate (40 ml) and the solution was stirred at room temperature for 6 hours. The mixture was concentrated under reduced pressure and the residue was purified by column-chromatography (ethyl acetate/hexane=1/3) to yield the compound 1-13 (190 mg, 25%).

$^1$H NMR(300 MHz, CDCl$_3$): δ 7.37(m, 2H), 7.22(m, 2H), 6.95(m, 1H), 6.43(m, 1H), 6.08(brs, 1H), 5.90(brs, 1H), 4.59 (s, 2H), 4.57(s, 2H), 3.83(s, 2H), 1.31(s, 9H)

EXAMPLE 10

Synthesis of 1-phenethyl-3-(4-sulfamoylbenzyl)thiourea (2-5)

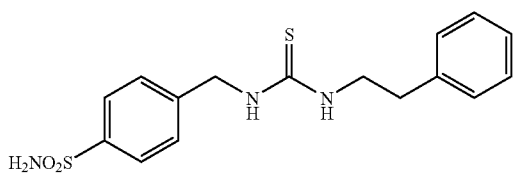

2-5

Step 1: Synthesis of 4-iodo-1-sulfamoylbenzene (2-2)

Pipsylchloride (100 mg) was dissolved in 28% ammonia solution (4 ml) and the solution was stirred at room temperature for 1 hours. The resulting mixture was extracted with ethyl acetate (20 ml), washed with water and saturated aqueous sodium chloride solution, dried over anhydrous magnesium sulfate, and then concentrated under reduced pressure. The residue was chromatographed on column eluting with ethyl acetate/hexane (1/2) to yield the compound 2-2 (89 mg, 100%).

$^1$H NMR(300 MHz, CD$_3$OD): δ 7.91(td, 1H, J=9.0 Hz), 7.63(td, 1H, J=9.0 Hz)

Step 2: Synthesis of 4-cyano-1-sulfamoylbenzene (2-3)

The compound 2-2 (58 mg) prepared in Step 1 was dissolved in dimethylformamide (2 ml) and to the solution were added zinc cyanide [Zn(CN)$_2$] (58 mg) and tetrakistriphenylphosphine palladium (10 mg), followed by stirring at 80° C. for 12 hours. The resulting mixture was basified with aqueous sodium bicarbonate solution, diluted with ethyl acetate (30 ml), washed with water and saturated aqueous sodium chloride solution, dried over anhydrous magnesium sulfate, and then concentrated under reduced pressure. The obtained residue was chromatographed on silica gel column eluting with ethyl acetate/hexane (1/2) to yield the compound 2-3 (30 mg, 80%).

$^1$H NMR(300 MHz, CDCl$_3$): δ 7.92-7.96 (m, 2H), 7.69-7.73 (m, 2H), 6.47 (s, 2H)

Step 3: Synthesis of 4-sulfamoylaminobenzene (2-4)

The compound 2-3 (52 mg) prepared in Step 2 was dissolved in methanol (2 ml) and to the solution were added a catalytic amount of 10% palladium/carbon and concentrated hydrochloric acid (10 μl), followed by stirring under hydrogen gas atmosphere at room temperature for 1 hour. The resulting mixture was diluted in ether, filtered through celite, neutralized with 1N aqueous sodium hyroxide solution, and then washed with water and saturate aqueous sodium chloride solution. The obtained residue was dried over anhydrous magnesium sulfate and then concentrated under reduced pressure to yield the compound 24 (26 mg, 50%).

$^1$H-NMR(300 MHz, CD$_3$OD): δ 7.77 (dd, 2H, J=1.7, 6.6 Hz), 7.41 (d, 2H, J =8.5 Hz), 3.80(s, 2H)

Step 4: Synthesis of 1-phenethyl-3-(4-sulfamoylbenzyl)thiourea (2-5)

The compound 24 (10 mg) prepared in Step 3 was dissolved in dimethylformamide (100 μl). The solution was diluted with dichloromethane (2 ml) and to the solution was added phenethylisothiocyanate (1.0 ml), followed by stirring at room temperature for 2 hours. The reaction solution was concentrated under reduced pressure and the obtained residue was chromatographed on a column eluting with ethyl acetate/hexane (1/1) to yield the compound 2-5 (11 mg, 59%).

$^1$H NMR(300 MHz, CD$_3$OD): δ 7.82-7.85 (m, 2H), 7.42 (d, 2H, J=8.5 Hz), 7.16-7.30 (m, 5H), 4.78 (br s, 2H), 3.72 (br s, 2H), 2.88 (t, 2H, J=7.1 Hz)

EXAMPLE 11

Synthesis of 1-phenethyl-3-(4-sulfamoylbenzyl)urea (2-6)

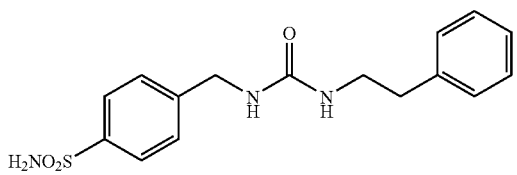

2-6

Compound 2-6 (13 mg, 79%) was synthesized according to the same procedure as described in Step 4 of Example 10 except that compound 2-4 (9 mg) was reacted with phenethylisocyanate (100 μl).

$^1$H NMR(300 MHz, CD$_3$OD): δ 7.82-7.84 (m, 2H), 7.39 (d, 2H, J=8.3 Hz), 7.15-7.32 (m, 5H), 4.35 (s, 2H)

EXAMPLE 12

Synthesis of 1-(4-t-butylbenzyl)-3-(4-sulfamoylbenzyl)thiourea (2-7)

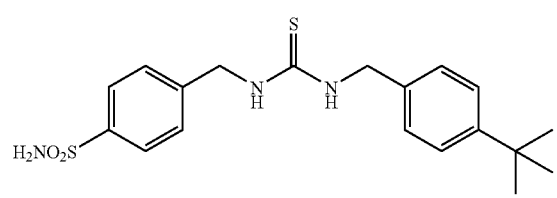

2-7

Compound 2-7 (7 mg, 96%) was synthesized according to the same procedure as described in Step 4 of Example 10 except that compound 24 (7 mg) and 4-t-butylbenzylisothiocyanate (10 mg) were used as reactants.

¹H NMR(300 MHz, acetone-4): δ 7.81 (d, 2H, J=8.3 Hz), 7.48 (d, 2H, J=8.3 Hz), 7.36 (dd, 2H, J=1.7, 6.3 Hz), 7.26 (d, 2H, J=8.3 Hz), 4.91 (br s, 2H), 4.75 (br s, 2H), 1.29 (s, 9H)

EXAMPLE 13

Synthesis of 1-(4-t-butylbenzyl)-3-(3-fluoro-4-methanesulfonylaminobenzylthiourea (3-5)

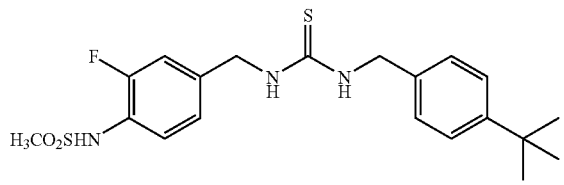

Step 1: Synthesis of 2-fluoro-4-iodo-1-methanesulfonylaminobenzene (3-2)

2-fluoro-4-iodophenylamine (1.50 g) was dissolved in dichloromethane (40 ml) and to the solution were added pyridine (1.02 ml) and methanesulfonylchloride (700 μl). The mixture was stirred at room temperature for 1 hour and 1.5 N aqueous hydrochloric acid was added thereto to quench the reaction. The resulting mixture was extracted with dichloromethane, dried over anhydrous magnesium sulfate, and then concentrated under reduced pressure. The obtained residue was column-chromatographed (ethyl acetate/hexane=1/1) to yield the compound 3-2 (1.89 g, 95%).

¹H NMR(300 MHz, CDCl₃): δ 7.47(dd, 2H, J=1.2, 1.7 Hz) 7.30(t, 1H, J=8.3 Hz) 6.51(s, 1H) 3.01(s, 3H)

Step 2: Synthesis of 4-cyano-2-fluoromethanesulfonylaminobenzene (3-3)

The compound 3-2 (1.81 g) prepared in Step 1 was dissolved in dimethylformamide (10 ml) and to the solution were added zinc (II) cyanide (845 mg) and tetrakistriphenylphosphine palladium (187 mg), followed by stirring at 80-90° C. for 1.5 hours. The resulting mixture was diluted with ethyl acetate (20 ml), washed with water and saturated aqueous sodium chloride solution, and then dried over anhydrous magnesium sulfate. The remaining liquid was concentrated under reduced pressure and the obtained residue was chromatographed on column eluting with ethyl acetate/hexane (1/2) to yield the compound 3-3 (1.03 g, 80%).

¹H NMR(300 MHz, CDCl₃): δ 7.65(t, 1H, J=8.0 Hz) 7.41 (d, 1H, J=9.8 Hz) 7.37(dd, 1H, J=9.5, 1.7 Hz) 6.83(s, 1H) 3.07(s, 3H)

Step 3: Synthesis of 3-fluoro-4-methanesulfonaminobenzylamine hydrochloride (3-4)

The compound 3-3 (1.03 g) prepared in Step 2 was dissolved in methanol (20 ml) and to the solution were added a catalytic amount of 10% palladium/carbon and concentrated hydrochloric acid (3 ml), followed by stirring at room temperature under hydrogen gas atmosphere for 1 hour. The resulting mixture was diluted in ether, filtered through celite, concentrated under reduced pressure, and then washed with ethyl acetate to yield the compound 3-4 (1.13 g, 92%).

¹H NMR(300 MHz, CD₃OD): δ 7.57(t, 1H, J=8.3 Hz) 7.33(dd, 1H, J=9.8, 1.8 Hz) 7.27(d, 1H, J=8.5 Hz) 4.11(s, 2H) 3.02(s, 3H)

Step 4: Synthesis of 1-(4-t-butylbenzyl)-3-(3-fluoro-4-methanesulfonylaminobenzyl)thiourea (3-5)

Compound 3-4 (1.13 g) prepared in Step 3 was dissolved in dimethylformamide (6 ml) and the solution were diluted in dichloromethane (35 ml). To the diluted solution was added 4-t-butylbenzylisothiocyanate (1.09 g) and triethylamine (1.2 ml) in order, and then the mixture was stirred at room temperature for 2 hours. The resulting mixture was concentrated under reduced pressure, diluted with ethyl acetate (20 ml), and then washed with water and saturated aqueous sodium chloride solution. The residue was dried over anhydrous magnesium sulfate, and concentrated under reduced pressure. The obtained residue was purified by chromatography on column eluting with ethyl acetate/hexane (2/3) to yield the compound 3-5 (1.23 g, 65%).

¹H NMR(300MHz, CDCl₃) : δ 7.41(t, 1H, J=8.2Hz) 7.34 (d, 2H, J=8.0Hz) 7.20(d, 2H, J=8.0Hz) 7.01(d, 1H, J=11.9Hz) 6.97(d, 1H, J=9.8Hz) 6.69(brs, 1H) 4.68(s, 2H) 4.54(s, 2H) 2.97(s, 3H) 1.28(s, 9H)

EXAMPLE 14

Synthesis of 1-phenethyl-3-(3-fluoro-4-methanesulfonaminobenzyl)urea (3-6)

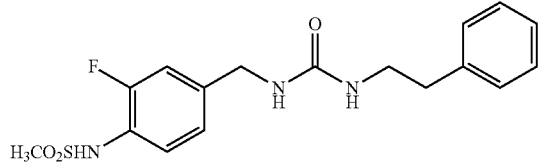

Compound 3-6 (17 mg, 36%) was synthesized according to the same procedure as described in Step 4 of Example 13 except that compound 3-4 (28 mg) was reacted with phenethylisocyanate (38 μl).

¹H NMR(300M:Hz, CD₃OD) : δ 7.40(t, 1H, J=8.2Hz) 7.28~7.06(m, 7H) 4.69(s, 2H, CH2) 3.87 (t, 2H) 2.98(s, 3H) 2.87(t, 2H, J=7.1Hz)

EXAMPLE 15

Synthesis of 1-phenethyl-3-(3-fluoro-4-methanesulfonylaminobenzyl)thiourea (3-7)

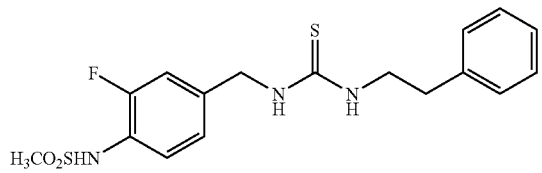

Compound 3-7 (8.3 mg, 24%) was synthesized according to the same procedure as described in Step 4 of Example 13 except that compound 3-4 (20 mg) and phenethylisothiocyanate (27 μl) were used as reactants.

¹H NMR(300 MHz, CD₃OD): δ 7.40(t, 1H, J=8.2 Hz) 7.29~7.14(m, 5H) 7.10~7.03(m, 2H) 4.26(s, 2H) 3.36 (t, 2H) 2.95(s, 3H) 2.76(t, 2H, J=7.1 Hz)

Compounds 3-8, 3-9 and 3-10 were synthesized according to the similar procedure as described in the Example 13, and NMR data thereof are shown below.

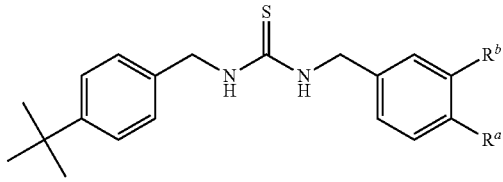

| Examples | Compounds No. | $R^a$ | $R^b$ | Spectral data |
|---|---|---|---|---|
| 16 | 3-8 | NHSO₂Me | CH₃ | ¹H NMR (300 MHz, CD₃OD): δ 7.32 (d, 2H, J = 8.0 Hz) 7.30 (d, 1H, J = 8.3 Hz) 7.17 (d, 2H, J = 8.3 Hz) 7.10 (s, 1H) 7.04 (d, 1H, J = 8.0 Hz) 6.37 (brs, 1H) 4.59 (s, 2H) 4.55 (s, 2H) 2.97 (s, 3H) 2.25 (s, 3H) 1.28 (s, 9H) |
| 17 | 3-9 | NHSO₂Me | Cl | ¹H NMR (300 MHz, CDCl₃): δ 7.50 (d, 1H, J = 8.3 Hz) 7.37 (d, 2H, J = 8.3 Hz) 7.35 (d, 1H, J = 2.0 Hz) 7.23 (d, 2H, J = 8.3 Hz) 7.13 (d, 1H, J = 7.1 Hz) 6.92 (brs, 1H) 4.69 (s, 2H) 4.58 (s, 2H) 2.978 (s, 3H) 1.30 (s, 9H) |
| 18 | 3-10 | NHSO₂Me | CO₂Me | ¹H NMR (400 MHz, CDCl₃): δ 10.38 (brs, 1H) 7.99 (s, 1H) 7.57 (d, 1H, J = 8.5 Hz) 7.41 (d, 1H, J = 8.4 Hz) 7.36 (d, 2H, J = 8.0 Hz) 7.23 (d, 2H, J = 8.0 Hz) 4.71 (s, 2H) 4.62 (s, 2H) 3.93 (s, 3H) 2.84 (s, 3H) 1.31 (s, 9H) |

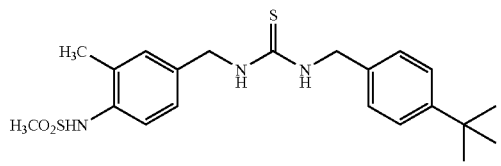

3-8

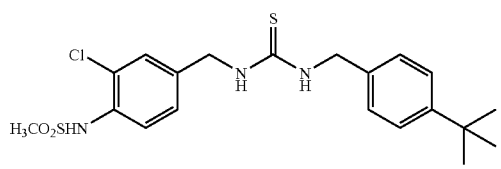

3-9

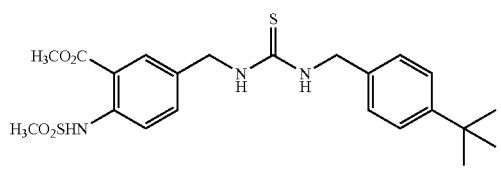

3-10

EXAMPLE 19

Synthesis of 1-(4-t-butylbenzyl)-3-(3-carboxyl-4-methanesulfonylaminobenzyl)thiourea (4-1)

Compond 3-10 (1.08 g) prepared according to the procedure as described in Example 13 was dissolved in acetone (20 ml) and to the solution was added 2.5 M aqueous lithium hydroxide solution (15 ml). The mixture was stirred at room temperature for 5 hours and the solvent was removed therefrom. The residue was dissolved in ethyl acetate and then extracted to yield the compound 4-1 (980 mg, 94%).

$^1$H NMR(300 MHz, CD$_3$CD): δ 8.07(d, 1H, J=2.2 Hz) 7.63(d, 1H, J=8.5 Hz) 7.51(d, 1H) 7.34(d, 2H, J=8.5 Hz) 7.20(d, 2H, J=8.0 Hz) 4.73(s, 2H) 4.66(s, 2H), 3.03(s, 3H) 1.29(s, 9H)

EXAMPLE 20

Synthesis of 1-(4-t-butylbenzyl)-3-((3-N-methoxyaminocarbonyl-4-methanesulfonylamino)benzyl)thiourea (4-2)

Compound 4-1 (50 mg) prepared according to the procedure as described in Example 19 was dissolved in benzene (2 ml) and to the solution was added dropwise oxalyl chloride (100 μl), followed by refluxing for 2 hours. The resulting mixture was concentrated under reduced pressure, and to the concentrate was added methoxylamine (92 mg). The mixture was dissolved in pyridine (2 ml), and the solution was stirred at room temperature for 24 hours and then concentrated under reduced pressure. To the concentrate was added ethyl ether, and the mixture was filtered and concentrated under reduced pressure. The obtained residue was chromatogrphed on column eluting ethyl acetate to yield the compound 4-2 (16 mg, 30%).

$^1$H NMR(300 MHz, CDCl$_3$): δ 10.14(s, 1H) 9.38(s, 1H) 7.55(m, 3H) 7.32(m, 4H) 5.04(s, 2H) 5.01(s, 2H) 3.82(s, 3H) 3.00(s, 3H) 1.25(s, 9H)

Compound 4-3 was synthesized according to the similar procedure as described in the Example 20, and NMR data thereof are shown below.

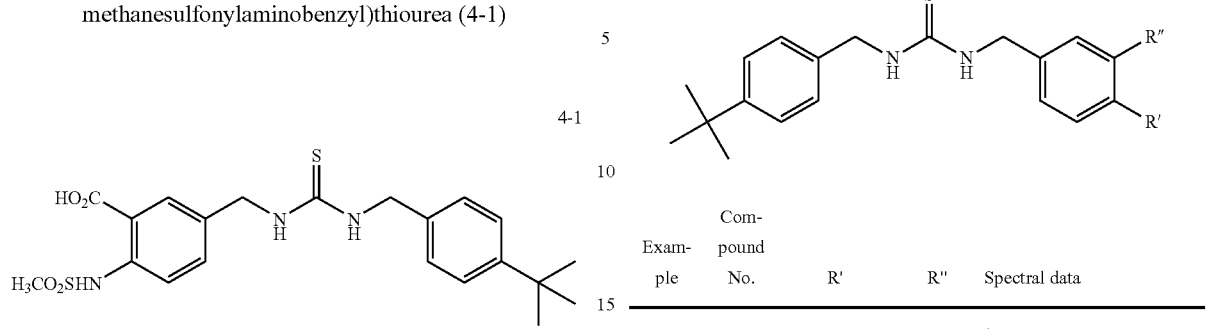

| Example | Compound No. | R' | R" | Spectral data |
|---|---|---|---|---|
| 21 | 4-3 | NHSO$_2$Me | CONHOH | $^1$H NMR (300 MHz, CD$_3$OD): δ 8.09 (d, 1H, J = 2.0 Hz) 7.51 (d, 1H, J = 8.3 Hz) 7.44 (dd, 1H, J = 2.2, 8.6 Hz) 7.31 (m, 4H) 5.05 (s, 4H) 2.92 (s, 3H) 1.27 (s, 9H) |

EXAMPLE 22

Synthesis of 1-(4-t-butylbenzyl)-3-(3-hydrazido-4-methanesulfonylaminobenzyl)thiourea (4-4)

Compound 4-1 (76 mg) prepared according to the procedure as described in Example 19 was dissolved in benzene (3 ml) and to the solution was added dropwise oxalyl chloride (200 μl), followed by refluxing for 3 hours. The resulting mixture was concentrated under reduced pressure and to the concentrate was added hydrazine (55 mg). The mixture was dissolved in tetrahydrofuran (3 ml), and the solution was stirred at 0° C. for 2 hours and then concentrated under reduced pressure. The obtained residue was chromatogrphed on silica gel column (ethyl acetate/hexane=1/1) to yield the compound 44 (5 mg, 6%).

$^1$H NMR(300 MHz, DMSO-d$_6$): δ 10.9(s, 1H), 10.2(s, 1H), 7.75(s, 1H), 7.64(d, 1H), 7.55(d, 1H), 7.41(s, 4H), 5.04(s, 2H), 5.00(s, 2H), 3.14(s, 3H), 1.20(s, 9H)

EXAMPLE 23

Synthesis of 1-(4-t-butylbenzyl)-3-(3-cyano-methanesulfonylaminobenzyl)thiourea (4-5)

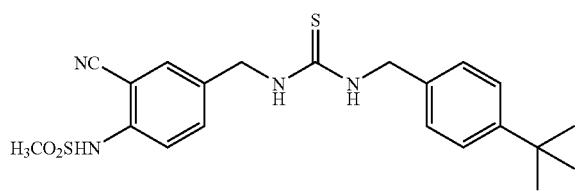

4-5

Compound 4-1 (50 mg) prepared according to the procedure as described in Example 19 was dissolved in benzene (3 ml) and to the solution was added dropwise oxalyl chloride (100 μl), followed by refluxing for 3 hours. The resulting mixture was concentrated under reduced pressure and to the concentrate was added sulfamide (106 mg). The mixture was dissolved in sulfolane (2 ml) and the solution was refluxed at 120° C. for 3 hours. To the reaction mixture was added 1 N-aqueous sodium hydroxide solution to quench the reaction. The resulting mixture was extracted with ether, washed several times with water, dried over anhydrous magnesium sulfate, and then concentrated under reduced pressure. The obtained residue was column-chromatogrphed (ethyl acetate/hexane=1/1) to yield the compound 4-5 (8 mg, 16%).

$^1$H NMR(300 MHz, CDCl$_3$): δ 10.8(s, 1H), 7.65(m, 2H), 7.58(m, 1H), 7.33(d, 4H), 5.05(s, 4H), 3.01(s, 3H), 1.24(s, 9H)

Compounds 4-6~4-13 were synthesized according to the similar procedure as described in the Example 13, and NMR data thereof are shown below.

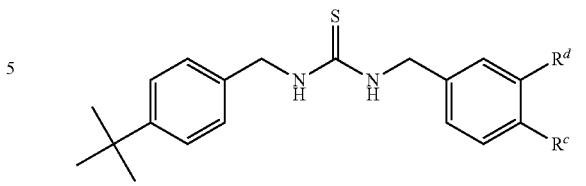

| Examples | Compounds No. | R$^c$ | R$^d$ | Spectral data |
|---|---|---|---|---|
| 24 | 4-6 | NHCO$_2$Me | F | $^1$H NMR (300 MHz, CDCl$_3$): δ 7.97 (t, 1H), 7.35 (d, 2H), 7.68 (d, 2H), 6.95 (d, 2H), 6.82 (s, 1H), 4.62 (s, 2H), 4.46 (s, 2H), 3.76 (s, 3H), 1.26 (s, 9H) |
| 25 | 4-7 | NHCOCH$_2$OMe | F | $^1$H NMR (300 MHz, CDCl$_3$): δ 8.49 (s, 1H), 8.07 (t, 1H, J = 8.0 Hz), 7.36 (d, 2H, J = 8.0 Hz) 7.23 (d, 2H, J = 8.0 Hz), 7.03 (d, 1H, J = 11.2 Hz), 6.93 (d, 1H, J = 8.3 Hz) 6.66 (brs, 1H) 4.67 (s, 2H), 4.62 (s, 2H), 3.49 (s, 3H), 1.32 (s, 9H) |
| 26 | 4-8 | NHCO$_2$Et | F | $^1$H NMR (300 MHz, CDCl$_3$): δ 7.95 (s, 1H) 7.33 (d, 2H, J = 8.0 Hz) 7.17 (d, 2H, J = 8.0 Hz) 6.94 (d, 2H) 6.77 (s, 1H), 4.60 (s, 2H) 4.55 (s, 2H), 4.19 (q, 2H, J = 7.2 Hz), 1.27 (m, 12H) |
| 27 | 4-9 | NHCH$_2$CO$_2$Et | F | $^1$H NMR (300 MHz, CDCl$_3$): δ 7.31 (d, 2H), J = 8.5 Hz), 7.15 (d, 2H, J = 8.3 Hz), 6.86 (s, 1H), 6.83 (s, 1H), 6.46 (t, 1H, J = 8.4 Hz), 6.10 (d, 1H), 4.53 (s, 2H), 4.48 (s, 2H), 4.20 (q, 2H, J = 7.1 Hz), 3.75 (s, 2H), 1.27 (m, 12H) |
| 28 | 4-10 | NHCH$_2$CO$_2$Me | F | $^1$H NMR (300 MHz, CDCl$_3$): δ 7.39 (d, 2H, J = 8.3 Hz), 7.23 (d, 2H, J = 8.3 Hz), 6.93 (s, 1H), 6.90 (s, 1H), 6.52 (t, 1H, J = 8.4 Hz), 6.36 (s, 1H), 4.60 (s, 2H), 4.53 (s, 2H), 3.83 (s, 2H), 3.74 (s, 3H), 1.34 (s, 9H) |
| 29 | 4-11 | NHCH$_2$CO$_2$H | F | $^1$H NMR (300 MHz, CD$_3$OD): δ 7.32 (d, 2H, J = 8.5 Hz), 7.18 (d, 2H, J = 8.3 Hz), 6.90 (m, 2H), 6.56 (t, 1H, J = 8.6 Hz), 4.65 (s, 2H), 4.55 (s, 2H), 3.70 (s, 2H), 1.28 (s, 9H) |
| 30 | 4-12 | H | CO$_2$Me | $^1$H NMR (300 MHz, CDCl$_3$): δ 7.95-7.98 (d, 2H, J = 7.3 Hz), 7.30-7.51 (m, 4H), 7.20-7.25 (d, 2H, J = 8.3 Hz), 4.75-4.79 (d, 2H, J = 5.4 Hz), 4.61-4.64 (d, 2H, J = 4.4 Hz), 3.92 (s, 3H), 1.33 (s, 9H) |
| 31 | 4-13 | H | CO$_2$H | $^1$H NMR (300 MHz, CD$_3$OD): δ 7.97-7.98 (s, 1H), 7.88-7.91 (d, 1H, J = 7.6 Hz), 7.32-7.53 (m, 4H), 7.18-7.22 (d, 2H, J = 8.0 Hz), 4.79 (s, 2H), 4.67 (s, 2H), 1.28 (s, 9H) |

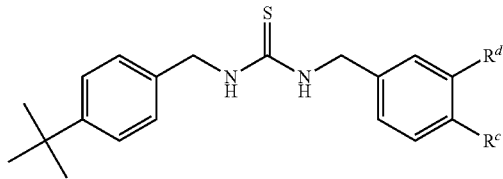

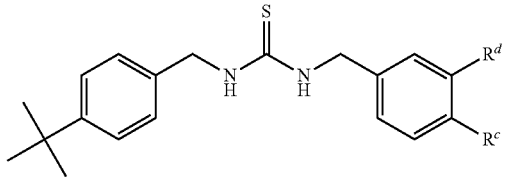

| Examples | Compounds No. | $R^c$ | $R^d$ | Spectral data |
|---|---|---|---|---|

| Examples | Compounds No. | $R^c$ | $R^d$ | Spectral data |
|---|---|---|---|---|

EXAMPLE 32

Synthesis of 1-(4t-butylbenzyl)-3-(2,3,5,6-tetrafluoro-4-methanesulfonylaminobenzyl)thiourea (5-4)

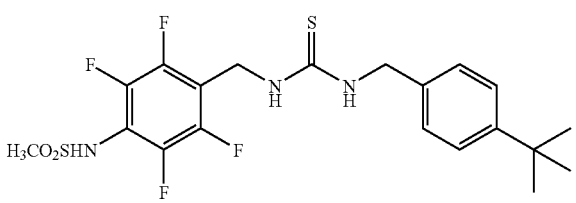

Step 1: Synthesis of 4-cyano-2,3,5,6-tetrafluoro-1-methanesulfonylaminobenzene 4-amino-2,3,4,5-tetrafluoronitrile (105 mg) was dissolved in tetrahydrofuran (4 ml) and the solution was cooled to 0° C. To the solution was added dropwise 1.6 M n-butyl lithium and the mixture was stirred for 10 minutes, followed by adding dropwise methanesulfonyl chloride (100 μl). After 1 hour, the reaction was quenched with 1.5 N aqueous hydrochloric acid. The resulting mixture was extracted with ethyl acetate, and then concentrated under reduced pressure. The obtained residue was chromatographed on column eluting with ethyl acetate/hexane (1/1) to yield 4-cyano-2,3,5,6-tetrafluoro-1-methanesulfonylaminobenzene (20 mg, 10%).

$^1$H NMR(300 MHz, CDCl$_3$): δ 6.84(brs, 1H) 3.08(s, 3H)

Step 2: Synthesis of 2,3,5,6-tetrafluoro-4-methanesulfonylaminobenzylamine hydrochloride 4-cyano-2,3,5,6-tetrafluoro-1-methanesulfonylaminobenzene (11 mg) prepared in Step 1 was dissolved in methanol (5 ml) and to the solution were added a catalytic amount of 10% palladium/carbon and concentrated hydrochloric acid (300 μl), followed by stirring at room temperature under hydrogen gas atmosphere for 1 hour. The resulting mixture was diluted in ether, filtered through celite, concentrated under reduced pressure, and then washed with ethyl acetate to yield 2,3,5,6-tetrafluoro-4-methanesulfonylaminobenzylamine hydrochloride (7.0 mg, 59%).

$^1$H NMR(300 MHz, CD$_3$OD): δ 4.32(s, 2H) 3.18(s, 3H)

Step 3: Synthesis of 1-(4-t-butylbenzyl)-3-(2,3,5,6-tetrafluoro-4-methanesulfonylaminobenzyl)thiourea (5-4)

2,3,5,6-tetrafluoro-4-methanesulfonylaminobenzylamine hydrochloride (20 mg) prepared in Step 2 was dissolved in dimethylformamide (800 µl), and the solution was diluted with dichloromethane (6 ml). To the diluted solution were added t-butylbenzylisothiocyanate (20 mg) and triethylamine (200 µl), and the mixture was stirred at room temperature for 2 hours. The mixture was concentrated under reduced pressure, diluted with ethyl acetate (20 ml), and then washed with water and saturated aqueous sodium chloride solution. The resulting mixture was dried over anhydrous magnesium sulfate and concentrated under reduced pressure, and the obtained residue was chromatographed on column eluting ethyl acetate/hexane (2/3) to yield the compound 54 (28 mg, 91%).

$^1$H NMR(300 MHz, CD$_3$OD): δ 7.34(dd, 2H, J=1.8, 6.5 Hz) 7.20(d, 2H, J=8.3 Hz) 4.87(s, 2H) 4.63(s, 2H) 3.13(s, 3H) 1.29(s, 9H)

EXAMPLE 33

Synthesis of 1-(4-t-butylbenzyl)-3-(2,5-difluoro-4-methanesulfonylaminobenzyl)thiourea (5-5)

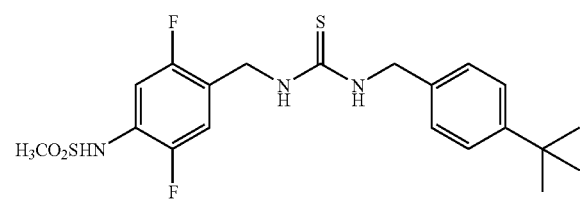

5-5

Step 1: Synthesis of 2,5-difluoro-4-cyano-1-methanesulfonylaminobenzene

To an ice-cold solution of 4-amino-2,5-difluorobenzonitrile (1.0 g) in anhydrous tetrahydrofuran (50 ml) was slowly added n-butyl lithium (2.6 ml) through an injector with stirring, followed by stirring 30 minutes. To the mixture was slowly added methanesulfonyl chloride (550 µl), followed by stirring at room temperature for 24 hours. After confirming the completion of the reaction using TLC, the resulting mixture was concentrated under reduced pressure, diluted with 1 N aqueous hydrochloric acid (100 ml), extracted with dichloromethane (50 ml×3). The combined organic layer was dried over magnesium sulfate, filtered, and then concentrated under reduced pressure. The obtained residue was purified by column-chromatography (ethyl acetate/hexane 2/3) to yield 2,5-difluoro-4-cyano-1-methanesulfonylaminobenzene (1.2 g, 79.6%).

$^1$H NMR(300 MHz, CDCl$_3$): δ 7.54(m, 1H), 7.40(m, 1H), 7.01(brs, 1H), 3.18(s, 3H)

Step 2: Synthesis of 2,5-difluoro-4-methanesulfonaminobenzyl hydrochloride 2,5-difluoro-4-cyano-1-methanesulfonylaminobenzene (250 mg), a catalytic amount of 10% palladium/carbon catalyst and methanol (20 ml) were added to a reactor. The reactor was filled with hydrogen gas while the mixture was stirred. Concentrated hydrochloric acid (250 µl) was slowly added thereto through an injector, followed by stirring for 18 hours. The reaction mixture was filtered through celite and the filtrate was concentrated under reduced pressure to afford a compound (250 mg, 85%) as a solid. The obtained compound was washed with ether, and the following procedure was carried out using the washed compound.

Step 3: Synthesis of 1-(4-t-butylbenzyl)-3-(2,5-difluoro-4-methanesulfonaminebenzyl)thiourea (5-5)

2,5-difluoro-4-methanesulfonaminobenzyl hydrochloride (250 mg) prepared by Step 2 was dissolved in dimethylformamide (5 ml) and to the solution was added triethylamine (128 µl) with stirring, followed by stirring for 30 minutes. To the mixture was added t-butylbenzylisothiocyanate (189 mg), followed by stirring for 6 hours. After the completion of the reaction, the resulting mixture was diluted with water (30 ml), and extracted with ethyl acetate (30 ml×3). The organic layer was dried over magnesium sulfate, filtered, and then concentrated under reduced pressure. The obtained residue was purified by column-chromatography (ethyl acetate/hexane=1/2) to yield the compound 5-5 (264 mg, 52.4%).

$^1$H NMR(300 MHz, CDCl$_3$): δ 7.36(m, 2H), 7.31(m, 1H), 7.23(m, 2H), 7.17(m, 1H), 6.69(brs, 1H), 6.31(brs, 1H), 6.04 (brs, 1H), 4.77(d, 2H, J=5.7 Hz), 4.53(d, 2H, J=4.8 Hz), 3.04(s, 3H), 1.31(s, 9H)

EXAMPLE 34

Synthesis of 1-(4-t-butylbenzyl)-3-[(5-methanesulfonylaminopyridin-2-yl)methyl]thiourea (5-6)

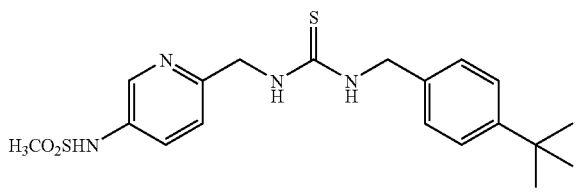

5-6

Step 1: Synthesis of 3-methanesulfonylamino-6-cyanopyridine

5-Amino-2-cyanopyridine (5 g) was dissolved in pyridine (30 ml). The solution was cooled to 0° C. and to the solution was added dropwise methanesulfonyl chloride (3.6 ml), followed by stirring at room temperature for 17 hours. The resulting mixture was concentrated under reduced pressure, extracted with water and dichloromethane, and then dried. The obtained residue was purified by column-chromatography (hexane/ethyl acetate=2/1) to yield an orange colored solid (6.4 g, 77%).

¹H NMR(300 MHz, CDCl₃): δ 8.47-8.46(m, 1H), 7.84-7.69(m, 2H), 6.89(brs, 1H), 3.16(s,3H)

Step 2: Synthesis of 1-(4-t-butylbenzyl)-3-[(5-methanesulfonylaminopyridin-2-yl)methyl]thiourea (5-6)

The compound (1.97 g) prepared in Step 1 was dissolved in methanol (50 ml) and to the solution were added concentrated hydrochloric acid (2 ml) and a catalytic amount of 5% palladium/carbon, followed by stirring under hydrogen atmosphere for 21 hours. The mixture was filtered through celite and the filtrate was concentrated under reduced pressure to obtain foamy compound (3 g). Part (135 mg) of the obtained compound was dissolved in dimethylformamide (5 ml) and to the solution were added triethylamine (101 mg) and 4-t-butylbenzylisothiocyanate (100 mg), followed by stirring at room temperature for 20 hours. The mixture was concentrated under reduced pressure, extracted with water and dichloromethane, and then purified by column-chromatography (ethyl acetate) to yield the compound 5-6 (98 mg, 48%) as a brown liquid.

¹H NMR(300 MHz, CDCl₃): δ 8.33-8.31(m, 1H), 7.66-7.62(m, 1H), 7.40-7.26(m, 5H), 6.99(brs, 1H), 6.76(brs, 1H), 4.77-4.60(m, 4H), 3.04(s, 3H), 1.32(s,9H)

EXAMPLE 35

Synthesis of 1-(4-t-butylbenzyl)-3-(3,5-dichloro-4-methanesulfonylaminobenzyl)thiourea (5-7)

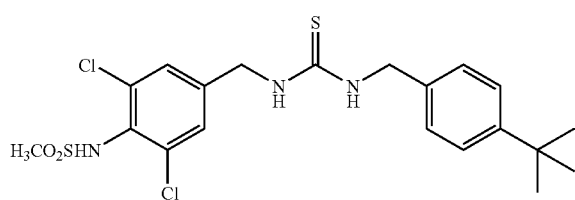

4-Amino-3,5-dichlorobenzonitrile (1 g) was dissolved in acetonitrile (50 ml) and to the solution were added triethylamine (890 μl) and methanesulfonyl chloride (670 mg), followed by refluxing for 8 hours. The mixture was extracted with water and dichloromethane, dried, concentrated, and then purified by column-chromatography (hexane/ethyl acetate=4/1) to obtain a compound (80 mg) as a liquid. The obtained compound was dissolved in methanol (10 ml), and then the solution was stirred for 15 hours in the presence of a small amount of concentrated hydrochloric acid and 5% palladium/carbon catalyst to hydrogenate the compound. The reaction solution was filtered through celite and concentrated. The concentrate was dissolved in dichloromethane (5 ml) and to the solution were added 4-t-butylbenzylisothiocyanate (54 mg) and triethylamine (500 μl), followed by stirring at room temperature for 15 hours. The resulting mixture was extracted with water and dichloromethane, and then purified by column-chromatography (hexane/ethyl acetate=2/1) to yield the compound 5-7 (38 mg) as a liquid.

¹H NMR(300 MHz, CDCl₃): δ 7.42-7.23(m, 6H), 6.23(brs, 1H), 5.87(brs, 1H), 4.85-4.82(m, 2H), 4.58-4.56(m, 2H), 3.57 (s, 3H), 1.31(s,9H)

EXAMPLE 36

Synthesis of 1-(4-t-butylbenzyl)-3-4-methanesulfonylaminophenethyl)thiourea (5-8)

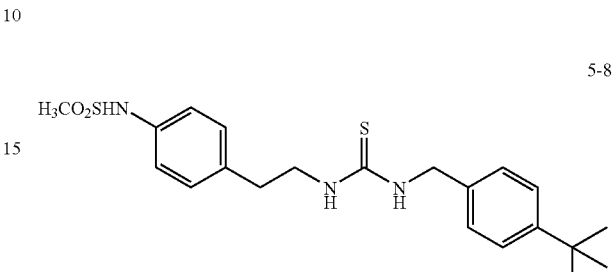

Step 1: Synthesis of 4-methanesulfonylaminobenzyl cyanide

To an ice-cold solution of 4-aminobenzyl cyanide (1 g) in dichloromethane (30 ml) were added dropwise triethylamine (1.58 ml) and methanesulfonyl chloride (700 μl), followed by stirring at room temperature for 12 hours. After confirming the completion of the reaction using TLC, to the mixture was added 1 N aqueous hydrochloric acid (50 ml). The resulting mixture was extracted with dichloromethane (30 ml×3), washed with saturated aqueous sodium chloride solution, dried over magnesium sulfate, and then filtered.

The filtrate was concentrated under reduced pressure and the obtained residue was purified by column-chromatography (ethyl acetate/hexane=2/3) to yield 4-methanesulfonylaminobenzyl cyanide (1.35 g, 85%).

¹H NMR(300 MHz, CDCl₃): δ7.34(d, 2H, J=8.4 Hz), 7.24 (d, 2H, J=8.7 Hz), 6.51(bs, 1H), 3.74(s, 2H), 3.03(s, 3H)

Step 2: Synthesis of 4-methanesulfonaminophenethylamine

4-Methanesulfonylbenzyl cyanide (200 mg) and Raney nickel (catalytic amount) were added to methanol (15 ml) and the mixture was stirred for 6 hours with the reactor filled with hydrogen gas. After confirming the completion of the reaction, the resulting mixture was filtered through celite and the filtrate was concentrated under reduced pressure. The following procedure was carried out using the concentrate which was not purified.

Step 3: Synthesis of 1-(4-t-butylbenzyl)-3-(4-methanesulfonylaminophenethyl)thiourea (5-8)

4-Methanesulfonaminophenethylamine (200 mg) prepared in Step 2 and 4-t-butylbenzylisothiocyanate (190 mg) were dissolved in ethyl acetate (30 ml) and the solution was subjected to reaction for 6 hours. After the completion of the reaction, the resulting mixture was concentrated under reduced pressure and the obtained residue was purified by column-chromatography (ethyl acetate/hexane=1/2) to yield the compound 5-8 (210 mg, 53%).

¹H NMR(300 MHz, CDCl₃): δ7.38(d, 2H, J=8.4 Hz), 7.21 (d, 2H, J=8.4 Hz), 7.14(s, 4H), 6.56(s, 1H), 6.05(brs, 1H), 5.69(brs, 1H), 4.51(brs, 2H), 3.72(d, 2H, J=4.8 Hz), 2.99(s, 3E), 2.86(t, 2H, J=6.9 Hz), 1.32(s, 9H)

EXAMPLE 37

Synthesis of 1-(4-t-butylbenzyl)-3-2-methanesulfonylaminophenethyl)thiourea (5-9)

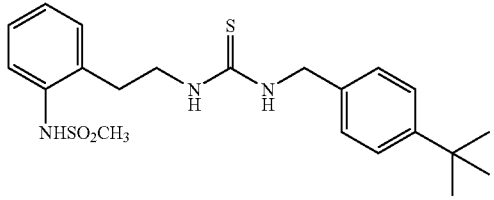

5-9

Step 1: Synthesis of (2-methanesulfonylaminophenyl)acetonitrile

To an ice-cold solution of 2-aminophenylacetonitrile (500 mg) in dichloromethane (20 ml) were added triethylamine (330 μl) and methanesulfonyl chloride (530 μl) and the mixture was stirred for 16 hours, under argon gas atmosphere. After confirming the completion of the reaction using TLC, the resulting mixture was diluted with 1 N aqueous hydrochloric acid solution (30 ml), and extracted with dichloromethane (50 ml×3). The organic layer was washed with brine, dried over magnesium sulfate, and then filtered. The filtrate was concentrated under reduced pressure and the obtained residue was purified by column-chromatography (ethyl acetate/hexane=1/2) to yield (2-methanesulfonylaminophenyl)acetonitrile (573 mg, 72%).

$^1$H NMR(300 MHz, CDCl$_3$): δ7.56(m, 1H), 7.37(m, 3H), 6.55(brs, 1H), 3.99(s, 2H), 3.06(s, 3H)

Step 2: Synthesis of 2-methanesulfonylaminophenethylamine (2-Methanesulfonylaminophenyl)acetonitrile (300 mg) was mixed with 10% palladium/carbon (catalytic amount) in methanol (20 ml) and the mixture was stirred under hydrogen gas atmospheres for 48 hours. After confirming the completion of the reaction using TLC, the resulting mixture was filtered through celite and the filtrate was concentrated under reduced pressure. The following procedure was carried out using the concentrate which was not purified.

Step 3: Synthesis of 1-(4-t-butylbenzyl)-3-(2-methanesulfonylaminophenethyl)thiourea (5-9)

2-Methanesulfonylaminophenethylamine (200 mg) prepared in Step 2 and t-butylbenzeneisothiocyanate (192 mg) were dissolved in ethyl acetate (20 ml) and the solution was stirred for 6 hours. After confirming the completion of the reaction, the resulting mixture was concentrated under reduced pressure and the concentrate was purified by column-chromatography (ethyl acetate/hexane=2/3) to yield the compound 5-9 (165 mg, 42%).

$^1$H NMR(300 MHz, CDCl$_3$): δ7.28(m, 8H), 6.38(brs, 1H), 4.74(s, 1H), 4.72(s, 1H), 3.79(m, 2H), 3.14(m, 4H), 3.01(s, 3H), 1.31(s, 9H)

EXAMPLE 38

Synthesis of 1-(4-t-butylbenzyl)-3-(4-methanesulfanylcarbonylaminobenzyl)thiourea (6-5)

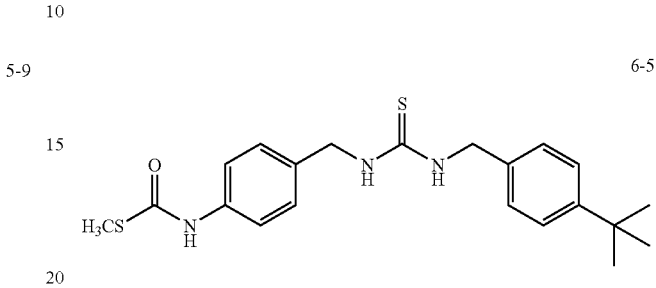

6-5

Step 1: Synthesis of (4-nitrobenzyl)carbamic acid t-butyl ester (6-2)

4-Nitrobenzylamine hydrochloride (110 mg) was dissolved in dichloromethane (2 ml) and to the solution were added dimethylaminopyridine (14 mg) and di-t-butyl dicarbonate (382 mg), followed by adding triethylamine (200 μl) thereto and stirring at room temperature for 3 hours. After the completion of the reaction, the resulting mixture was concentrated under reduced pressure and the obtained residue was chromatographed on column eluting with ethyl acetate/hexane (1/3) to yield the compound 6-2 (88.3 mg, 66%).

$^1$H NMR(300 MHz, CDCl$_3$): δ 8.18 (d, 2H, J=8.5 Hz), 7.43 (d, 2H, J=8.8 Hz) 4.40 (d, 2H, J=6.3 Hz), 1.45 (s, 9H)

Step 2: Synthesis of (4-methylsulfanylcarbonylaminobenzyl)carbamic acid t-butyl ester (6-3)

The compound 6-2 (88.3 mg) prepared in Step 1 was dissolved in methanol (2 ml) and to the solution was added catalytic amount of 10% palladium/carbon, followed by stirring at room temperature under hydrogen gas atmosphere for 30 minutes. The resulting mixture was diluted with ether, and filtered through celite. The filtrate was concentrated under reduced pressure to yield compound (76 mg). The obtained compound, which was not purified, was dissolved in dichloromethane (1 ml) and to the solution were added methylchlorothiolformate (100 μl) and pyridine (49 μl). After stirring the mixture at room temperature for 1 hour, the resulting mixture was extracted with dichloromethane, dried over anhydrous magnesium sulfate, and then concentrated under reduced pressure. The obtained residue was column-chromatographed (ethyl acetate/hexane=1/1) to yield the compound 6-3 (22 mg, 22%).

$^1$H NMR(300 MHz, CDCl$_3$): δ 7.36 (d, 1H, J=8.5 Hz), 7.20-7.25 (m, 2H), 7.03 (d, 1H, J=8.3 Hz), 4.25 (s, 2H), 2.40 (s, 3H), 1.44 (s, 9H)

Step 3: Synthesis of 4-methylsulfanylcarbonylaminobenzylamine hydrochloride (6-4)

The compound 6-3 (22 mg) prepared in Step 2 was dissolved in ethyl acetate (1 ml) and to the solution was added 5

N aqueous hydrochloric acid (1 ml). The mixture was stirred at 60° C. for 1 hour and concentrated under reduced pressure to yield the compound 6-4 (15 mg, 100%).

$^1$H N(300 MHz, CD$_3$OD): δ 7.65 (d, 1H, J=8.5 Hz), 7.57 (d, 1H, J=8.3 Hz), 7.49 (d, 1H, J=8.5 Hz), 7.38 (d, 1H, J=8.8 Hz), 4.05(s, 2H) 2.35(s, 3H)

Step 4: Synthesis of 1-(4-t-butylbenzyl)-3-(4-methyl-sulfanylcarbonylaminobenzyl)thiourea (6-5)

The compound 6-4 (15 mg) prepared in Step 3 was diluted in dichloromethane (1 ml) and to the solution were added 4-t-butylisothiocyanate (20 mg) and triethylamine (100 μl), followed by stirring at room temperature for 1 hour. The resulting mixture was concentrated under reduced pressure and the obtained residue was chromatographed on column eluting with ethylacetate/hexane (1/3) to yield the compound 65 (20 mg, 83%).

$^1$H NMR(300 MHz, CDCl$_3$): δ 7.16-7.35 (m, 8H), 4.56 (br, 4H), 2.35 (s, 3H), 1.26 (s, 9H)

EXAMPLE 39

Synthesis of 1-(4-t-butylbenzyl)-3-(4-guanidinobenzyl)thiourea (7-6)

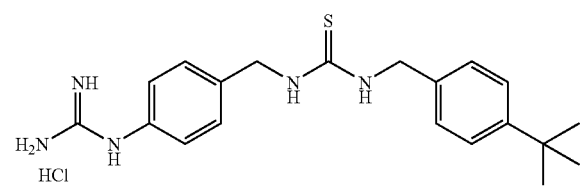

7-6

Step 1: Synthesis of 4-(1,3-bis(t-butoxycarbonyl)-2-guanidino)phenyliodide (7-2)

4-Iodoaniline 7-1 (100 mg) was dissolved in dimethylformamide (2 ml) and to the solution were added 1,3-bis(t-butoxycarbonyl)-2-methyl-2-thiopseudourea (200 mg), mercury (II) chloride (186 mg) and triethylamine (200 μl), followed by stirring for 1 hour. After the completion of the reaction, the resulting mixture was concentrated under reduced pressure at the temperature not more than 50° C. and the obtained residue was chromatographed eluting with ethyl acetate/hexane (1/3) to yield the compound 7-2 (137 mg, 66%).

$^1$H NMR(300 MHz, CDCl$_3$): δ 11.60 (br, 1H) 10.33 (br, 1H), 7.58-7.63 (d, 2H, J=8.8 Hz), 7.35-7.38 (d, 2H, J=8.8 Hz), 1.51 (s, 9H), 1.48 (s, 9H)

Step 2: Synthesis of 4-[1,3-bis(t-butoxycarbonyl)-2-guanidino]benzonitrile (7-3)

The compound 7-2 (137 mg) prepared in Step 1 was dissolved in dimethylformamide (2 ml) and to the solution were added zinc (II) cyanide (40 mg) and tetrakistriphenylphosphine palladium (14 mg), followed by stirring at 80° C. for 1 hour. The reaction was quenched with water. The resulting mixture was extracted with ethyl acetate, and the organic phase was dried over anhydrous magnesium sulfate, and then concentrated under reduced pressure. The obtained residue was chromatographed on column eluting with ethyl acetate/hexane (1/3) to yield the compound 7-3 (95 mg, 89%).

$^1$H NMR(300 MHz, CDCl$_3$): δ 11.58 (br, 1H) 10.62 (br, 1H), 7.76-7.79 (d, 2H, J=8.8 Hz), 7.58-7.61 (dd, 2H, J=2.0, 6.8 Hz), 1.52 (s, 9H), 1.50 (s, 9H)

Step 3: Synthesis of 1-(4-t-butylbenzyl)-3-[4-{1,3-bis(t-butoxycarbonyl)-2-guanidino}benzyl]thiourea (7-5)

The compound 7-3 (20 mg) prepared in Step 2 was dissolved in methanol (2 ml) and to the solution was added catalytic amount of palladium/carbon, followed by stirring at room temperature under hydrogen gas atmosphere for 30 minutes. The resulting mixture was diluted with ether, filtered through celite, and then concentrated under reduced pressure to give the compound 7-4. The compound 7-4 was diluted with dichloromethane (3 ml). To the solution was added 4-t-butylbenzylisothiocyanate (40 mg) and the mixture was stirred at room temperature for 1 hour. The resulting mixture was concentrated under reduced pressure and the obtained residue was chromatographed eluting with ethyl acetate/hexane (1/3) to yield the compound 7-5 (35 mg, 95%).

$^1$H NMR(300 MHz, CD$_3$OD): δ 7.18-7.49 (m, 8H), 4.66-4.69 (br, 4H), 1.56 (s, 9H), 1.45 (s, 9H), 1.29 (s, 9H)

Step 4: Synthesis of 1-(4-t-butylbenzyl)-3-(4-guanidinobenzyl)thiourea (7-6)

The compound 7-5 (35 mg) prepared in Step 3 was dissolved in ethyl acetate (1.0 ml) and to the solution was added 5 N aqueous hydrochloric acid (1 ml). The mixture was stirred at 60° C. for 1 hour and concentrated under reduced pressure to yield the compound 7-6 (18 mg, 100%).

$^1$H NMR(300 MHz, acetone-d$_6$): δ 7.07-7.37 (m, 8H), 4.73(s, 2H), 4.66 (s, 2H), 1.17 (s, 9H)

EXAMPLE 40

Synthesis of 1-[2-(1-methyl-1H-pyrrol-2-yl)ethyl]-3-(4-methanesulfonylaminobenzyl)thiourea (8-4)

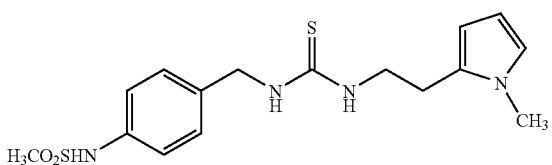

8-4

Step 1: Synthesis of (4-aminobenzyl)carbamic acid t-butyl ester (8-1)

4-Aminobenzylamine (1.02 g) was dissolved in anhydrous tetrahydrofuran (10 ml) and to the solution was added di-t-butyldicarbonate (2.002 g), followed by stirring at room temperature for 2 hours. The resulting mixture was concentrated under reduced pressure to remove the solvent. The obtained residue was purified by column-chromatography (ethyl acetate/hexane=2/3) to yield the compound 8-1 (1.78 g, 96%) as a yellow solid.

¹H NMR (300 MHz, CDCl₃): δ7.09-7.05 (m, 2H), 6.6-6.62 (m, 2H), 4.70 (brs, 1H), 4.18(d, 2H, J=5.7 Hz), 3.64(brs, 2H), 1.45 (s, 9H)

Step 2: Synthesis of (4-methanesulfonylaminobenzyl)carbamic acid t-butyl ester (8-2)

Compound 8-1 (1 g) was dissolved in anhydrous dichloromethane and the solution was cooled to 0° C. To the solution was added triethylamine (630 μl) and methanesulfonyl chloride (350 μl) in order and the mixture was stirred at room temperature for 24 hours. After confirming the completion of the reaction using TLC, the resulting mixture was neutralized with hydrochloric acid solution, diluted with water, and then extracted three times with dichloromethane. The extracted organic layer was washed with water and saturated aqueous sodium chloride solution, dried over magnesium sulfate, and then dried under reduced pressure. The obtained residue was purified by column-chromatography (hexane/ethyl acetate=2/1) to yield the compound 8-2 (1.28 g, 95%) as a white solid.

¹H NMR (300 MHz, CDCl₃): δ 7.1-7.3 (m, 4H), 6.77 (s, 1H), 4.88 (brs, 1H), 4.28 (d, 2H), 2.99 (s, 3H), 1.46 (s, 9H)

Step 3: Synthesis of 4-methanesulfonylaminobenzylammonium trifluoroacetate (8-3)

(4-Methanesulfonylaminobenzyl)carbamic acid t-butyl ester 8-2 (500 mg) was dissolved in anhydrous dichloromethane (30 ml) and the solution was cooled to 0° C., followed by slowly adding trifluoroacetic acid (5 ml) thereto. The mixture was stirred at 0° C. for 1 hour and 30 minutes and then, after confirming the completion of the reaction using TLC, concentrated under reduced pressure to yield an orange colored residue. The residue was washed with ether and filtered to yield the compound 8-3 (420 mg, 80%) as a pink solid.

¹H NMR (300 MHz, DMSO-d₆): δ 8.14 (brs, 3H), 7.39 (d, 2H), 7.22 (d, 2H), 3.97 (s, 2H), 2.99 (s, 3H)

Step 4: Synthesis of 1-[2-(1-methyl-1H-pyrrol-2-yl)ethyl]-3-(4-methanesulfonylaminobenzyl)thiourea (8-4)

Compound 8-3 (500 mg) was dissolved in dimethylformamide (2 ml) and to the solution was added triethylamine (230 μl), followed by stirring for 1 hour. To the mixture was added 2-(2-isothiocyanatoethyl)-1-methyl-1H-pyrrole (280 mg), followed by adding ethyl acetate (10 ml) thereto. The mixture was stirred for 12 hours, filtered under reduced pressure, and then purified by column-chromatography (ethyl acetate/hexane=4/1) to yield the compound 84 (146 mg, 25%) as a red solid.

¹H NMR (300 MHz, CH₃COCH₃-d₆): δ 7.32(m, 4H), 7.16 (m, 1H), 6.42(d, 1H, J=2.1 Hz), 6.02(d, 1H, J=1.95 Hz), 4.76(m, 2H), 3.89(m, 2H), 3.81(m, 2H), 3.01(m, 2H), 2.96(s, 3H)

EXAMPLE 41

Synthesis of 1-(4-aminobenzyl)-3-(4-t-butylbenzyl)thiourea (9a)

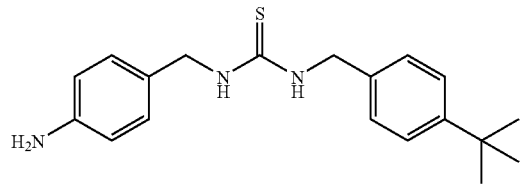

9a 4-t-Butylbenzylisothiocyanate (100 mg) was dissolved in dichloromethane (3 ml) and then cooled to 0° C. To the solution was added 4-nitrobenzylamine (75 mg), followed by stirring at room temperature for 6 hours. After the completion of the reaction, dichloromethane was evaporated therefrom under reduced pressure and the residue was dissolved in methanol (3 ml). To the solution was added catalytic amount of 5% platinum/carbon and the mixture was subjected to hydrogenation reaction under atmospheric pressure. After the completion of the reaction, the methanol was evaporated under reduced pressure and the obtained residue was column-chromatographed (hexane/ethyl acetate=1/1) to yield the compound 9a (137 mg, 85%) as a white solid.

¹H NMR (300 MHz,CDCl₃): δ 6.70-7.40(m, 8H), 6.00-6.40(br, 2H), 4.55(br, 2H), 4.45(br, 2H), 1.28(s, 9H)

MS (E) m/e 327 [M+]

EXAMPLE 42

Synthesis of 1-(4-acetylaminobenzyl)-3-(4-t-butylbenzyl)thiourea (9b)

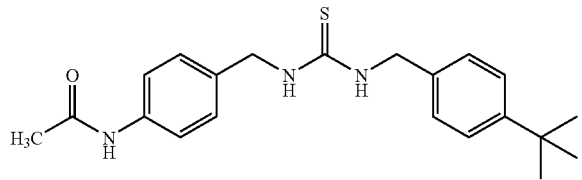

9b

Compound 9a (100 mg) and triethylamine (50 mg) were dissolved in dichloromethane (3 ml) and cooled to 0° C. To the solution was added anhydrous acetic acid (35 mg). After the completion of the reaction, dichloromethane was evaporated under reduced pressure and the obtained residue was column-chromatographed (hexane/ethyl acetate=1/1) to yield the compound 9b (107 mg, 95%) as a white solid.

¹H NMR (300 MHz, DMSO-d): δ 8.31(s, 1H), 7.87(br, 2H), 7.50(d, 2H, J=8.40 Hz), 7.32(d, 2H, J=8.25 Hz), 7.16-7.17(m, 4H), 4.59(br, 4H), 2.01(s, 3H), 1.25(s, 9H)

MS (E) m/e 369 [M+]

EXAMPLE 43

Synthesis of 1-(4-(N,N-dimethanesulfonyl)aminobenzyl)-3-(4-t-butylbenzyl)thiourea (9c)

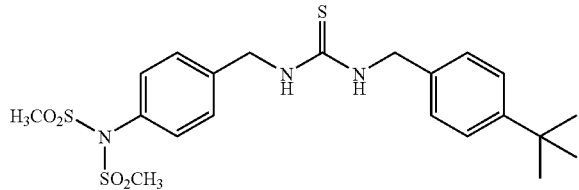

4-t-Butylbenzylisothiocyanate (100 mg) was dissolved in dichloromethane (3 ml) and cooled to 0° C. To the solution was added (N,N-dimethylsulfonyl-4-amino)benzylamine (136 mg), followed by stirring at room temperature for 6 hours. After the completion of the reaction, dichloromethane was evaporated under reduced pressure and the obtained residue was column-chromatographed (hexane/ethyl acetate=1/1) to yield the compound 9c (184 mg, 75%) as a white solid.

$^1$H NMR (300 MHz, CDCl$_3$): δ 7.00-7.35(m, 8H), 6.30(br, 2H), 4.66(s, 2H), 4.49(s, 2H), 3.26(s, 6H), 1.22(s, 9H); MS (EI) m/e 469 [M+]

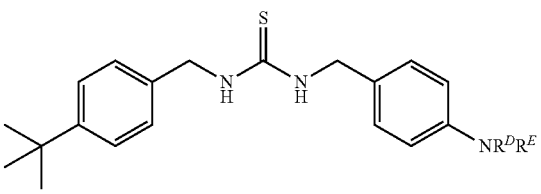

| Examples | Compounds No. | R$^D$<br>R$^E$ | Spectral data |
|---|---|---|---|
| 44 | 9d | H—<br>CH$_3$SO$_2$— | $^1$H NMR (300 MHz, CDCl$_3$): δ 7.37 (d, 2H), 7.1-7.3 (m, 6H), 6.39 (s, 1H), 5.99 (brs, 1H), 4.66 (d, 2H), 4.56 (m, 2H), 3.00 (s, 3H), 1.31 (s, 9H)<br>MS (EI) m/e 405 [M+] |
| 45 | 9e | H—<br>CF$_3$SO$_2$— | $^1$H NMR (300 MHz, DMSO-d$_6$): δ 7.90 (br, 1H), 7.25 (m, 8H), 4.50-4.70 (br, 4H), 1.25 (s, 9H)<br>MS (EI) m/e 459 [M+] |
| 46 | 9f | —H<br>—CHO | $^1$H NMR (300 MHz, CDCl$_3$): δ 8.20-8.40 (br, 2H), 8.05 (s, 1H), 6.80-7.30 (m, 8H), 4.52 (br, 4H), 1.19 (s, 9H)<br>MS (EI) m/e 355 [M+] |
| 47 | 9g | —H<br>—C(=S)NH$_2$ | $^1$H NMR (300 MHz, DMSO-d$_6$): δ 9.64 (s, 1H), 7.86 (br, 2H), 7.20-7.40 (m, 8H), 4.61 (br, 4H), 1.26 (s, 9H)<br>MS (EI) m/e 386 [M+] |
| 48 | 9h | —H<br>—CO$_2$Et | $^1$H NMR (300 MHz, DMSO-d$_6$): δ 9.56 (s, 1H), 7.81 (br, 2H), 7.15-7.45 (m, 8H), 4.58 (br, 4H), 4.10 (q, 2H, J = 7.05 Hz), 1.25 (s, 9H), 1.23 (t, 3H, J = 7.05 Hz)<br>MS (EI) m/e 399 [M+] |

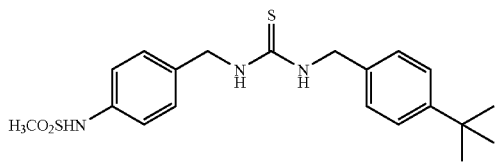

9d

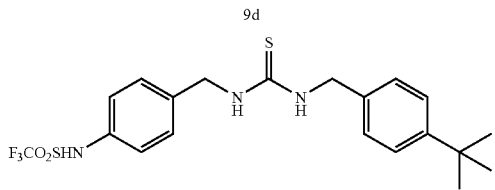

9e

| Examples | Compounds No. | $R^D$ $R^E$ | Spectral data |
|---|---|---|---|

9f

9g

9h

EXAMPLE 49

Synthesis of 1-(4-t-butylbenzyl)-3-[2-hydroxy-4-(N-t-butoxycarbonyl)aminobenzyl]thiourea (10-4)

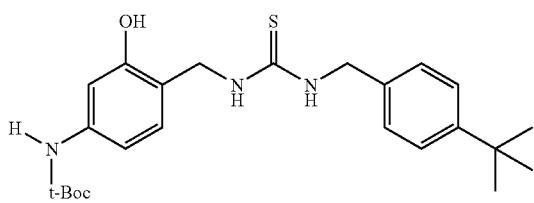

10-4

2-Hydroxy-4-nitrobenzaldehyde (1.67 g), t-butyldiphenylsilylchloride (TBDPSCI) (2.65 g) and imidazole (681 mg) were dissolved in dichloromethane (100 ml) and the solution was stirred at room temperature for 18 hours. The precipitate was filtered off and the filtrate was concentrated under reduced pressure. The obtained residue was purified by column-chromatography (hexane/ethyl acetate=3/1) to yield the compound 10-1 (4.00 g, 99%). The compound 10-1 (3.00 g) was reduced in the presence of palladium/carbon catalyst to yield an amine. The amine was dissolved in tetrahydrofuran (15 ml) and to the solution was added Boc$_2$O (950 mg), followed by stirring at room temperature for 18 hours. To the mixture were added water (20 ml) and ethyl acetate (10 ml). From the mixture, an organic layer was separated and an aqueous layer was extracted with ethyl acetate (10 ml×2). The combined organic layer was washed with brine, dried over magnesium sulfate and then concentrated under reduced pressure. The obtained residue was purified by column-chromatography (hexane/ethyl acetate=3/1) to yield the compound 10-2 (380 mg, 20%) and 10-3 (764 mg, 41%). The compound 10-2 was dissolved in ethyl acetate (10 ml) and to the solution was added t-butylbenzylisothiocyanate (150 mg), followed by stirring at room temperature for 18 hours. The resulting mixture was concentrated under reduced pressure and the obtained residue was purified by column-chromatography (hexane/ethyl acetate=3/1) to yield thiourea compound (300 mg, 56%). The compound (300 mg) was dissolved in THF (5.0 ml) and to the solution was added tetrabutylammonium fluoride (131 mg), followed by stirring at room temperature for 45 minutes. The reaction was quenched with saturated sodium bicarbonate and an aqueous solution layer was extracted with ethyl acetate (10 ml×2). The combined organic layer was washed with saturated aqueous sodium chloride solution, dried over magnesium sulfate, and then concentrated under reduced pressure. The obtained residue was purified by column-chromatography (hexane/ethyl acetate=1/1) to yield the compound 10-4 (52 mg, 27%).

$^1$H NMR (300 MHz, CDCl$_3$): δ 7.35(d, J=8.4 Hz, 2H), 7.20(d, J=8.4 Hz, 2H), 7.07(dd, J=2.7, 8.4 Hz, 1H), 6.94(d, J=8.4 Hz, 1H), 6.89(d, J=2.7 Hz, 1H), 6.01(bs, 1H), 5.19(bs, 1H), 4.83(d, J=5.7 Hz, 2H), 4.15(d, J=6.6 Hz, 2H), 1.44(s, 9H), 1.30(s, 9H)

EXAMPLE 50

Synthesis of 1-(4-t-butylbenzyl)-3-[2-hydroxy-4-methanesulfonylaminobenzyl]thiourea (10-6)

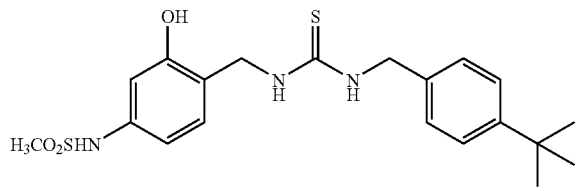

Step 1: Synthesis of 2-(N-t-butyloxycarbonylamino)methyl-4-methanesulfonylamino-1-t-butyldiphenylsilyloxybenzene (1-5)

The compound 10-3 (700 mg) prepared by Example 49 was dissolved in dichloromethane (10 ml) and the solution was cooled to 0° C., followed by adding trifluoroacetic acid (2.0 ml) thereto. The mixture was stirred for 2 hours and concentrated under reduced pressure. The obtained residue (186 mg) was dissolved in THF (2.0 ml) and to the solution was added triethylamine (90 μl), followed by stirring for 12 hours. To the solution was added Boc$_2$O (68 mg) and the mixture was stirred at room temperature for 10 hours. To the resulting mixture were added water (10 ml) and ethyl acetate (10 ml). The organic layer was separated and the aqueous layer was extracted with ethyl acetate (10 ml×2). The combined organic layer was washed with saturated aqueous sodium chloride solution, dried over magnesium sulfate, and then concentrated under reduced pressure. The obtained residue was purified by column-chromatography (hexane/ethyl acetate=1/2) to yield an alkylamine intermediate (100 mg, 69%), protected with Boc group. The intermediate and triethylamine (40 μl) were dissolved in dichloromethane (2.0 ml) and the solution was cooled to 0° C. To the solution was added methanesulfonyl chloride (20 μl) and the mixture was stirred at room temperature for 2 hours. The water was added thereto to quench the reaction. An organic layer was separated, dried over magnesium sulfate, and then concentrated under reduced pressure. The obtained residue was purified by column-chromatography (hexane/ethyl acetate=3/2) to yield the compound 10-5 (69 mg, 60%).

$^1$H NMR (300 MHz, CDCl$_3$): δ 7.68(m, 4H), 7.40(m, 6H), 7.12(d, J=3.0 Hz, 1H), 6.73(dd, J=3.0, 8.7 Hz, 1H), 6.40(d, J=8.7 Hz, 1H), 6.04(s, 1H), 4.94(bs, 1H), 4.46(d, J=5.4 Hz, 2H), 2.90(s, 3H), 1.48(s, 9H), 1.11(s, 9H).

Step 2: Synthesis of 1-(4-t-butylbenzyl)-3-[2-hydroxy-4-methanesulfonylaminobenzyl]thiourea (10-6)

Compound 10-5 (90 mg) was dissolved in THF (2.0 ml) and to the solution was added tetrabutylammoniumfluoride (200 μl), followed by stirring at room temperature for 45 minutes. The reaction was quenched with saturated aqueous sodium bicarbonate solution and the aqueous layer was extracted with ethyl acetate (10 ml×2). The combined organic layer was washed with saturated aqueous sodium chloride solution, dried over magnesium sulfate, and then concentrated under reduced pressure. The obtained residue was purified by column-chromatography (hexane/ethyl acetate=1/1) to yield a phenol compound (38 mg, 71%). The compound was dissolved in dichloromethane (3.0 ml) and the solution was cooled to 0° C. To the solution was added trifluoroacetic acid (500 μl), and the mixture was stirred for 2 hours and concentrated under reduced pressure. The concentrate was dissolved in ethyl acetate (2.0 ml) and to the solution was added triethylamine (16 μl), followed by stirring for 1 hour. To the solution was slowly added a solution of t-butylbenzyl-isothiocyanate (25 mg) in ethyl acetate (1.0 ml), and the mixture was stirred at room temperature for 18 hours and concentrated under reduced pressure. The obtained residue was purified by column-chromatography (hexane/ethyl acetate=1/3) to yield the compound 10-6 (37 mg, 73%).

$^1$H NMR (300 MHz, CDCl$_3$): δ 7.35(d, J=8.1 Hz, 2H), 7.19(d, J=8.1 Hz, 2H), 7.06(d, J=2.4 Hz, 1H), 7.00(dd, J=2.4, 8.4 Hz, 1H), 6.89(d, J=8.4 Hz, 1H), 6.31(bs, 1H), 6.23(bs, 1H), 4.80(d, J=6.3 Hz, 2H), 4.49(bs, 2H), 2.94(s, 3H), 1.30(s, 9H)

EXAMPLE 51

Synthesis of 1-(4-t-butylbenzyl)-3-(2,6-difluoro-3-methanesulfonylaminobenzyl)thiourea (11-2)

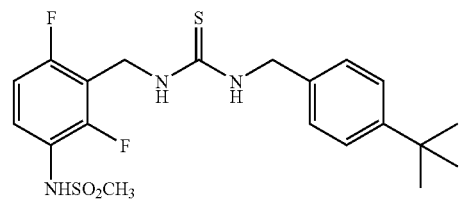

Step 1: Synthesis of 2,4-difluoro-3-[N-(t-butoxycarbonylamino)methyl]aniline (11-1)

2,6-Difluoro-3-nitrobenzonitrile (921 mg) and 10% palladium/carbon (200 mg) were mixed in methanol (15 ml) and to the mixture was added c-HCl (900 μl), followed by stirring under hydrogen atmosphere for 1 day. The mixture was diluted with ethyl acetate (30 ml) and filtered through celite pad. The filtrate was neutralized with 1 N aqueous sodium hydroxide solution and the organic layer was separated. The aqueous layer was extracted with ethyl acetate (10 ml×2). The combined organic layer was washed with saturated aqueous sodium chloride solution, dried over magnesium sulfate, and then concentrated under reduced pressure. The residue was purified by column-chromatography (methanol/ethyl acetate=2/1) to yield an amine salt (580 mg, 50%). The obtained amine salt was dissolved in tetrahydrofiran (5.0 ml) and to the solution was added triethylamine (700 μl), followed by stirring at room temperature for 12 hours. To the solution was added Boc$_2$O (548 mg) and the mixture was stirred at room temperature for 10 hours. To the resulting mixture were added water (10 ml) and ethyl acetate (10 ml) and then the organic layer was separated. The aqueous layer was extrated with ethyl acetate (10 ml×2). The combined organic layer was washed with saturated aqueous sodium chloride solution, dried over magnesium sulfate, and then concentrated under reduced pressure. The obtained residue was purified by column-chromatography (hexane/ethyl acetate=1/1) to yield intermediate material 11-1 (531 mg, 82%) protected with Boc.

$^1$H NMR (300 MHz, CDCl$_3$) δ 6.67(m, 2H), 4.86(bs, 1H), 4.39(d, J=4.8 Hz, 2H), 3.59(bs, 2H), 1.44(s, 9H)

Step 2: Synthesis of 1-(4t-butylbenzyl)-3-(2,6-difluoro-3-methanesulfonylaminobenzyl)thiourea (11-2)

Compound 11-1 (531 mg) was mesylated and treated with trifluoroacetic acid to remove Boc group therefrom. 4-t-butylbenzylisothiocyanate was reacted therewith to yield the compound 11-2 (145 mg, 16%).

$^1$H NMR (300MHz, CDCl$_3$): δ 7.50(dt, J=5.7, 9.0 Hz, 1H), 7.38(d, J=8.1 Hz, 2H), 7.22(d, J=8.1 Hz, 2H), 6.90(dt, J=1.8, 9.0 Hz, 1H), 6.41(bs, 1H), 6.14(bs,1H), 6.02(bs, 1H), 4.79(d, J=5.7 Hz, 2H), 4.55(bs, 2H), 3.00(s, 3H), 1.32(s, 9H)

EXAMPLE 52

Synthesis of 1-(4-t-butylbenzyl)-3-(3-methanesulfonylaminobenzyl)thiourea (12-3b)

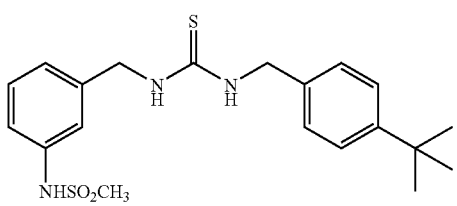

12-3b

Step 1: Synthesis of 3-aminomethyl-phenylamine (12-1b)

3-Nitrobenzaldehyde (1.51 g) and hydroxylamine hydrochlride (1.29 g) were dissolved in methanol (100 ml), and to the solution was slowly added pyridine (2.37 g) at room temperature, followed by stirring for 18 hours. The resulting mixture was concentrated under reduced pressure. The residue was dissolved in ethyl acetate (30 ml), washed with water (10 ml×2) and saturated aqueous copper sulfate solution (10 Ml), dried over magnesium sulfate, concentrated under reduced pressure, and then the residue was purified by column-chromatography (hexane/ethyl acetate=3/1) to yield oxime (1.66 g). The obtained oxime was dissolved in methanol (20 ml) and to the solution was added 10% palladium/carbon (414 mg), followed by stirring at room temperature under hydrogen atmosphere for 3 days. The reaction mixture was filtered to remove the precipitate and the filtrate was concentrated under reduced pressure to yield the compound 12-1b (643 mg, 53%).

$^1$H NMR(300 MHz, DMSO-d$_6$): δ 7.08(t, J=8.1 Hz, 1H), 6.66(m, 2H), 6.55(d, J=8.1 Hz, 1H), 2.40 (bs, 2H)

Step 2: Synthesis of 1-(4-t-butylbenzyl)-3-(3-methanesulfonylaminobenzyl)thiourea (12-3b)

Compound 12-1b (643 mg) was dissolved in tetrahydrofuran (6.0 ml) and to the solution was slowly added Boc$_2$O (1.26 g) at room temperature, followed by stirring for 18 hours. The resulting mixture was concentrated under reduced pressure and the obtained residue was purified by column-chromatography (hexane/ethyl acetate=2/1) to yield an intermediate compound (622 mg) protected with Boc group. The intermediate compound and triethylamine (500 μl) were dissolved in dichloromethane (20 ml) and the solution was cooled to 0° C. To the solution was added methanesulfonyl chloride (300 μl) and the mixture was stirred at room temperature for 50 minutes. The water was added thereto to quench the reaction. The organic layer was separated, dried over magnesium sulfate, concentrated under reduced pressure, and then the residue was purified by column-chromatography (hexane/ethylacetate=1/1) to yield the compound 12-2b (871 mg, 47%). The compound 12-2b was dissolved in dichloromethane (15 ml) and the solution was cooled to 0° C., followed by adding trifluoroacetic acid (3.0 ml) thereto and stirring for 2 hours. The resulting mixture was concentrated under reduced pressure and the residue was dissolved in ethyl acetate (10 ml), followed by adding triethylamine (140 μl) thereto and stirring for 1 hour. To the solution was slowly added a solution of t-butylbenzylisothiocyanate (421 mg) in ethyl acetate (2 ml) and the mixture was stirred at room temperature for 18 hours. The resulting mixture was concentrated under reduced pressure and the obtained residue was purified by column-chromatography (hexane/ethyl aceate=1/1) to yield the compound 12-3b (385 mg, 95%).

$^1$H NMR (300 MHz, CDCl$_3$): δ7.33(d, J=8.4 Hz, 2H), 7.25(t, J=8.1 Hz, 1H), 7.18(d, J=8.4 Hz, 2H), 7.13(m, 2H), 7.03(d, J=7.5 Hz, 1H), 6.31(bs, 2H), 4.66(d, J=5.1 Hz, 2H), 4.58(d, J=4.8 Hz, 2H), 2.95(s, 3H), 1.29(s, 9H).

Compounds 12-3a and 12-3c~12-3g of Example 53~Example 59 were synthesized according to the synthesizing procedure as described above.

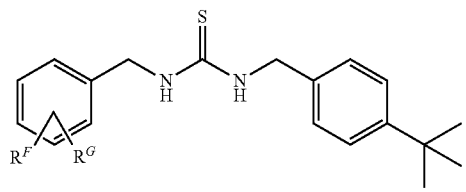

12-3

| Examples | Compounds No. | $R^F$ = $R^G$ = | Spectral data |
|---|---|---|---|
| 53 | 12-3a | H 2-NHMs | $^1$H NMR (300 MHz, CDCl$_3$): δ 8.13 (bs, 1H), 7.46 (d, J = 8.1 Hz, 1H), 7.31 (m, 2H), 7.31 (d, J = 8.4 Hz, 2H), 7.17 (d, J = 5.4 Hz, 1H), 7.16 (d, J = 8.4 Hz, 2H), 6.34 (m, 2H), 4.87 (d, J = 6.0 Hz, 2H), 4.47 (bs, 2H), 2.99 (s, 3H), 1.28 (s, 9H). |

12-3

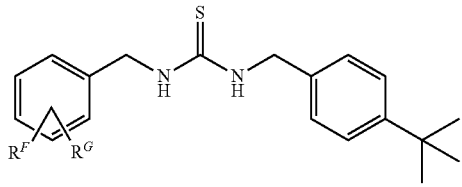

| Examples | Compounds No. | $R^F =$<br>$R^G =$ | Spectral data |
|---|---|---|---|
| 54 | 12-3c | H<br>2-NMs$_2$ | $^1$H NMR (300 MHz, CDCl$_3$): δ 7.62 (d, J = 7.5 Hz 1H), 7.47 (t, J = 7.5 Hz, 1H), 7.40 (t, J = 8.4 Hz, 1H), 7.34 (d, J = 8.4 Hz, 3H), 7.17 (d, J = 8.4 Hz, 2H), 6.49 (bs 1H), 6.31 (bs, 1H), 4.86 (d, J = 4.2 Hz, 2H), 4.50 (bs, 2H) 3.43 (s, 6H), 1.29 (s, 9H). |
| 55 | 12-3d | H<br>3-NMs$_2$ | $^1$H NMR (300 MHz, CDCl$_3$): δ 7.43 (d, J = 7.2 Hz, 1H), 7.38 (m, 1H), 7.38 (d, J = 8.4 Hz, 2H), 7.31 (m, 1H), 7.29 (m, 1H), 7.22 (d, J = 8.4 Hz, 2H), 6.16 (bs, 1H), 6.04 (bs, 1H), 4.78 (d, J = 5.7 Hz, 2H), 4.57 (bs, 2H), 3.40 (s, 6H), 1.30 (s, 9H). |
| 56 | 12-3e | 4-F<br>3-NHMs | $^1$H NMR (300 MHz, CDCl$_3$): δ 7.46 (d, J = 8.1 Hz, 1H), 7.47 (d, J = 8.4 Hz, 2H), 7.22 (d, J = 8.4 Hz, 2H), 7.08 (d, J = 8.1 Hz, 2H), 6.50 (bs, 1H), 6.12 (bs, 1H), 5.97 (bs, 1H), 4.71 (d, J = 5.4 Hz, 2H), 4.57 (d, J = 4.8 Hz, 2H), 3.03 (s, 3H), 1.31 (s, 9H). |
| 57 | 12-3f | 4-F<br>3-NMs$_2$ | $^1$H NMR (300 MHz, CDCl$_3$): δ 7.37 (d, J = 8.4 Hz, 2H), 7.36 (m, 2H), 7.24 (d, J = 8.4 Hz, 2H), 7.15 (d, J = 9.3 Hz 1H), 6.20 (bs, 1H), 6.04 (bs, 1H), 4.74 (d, J = 5.4 Hz, 2H), 4.55 (d, J = 5.1 Hz, 2H), 3.43 (s, 6H), 1.31 (s, 9H). |
| 58 | 12-3g | 6-F<br>3-NHMs | $^1$H NMR (300 MHz, CDCl$_3$): δ 7.36 (d, J = 8.1 Hz, 2H), 7.28 (dd, J = 2.4, 6.4 Hz, 1H), 7.21 (d, J = 8.1 Hz, 2H), 7.08 (m, 1H), 7.00 (t, J = 9.2 Hz, 1H), 6.88 (bs, 1H), 6.34 (bs, 1H), 6.18 (bs, 1H), 4.76 (d, J = 5.7 Hz, 2H), 4.55 (d, J = 4.5 Hz, 2H), 2.97 (s, 3H), 1.30 (s, 9H). |

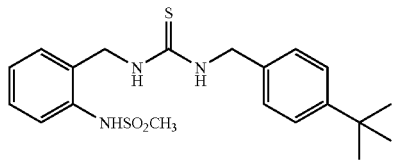

12-3a

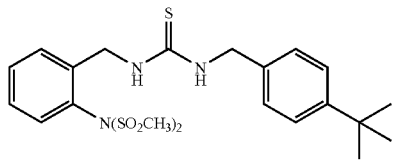

12-3c

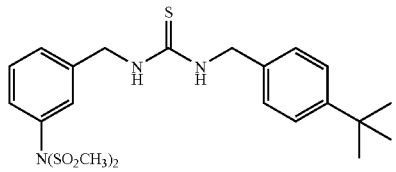

12-3d

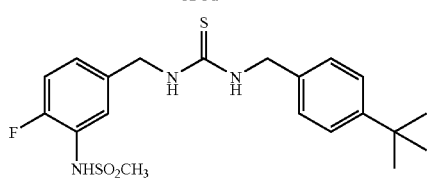

12-3e

-continued 12-3

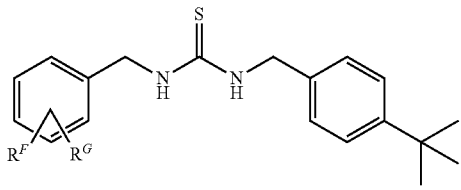

| Examples | Compounds No. | $R^F =$ $R^G =$ | Spectral data |
|---|---|---|---|

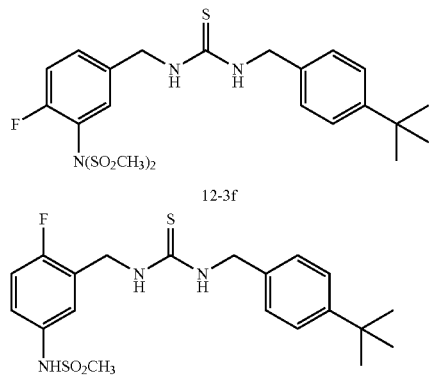

12-3f 12-3g

EXAMPLE 59

Synthesis of 1-(4-t-butyl-2-methoxybenzyl)-3-(4-methanesulfonylaminobenzyl)thiourea (13-4a)

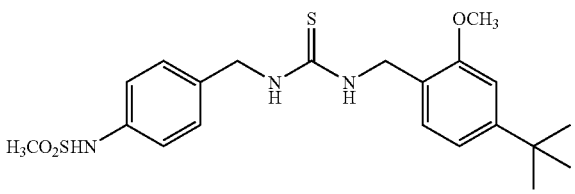

13-4a

Step 1: Synthesis of 4-t-butyl-2-methoxybenzonitrile (13-2a)

4-t-Butyl-2-hydroxybenzonitrile (1.16 g) and potassium carbonate (376 mg) were dissolved in dimethylformamide (4 ml) and to the solution was added dropwise iodomethane (226 μl), followed by stirring at 50° C. for 2 hours. The resulting mixture was filtered to remove the remaining potassium carbonate and concentrated under reduced pressure. The obtained residue was purified by column-chromatography (hexane/ethyl acetate=10/1) to yield the compound 13-2a (167 mg, 97%).
$^1$H NMR(300 MHz, CDCl$_3$): δ7.45(d, 1H, J=8.0 Hz), 7.01 (dd, 1H, J=1.7, 8.2 Hz), 6.94(d, 1H, J=1.5 Hz), 3.92(s, 3H), 1.31(s, 9H)

Step 2: Synthesis of 4-t-butyl-2-methoxybenzylamine (13-3a)

Lithium aluminium hydride (50 mg) was suspended in ether (2 ml) and the suspension was cooled to 0° C. To the suspension was added dropwise a solution of the compound 13-2a (167 mg) prepared by Step 1 in ether (2 ml) and the mixture was refluxed for 2 hours. After the completion of the reaction, the reaction solution was basified with 5 N aqueous sodium hydroxide solution. Then, aqueous Rochel solution was added thereto and stirred for 1 hour, at room temperature. Then, resulting mixture was extracted with ether (50 ml×3) and concentrated under reduced pressure to yield the compound 13-3a (120 mg, 71%). The following Step 3 was proceeded using the compound 13-3a which was not purified.

Step 3: Synthesis of 1-(4-t-butyl-2-methoxybenzyl)-3-(4-methanesulfonylaminobenzyl)thiourea (13-4a)

The compound 13-3a (132 mg) prepared according to the same procedure as described in Step 2 was dissolved in dichloromethane (5 ml) and to the solution were added triethylamine (143 μl) and 4-methanesulfonaminobenzyl-isothiocyanate (165 mg) in order, followed by stirring at room temperature for 3 hours. The reaction solution was evaporated under reduced pressure and the obtained residue was purified by column-chromatography (hexane/ethyl acetate=2/1) to yield the compound 13-4a (190 mg, 70%),
$^1$H NMR(300 MHz, CDCl$_3$): δ7.11-7.32(m, 5H), 6.96(d, 1H, J=7.0 Hz), 6.82(s, 1H), 4.67(s, 2H), 4.45(s, 2H), 3.62(s, 3H), 3.00(s, 3H), 1.2(s, 9H); MS (FAB) m/e 436[M$^+$+1]

Compounds of Example 60~69 are shown in the Scheme 13. In Step 1 of the Examples, compounds 13-2b~13-2k were synthesized according to the similar procedure as described in Step 1 of Example 59, and properties and spectral data thereof are shown in below table. And in Step 2 of the respective examples, amines were synthesized according to the similar procedure as described in Step 2 of Example 59, and the following Step 3 were proceeded using the obtained amine compounds which was not purified. In the Example 60~69, the final compounds 13-4b~13-4k were synthesized according to the similar procedure as described in Step 3 of Example 59 except that amines prepared by Step 2 were used, and properties and spectral data thereof are shown in below table.

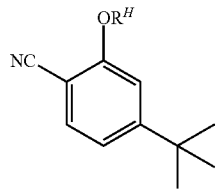

13-2b~13-2k

| Examples-step | Compounds | $R^H$ | Spectral data |
|---|---|---|---|
| 60-1 | 13-2b | ethyl | H NMR (300 MHz, CDCl$_3$): δ 7.45 (d, 1H, J = 8.1 Hz), 6.98 (dd, 1H, J = 1.7, 8.1 Hz), 6.92 (d, 1H, J = 1.5 Hz), 4.15 (q, 2H, J = 6.8 Hz), 1.46 (t, 3H, J = 7.1 Hz), 1.30 (s, 9H); MS (FAB) m/e 450 [M$^+$ + 1] |
| 61-1 | 13-2c | n-propyl | $^1$H NMR (300 MHz, CDCl$_3$): δ 7.45 (d, 1H, J = 8.3 Hz), 6.98 (dd, H, J = 1.7, 8.2 Hz), 6.91 (d, 1H, J = 1.7 Hz), 4.02 (t, 2H, J = 6.6 Hz), 1.78-1.92 (m, 2H), 1.30 (s, 9H), 1.07 (t, 3H, 7.3 Hz) |
| 62-1 | 13-2d | n-butyl | $^1$H NMR (300 MHz, CDCl$_3$): δ 7.44 (d, 1H, J = 8.0 Hz), 6.98 (dd, 1H, J = 1.7, 8.0 Hz), 6.92 (d, 1H, J = 1.5 Hz) 4.04 (t, 2H, J = 3.4 Hz), 1.70-1.88 (m, 2H), 1.40-1.62 (m, 2H), 1.30 (s, 9H), 0.97 (t, 3H, J = 7.3 Hz) |
| 63-1 | 13-2e | n-pentyl | $^1$H NMR (300 MHz, CDCl$_3$): δ 7.44 (d, 1H, J = 8.0 Hz), 6.98 (dd, 1H, J = 1.7, 8.0 Hz), 6.91 (d, 1H, J = 1.7 Hz), 4.05 (t, 2H, J = 6.6 Hz), 1.84 (m, 2H, J = 6.8 Hz), 1.34-1.53 (m, 4H), 1.30 (s, 9H), 0.92 (t, 3H, J = 7.1 Hz) |
| 64-1 | 13-2f | isopropyl | $^1$H NMR (300 MHz, CDCl$_3$): δ 7.44 (d, H, J = 8.0 Hz), 6.97 (dd, 1H, J = 1.7, 8.0 Hz), 6.94 (d, 1H, J = 1.7 Hz) 4.65 (m, 1H, J = 5.9 Hz), 1.38 (d, 6H, J = 6.1 Hz), 1.29 (s, 9H) |
| 65-1 | 13-2g | isobutyl | $^1$H NMR (300 MHz, CDCl$_3$): δ 7.45 (d, 1H, J = 8.3 Hz), 6.8 (dd, 1H, J = 1.7, 8.0 Hz), 6.90 (d, 1H, J = 1.5 Hz), 3.81 (d, 2H, J = 6.4 Hz), 2.08-2.20 (m, 1H), 1.30 (s, 9H), 1.06 (d, 6H, J = 6.8 Hz) |
| 66-1 | 13-2h | neo-pentyl | $^1$H NMR (300 MHz, CDCl$_3$): δ 7.45 (d, 1H, J = 8.0 Hz), 6.98 (dd, 1H, J = 1.7, 8.0 Hz), 6.89 (d, 1H, 1.7 Hz), 3.68 (s, 2H), 1.30 (s, 9H), 1.08 (s, 9H) |
| 67-1 | 13-2i | MOM | $^1$H NMR (400 MHz, CDCl$_3$): δ 7.51 (d, 1H, J = 8.1 Hz), 7.19 (dd, 1H, J = 1.5, 5.2 Hz), 7.10 (d, 1H, J = 1.6 Hz), 5.31 (s, 2H), 3.56 (s, 3H), 1.34 (s, 9H) |
| 68-1 | 13-2j | methoxy-ethoxy-methyl | $^1$H NMR (300 MHz, CDCl$_3$): δ 7.45 (d, 1H, J = 7.8 Hz), 7.02 (d, 1H, J = 1.7 Hz), 6.99 (dd, 1H, J = 1.7, 3.0 Hz), 4.23 (t, 2H, J = 4.6 Hz), 3.80 (t, 2H, J = 4.5 Hz), 3.47 (s, 3H), 1.29 (s, 9H) |
| 69-1 | 13-2k | benzyl | $^1$H NMR (300 MHz, CDCl$_3$): δ 7.50-7.27 (m, 6H), 7.02 (d, 1H, J = 0.7 Hz), 6.98 (dd, 1H, J = 1.7, 5.3 Hz), 5.21 (s, 2H), 1.25 (s, 9H), 3.47 (s, 3H) |

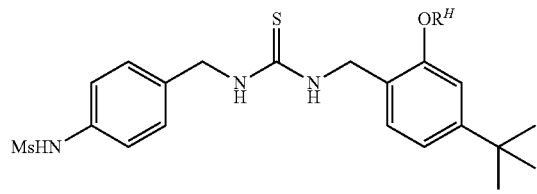

13-4b~13-4k

| Examples-step | Compounds | $R^H$ | Spectral data |
|---|---|---|---|
| 60-3 | 13-4b | ethyl | $^1$H NMR (300 MHz, CDCl$_3$): δ 7.01-7.10 (m, 5H), 6.91 (d, 1H, J = 7.6 Hz), 6.77 (s, 1H), 4.64 (s, 2H), 4.42 (s, 2H), 3.87 (q, 2H, J = 7.1 Hz), 2.94 (s, 3H), 1.15-1.24 (m, 12H); MS (FAB) m/e 450 [M$^+$ + 1] |
| 61-3 | 13-4c | n-propyl | $^1$H NMR (300 MHz, CDCl$_3$): δ 7.06-7.20 (m, 5H), 6.95 (dd, 1H, J = 1.7, 7.9 Hz), 6.1 (d, 1H, J = 1.5 Hz), 4.68 (s, 2H), 4.44 (s, 2H), 3.80 (t, 2H, J = 6.6 Hz), 2.98 (s, 3H), 1.52-1.74 (m, 2H), 1.29 (s, 9H), 0.95 (t, 3H, J = 7.6 Hz); MS (FAB) m/e 464 [M$^+$ + 1] |
| 62-3 | 13-4d | n-butyl | $^1$H NMR (300 MHz, CDCl$_3$): δ 7.08-7.33 (m, 5H), 6.96 (d, 1H, J = 7.8 Hz), 6.83 (s, 1H), 4.68 (s, 2H), 4.47 (s, 2H), |

-continued

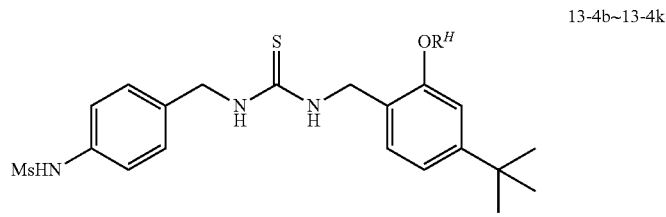

13-4b~13-4k

| Examples-step | Compounds | $R^H$ | Spectral data |
|---|---|---|---|
| | | | 3.85 (t, 2H, J = 6.8 Hz), 2.98 (m, 3H), 1.39-1.80 (m, 4H), 1.29 (s, 9H), 0.91 (t, 3H, J = 7.3 Hz); MS (FAB) m/e 478 [M⁺ + 1] |
| 63-3 | 13-4e | n-pentyl | $^1$H NMR (300 MHz, CDCl$_3$): δ .05-7.35 (m, 5H), 6.75-7.00 (m, 2H), 4.61 (s, 2H), 4.49 (s, 2H), 2.96 (s, 3H), 1.55-1.70 (m, 2H), 1.10-1.48 (m, 13H), 0.92 (t, 3H, J = 7.1 Hz); MS (FAB) m/e 492 [M⁺ + 1] |
| 64-3 | 13-4f | isopropyl | $^1$H NMR (300 MHz, CDCl$_3$): δ 7.06-7.37 (m, 5H), 6.95 (dd, H, J = 1.7, 7.8 Hz), 4.69 (s, 2H), 4.33-4.60 (m, 3H), 2.97 (s, 3H), 1.29 (s, 9H), 1.23 (d, 6H, J = 6.1 Hz); MS (FAB) m/e 464 [M⁺ + 1] |
| 65-3 | 13-4g | isobutyl | $^1$H NMR (300 MHz, CDCl$_3$): δ 7.06-7.33 (m, 5H), 6.95 (d, 1H, J = 8.0 Hz), 6.81 (d, 1H, J = 1.7 Hz), 4.68 (s, 2H), 4.48 (s, 2H), 3.62 (d, 2H, J = 6.3 Hz), 2.98 (s, 3H), 1.30 (s, 9H), 0.96 (d, 6H, J = 6.8 Hz); MS (FAB) m/e 478 [M⁺ + 1] |
| 66-3 | 13-4h | neo-pentyl | $^1$H NMR (300 MHz, CDCl$_3$): δ 7.04-7.21 (m, 5H), 6.95 (d, 1H, J = 8.1 Hz), 6.82 (d, 1H, J = 1.7 Hz), 4.68 (s, 2H), 4.53 (s, 2H), 3.54 (s, 2H), 2.97 (s, 3H), 1.30 (s, 9H), 0.99 (s, 9H); MS (FAB) m/e 492 [M⁺ + 1] |
| 67-3 | 13-4i | MOM | $^1$H NMR (300 MHz, CDCl$_3$): δ 6.96-7.30 (m, 7H), 5.06 (s, 2H), 4.66 (s, 2H), 4.51 (s, 2H), 3.39 (s, 3H), 2.98 (s, 3H), 1.28 (s, 9H); MS (FAB) m/e 466 [M⁺ + 1] |
| 68-3 | 13-4j | methoxy-ethoxy-methyl | $^1$H NMR (300 MHz, CDCl$_3$): δ 7.10-7.37 (m, 5H), 6.98 (d, 1H, J = 7.8 Hz), 6.85 (s, 1H), 4.68 (s, 2H), 4.61 (s, 2H), 4.00-4.15 (m, 2H), 3.60-3.75 (m, 2H), 3.30 (s, 3H), 2.97 (s, 3H), 1.28 (s, 9H); MS (FAB) m/e 480 [M⁺ + 1] |
| 69-3 | 13-4k | benzyl | $^1$H NMR (400 MHz, CDCl$_3$): δ 7.50-6.95 (m, 12H), 5.01 (s, 2H), 4.68-4.40 (m, 4H), 3.00 (s, 3H), 1.33 (s, 9H); MS (FAB) m/e 512 [M⁺ + 1] |

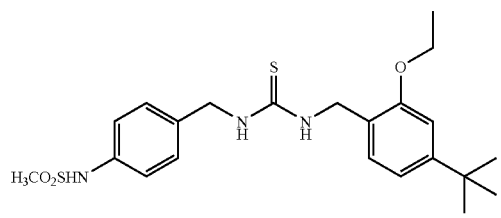

13-4b

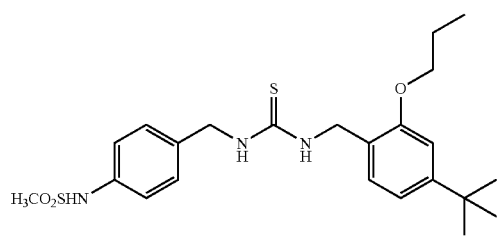

13-4c

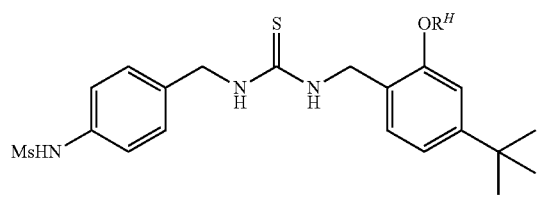
13-4b~13-4k
| Examples-step | Compounds | R^H | Spectral data |
|---|---|---|---|
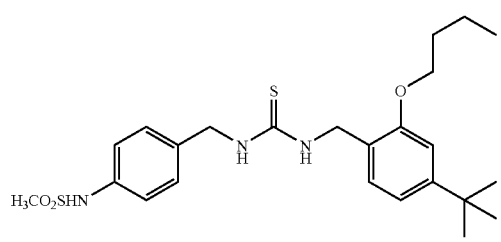
13-4d
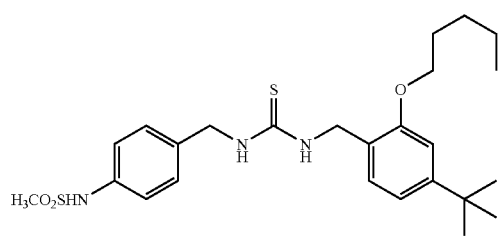
13-4e
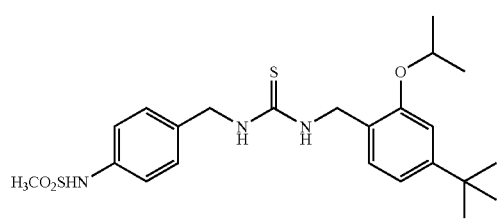
13-4f
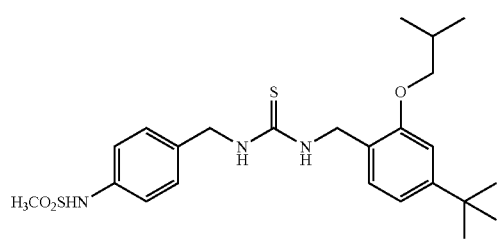
13-4g -continued
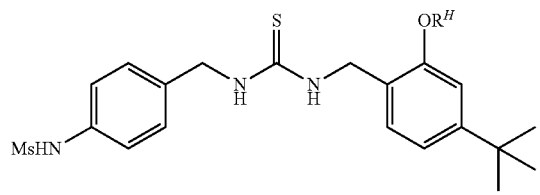
13-4b~13-4k
Examples-
step   Compounds   $R^H$   Spectral data
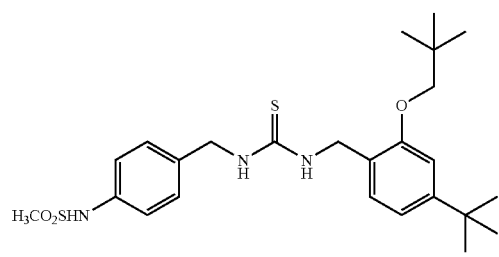
13-4h
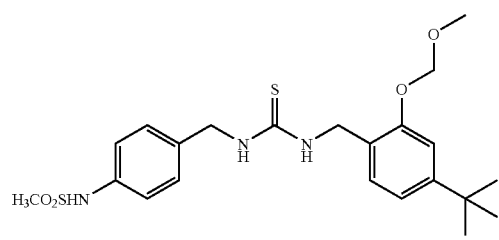
13-4i
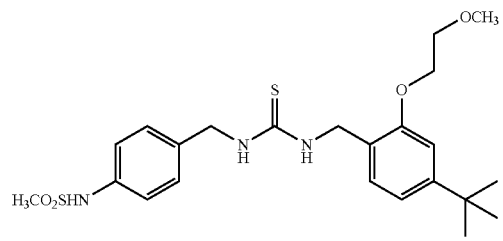
13-4j
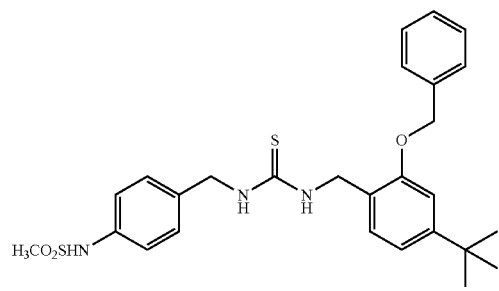
13-4k

EXAMPLE 70

Synthesis of 1-(2-acetoxymethyl-4-t-butylbenzyl)-3-(4-methanesulfonylaminobenzene)thiourea (13-9a)

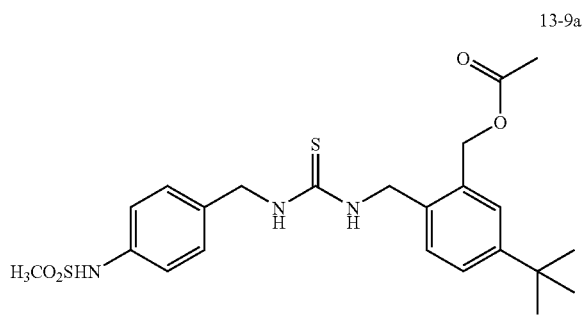

Step 1: Synthesis of 4-t-butyl-2-trifluoromethane-sulfonyloxybenzonitrile (13-5)

4-t-butyl-2-hydroxybenzonitrile (800 mg) was dissolved in dichloromethane (16 ml) and cooled to 0° C. To the solution were added triethylamine (663 µl) and trifluoromethanesulfonic anhydride (764 µl) in order, followed by stirring for 1 hour. The reaction solution was evaporated under reduced pressure and the obtained residue was purified by column-chromatography (hexane/ethyl aceate=10/1) to yield the compound 13-5 (1.30 g, 93%).

$^1$H NMR(300 MHz, CDCl$_3$): δ7.67(d, 1H, J=8.0 Hz), 7.49 (dd, 1H, J=1.7, 8.3 Hz), 7.43(d, 1H, J=1.5 Hz), 1.34(s, 9H)

Step 2: Synthesis of methyl 5-t-butyl-2-cyanobenzoate (13-6)

The compound 13-5 (1.30 g) prepared according to the same procedure as described in Step 1 was mixed with palladium acetate (28 mg) and 1,1'-bis(diphenylphosphino)ferrocene (141 mg), and the atmosphere of the reactor was brought into an atmosphere of carbon monoxide. To the mixture was added dimethylsulfoxide (25 ml) to dissolve the mixture. To the solution was added triethylamine (1.77 ml) and methanol (3.42 ml) successively with stirring and the mixture was stirred at 50° C. for 4 hours. The resulting mixture was filtered to remove the catalyst and the filtrate was evaporated under reduced prssure. The obtained residue was purified by column-chromatography (hexane/ethyl acetate=20/1) to yield the compound 13-6 (400 mg, 44%).

$^1$H NMR(300 MHz, CDCl$_3$): δ8.13(d, 1H, J=2.0 Hz), 7.72 (d, 1H, J=8.1 Hz), 7.64(dd, 1H, J=2.2, 8.2 Hz), 3.99(s, 3H), 1.34(s, 9H)

Step 3: Synthesis of (2-aminomethyl-5-t-butylphenyl)methanol (13-7)

Lithium aluminium hydride (105 mg) was supended in ether (3 ml) and the suspension was cooled to 0° C. To the suspension was added dropwise a solution of the compound 13-6 (140 mg) prepared by Step 2 in ether (4 ml) and the mixture was refluxed for 2 hours. After the completion of the reaction, the reaction mixture was basified with 5 N aqueous sodium hydroxide solution, followed by adding aqueous Rochel solution thereto and then stirring for 1 hour. Then, the resulting mixture was extracted with ether (50 ml×3) and concentrated under reduced pressure to yield the compound 13-7 (320 mg, 90%). The following Step 4 was proceeded using the compound 13-7 which was not purified

Step 4: Synthesis of 1-(4-t-butyl-2-hydroxymethyl-benzyl)-3-(4-methanesulfonylaminobenzyl)thiourea (13-8)

The compound 13-7a (320 mg) prepared according to the same procedure as described in Step 3 was dissolved in dichloromethane (7 ml) and to the solution were added triethylamine (231 µl) and 4-methanesulfonaminobenzyl-isothiocyanate (401 mg) successively, followed by stirring at room temperature for 3 hours. The reaction solution was evaporated under reduced pressure and the obtained residue was purified by column-chromatography (hexane/ethyl acetate=1/1) to yield the compound 13-8 (460 mg, 64%).

$^1$H NMR(300 MHz, CDCl$_3$) δ7.38-7.00 (m, 7H), 4.75-4.60 (m, 4H), 4.50(s, 2H), 2.92(s, 3H), 1.25(s, 9H)

Step 5: Synthesis of 1-(2-acetoxymethyl-4-t-butyl-benzyl)-3-(4-methanesulfonylaminobenzene)thiourea (13-9a)

1,3-Dicyclohexylcarbodiimide (68 mg) was dissolved in dichloromethane (1 ml), and the solution was stirred and cooled to 0° C. To the solution were added dropwise a mixed solution of the compound 13-8 (130 mg) prepared according to the same procedure as described in Step 4 and 4-(dimethylamino)pyridine (4 mg) in dichloromethane (3 ml), followed by adding acetic acid (34 µl) thereto. The mixture was stirred at room temperature for 12 hours and concentrated under reduced pressure. The obtained residue was purified by column-chromatograpohy (hexane/ethyl acetate=3/2) to yield the compound 13-9a (52 mg, 37%).

$^1$H NMR(300 MHz, CDCl$_3$): δ7.40-7.06(m, 7H), 5.10(s, 2H), 4.68(s, 4H), 2.30(s, 3H), 2.01(s, 3H), 1.30(s, 9H); MS (FAB) m/e 478 [M$^+$+1]

EXAMPLE 71

Synthesis of 1-(2-trimethylacetoxymethyl-4-t-butyl-benzyl)-3-(4methanesulfonylaminobenzene)thiourea (13-9b)

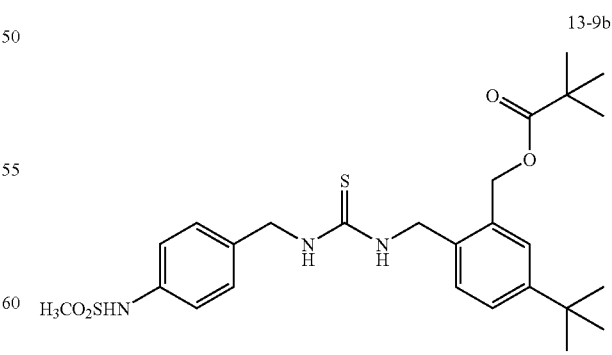

Compound 13-9b (110 mg, 71%) was synthesized by reacting compound 13-8 (130 mg) with trimethylacetic acid (45 mg) according to the similar procedure as described in Step 5 of Example 70.

$^1$H NMR(300 MHz, CDCl$_3$): δ7.43-7.07(m, 7H), 5.10(s, 2H), 4.72(s, 2H), 4.66(s, 2H), 2.97(s, 3H), 1.29(s, 9H), 1.12(s, 9H); MS (FAB) m/e 520 [M$^+$+1]

EXAMPLE 72

Synthesis of 1-(4-t-butylbenzyl)-3-(4-methylthiobenzyl)thiourea (14-3)

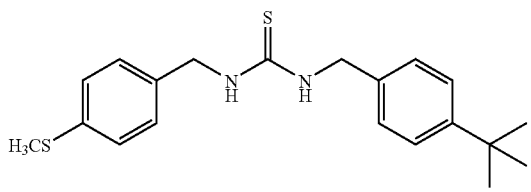

Step 1: Synthesis of 2-(4-methylthiobenzyl)isoindol-1,3-dione (14-1)

(4-methylthio)benzylalcohol (1.54 g) was dissolved in anhydrous tetrahydrofuran (10 ml) and to the solution were added phthalimide (1.47 g) and triphenylphosphine (2.62 g). To the mixture was slowly added dropwise a solution of diisopropylazodicarboxylate (DIAD) (2.02 g) in anhydrous tetrahydrofuran (4 ml), while the mixture was stirred at room temperature. After 18 hours, the reaction mixture was concentrated and the residue was purified by column-chromatography (hexane/ethyl acetate=5/1) to yield a white solid (2.00 g, 71%).

$^1$H NMR(300 MHz, CDCl$_3$): δ 7.86-7.68(m, 4H), 7.38-7.35(m, 2H), 7.22-7.18(m, 2H), 4.79(s, 2H), 2.44(s, 3H)

Step 2: Synthesis of 1-(4-t-butylbenzyl)-3-(4-methylthiobenzyl)thiourea (14-3)

2-(4-methylthiobenzyl)isoindol-1,3-dione (14-1) (1.67 g) was dissolved in ethanol (10 ml) and to the solution was added hydrazine hydrate (300 mg), followed by refluxing. After 24 hours, the resulting mixture was diluted with dichloromethane (50 ml) and washed with 2 N hydrochloric acid solution. An organic layer was washed with aqueous sodium chloride solution, dried over anhydrous magnesium sulfate, concentrated under reduced pressure. The residue was purified by column-chromatography to obtain a liquid (0.8 g). The obtained liquid mixture (400 mg) was dissolved in dichloromethane (20 ml) and to the solution was added 4-t-butylbenzylisothiocyanate (0.54 g), followed by stirring at room temperature for 24 hours. The reaction mixture was concentrated and the residue was purified by column-chromatography (dichloromethane) to yield the compound 14-3 (0.52 g, 56%) as a white solid.

$^1$H NMR(300 MHz, CDCl$_3$): δ 7.37-7.15(m, 8H), 6.00(brs, 2H), 4.60-4.50(m, 4H), 2.47(s, 3H), 1.31(s, 9H)

EXAMPLE 73

Synthesis of 1-(4-t-butylbenzyl)-3-[2-(4-methylthiazol-5-yl)ethyl]thiourea (14-6)

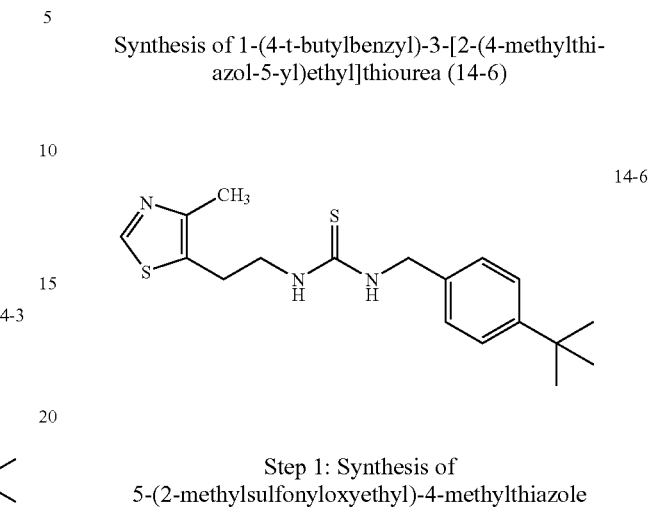

Step 1: Synthesis of 5-(2-methylsulfonyloxyethyl)-4-methylthiazole 2-(4-methylthiazol-5-yl)ethanol (5.01 g) was dissolved in dichloromethane (100 ml) and to the solution was added triethylamine (5.06 g), followed by adjusting the temperature of reactor to 0° C. To the obtained solution was added dropwise methanesulfonyl chloride (4.58 g), and the mixture was stirred for 21. hours while allowed to warm up to room temperature. The reaction solution was washed with water, concentrated under reduced pressure, and then purified by column-chromatography (hexane/ethyl acetate=1/3) to yield 5-(2-methylsulfonyloxyethyl)-4-methylthiazole (5.18 g, 67%) as a pale yellow liquid.

$^1$H NMR(300 MHz, CDCl$_3$): δ 8.63(s, 1H), 4.37(t, 3H, J=6 Hz), 3.23(t, 3H, J=6 Hz), 2.97(s, 3H), 2.43(s, 3H)

Step 2: Synthesis of 2-[2-(4-methylthiazol-5-yl)ethyl]isoindol-1,3-dione (14-4)

5-(2-methylsulfonyloxyethyl)-4-methylthiazole (4.17 g) was dissolved in dimethylformamide (20 ml) and to the solution was added potassium phthalimide (3.84 g), followed by stirring at 70° C. for 5 hours. The mixture was concentrated under reduced pressure and water was added thereto to form precipitate. The resulting mixture was filtered to collect the precipitate. The obtained precipitate was dissolved in dichloromethane. The solution was dried over anhydrous magnesium sulfate, concentrated, and then crystallized (dichloromethane/petroleum ether) to yield the compound 144 (3.77 g, 74%) as a pale yellow solid.

$^1$H NMR(300 MHz, CDCl$_3$): δ 8.57(s, 1H), 7.86-7.70(m, 4H), 3.91(t, 3H, J=6 Hz), 3.18(t, 3H, J=6 Hz), 2.38(s, 3H)

Step 3: Synthesis of 1-(4-t-butylbenzyl)-3-[2-(4-methylthiazol-5-yl)ethyl]thiourea (14-6)

2-[2-(4-methylthiazol-5-yl)ethyl]isoindol-1,3-dione (3 g) was dissolved in a mixture of methanol (10 ml) and tetrahydrofuran (10 ml) and to the solution was added dropwise hydrazine hydrate (610 mg), followed by stirring for 20 hours. To the obtained solution was added 2 N aqueous hydrochloric acid solution (6 ml), and the mixture was stirred for 3 hours and concentrated under reduced pressure to obtain reaction mixture (3.5 g) as a yellow solid. The obtained mixture (140 mg) was dissolved in dimethylformamide (5 ml)

and to the solution were added 4-t-butylbenzylisothiocyanate (0.2 g) and a small amount of triethylamine, followed by stirring at room temperature for 21 hours. The resulting mixture was diluted with dichloromethane, washed with water, dried, concentrated under reduced pressure, and then purified by column-chromatography (hexane/ethyl acetate=1/1) to yield the compound 14-6 (0.07 g) as a liquid.

$^1$H NMR(300 MHz, CDCl$_3$): δ 8.53(s,1H), 7.38-7.18(m, 4H), 6.25(brs, 1H), 5.77(brs, 1H), 4.49(s,2H), 3.78-3.73(m, 2H), 3.08(t, 2H, J=6 Hz), 2.36(s, 3H), 1.31(s, 9H)

EXAMPLE 74

Synthesis of 1-(4-t-butylbenzyl)-3-((2-chloro-5-pyridinyl)methyl)thiourea (14-9)

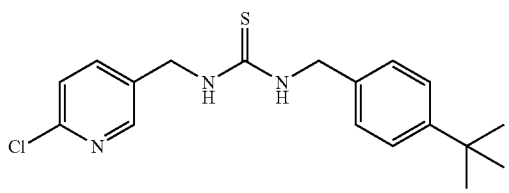

14-9

Step 1: Synthesis of ((2-chloro-5-pyridinyl)methyl)isoindol-1,3-dione (14-7)

2-chloro-5-chloromethylpyridine (5 g) was dissolved in dimethylformamide (60 ml) and to the solution was added phthalimide (6.29 g), followed by stirring at room temperature for 17 hours. The solvent of the reaction solution was removed under reduced pressure and the residue was extracted with water and dichloromethane to yield a white solid (6.2 g, 74%).

$^1$H NMR(300 MHz, CDCl$_3$): δ 8.50-8.49(m, 1H), 7.88-7.72(m, 5H), 7.30-7.26(m, 1H), 4.83(s, 2H), 2.44(s, 3H)

Step 2: Synthesis of 1-(4-t-butylbenzyl)-3-((2-chloro-5-pyridinyl)methyl)thiourea (14-9)

((2-chloro-5-pyridinyl)methyl)isoindol-1,3-dione (4.7 g) was dissolved in methanol (100 ml) and to the solution was added hydrazine hydrate (7.7 ml), followed by stirring at room temperature for 2 hours. The reaction slolution was extracted with water and dichloromethane and concentrated under reduced pressure to obtain a liquid (1.4 g). The obtained liquid mixture (66 mg) was dissolved in dichloromethane (5 ml) and to the solution was added 4-t-butylbenzylisothiocyanate (95 mg), followed by stirring at room temperature for 24 hours. The reaction mixture was concentrated and purified by column-chromatography (hexane/ethyl acetate=2/1) to yield the compound 14-9 (45 mg, 28%) as a white solid.

$^1$H NMR(300 MHz, CDCl$_3$): δ 8.16-8.15(m, 1H), 7.61-7.57(m, 1H), 7.38-7.18(m, 4H), 6.48(brs, 2H), 6.21(brs, 2H), 4.74(d, 2H, J=5.7 Hz), 4.54(d,2H, J=4.5 Hz), 1.29(s, 9H)

EXAMPLE 75

Synthesis of 1-(4-t-butylbenzyl)-3-(2-(thiomorpholinyl)ethyl)thiourea (15-3)

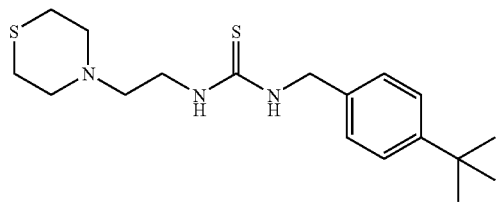

15-3

Step 1: Synthesis of 2-(2-thiomorpholin-4-yl)ethyl)isoindol-1,3-dione (15-1)

Thiomorpholine (3.75 g) was dissolved in acetone (100 ml) and to the solution were added anhydrous potassium carbonate (5.52 g) and 2-(bromoethyl)phthalimide (9.22 g), followed by refluxing for 26 hours. The obtained mixture was filtered, concentrated, and then dissolved in dichloromethane. The solution was washed with water, dried, concentrated under reduced pressrure, and then purified by column-chromatography (hexane/ethyl acetate=1/1) to yield the compound 15-1 (2 g, 20%) as a yellow solid.

$^1$H NMR(300 MHz, CDCl$_3$): δ 7.87-7.70(m, 4H), 3.80(t, 2H, J=6.6 Hz), 2.79-2.57(m, 10H)

Step 2: Synthesis of 1-(4-t-butylbenzyl-3-(2-(thiomorpholin-4-yl)ethyl)thiourea (15-3)

2-(2-thiomorpholin-4-ylethyl)isoindol-1,3-dione 15-1 (2.76 g) was dissolved in a mixture of methanol (20 ml) and tetrahydrofuran (20 ml) and to the solution was added dropwise hydrazine hydrate (550 mg), followed by stirring for 21 hours. To the obtained solution was added 2 N aqueous hydrochloric acid solution (6 ml), and the mixture was stirred for 3 hours and then concentrated under reduced pressure. To the concentrate was added water (15 ml) and the undissolved material was filtered off. The filtrate was concentrated to obtain reaction mixture (1.62 g) as a solid. The obtained mixture (150 mg) was dissolved in dimethylformamide (5 ml) and to the solution was added 4-t-butylbenzylisothiocyanate (210 mg) and a small amount of triethylamine, followed by stirring at room temperature for 23 hours. The resulting mixture was diluted with dichloromethane, washed with water, and concentrated under reduced pressure. The residue was purified by column-chromatography (hexane/ethyl acetate=1/3) to the compound 15-3 (0.12 g) as a white solid.

$^1$H NMR(300 MHz, CDCl$_3$): δ 7.42-7.26(m, 4H), 6.32(brs, 1H), 4.60(s,2H), 3.40(s, 2H), 2.62-2.20(m, 10H), 1.32(s, 9H)

EXAMPLE 76

Synthesis of 1-(furan-2-ylmethyl)-3-(4-methoxybenzyl)thiourea (16-1)

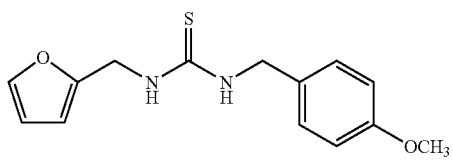

16-1

Furan-2-ylmethylamine (190 mg) was dissolved in dimethylformamide (5 ml) and to the solution were added triethylamine (200 mg) and 4-methoxybenzylisothiocyanate (360 mg), followed by stirring at room temperature for 24 hours. Then, the resulting mixture was diluted with ethyl acetate, washed with water, dried, and concentrated under reduced pressure. The residue was purified by column-chromatography (hexane/ethyl acetate=1/1) to yield the compound 16-1 (0.5 g, 90%) as a liquid.

$^1$H NMR(300 MHz, CDCl$_3$): δ 7.33-7.32(m, 1H), 7.23-7.19(m, 2H), 6.89-6.85(m, 2H), 6.32-6.23(m, 2H), 6.20(brs, 1H), 6.05(brs,1H), 4.67-4.64(m, 2H), 4.55-4.53(m, 2H), 3.80 (s, 3H)

EXAMPLE 77

Synthesis of 1-(4-t-butylbenzyl)-3-(furan-2-ylmethyl)thiourea (16-2)

16-2

Furan-2-ylmethylamine (0.58 g) was dissolved in dichloromethane (50 ml) and to the solution was added 4-t-butylbenzylisothiocyanate (1.23 g), followed by stirring at room temperature for 8 hours. Then, the resulting mixture was diluted with ethyl acetate, washed with water, dried, and concentrated under reduced pressure. The residue was purified by column-chromatography (dichloromethane) to yield the compound 16-2 (1.57 g, 87%) as a liquid.

$^1$H NMR(300 MHz, CDCl$_3$): δ 7.37-7.20(m, 5H), 6.31-6.29(m, 1H), 6.21-6.19(m, 1H), 6.10(brs,1H), 4.65-4.63(m, 2H), 4.58-4.50(m, 2H), 1.30(s, 9H)

EXAMPLE 78~EXAMPLE 121

Compounds of Example 78~Example 121 are shown in the Scheme 16. The compounds were synthesized according to the similar procedure as described in Example 76 or Example 77, and properties and spectral data are shown in below table.

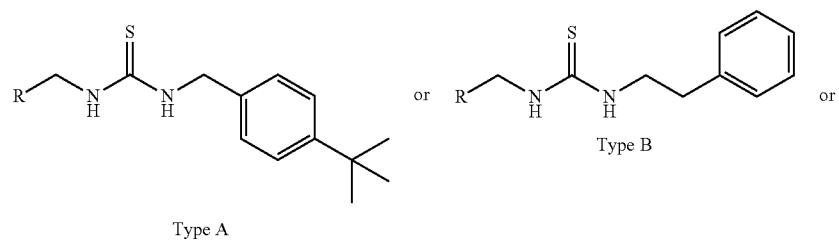

Type A / Type B

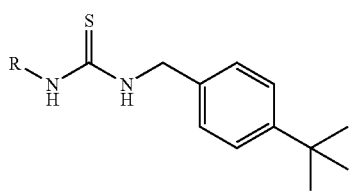

Type C

| Examples | Compounds | R = | Types | Spectral data |
|---|---|---|---|---|
| 78 | 16-3 | furan-2-yl | B | $^1$H NMR (300 MHz, CDCl$_3$): δ 7.34-7.18 (m, 6H), 6.31-6.28 (m, 1H), 6.21-6.20 (m, 1H), 5.92 (brs, 2H), 4.60-4.50 (m, 2H), 3.75-3.65 (m, 2H), 2.91 (t, 2H, J = 6.6 Hz) |
| 79 | 16-4 | pyridin-2-yl | A | $^1$H NMR (300 MHz, CDCl$_3$): δ 8.41-8.39 (m, 1H), 7.70-7.64 (m, 1H), 7.38-7.17 (m, 6H). 4.73 (m, 2H), 4.64 (m, 2H), 1.31 (s, 9H) |

-continued

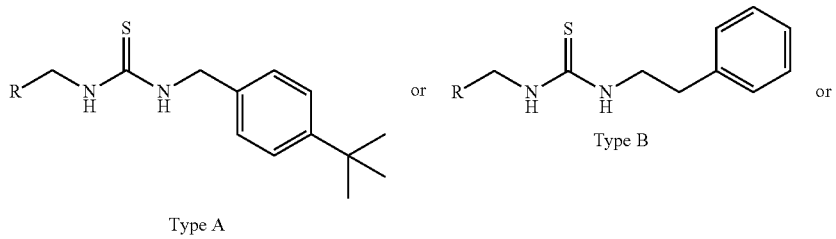

Type A or Type B or

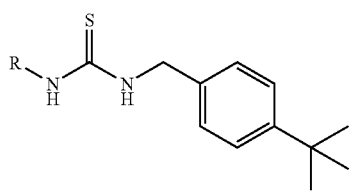

Type C

| Examples | Compounds | R = | Types | Spectral data |
|---|---|---|---|---|
| 80 | 16-5 | pyridin-2-yl | B | $^1$H NMR (300 MHz, CDCl$_3$): δ 8.41-8.38 (m, 1H), 7.72-7.66 (m, 1H), 7.34-7.05 (m, 9H), 4.69 (m, 2H), 3.77 (m, 2H), 2.96 (t, 2H, J = 6.9 Hz) |
| 81 | 16-6 | pyridin-3-yl | A | $^1$H NMR (300 MHz, CDCl$_3$): δ 8.52-8.48 (m, 2H), 7.63-7.59 (m, 1H), 7.39-7.35 (m, 2H), 7.24-7.20 (m, 3H), 6.22 (brs, 1H), 5.95 (brs, 1H), 4.79-4.76 (m, 2H), 4.57-4.55 (m, 2H), 1.31 (s, 9H) |
| 82 | 16-7 | pyridin-4-yl | A | $^1$H NMR (300 MHz, CDCl$_3$): δ 8.51-8.49 (m, 2H), 7.40-7.37 (m, 2H), 7.25-7.21 (m, 2H), 7.10-7.07 (m, 2H), 6.30 (brs, 1H), 6.00 (brs, 1H), 4.80-4.77 (m, 2H), 4.58-4.56 (m, 2H), 1.31 (s, 9H) |
| 83 | 16-8 | (pyridin-2-yl)methyl | A | $^1$H NMR (300 MHz, CDCl$_3$): δ 8.16-8.14 (m, 1H), 7.62-7.55 (m, 1H), 7.37-7.22 (m, 4H), 7.16-7.05 (m, 2H), 4.54 (m, 2H), 3.91 (m, 2H), 3.04 (t, 2H, J = 6 Hz), 1.32 (s, 9H) |
| 84 | 16-9 | (pyridin-2-yl)methyl | B | $^1$H NMR (300 MHz, CDCl$_3$): δ 8.41-8.38 (m, 1H), 7.66-7.60 (m, 1H), 7.33-7.13 (m, 7H), 6.31 (br, 2H), 3.87 (m, 2H), 3.66 (m, 2H), 3.04 (t, 2H, J = 6 Hz), 2.92 (t, 2H, J = 6.9 Hz), |
| 85 | 16-10 | 2-fluorophenyl | A | $^1$H NMR (300 MHz, CDCl$_3$): δ 7.37-7.19 (m, 6H), 7.12-6.99 (m, 2H), 6.11 (brs, 1H), 6.01 (brs, 1H), 4.75-4.73 (m, 2H), 4.57-4.55 (m, 2H), 1.31 (s, 9H) |

-continued
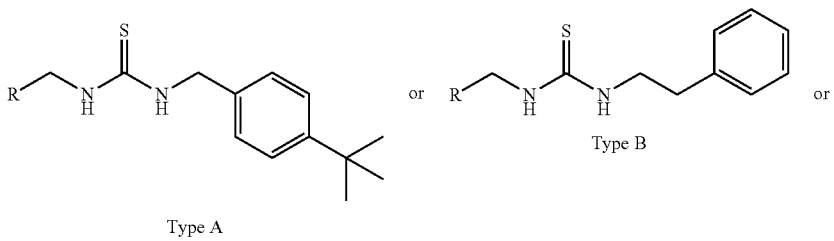
Type A    Type B
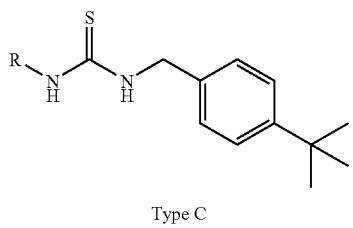
Type C
| Examples | Compounds | R = | Types | Spectral data |
|---|---|---|---|---|
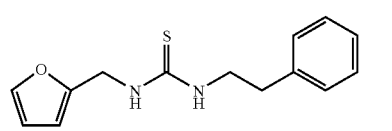
16-3
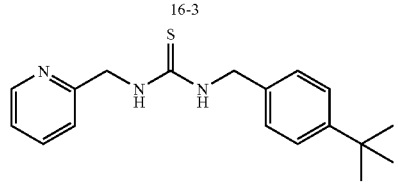
16-4
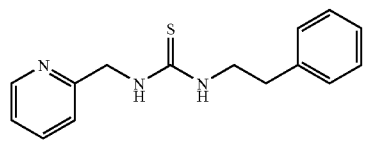
16-5
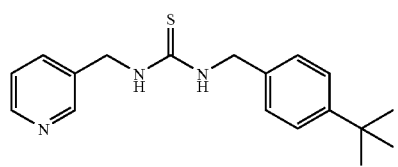
16-6
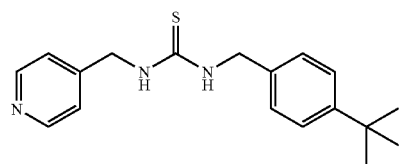
16-7
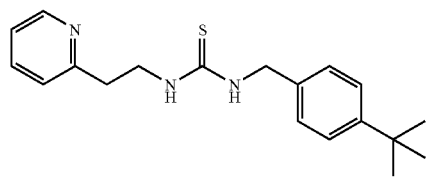
16-8

-continued
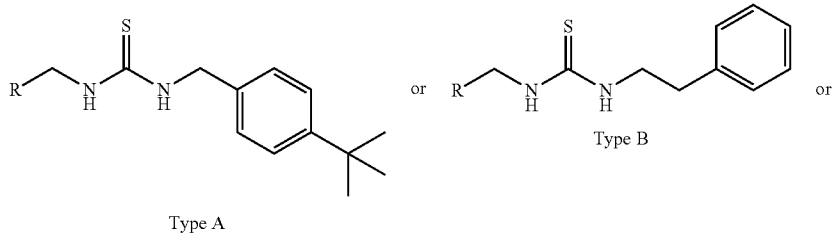
Type A        Type B
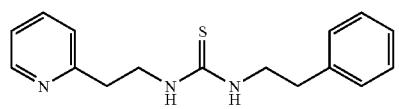
Type C
| Examples | Compounds | R = | Types | Spectral data |
|---|---|---|---|---|
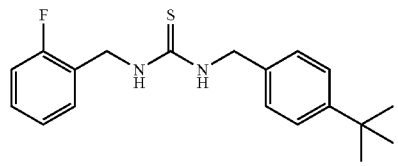
16-9
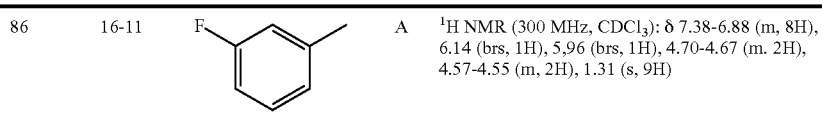
16-10
| Examples | Compounds | R = | Types | Spectral data |
|---|---|---|---|---|
| 86 | 16-11 | 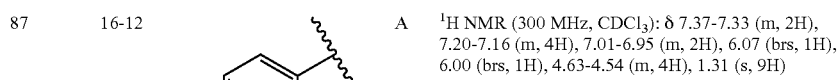 | A | $^1$H NMR (300 MHz, CDCl$_3$): δ 7.38-6.88 (m, 8H), 6.14 (brs, 1H), 5,96 (brs, 1H), 4.70-4.67 (m. 2H), 4.57-4.55 (m, 2H), 1.31 (s, 9H) |
| 87 | 16-12 | 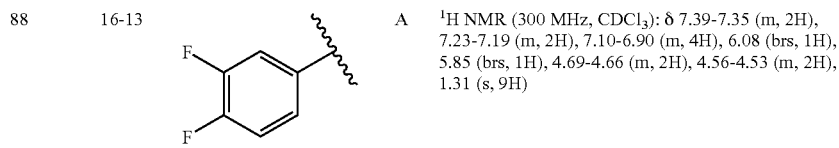 | A | $^1$H NMR (300 MHz, CDCl$_3$): δ 7.37-7.33 (m, 2H), 7.20-7.16 (m, 4H), 7.01-6.95 (m, 2H), 6.07 (brs, 1H), 6.00 (brs, 1H), 4.63-4.54 (m, 4H), 1.31 (s, 9H) |
| 88 | 16-13 | 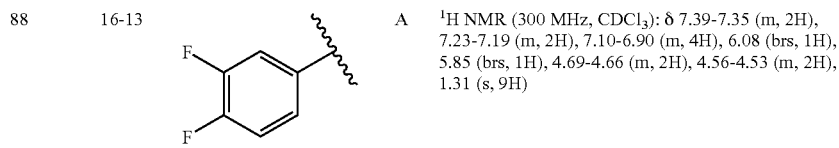 | A | $^1$H NMR (300 MHz, CDCl$_3$): δ 7.39-7.35 (m, 2H), 7.23-7.19 (m, 2H), 7.10-6.90 (m, 4H), 6.08 (brs, 1H), 5.85 (brs, 1H), 4.69-4.66 (m, 2H), 4.56-4.53 (m, 2H), 1.31 (s, 9H) |
| 89 | 16-14 | 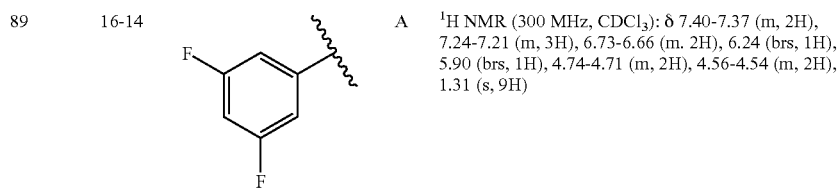 | A | $^1$H NMR (300 MHz, CDCl$_3$): δ 7.40-7.37 (m, 2H), 7.24-7.21 (m, 3H), 6.73-6.66 (m. 2H), 6.24 (brs, 1H), 5.90 (brs, 1H), 4.74-4.71 (m, 2H), 4.56-4.54 (m, 2H), 1.31 (s, 9H) |

| Examples | Compounds | R = | Types | Spectral data |
|---|---|---|---|---|
| 90 | 16-15 | 2,5-difluorophenyl | A | $^1$H NMR (300 MHz, CDCl$_3$): δ 7.39-7.36 (m, 2H), 7.24-7.22 (m, 2H), 7.02-6.94 (m, 3H), 6.16 (brs, 1H), 5.92 (brs, 1H), 4.78-4.76 (m, 2H), 4.56-4.54 (m, 2H), 1.31 (s, 9H) |
| 91 | 16-16 | 2,4-difluorophenyl | A | $^1$H NMR (300 MHz, CDCl$_3$): δ 7.38-7.20 (m, 5H), 6.90-6.74 (m, 2H), 6.10 (brs, 1H), 5.91 (brs, 1H), 4.75-4.72 (m, 2H), 4.55-4.50 (m, 2H), 1.31 (s, 9H) |
| 92 | 16-17 | 2,6-difluorophenyl | A | $^1$H NMR (300 MHz, CDCl$_3$): δ 7.38-7.34 (m, 2H), 7.27-7.20 (m, 3H), 6.91-6.85 (m, 2H), 6.05 (brs, 1H), 6.02 (brs, 1H), 4.71-4.70 (m, 2H), 4.61-4.60 (m, 2H), 1.31 (s, 9H) |

16-11

16-12

16-13

16-14

16-15

-continued

| Examples | Compounds | R = | Types | Spectral data |
|---|---|---|---|---|
| | 16-16 | 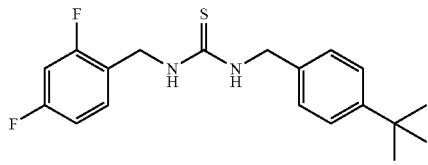 | | |
| | 16-17 | 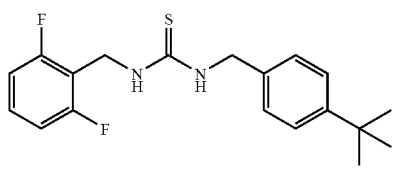 | | |

| Examples | Compounds | R = | Types | Spectral data |
|---|---|---|---|---|
| 93 | 16-18 | 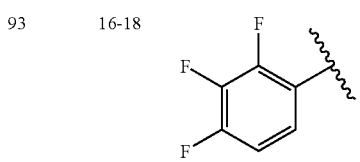 | A | $^1$H NMR (300 MHz, CDCl$_3$): δ 7.39-7.35 (m, 2H), 7.25-7.20 (m, 3H), 7.15-7.05 (m, 1H), 6.95-6.85 (m, 1H), 6.16 (brs, 1H), 5.88 (brs, 1H), 4.80-4.78 (m, 2H), 4.53-4.51 (m, 2H), 1.31 (s, 9H) |
| 94 | 16-19 | 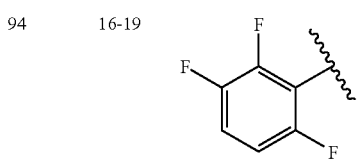 | A | $^1$H NMR (300 MHz, CDCl$_3$): δ 7.39-7.35 (m, 2H), 7.25-7.06 (m, 3H), 6.86-6.78 (m, 1H), 6.14 (brs, 1H), 5.95 (brs, 1H). 4.79-4.76 (m, 2H), 4.56-4.50 (m, 2H), 1.31 (s, 9H) |
| 95 | 16-20 | 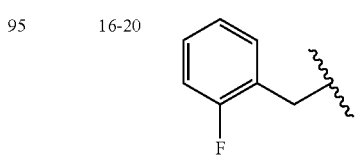 | A | $^1$H NMR (300 MHz, CDCl$_3$): δ 7.39-7.35 (m, 2H), 7.26-6.98 (m, 6H), 5.97 (brs, 1H), 5.68 (brs, 1H), 4.51-4.49 (m, 2H), 3.75-3.74 (m, 2H), 2.94 (t, 2H, J = 6.6 Hz), 1.32 (s, 9H) |
| 96 | 16-21 | 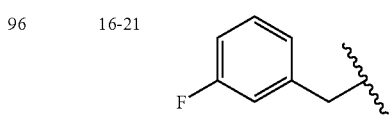 | A | $^1$H NMR (300 MHz, CDCl$_3$): δ 7.38-7.19 (m, 6H), 6.92-6.84 (m, 2H), 6.03 (brs, 1H), 5.59 (brs, 1H), 4.46 (m, 2H), 3.78 (m, 2H), 2.89 (t, 2H, J = 6.6 Hz), 1.32 (s, 9H) |
| 97 | 16-22 | 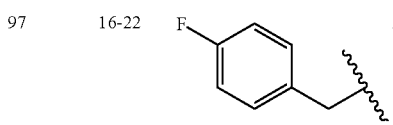 | A | $^1$H NMR (300 MHz, CDCl$_3$): δ 7.37-6.92 (m, 8H), 5.94 (brs, 1H), 5.58 (brs, 1H), 4.46 (m, 2H). 3.73 (m, 2H), 2.85 (t, 2H, J = 6 Hz), 1.32 (s, 9H) |
| 98 | 16-23 | 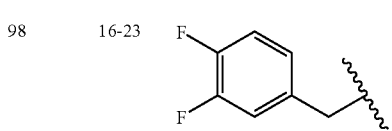 | A | $^1$H NMR (300 MHz, CDCl$_3$): δ 7.40-7.35 (m, 2H), 7.19-7.16 (m, 2H), 7.10-6.83 (m, 3H), 6.08 (brs, 1H), 5.58 (brs, 1H), 4.47-4.44 (m, 2H), 3.77-3.70 (m, 2H), 2.84 (t, 2H, J = 6.9 Hz), 1.31 (s, 9H) |

| Examples | Compounds | R = | Types | Spectral data |
|---|---|---|---|---|
| | 16-18 | 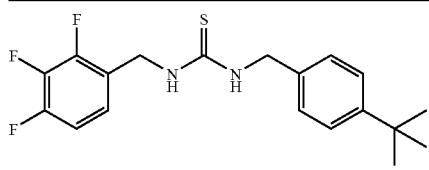 | | |
| | 16-19 | 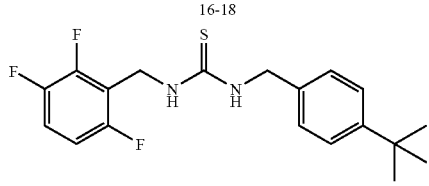 | | |
| | 16-20 | 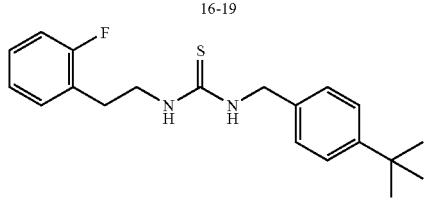 | | |
| | 16-21 | 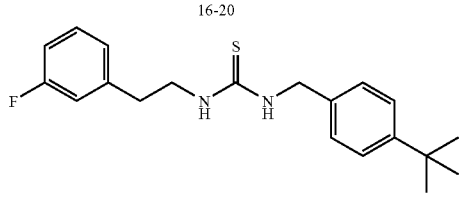 | | |
| | 16-22 | 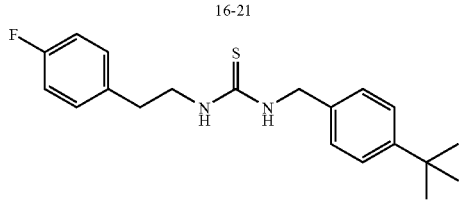 | | |
| | 16-23 | 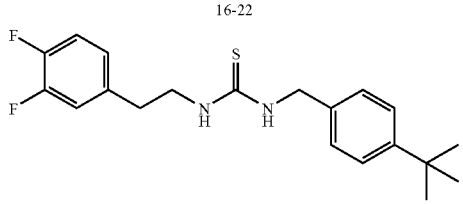 | | |
| Examples | Compounds | R = | Type | Spectral data |
|---|---|---|---|---|
| 99 | 16-24 | 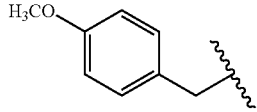 | A | $^1$H NMR(300 MHz, CDCl$_3$): δ 7.38-7.34(m, 2H), 7.19-7.16(m, 2H), 7.08-7.04(m, 2H), 6.84-6.80(m, 2H), 5.90(brs, 1H), 5.62(brs, 1H), 4.48-4.46(m, 2H), 3.79(s, 3H), 3.70-3.68(m, 2H), 2.81(t, 2H, 36.6 Hz), 1.31(s, 9H) |
| 100 | 16-25 | 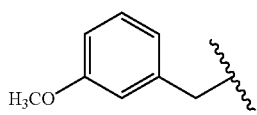 | A | $^1$H NMR(300 MHz, CDCl$_3$): δ 7.37-7.33(m, 2H), 7.22-7.15(m, 3H), 6.79-6.71(m, 3H), 5.93(brs, 1H), 5.64(brs, 1H), 4.47-4.45(m, 2H), 3.79(s, 3H), 3.78-3.72(m, 2H), 2.85(t, 2H, J = 6.6 Hz), 1.31(s, 9H) |

-continued

| Examples | Compounds | R = | Type | Spectral data |
|---|---|---|---|---|
| 101 | 16-26 | 2-methoxybenzyl | A | $^1$H NMR(300 MHz, CDCl$_3$): δ 7.39-7.35(m, 2H), 7.25-7.18(m, 3H), 7.10-7.07(m, 1H), 6.92-6.87(m, 1H), 6.82-6.79(m, 1H), 6.23(brs, 1H), 6.04(brs, 1H), 4.60-4.59(m, 2H), 3.61(s, 3H), 3.61-3.50(m, 2H), 2.89(t, 2H, J = 6.9 Hz), 1.32(s, 9H) |
| 102 | 16-27 | 3,4-dimethoxybenzyl | A | $^1$H NMR(300 MHz, CDCl$_3$): δ 7.36-7.33(m, 2H), 7.18-7.15(m, 2H), 6.79-6.75(m, 1H), 6.69-6.66(m, 2H), 6.03(brs, 1H), 5.77(brs, 1H), 4.48-4.46(m, 2H), 3.84(s, 3H), 3.83(s, 3H), 3.72-3.70(m, 2H), 2.81(t, 2H, J = 6.9 Hz), 1.30(s, 9H) |
| 103 | 16-28 | 3,4,5-trimethoxybenzyl | A | $^1$H NMR(300 MHz, CDCl$_3$): δ 7.37-7.33(m, 2H), 7.20-7.17(m, 2H), 6.48(s, 2H), 6.00(brs, 2H), 4.60-4.55(m, 4H), 3.82-3.79(m, 9H), 1.30(s, 9H) |

16-24

16-25

16-26

16-27

16-28

| Examples | Compounds | R = | Type | Spectral data |
|---|---|---|---|---|
| 104 | 16-29 | 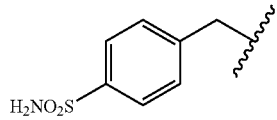 | A | $^1$H NMR(300 MHz, CDCl$_3$): δ 7.83-7.79(m, 2H), 7.39-7.18(m, 6H), 6.13(brs. 1H), 5.71(brs, 1H), 4.85(s, 2H), 4.50(m, 2H), 3.80-3.75(m, 2H), 2.97(t, 2H, J = 7.2 Hz), 1.31(s, 9H) |
| 105 | 16-30 | 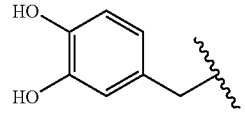 | A | $^1$H NMR(300 MHz, CDCl$_3$): δ 7.40-7.35(m, 2H), 7.20-7.16(m, 2H), 6.78-6.75(m, 1H), 6.66-6.65(m, 1H), 6.58-6.54(m, 1H), 5.94(brs, 1H), 5.67(brs, 1H), 4.48-4.46(m, 2H), 3.65-3.64(m, 2H), 2.74(t, 2H, J = 6.6 Hz), 1.31(s, 9H) |
| 106 | 16-31 | 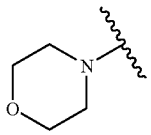 | C | $^1$H NMR(300 MHz, CDCl$_3$): δ 7.56(brs. 1H), 7.41-7.25(m, 4H), 6.63(brs. 1H), 4.86(d, 2H, J = 6 Hz), 3.90-3.86(m, 2H), 3.63-3.55(m, 2H), 2.98-2.93(m, 2H), 2.67-2.60(m, 2H), 1.33(s, 9H) |
| 107 | 16-32 | 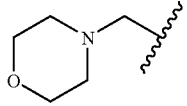 | A | $^1$H NMR(300 MHz. CDCl$_3$): δ 7.29-7,32(m, 2H), 7.21(d, 2H, J = 8.0 Hz), 6.39(br s, 1H), 4.55(br s, 2H), 2.86-2.94(m, 6H), 2.42(t, 2H, J = 5.4 Hz), 2.29(t, 2H, J = 4.7 Hz), 1.24(s, 9H) |
| 108 | 16-33 | 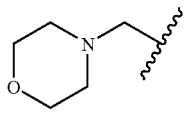 | B | $^1$H NMR(300 MHz, CDCl$_3$): δ 7.34-7.20(m, 5H), 6.29(s, 1H), 3.80-3.70(m, 2H), 3.60-3.50(m, 4H), 3.40-3.30(m, 2H), 2.96(t, 2H, J = 6.9 Hz), 2.51-2.35(m, 6H) |
| 109 | 16-34 | 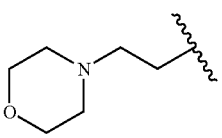 | A | $^1$H NMR(300 MHz, CDCl$_3$): δ 7.40-7.26(m, 4H), 6.40(brs, 1H), 4.63(m, 2H), 3.50-3.30(m, 6H), 2.52-2.36(m, 6H), 1.31(s, 9H) |
| 110 | 16-35 | 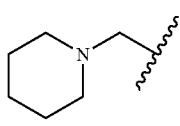 | A | $^1$H NMR(300 MHz, CDCl$_3$): δ 7.37-7.26(m, 4H), 6.40(brs, 1H), 4.68(m, 2H), 3.34(m, 2H), 2.42(t, 2H, J = 5.1 Hz), 2.30(m, 4H), 1.60(m, 2H), 1.30(s, 9H), 1.29-1.09(m, 4H) |
| 111 | 16-36 | 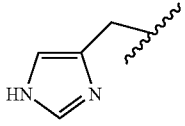 | A | $^1$H NMR(300 MHz, CD$_3$OD): δ 7.57(d, 1H, J = 1.0 Hz), 7.32-7.36(m, 2H), 7.21(d, 1H, J = 8.6 Hz), 4.63(br s, 2H), 3.72(br s, 2H), 2.83(t, 2H, J = 7.1 Hz), 1.29(s, 9H). |
| 112 | 16-37 | 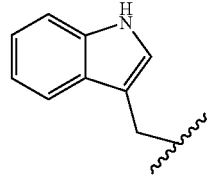 | A | $^1$H NMR(300 MHz, CDCl$_3$): δ 7.97(brs, 1H), 7.59-7.56(m, 1H), 7.38-7.09(m, 8H), 6.96(brs, 1H), 5.85(brs, 1H), 5.72(brs, 1H), 4.40(m, 2H), 3.79(m, 2H), 3.04(t, 2H, J = 6.6 Hz), 1.30(s, 9H) |

| Examples | Compounds | R = | Type | Spectral data |
|---|---|---|---|---|
| | 16-29 | | | |
| | 16-30 | | | |
| | 16-31 | | | |
| | 16-32 | | | |
| | 16-33 | | | |
| | 16-34 | | | |
| | 16-35 | | | |
| | 16-36 | | | |

| Examples | Compounds | R = | Type | Spectral data |
|---|---|---|---|---|
| | | 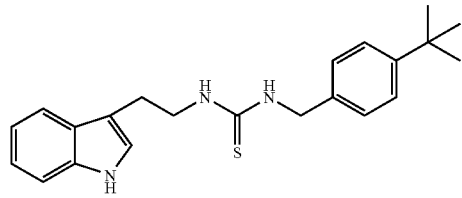<br>16-37 | | |

| Examples | Compounds | R = | Type | Spectral data |
|---|---|---|---|---|
| 113 | 16-38 | 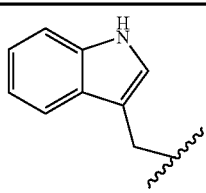 | B | $^1$H NMR(300 MHz, CDCl$_3$): δ 8.03(brs, 1H), 7.60-7.05(m, 9H), 5.67(brs, 1H), 5.51(brs, 1H), 3.68(m, 2H), 3.54(m, 2H), 3.03(t, 2H, J = 6.6 Hz), 2.75(t, 2H, J = 6.6 Hz) |
| 114 | 16-39 | 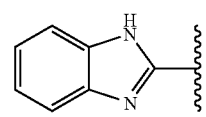 | A | $^1$H NMR(300 MHz, CDCl$_3$): δ 7.52-7.15(m, 9H), 5.10-4.90(m, 2H), 4.60-4.55(m, 2H), 2.67(brs, 2H), 1.25(s, 3H) |
| 115 | 16-40 | 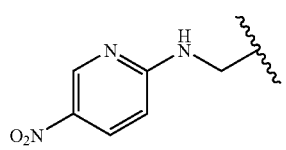 | A | $^1$H NMR(300 MHz, CDCl$_3$): δ 8.70(brs, 1H), 8.14-8.09(m, 1H), 7.38-7.20(m, 5H), 6.42-6.30(m, 2H), 5.91(brs, 1H), 4.58(m. 2H), 3.79-3.66(m, 4H), 1.30(s, 9H) |
| 116 | 16-41 | 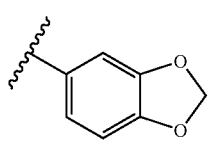 | A | $^1$H-NMR(300 MHz, CDCl$_3$): δ 7.37-7.47(m, 2H), 7.21-7.24(d, 2H, J = 8.3 Hz), 6.70-6.78 (m, 3H), 5.98(s, 2H), 4.57-4.60(br, 4H), 1.35 (s, 9H) |
| 117 | 16-42 | 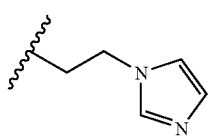 | A | $^1$H-NMR(300 MHz, acetone-d$_6$): δ 7.50(s, 1H), 7.32(dd, 2H, J = 1.9, 6.3 Hz), 7.22(d, 2H, J = 8.5 Hz), 7.05(s, 1H), 6.86(s, 1H), 4.66(br s, 2H), 4.01(t, 2H, J = 7.1 Hz), 3.50(t, 2H, J = 6.6 Hz), 1.99-2.08(m, 2H), 1.24(s, 9H) |
| 118 | 16-43 | 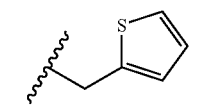 | A | $^1$H-NMR(300 MHz, CDCl$_3$): δ 7.32-7.35(m, 2H), 7.11-7.18(m, 3H), 6.88(dd, 1H, J = 3.4, 5.1 Hz), 6.74(d, 1H, J = 2.9 Hz), 6.09(br s, 1H), 5.75(br s, 1H), 4.44(br s, 2H), 4.08(t, 2H, J = 7.3 Hz), 3.07(t, 2H, J = 6.6 Hz), 1.29 (s, 9H) |
| 119 | 16-44 | 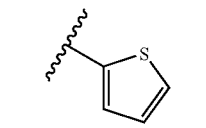 | A | $^1$H-NMR(300 MHz, CDCl$_3$): δ 7.36-7.39(m, 2H), 7.21-7.26(m, 3H), 6.94-6.96(m, 2H), 6.24(br s, 1H), 6.04(br s, 1H), 4.88(d, 2H, J = 4.8 Hz), 4.57(br s, 2H), 1.33(s, 9H) |
| 120 | 16-45 | 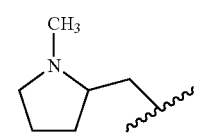 | A | $^1$H NMR(CDCl$_3$): δ 7.37(m, 2H), 7.23(m, 2H), 4.45(bs, 2H), 3.50(m, 2H), 2.73(m, 2H), 2.50(bs, 1H), 2.21(s, 3H), 2.13(m, 1H), 1.88(m, 3H), 1.68(m, 4H), 1.30(s, 9H) |

| Examples | Compounds | R = | Type | Spectral data |
|---|---|---|---|---|
| | 16-38 | 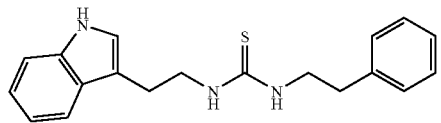 | | |
| | 16-39 | 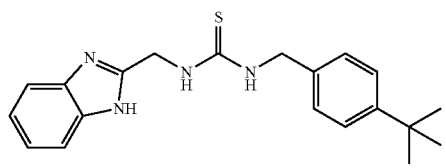 | | |
| | 16-40 | 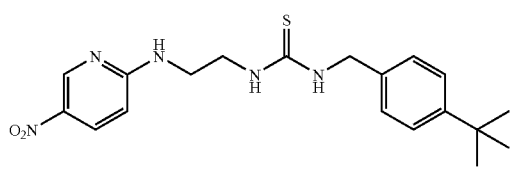 | | |
| | 16-41 | 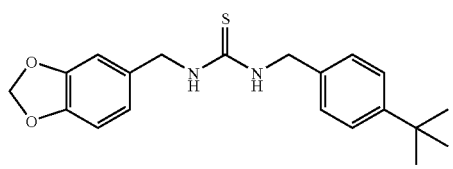 | | |
| | 16-42 | 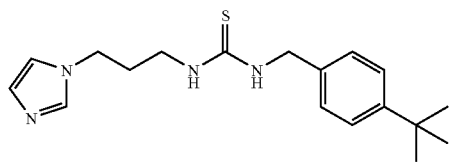 | | |
| | 16-43 | 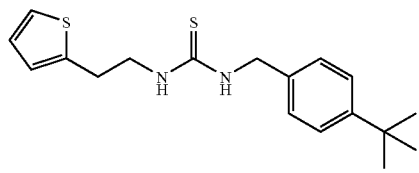 | | |
| | 16-44 | 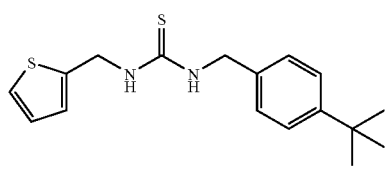 | | |
| | 16-45 | 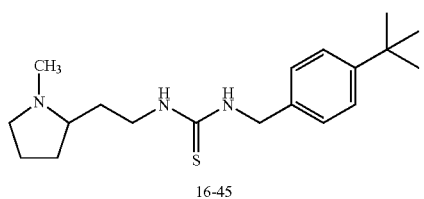 | | |

EXAMPLE 121

Synthesis of 1-(4-t-butylbenzyl)-3-(2-pyridinyl)thiourea (16-46)

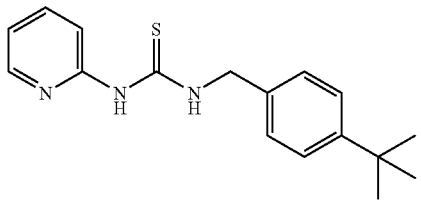

16-46

2-aminopyridine (86 mg) was dissolved in acetonitrile (10 ml) and to the solution were added 4-t-butylbenzylisothiocyanate (190 mg) and triethylamine (140 µl), followed by refluxing for 27 hours. The resulting mixture was extracted with water and dichloromethane, dried, concentrated under reduced pressure, and then crystallized (dichloromethane/petroleum ether) to yield the compound (90 mg, 33%) as a white solid.

$^1$H NMR(300 MHz, CDCl$_3$): δ 11.99(brs, 1H), 8.13-8.11 (m, 1H), 7.67-7.61(m, 1H), 7.41-7.27(m, 4H), 6.96-6.92(m, 1H), 6.68-6.64(m, 1H), 4.99-4.96 (m, 2H), 1.32(s, 9H)

EXAMPLE 122

Synthesis of 1-(4-t-butylbenzyl)-3-((2-hydroxy-1-methyl-2-phenyl)ethyl)thiourea (16-47)

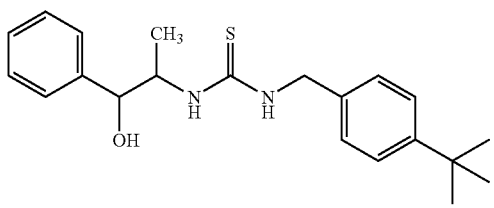

16-47

Phenylpropanolamine hydrochloride (100 mg) was dissolved in dimethylformamide (5 ml) and to the solution was added triethylamine (80 µl), followed by stirring for 30 minutes. To the obtained reaction mixture was added t-butylbenzeneisothiocyanate (135 mg), and the mixture was stirred for 4 hours, diluted with water (20 ml), extracted with dichloromethane (30 ml×3), dried over magnesium sulfate, and then flitered. The filtrate was concentrated under reduced pressure and the obtained residue was purified by column-chromatography (ethyl acetate/hexane=1/3) to yield the compound 1647 (159 mg, 83.7%).

$^1$H NM(300 MHz, CDCl$_3$): δ7.32(m, 9H), 6.65(brs, 1H), 5.69(d, 1H, J=7.8 Hz), 4.92(s, 1H), 4.57(s, 2H), 2.66(s, 1H), 1.58(s, 1H), 1.31(s, 9H), 0.98(d, 3H, J=6.9 Hz)

EXAMPLE 123

Synthesis of 1-(4-t-butylbenzyl)-3-(1H-pyrrol-2-ylmethyl)thiourea (17-1)

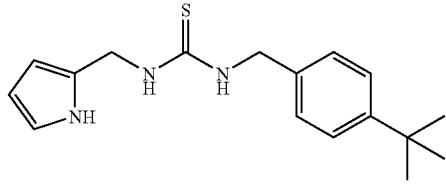

17-1

Step 1: Synthesis of 1H-pyrrol-2-carboxaldehyde oxime

Pyrrole-3-carboxaldehyde (120.4 mg) was dissolved in methanol (4 ml) and to the solution were added hydroxylamine hydrochloride (106 mg) and sodium acetate (127 mg), followed by stirring for 1 hour. The resulting mixture was extracted with ethyl acetate, and then dried over anhydrous magnesium sulfate. The filtrate was concentrated under reduced pressure, and then column-chromatographed (ethyl acetate/hexane=1/3) to yield the compound (122 mg, 100%).

$^1$H NMR(300 MHz, CD$_3$OD): δ 7.19(s, 1H), 6.92 (t, 1H, J=2.1 Hz), 6.52 (q, 1H, J=3.7 Hz), 6.15 (q, 1H J=3.7 Hz)

Step 2: Synthesis of (1H-pyrrol-2-yl)methylamine hydrochloride 1H-pyrrol-2-carboxaldehyde oxime (60 mg) prepared according to the same procedure as described in Step 1 was dissolved in methanol (2 ml) and to the solution were added a catalytic amount of 10% palladium/carbon and concentrated hydrochloric acid (100 µl), followed by stirring at room temperature under hydrogen gas atmosphere for 1 hour. The resulting mixture was diluted with ether, and then filtered through celite. The filtrate was concentrated under reduced pressure to yield (1H-pyrrol-2-yl)methylamine hydrochloride (60 mg, 100%).

$^1$H NMR(300 MHz, CD$_3$OD): δ 6.78 (q, 1H,J=4.2 Hz), 6.23 (s, 1H), 6.10 (q, 1H, J=5.9 Hz), 4.08 (s, 2H)

Step 3: Sythesis of 1-(4-t-butylbenzyl)-3-(1H-pyrrol-2-ylmethyl)thiourea (17-1)

(1H-pyrrol-2-yl)methylamine hydrochloride (60 mg) prepared according to the same procedure as described in Step 2 was dissolved in dichloromethane (2 ml) and to the solution was added 4-t-butylbenzylisothiocyanate (155 mg), followed by stirring at room temperature for 1 hour. The resulting mixture was concentrated under reduced pressure and the obtained residue was column-chromatographed (ethyl acetate/hexane=1/3) to yield the compound 17-1 (120 mg, 65%).

¹H-NMR(300 MHz, CD₃OD): δ 7.23-7.35 (t, 2H, J=7.4 Hz), 7.18-7.21 (d, 2H, J=8.5 Hz), 6.65 (d, 1H, J=2.2 Hz), 5.97-5.98 (d, 2H, J=2.0 Hz), 4.61 (br, 4H), 1.29 (s, 9H)

EXAMPLE 124

Synthesis of 1-(4-t-butylbenzyl)-3-(1-methyl-1H-pyrrol-2-yl)methylthiourea (17-2)

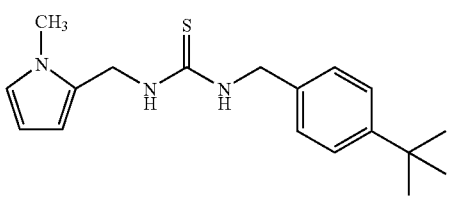

17-2

Step 1: Synthesis of methyl-1H-pyrrol-2-carboxaldehyde oxime

Methyl-2-pyrrolecarboxaldehyde (5 g), hydroxylamine hydrochloride (9.55 g) and sodium acetate (11.28 g) were dissolved in methanol (100 ml) and the solution was refluxed for 12 hours. Aftre confirming the completion of the reaction using TLC, the resulting mixture was purified by column-chromatography (ethyl acetate/hexane=3/1) to yield the compound (5.01 g, 88%) as a brown solid.

¹H NMR (300 MHz, CDCl₃): δ 7.40(s, 1H), 7.31(m, 1H), 6.70(m, 1H), 6.23(m, 1H), 3.74(s, 3H)

Step 2: Synthesis of (1-methyl-1H-pyrrol-2-yl)methylamine

Sodium borohydride (310 mg) was dried under vacuum and anhydrous tetrahydrofuran (30 ml) was added thereto through an injector, followed by adjusting the temperature down to −15° C. To the mixture at −15° C. was added a solution of methyl-1H-pyrrol-2-carboxaldehyde oxime (500 mg) and nickel (II) chloride hexahydrate (catalytic amount) in anhydrous methanol (30 ml) and the mixture was stirred, followed by stirring at room temperature for 12 hours. After confirming the completion of the reaction, the resulting mixture was filtered and the obtained brown oil was purified by column-chromatography (ethyl acetate) to yield (1-mehtyl-1H-pyrrol-2-yl)methylamine (275 mg, 62%) as solid.

¹H NMR (300 MHz, CDCl₃): δ 6.6.3(m, 1H), 6.11(m, 2H), 3.94(m, 2H), 3.72(brs, 2H), 3.64(s, 3H)

Step 3: Synthesis of 1-(4-t-butylbenzyl)-3-(1-methyl-1H-pyrrol-2-yl)methylthiourea (17-2)

(1-methyl-1H-pyrrol-2-yl)methylamine (65 mg) and 4-t-butylbenzylisothiocyanate (120 mg) were dissolved in ethyl acetate (30 ml) and the solution was stirred for 12 hours. After the completion of the reaction, the resulting mixture was purified by column-chromatography (ethyl acetate/hexane=1/3) to yield the compound 17-2 (140 mg, 75%)

¹H NMR (300 MHz, CDCl₃): δ 7.36(m, 2H), 7.19(m, 2H), 6.58(m, 1H), 6.18(brs, 1H), 6.01(m, 2H), 5.69(brs, 1H), 4.63 (d, 2H, J=2.1 Hz), 4.52(d, 2.4 Hz), 3.52(s, 3H), 1.31(s, 9H)

EXAMPLE 125

Synthesis of 1-(1-methyl-1H-pyrrol-2-ylmethyl)-3-phenethylthiourea (17-3)

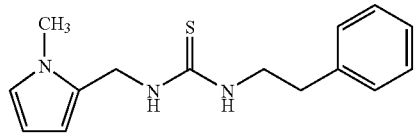

17-3

(1-methyl-1H-pyrrol-2-yl)methylamine (65 mg) and (2-isothiocyanatoethyl)benzene (100 mg) were dissolved in ethyl acetate (20 ml) and the solution was stirred for 12 hours. After the completion of the reaction, the resulting mixture was purified by column-chromatography (ethyl acetate/hexane=1/3) to yield the compound 17-3 (97 mg, 60%) as a brown liquid.

¹H NMR (300 MHz, CDCl₃): δ 7.25(m, 5H), 6.60(m, 1H), 6.02(m, 1H), 5.97(s, 1H), 4.51(brs, 2H), 3.69(brs, 2H), 2.87(t, 2H, J=6.9 Hz)

EXAMPLE 126

Synthesis of 1-(4-t-butylbenzyl)-3-(5-nitrothiophen-2-ylmethyl)thiourea (17-4)

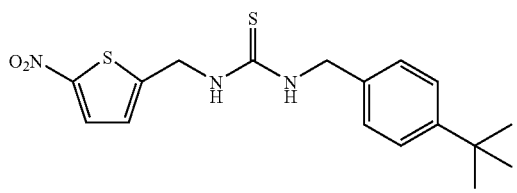

17-4

Step 1: Synthesis of 5-nitrothiophen-2-carboxaldehyde oxime

5-Nitrothiophen-2-carboxaldehyde oxime (yield: 85%, pale yellow solid) was synthesized according to the similar procedure as described in Step 1 of Example 124 except that 5-nitrothiophen-2-carboxaldehyde was usded as a starting material.

¹H NMR (300 MHz, CDCl₃): δ 8.21(s, 1H), 7.91(d, 1H, J=2.1 Hz), 7.85(d, 1H, J=2.25 Hz), 7.76(s, 1H), 7.26(s, 1H), 7.11(d, 1H, J=2.1 Hz)

Step 2: Synthesis of (5-nitrothiophen-2-yl)methylamine

Sodium borohydride (132 mg) was dried under vacuum and then anhydrous tetrahydrofuran (30 ml) was added thereto through an injector, followed by adjusting the temperature down to −15° C. To the mixture at −15° C. was added a solution of 5-nitrothiophen-2-carboxaldehyde oxime (200 mg; synthesized in Step 1) and nickel chloride (II) hexahydrate (catalytic amount) in anhydrous methanol (20 ml), and the mixture was stirred for 12 hours. After confirming the completion of the reaction, the resulting mixture was filtered to obtain the compound as a brown liquid.

Step 3: Synthesis of 1-(4-t-butylbenzyl)-3-(5-nitrothiophen-2-ylmethyl)thiourea (17-4)

The compound 17-4 (yield: 40%, yellow solid) was synthesized by reacting the compound prepared in Step 2 with 4-t-butylbenzylisothiocyanate according to the similar procedure as described in Step 3 of Example 124.

$^1$H NMR (300 MHz, CDCl$_3$): δ 7.71(d, 1H, J=1.95 Hz), 7.37(m, 2H), 7.23(m, 2H), 6.85(d, 1H, J=1.95 Hz), 6.59(brs, 1H), 6.30(brs, 1H), 4.96(d, 2H, J=3 Hz), 4.55(brs, 2H), 1.29 (s, 9H)

EXAMPLE 127

Synthesis of 1-(4-t-butylbenzyl)-3-(2-methyl-pyridin-3-ylmethyl)thiourea (18-5)

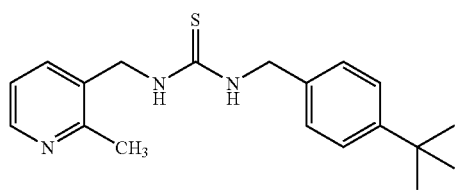

18-5

Step 1: Synthesis of (2-methylpyridin-3-yl)methanol (18-2)

Ethyl 2-methylnicotinate 18-1 (257 mg) was mixed with dichloromethane (4 ml) and to the mixture at −78° C. was added dropwise 1 M diisobutyl aluminium hydride (4 ml), followed by siring for 1 hour. The reaction was quenched with methanol and to the mixture was added aqueous Rochel solution (20 ml), followed by stirring for 2 hours. The resulting mixture was extracted with dichloromethane, dried over anhydrous magnesium sulfate, and concentrated under reduced pressure. The residue was column-chromatographed (ethyl acetate/hexane=1/1) to yield the compound 18-2 (166 mg, 87%).

$^1$H NMR(300 MHz, CDCl$_3$): δ 8.34 (d, 1H, J=3.4 Hz), 7.74 (d, 1H, J=7.6 Hz), 7.15 (dd, 1H, J=5.1 Hz, J=7.8 Hz), 4.70 (s, 2H), 3.21 (br, 1H), 2.51 (s, 3H)

Step 2: Synthesis of (2-methylpyridin-3-yl)methylaminophthalimide (18-3)

Compound 18-2 (166 mg) prepared in Step 1 was dissolved in tetrahydrofuran (4 ml) and to the solution were added phthalimide (401 mg) and triphenylphosphine (716 mg), followed by adding diethylazodicarbonate (0.24 ml) thereto and stirring for 30 minutes. After the completion of the reaction, the resulting mixture was concentrated under reduced pressure and the obtained residue was column-chromatographed (ethyl acetate/hexane=1/1) to yield the compound 18-3 (300 mg, 88%).

$^1$H NMR(300 MHz, CDCl$_3$): δ 8.40 (dd, 1H, J=1.7 Hz, J=3.2 Hz), 7.87-7.83 (m, 2H), 7.76-7.72 (m, 2H), 7.61 (d, 1H, J=6.6 Hz), 7.10 (dd, 1H, J=4.9 Hz, J=7.8 Hz) 4.80 (s, 2H), 2.72 (s, 3H)

Step 3: Synthesis of 1-(4-t-butylbenzyl)-3-(2-methylpyridin-3-ylmethyl)thiourea (18-5)

The compound 18-3 (19 mg) prepared in Step 2 was dissolved in ethanol and to the solution was added a drop of methylamine. After stirring the mixture at 55° C. for 30 hours, t-butylbenzylisothiocyanate (62 mg) was added thereto, and the mixture was stirred at room temperature for 1 hour. The resulting mixture was concentrated under reduced pressure and the obtained residue was column-chromatographed (methanol/dichloromethane=1/10) to yield the compound 18-5 (26.2 mg, 100%).

$^1$H NMR(300 MHz, CDCl$_3$): δ 8.56-8.55 (m, 1H), 8.37-8.30 (m, 1H), 7.75-7.67(m, 1H), 7.40-7.10 (m, 4H), 4.74 (s, 2H), 4.44 (s, 2H), 3.05 (s, 3H), 1.30 (s, 9H)

EXAMPLE 128

Synthesis of 1-(1H-indazol-5-yl)-3-phenethylthiourea (19-1)

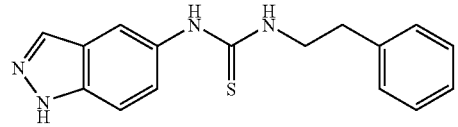

19-1

Step 1: Synthesis of 5-amino-1H-indazole

5-Nitro-1H-indazole (20 mg) was dissolved in methanol (1 ml) and to the solution was added a catalytic amount of palladium/carbon, followed by stirring at room temperature under hydrogen gas atmosphere for 30 minutes. The resulting mixture was diluted with ether, filtered through celite, and then concentrated under reduced pressure to yield 5-amino-1H-indazole (16 mg, 100%).

$^1$H NMP(300 MHz, CD$_3$OD): δ 7.78 (s, 1H), 7.32 (d, 1H, J=8.7 Hz), 7.01-6.95 (m, 2H)

Step 2: Synthesis of 1-(1H-indazol-5-yl)-3-phenethylthiourea (19-1)

5-Amino-1H-indazole (9 mg) prepared according to the same procedure as described in Step 1 was dissolved in dichloromethane (1 ml) and the solution was stirred at room temperature for 3 hours. The resulting mixture was concentrated under reduced pressure and the obtained residue was column-chromatographed eluting with ethyl acetate/hexane (1/2) to yield the compound 19-1 (10 mg, 60%).

¹H NMR(300 MHz, CD₃OD): δ 7.99 (d, 1H, J=1.0 Hz), 7.51-7.47 (m, 2H), 7.27-7.13 (m, 6H), 3.78 (t, 2H, J=6.8 Hz), 2.90 (t, 2H, J=7.3 Hz)

EXAMPLE 129

Synthesis of 1-(4-t-butylbenzyl)-3-(1H-indazolyl) thiourea (19-2)

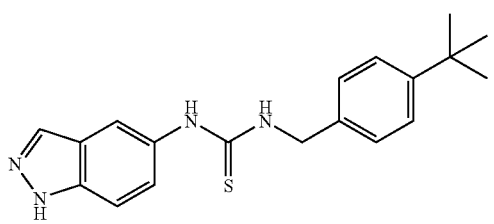

19-2

Compound 19-2 (25 mg, 65%) was synthesized using 5-amino-1H-indazole (15 mg) and t-butylbenzylisothiocyanate (30 mg) according to the similar procedure as described in Step 2 of Exmaple 128.

¹H NMR(300 MHz, CD₃OD): δ 7.99(s, 1H), 7.65 (s, 1H), 7.50 (d, 1H, J=8.8 Hz), 7.33-7.21 (m, 5H), 4.73 (brs, 2H), 1.27 (s, 9H)

EXAMPLE 130

Synthesis of 1-(4-t-butylbenzyl)-3-(2-fluoro-4-methanesulfonyloxybenzyl)thiourea (20-2a)

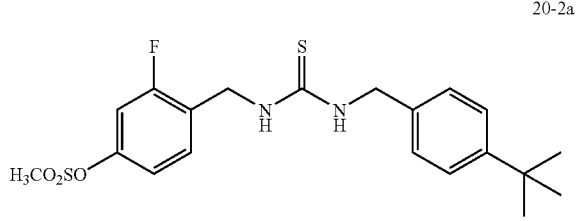

20-2a

Step 1: Synthesis of 3-fluoro-4-(N-t-butyloxycarbonylaminomethyl)phenol (20-1a) and 3-fluoro-(N-t-butyloxycarbonylaminomethyl)phenol t-butyloxycarbonyl ether (20-1b)

2-Fluoro-4-hydroxybenzonitrile (686 mg), nickel chloride (II) (1.18 g) and Boc₂O (2.18 mg) were dissolved in methanol (40 ml) and the solution was cooled to 0° C. To the solution was slowly added sodium borohydride (1.32 g), and the mixture was stirred at 0° C. for 10 minutes and then at room temperature for 24 hours. The resulting mixture was concentrated under reduced pressure and to the concentrate were added ethyl acetate (60 ml) and sodium borohydride (300 mg), followed by filtering. The filtrate was extracted twice with ethyl acetate. The total filtrate was concentrated under reduced pressure, and then purified by column-chromatography (hexane/ethyl acetate=3/1) to yield the compound 20-1a (134 mg, 11%) and 20-1b (710 mg, 42%).

20-1a: ¹H NMR (300 MHz, CDCl₃) δ 7.11(t, J=8.2 Hz, 1H), 6.62(bs, 1H), 6.61(d, J=9.6 Hz, 2H), 4.91(bs, 1H), 4.24 (d, J=4.8 Hz, 2H), 1.46(s, 9H)

20-1b: ¹H NMR (300 MHz, CDCl₃) δ 7.37(t, J=8.3 Hz, 1H), 6.93(m, 2H), 4.88(bs, 1H), 4.32(d, J=5.7 Hz, 2H), 1.55 (s, 9H), 1.44(s, 9H)

Step 2: Synthesis of 1-(4-t-butylbenzyl)-3-(2-fluoro-4-methanesulfonyloxybenzyl)thiourea (20-2a)

Compound 20-1a (134 mg) prepared in Step 1 was dissolved in dichloromethane (2 ml) and to the solution at 0° C. were added dropwise methanesulfonyl chloride (44 μl) and pyridine (45 μl), followed by stirring at room temperature for 24 hours. The resulting mixture was concentrated under reduced pressure and the obtained residue was purified by column-chromatography (hexane/ethyl acetate=3/1) to obtain methanesulfonyl compound (55 mg, 31%). The obtained compound was dissolved in dichlorormethane (2.0 ml) and the solution was cooled to 0° C., followed by adding trifluoroacetic acid (100 μl) thereto and stirring for 2 hours. The resulting mixture was concentrated under reduced pressure and dissolved in dimethylformamide (5.0 ml). To the solution was added triethylamine (30 μl) and the mixture was stirred for 1 hour. To the obtained solution was added 4-t-butylbenzylisothiocyanate (40 mg) and the mixture was stirred at room temperature for 18 hours. The resulting mixture was concentrated under reduced pressure and the obtained residue was purified by column-chromatography (hexane/ethyl acetate=2/1) to yield the compound 20-2a (61 mg, 85%).

¹H NMR (300 MHz, CDCl₃) δ 7.43(t, J=8.7 Hz, 1H), 7.37(d, J=8.1 Hz, 2H), 7.22(d, J=8.1 Hz, 2H), 7.02(m, 2H), 6.20(bs, 1H), 6.00(bs, 1H), 4.79(d, J=5.4 Hz, 2H), 4.53(d, J=4.2 Hz, 2H), 3.16(s, 3H), 1.31(s, 9H).

EXAMPLE 131

Synthesis of 1-(4-t-butylbenzyl)-3-(2-fluoro-4-hydroxy)thiourea (20-2b)

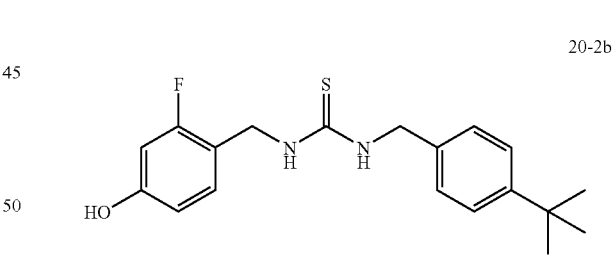

20-2b

The compound 20-1b (710 mg) prepared in Step 1 of Example 130 was dissolved in dichloromethane (10 ml) and the solution was cooled to 0° C., followed by adding trifluoroacetic acid (1.0 ml) thereto and stirring for 2 hours. The resulting mixture was concentrated under reduced pressure and part (211 mg) of the obtained residue was dissolved in dimethylformamide (5.0 ml). To the solution was added triethylamine (120 μl) and the mixture was stirred for 1 hour. To the obtained solution was slowly added 4-t-butylbenzylisothiocyanate (170 mg) and the mixture was stirred at room temperature for 18 hours. The resulting mixture was concentrated under reduced pressure and purified by column-chromatography (hexane/ethyl acetate=1/1) to yield the compound 20-2b (196 mg, 68%).

¹H NMR (300 MHz, CDCl₃): δ 7.35(d, J=8.4 Hz, 2H), 7.20(d, J=8.4 Hz, 2H), 7.13(t, J=8.4 Hz, 1H), 6.54(m, 2H), 6.08(bs, 1H), 6.02(bs, 1H), 5.75(bs, 1H), 4.59(m, 4H), 1.31(s, 9H)

EXAMPLE 132

Synthesis of 1-(4t-butylbenzyl)-3-[(6-methanesulfonylaminopyridin-2-yl)methyl]thiourea (21-7)

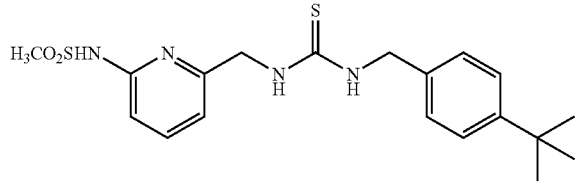

21-7

Step 1: Synthesis of 2,2-dimethyl-N-(6-methyl-2-pyridinyl)propaneamide (21-1)

2-amino-6-picoline (26 g) was dissolved in dichloromethane (280 ml) and the reactor was cooled to 0° C., followed by adding triethylamine (30 g) thereto. To the obtained solution was slowly added dropwise a solution of trimethylacetylchloride (31.8 g) in dichloromethane (20 ml) and the mixture was stirred at room temperature for 3 hours. The resulting mixture was filtered, washed with water, dried over anhydrous magnesium sulfate, concentrated under reduced pressure and then crystallized (dichloromethane/petroleum ether) to yield a pale yellow solid (38 g, 82%).

Step 2: Synthesis of N-[6-(bromomethyl)-2-pyridinyl]-2,2-dimethylpropaneamide (21-2)

2,2 ethyl-N-(6-methyl-2-pyridinyl)propaneamide (21-1) (32 g) and N-bromosuccinimide (29.6 g) were added to carbon tetrachloride (300 ml) and to the mixture was added AIBN (15 mg), followed by reluxing for 20 hours under light emitted by 500 W lamp. The resulting mixture was cooled to room temperature, filtered, and concentrated under reduced pressure. The residue was purified by column-chromatography (hexane/ethyl acetate=10/1) to yield the compound 21-2 (1.94 g, 5%) as a pure white solid.
¹H NMR(300 MHz, CDCl₃): δ 8.20-8.17(m, 1H), 8.00(brs, 1H), 7.72-7.66(m, 1H), 7.16-7.13(m, 1H), 4.42(s, 2H), 1.34 (s, 9H)

Step 3: Synthesis of N-[6-{(1,3-dihydro-1,3-dioxo-2H-isoindol-2-yl)methyl}-2-pyridinyl]-2,2-dimethylpropaneamide (21-3)

N-[6-(bromomethyl)-2-pyridinyl]-2,2-dimethylpropaneamide (21-2) (1.9 g) was dissolved in dimethylformamide (20 ml) and to the solution was added potassium phthalimide (1.43 g), followed by stirring at room temperature for 24 hours. The resulting mixture was concentrated under reduced pressure and extrated with water and dichloromethane. An organic layer was concentrated under reduced pressure to yield the compound 21-3 (2.27 g, 96%) as a bright yellow solid.

¹H NMR(300 MHz, CDCl₃): δ 8.15-8.12(m, 1H), 7.92-7.74(m, 4H), 7.66-7.60(m, 1H), 7.00-6.97(m, 1H), 4.90(s, 2H), 1.29(s, 9H)

Step 4: Synthesis of 2-[(2-amino-6-pyridinyl)methyl]-1H-isoindol-1,3(2H)-dione (21-4)

N-[6-{(1,3-dihydro-1,3-dioxo-2H-isoindol-2-yl)methyl}-2-pyridinyl]-2,2-dimethylpropaneamide 21-3 was dissolved in ethanol (20 ml) and to the solution was added concentrated sulfuric acid (2 ml), followed by refluxing for 6 hours. The obtained solution was basified with ammonia solution, extracted with dichloromethane, and then dried over anhydrous magnesium sulfate. The residue was concentrated under reduced pressure and purified by column-chromatography (hexane/ethyl acetate=1/1) to yield the compound 214 (400 mg, 23%) as a pale yellow solid.
¹H NMR(300 MHz, CDCl₃): δ 7.90-7.71(m, 4H), 7.38-7.32(m, 1H), 6.59-6.56(m, 1H), 6.37-6.33(m, 1H), 4.83(s, 2H), 4.36(brs, 2H)

Step 5: Synthesis of 2-[(2-methanesulfonylamino-6-pyridinyl)methyl]-1H-isoindol-1,3(2H)-dione (21-5)

The compound 21-4 (200 mg) prepared in Step 4 was dissolved in dichloromethane (10 ml) and to the solution were added triethylamine (130 µl) and methanesulfonyl chloride (67 g), followed by stirring at room temperature for 24 hours. The resulting mixture was extracted with water and dichloromethane, dried, concentrated under reduced pressure, and then crystallized (dichloromethane/petroleum ether) to yield the compound 21-5 (260 mg, 99%) as a white solid.

Step 6: Synthesis of 1-(4-t-butylbenzyl)-3-[(2-methanesulfonylamino-6-pyridinyl)methyl]thiourea (21-7)

The compound 21-5 (220 mg) prepared in Step 5 was dissolved in methanol (5 ml) and to the solution was added hydrazine hydrate (270 µl), followed by stirring at room temperature for 2 hours. The obtained reaction solution was concentrated under reduced pressure to obtain the compound 21-6. The compound 21-6 (690 mg) was dissolved in dimethylformamide (20 ml) and to the solution was added 4-t-butylbenzylisothiocyanate (370 mg), followed by stirring at 100° C. for 7 hours. The reaction mixture was concentrated and purified by column-chromatography (hexane/ethyl acetate=1/2) to yield the compound 21-7 (58 mg, 23%) as a green foamy solid.
¹H NMR(300 MHz, CDCl₃): δ 7.69-7.63(m, 1H), 7.42-7.38(m, 2H), 7.31-7.25(m, 3H), 7.04-6.65(m, 3H), 4.76-4.60 (m, 4H), 3.07(s, 3H), 1.31(s,9H)

EXAMPLE 133

Synthesis of (4-t-butylbenzyl)thiocarbamic acid (1-methyl-4-nitro-1H-pyrrol-2-yl)methyl ester (22-3)

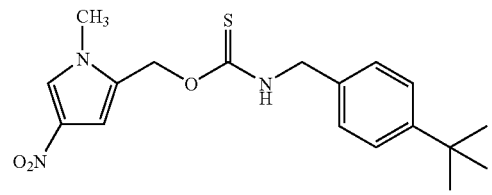

22-3

Step 1: Synthesis of N-methyl-4-nitro-pyrrol-2-carboxaldehyde (22-1)

N-methylpyrrol-2-carboxaldehyde (5 g) was dissolved in anhydrous acetic acid (50 ml), and to an ice-cold of the solution was slowly added dropwise nitric acid (1.84 ml) with stirring. The mixture was stirred at this temperature for 1 hour, and then at room temperature for 18 hours. After confirming the completion of the reaction, to the mixture was added an ice-water (200 ml), followed by slowly adding solid sodium hydroxide (20 g) thereto and stirring for 1 hour. The obtained mixture was extracted with ether (150 ml×3). The obtained organic layer was washed with aqueous sodium bicarbonate solution and saturated aqueous sodium chloride solution, dried over sodium sulfate, and then filtered. The filtrate was concentrated under reduced pressure and purified by column-chromatography (ethyl acetate/hexane=1/4) to yield the compound 22-1 (3.5 g, 49.6%).

$^1$H NMR(300 MHz, CDCl$_3$): δ9.63(s, 1H), 7.68(s, 1H), 7.43(s, 1H), 4.03(s, 3H)

Step 2: Synthesis of 2-hydroxymethyl-N-methyl-4-nitro-pyrrole (22-2)

Compound 22-1 (550 mg) was dissolved in anhydrous tetrahydrofuran (30 ml) and cooled to 0° C. To the solution was slowly added dropwise 1M borane-tetrahydrofuran (3.25 ml), followed by refluxing at 80° C. for 3 hours. After the completion of the reaction, the solvent was evaporated under reduced pressure to be removed, and then the residue was purified by column-chromatography (ethyl acetate/hexane=2/1) to yield the compound 22-2 (500 mg, 90%).

$^1$H NMR(300 MHz, CDCl$_3$): δ 7.51(s, 1H), 6.65(s, 1H), 4.59(s, 2H), 3.75(s, 3H)

Step 3: Synthesis of (4-t-butylbenzyl)thiocarbamic acid (1-methylnitro-1H-pyrrol-2-yl)methyl ester (22-3)

Compond 22-2 (100 mg) was dissolved in anhydrous tetrahydrofuran (15 ml) and cooled to 0° C. To the solution was slowly added sodium hydride (190 mg) with stirring, followed by stirring for 30 minutes. To the mixture was added t-butylbenzylisothiocyanate (130 mg), followed by stirring for 6 hours. The solvent was evaporated under reduced pressure to be removed, and then the residue was diluted with water (20 ml). The obtained mixture was extracted with ethyl acetate (20 ml×3), dried over magnesium sulfate, and then filtered. The filtrate was evaporated under reduced pressure and the obtained residue was purified by column-chromatography (ethyl acetate/hexane=1/3) to yield the compound 22-3 (130 mg, 56.2%).

$^1$H NMR(300 MHz, CDCl$_3$): δ7.51(m, 1H), 7.31(m, 3H), 7.10(m, 1H), 6.83(m, 1H), 6.47(brs, 1H), 5.44(s, 2H), 4.71(d, 2H, J=5.7 Hz), 3.68(s, 3H), 1.31(s, 9H)

EXAMPLE 134

Synthesis of 1-(4-t-butylbenzyl-3-(4-methanesulfonylamino-1-methyl-1H-pyrrol-2-yl)thiourea (22-9)

22-9

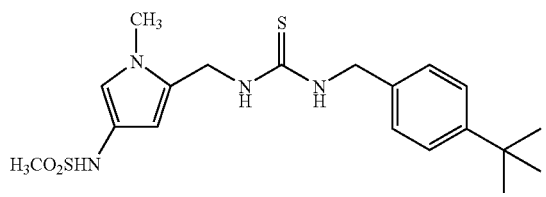

Step 1: Synthesis of 2-cyano-N-methylpyrrole (22-4)

N-methyl-2-pyrrolcarboxaldehyde (5 g) and hydroxylamine hydrochloride (3.82 g) were mixed in 1-methyl-2-pyrrolidinone (50 ml) and the mixture was refluxed at 110° C. for 2 hours. After confirming the completion of the reaction, to the reaction mixture was slowly added an ice-water (200 ml) and the resulting mixure was extracted with ethyl acetate (150 ml×3), washed with brine, dried over sodium sulfate, and then filtered. The filtrate was concentrated under reduced pressure and the obtained residue was purified by column-chromatography (ethyl acetate/hexane=1/4) to yield the compound 22-4 (3.5 g, 72%).

$^1$H NMR(300 MHz, CDCl$_3$): δ 6.79(m, 2H), 6.16(m, 1H), 3.78(s, 3H)

Step 2: Synthesis of 4nitro-2-cyano-N-methylpyrrole (22-5)

Compound 22-4 (1 g) was dissolved in anhydrous acetic acid (100 ml), and cooled to 0° C. To the solution was slowly added dropwise nitric acid (380 μl) with stirring, followed by stirring at the same temperature for 1 hour and subsequently at room temperature for 18 hours. After confining the completion of the reaction, to the mixture was added an ice-water (200 ml), followed by slowly adding solid sodium hydroxide (20 g) thereto and stirring for 1 hour. The obtained mixture was extracted with ether (50 ml×3). The obtained organic layer was washed with aqueous sodium bicarbonate solution and saturated aqueous sodium chloride solution, dried over sodium sulfate, and then filtered. The filtrate was concentrated under reduced pressure and purified by column-chromatography (ethyl acetate/hexane=1/3) to yield the compound 22-5 (1.05 g, 73.7%).

$^1$H NMR(300 MHz, CDCl$_3$): δ 7.65(s, 1H), 7.32(s, 1H), 3.88(s, 3H)

Step 3: Synthesis of 2-cyano-4-amino-N-methylpyrrole (22-6)

Compound 22-5 (500 mg) and 10% palladium/carbon (50 mg) were poured into the reactor and dissolved in methanol (10 ml), and then reacted under hydrogen gas atmosphere for 2 hours. After confirming the completion of the reaction, the resulting mixture was filtered through celite, and the filtrate was concentrated under reduced pressure and purified by column-chromatography (ethyl acetate/hexane=3/1) to yield the compound 22-6 (310 mg, 77.4%).

$^1$H NMR(300 MHz, CDCl$_3$): δ6.36(d, 1H, J=2.1 Hz), 6.30 (d, 1H, J=4.2 Hz), 3.66(s, 3H)

Step 4: Synthesis of 4-methanesulfonylamino-2-cyano-N-methylpyrrole (22-7)

Compound 22-6 (310 mg) was dissolved in dichloromethane (30 ml) and cooled to 0° C. To the solution were added triethylamine (430 μl) and methanesulfonyl chloride (210 μl) successively through an injector, followed by stirring at room temperature for 24 hours. The resulting mixture was diluted with 1 N aqueous hydrochloric acid, and an organic layer was dried over magnesium sulfate and filtered. The filtrate was concentrated under reduced pressure and the obtained residue was purified by column-chromatography (ethyl aceate/hexane=1/1) to yield the compound 22-7 (400 mg, 78.5%)

$^1$H NMR(300 MHz, CDCl$_3$): δ 6.78(d, 1H, J=1.8 Hz), 6.53(d, 1H, J=1.8 Hz), 5.95(brs, 1H), 3.92(s, 3H), 2.97(s, 3H)

Step 5: Synthesis of (4-methanesulfonylamino-1-methyl-1H-pyrrol-2-yl)methylamine (22-8)

Compound 22-7 (150 mg) and 10% palladium/carbon (catalytic amount), together with methanol (10 ml), were poured into reactor and the reactor was filled with hydrogen gas, followed by stirring at room temperature for 24 hours. After the completion of the reaction, the resulting mixture was filtered through celite and concentrated under reduced pressure. The following procedure was carried out using the obtained residue which was not purified.

Step 6: Synthesis of 1-(4-t-butylbenzyl)-3-(4-methanesulfonylamino-1-methyl-1H-pyrrol-2-yl)thiourea (22-9)

The compound 22-8 (95 mg) prepared in Step 5 and 4-t-butylbenzylisothiocyanate (96 mg) were added to ethyl acetate (20 ml) and the mixture was stirred for 16 hours. The resulting mixture was concentrated under reduced pressure and the obtained residue was purified by column-chromatography (ethyl acetate/hexane=3/2) to yield the compound 22-9 (105 mg, 55%).

$^1$H NMR(300 MHz, CDCl$_3$): δ7.37(d, 2H, J=8.1 Hz), 7.22 (d, 2H, J=8.1 Hz), 6.61(d, 1H, J=1.8 Hz), 5.95(d, 1H, J=2.1 Hz), 6.26(brs, 1H), 5.87(brs, 1H), 5.77(brs, 1H), 4.64(d, 2H, J=4.8 Hz), 4.54(d, 2H, J=3.9 Hz), 3.48(s, 3H), 2.91(s, 3H), 1.31(s, 9H)

EXAMPLE 135

Synthesis of 1-(4-t-butylbenzyl)-3-[(4-methanesulfonylaminomethyl)phenyl]thiourea (23-2)

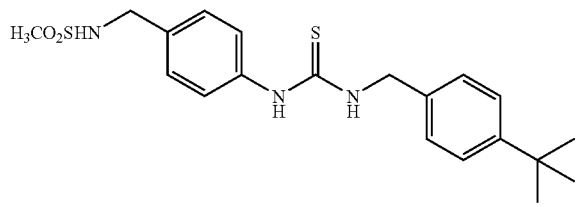

Step 1: Synthesis of (4-methanesulfonylaminomethyl)-1-nitrobenzene (23-1)

4-nitrobenzylamine hydrochloride (3.77 g) was dissolved in dichloromethane (20 ml) and to the solution at 0° C. was added triethylamine (6.14 ml), followed by adding dropwise methanesulfonyl chloride (1.7 ml) thereto and stirring at room temperature for 23 hours. After the completion of the reaction, the resulting mixture was extracted with water and dichloromethane, concentrated under reduced pressure, and then crystallized (dichloromethane/petroleum ether) to yield an ocherous solid (1.2 g, 26%).

Step 2: Synthesis of 1-(4-t-butylbenzyl)-3-[(4-methanesulfonylaminomethyl)phenyl]thiourea (23-2)

The compound 23-1 prepared in Step 1 was dissolved in ethyl acetate (30 ml) and to the solution was added tin (II) chloride dihydrate (6.1 g), followed by refluxing at 50° C. for 2 hours. After allowed to cool down to room temperature, the resulting mixture was basified with saturated aqueous sodium bicarbonate solution, washed with water and brine, dried, and then concentrated under reduced pressure to obtain a yellow solid (610 mg, 59%). The obtained compound (107 mg), which was not purified, was dissolved in acetonitrile (10 ml) and to the solution were added triethylamine (100 μl) and 4-t-butylbenzylisothiocyanate (110 mg), followed by refluxing for 24 hours. The resultant mixture was concentrated under reduced pressure and purified by column-chromatography (hexane/ethyl acetate=1/2) to yield the compound 23-2 (73 mg, 34%) as a solid.

$^1$H NMR(300 MHz, CDCl$_3$): δ 7.84(brs, 1H), 7.46-7.18(m, 8H), 6.26(brs, 1H), 5.00-4.81(m, 3H), 4.31-4.28(m, 2H), 2.92 (s, 3H), 1.29(s,9H)

EXAMPLE 136~EXAMPLE 141

Compounds of Example 136 Example 141, which are shown in the Scheme 24, were synthesized according to the similar procedure as described in Example 76 or Example 77, and properties and spectral data thereof are shown in below table.

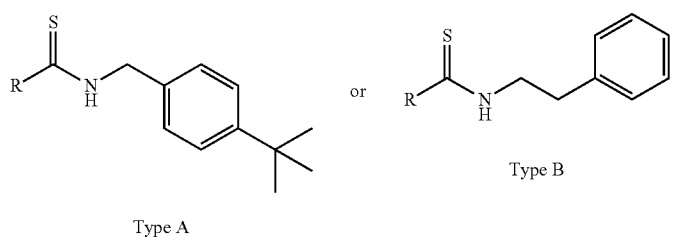

Type A    Type B

| Examples | Compounds | R = | Type | Spectral data |
|---|---|---|---|---|
| 136 | 24-1 | (benzyl-piperazinyl-methyl group) | A | $^1$H NMR(300 MHz, CDCl$_3$): δ 7.39 7.26(m, 9H), 5.55(brs, 1H), 4.81(d, 2H, J = 4.8 Hz), 3.83-3.79(m, 4H), 3.53(s, 2H), 2.51-2.47(m, 4H), 1.32(s, 9H) |

-continued

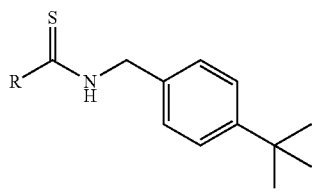

Type A

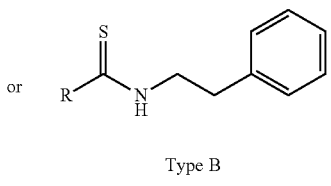

Type B

| Examples | Compounds | R = | Type | Spectral data |
|---|---|---|---|---|
| 137 | 24-2 | benzyl-N-methylpiperazine | B | $^1$H NMR(300 MHz, CDCl$_3$): δ 7.33-7.19(m, 10 H), 5.40(brs, 1H), 3.97-3.90(m, 2H), 3.72-3.69(m, 4H), 3.52(s, 2H), 2.94(t, 2H, J = 6.9 Hz), 2.46-2.42(m, 4H), 1.32(s, 9H) |
| 138 | 24-3 | 2-(4-methylpiperazin-1-yl)pyrimidine | A | $^1$H NMR(300 MHz, CDCl$_3$): δ 8.34-8.32(m, 1H), 7.40-7.26(m, 5H), 6.55(t, 1H, J = 4.5 Hz), 5.51(brs, 1H), 4.85(d, 2H, J = 4.2 Hz), 3.96-3.94(m, 8H), 1.32(s, 9H) |
| 139 | 24-4 | 2-(4-methylpiperazin-1-yl)pyridine | A | $^1$H NMR(300 MHz, CDCl$_3$): δ 8.19-8.16(m. 1H), 7.53-7.26(m, 5H), 6.68-6.56(m, 2H), 5.58(brs, 1H), 4.85(d, 2H, J = 4.8 Hz), 4.04-4.00(m, 4H), 3.74-3.70(m, 4H), 1.32(s, 9H) |
| 140 | 24-5 | 1H-pyrazole-4-carboxylic acid | A | $^1$H-NMR(300 MHz, CDCl$_3$): δ 9.15(s, 1H), 9.10(m, 1H), 7.95(s, 1H), 7.34(d, 2H, J = 8.6 Hz), 7.25(d, 2H, J = 8.6 Hz), 4.84(d, 2H, J = 5.6 Hz), 1.25(s, 9H) |
| 141 | 24-6 | 1,2,3,4-tetrahydroisoquinoline | A | $^1$H NMR(CDCl$_3$): δ 7.35(m, 2H), 7.18(m, 4H), 5.62(bs, 1H), 4.92(s, 2H), 4.87(d, 2H, d = 2.25 Hz), 3.98(m, 2H), 2.94(m, 2H), 1.32(s, 9H) |

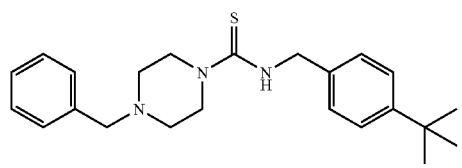

24-1

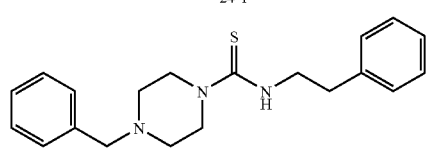

24-2

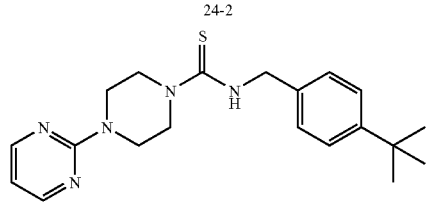

24-3

-continued

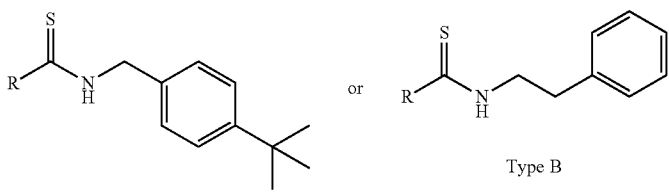

Type A or Type B

| Examples | Compounds | R = | Type | Spectral data |
|---|---|---|---|---|

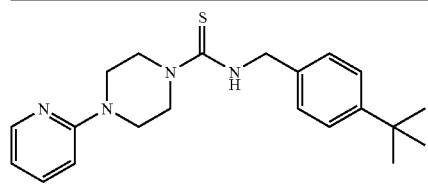

24-4

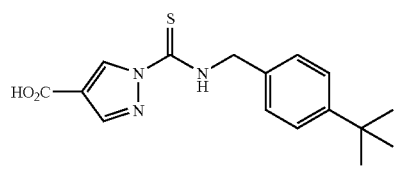

24-5

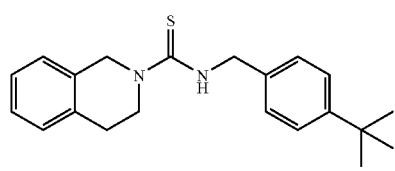

24-4

EXAMPLE 142

Synthesis of 1-benzyl-1-(4-hydroxy-3-methoxybenzyl)-3-phenethylthiourea (25-1)

25-1

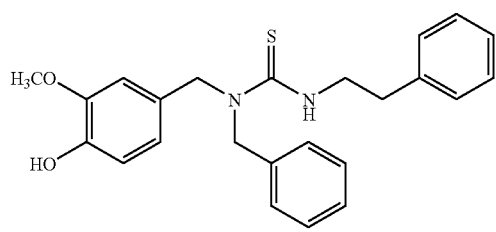

Vaniline (200 mg) and benzylamine (129 mg) were dissolved in methanol (3 ml) and the solution was stirred for 30 minutes. To the solution was added a catalytic amount of 10% platinum/carbon to be subjected to the hydrogenation reaction (1 atm). After the completion of the reaction, the resulting mixture was filtered and evaporated under reduced pressure to remove methanol. The obtained residue was dissolved in dichloromethane (3 ml) and to the solution was added phenethylisothiocyanate (196 mg, 1.2 mmol), followed by stirring at room temperature for 5 hours. Then, dichloromethane was evaporated under reduced pressure and the obtained residue was column-chromatographed (hexane/ethyl acetate=1/1) to yield the compound 25-1 (400 mg, 82%) as a white solid.

$^1$H NMR (300 MHz, CDCl$_3$): δ 7.25 (m, 10H), 6.94 (m, 3H), 6.69(m, 2H), 5.69(s, 1H), 5.51(t, 1H, J=4.68 Hz), 4.88(s, 2H), 4.75(s, 2H), 3.89(m, 2H), 3.75(s, 3H), 2.78(t, 2H, J=6.57 Hz): MS (EI) m/e 406 [M$^+$]

EXAMPLE 143~EXAMPLE 167

Compounds 25-2~25-26 of Example 143~Example 167, which are shown in the Scheme 25, were synthesized according to the similar procedure as described in Example 142, and properties and spectral data thereof are shown in below table.

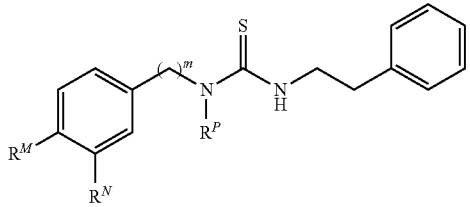

| Examples | Compounds No. | $R^M$, $R^N$, $R^P$, m | Spectral data |
|---|---|---|---|
| 143 | 25-2 | $R^M$ = —OH<br>$R^N$ = —OCH$_3$<br>$R^P$ = —(CH$_2$)$_2$Ph<br>m = 1 | $^1$H NMR(300 MHz, CDCl$_3$): δ 7.20(m, 1H), 6.82(d, 1H, J = 8.04 Hz), 6.66(s, 1H), 6.58(d, 1H, J = 8.04 Hz) 5.59(s, 1H), 5.30(t, 1H), 4.59(s, 2H), 3.88(m, 4H), 3.81(s, 3H), 2.84(m, 6H); MS(EI) m/e 420 [M$^+$] |
| 144 | 25-3 | $R^M$ = —OH<br>$R^N$ = —OCH$_3$<br>$R^P$ = —(CH$_2$)$_3$Ph<br>m = 1 | $^1$H NMR(300 MHz, CDCl$_3$): δ 7.20(m, 10 H), 6.83(d, 1H, J = 8.04 Hz), 6.72(s, 1H), 6.57(d, 1H, J = 8.04 Hz) 5.58(s, 2H), 5.21(t, 1H, J = 4.62 Hz), 4.72(s, 2H), 3.85(t, 2H, J = 6.57 Hz), 3.81(s, 3H), 2.82(t, 2H, J = 7.68 Hz) 2.51(t, 2H, J = 8.55 Hz) MS(EI) m/e 434 [M$^+$] |
| 145 | 25-4 | $R^M$ = —OH<br>$R^N$ = —OCH$_3$<br>$R^P$ = —(CH$_2$)$_4$Ph<br>m = 1 | $^1$H NMR(300 MHz, CDCl$_3$): δ 7.19(m, 10H), 6.70(m, 3H), 5.58(s, 1H) 4.69(s, 2H), 3.79(s, 3H), 3.87(m, 2H), 3.38(m, 2H), 2.84(t, 2H, J = 6.6 Hz), 2.58(t, 2H, J = 7.7 Hz), 1.55(m, 4H); MS(EI) m/e 448 [M$^+$] |
| 146 | 25-5 | $R^M$ = —OH<br>$R^N$ = —OCH$_3$<br>$R^P$ = —C$_8$H$_{17}$<br>m = 1 | $^1$H NMR(300 MHz, CDCl$_3$): δ 7.20(m, 5H), 6.74(m, 3H), 5.63(s, 1H) 5.36(t, 1H), 4.77(s, 2H), 3.94(m, 2H), 3.85(s, 3H), 3.49(t, 2H, J = 7.8 Hz), 2.89(t, 2H, J = 6.57 Hz), 1.48(t, 2H), 1.28(m, 2H), 0.90(t, 3H) MS(EI) m/e 428 [M$^+$] |

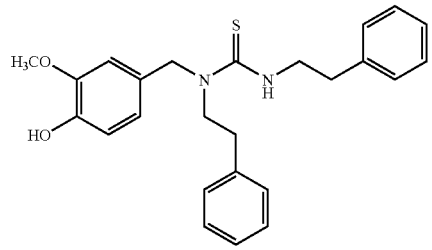

25-2

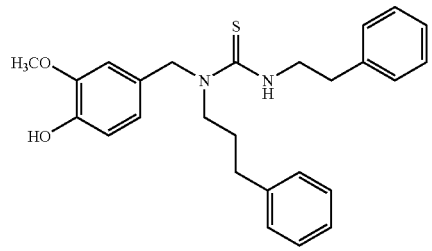

25-3

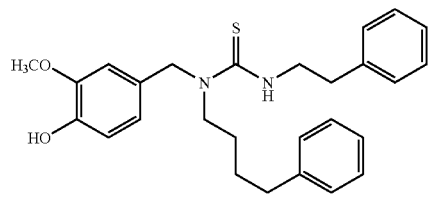

25-4

-continued

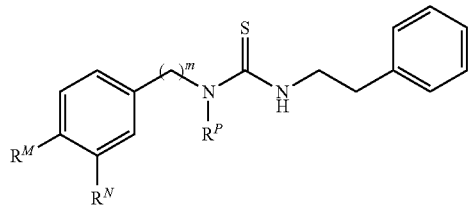

| Examples | Compounds No. | $R^M, R^N, R^P$, m | Spectral data |
|---|---|---|---|

| Examples | Compounds No. | $R^M, R^N, R^P$, m | Spectral data |
|---|---|---|---|
| | 25-5 | | |
| 147 | 25-6 | $R^M$ = —OH<br>$R^N$ = —OCH$_3$<br>$R^P$ = isopropyl<br>m = 1 | $^1$H NMR(300 MHz, CDCl$_3$): δ 6.86(m, 8H), 5.75(s, 1H), 5.59(s, 1H) 5.35(s, 1H), 4.32(s, 2H), 3.80(s, 3H), 3.85(m, 3H), 2.74(t, 2H, J = 6.71 Hz), 1.18(d, 6H); MS (EI) m/e 358 [M$^+$] |
| 148 | 25-7 | $R^M$ = —OH<br>$R^N$ = —OCH$_3$<br>$R^P$ = cyclohexyl<br>m = 1 | $^1$H NMR(300 MHz, CDCl$_3$): δ 7.07(m, 5H), 6.67(m, 3H), 5.56(s, 2H) 5.34(m, 4H), 4.37(s, 2H), 3.86(m, 2H), 3.79(s, 3H), 2.74(t, 2H, J = 6.71 Hz), 1.43(m, 10H); MS(EI) m/e 398 [M$^+$] |
| 149 | 25-8 | $R^M$ = —OH<br>$R^N$ = —OH<br>$R^P$ = —(CH$_2$)$_3$Ph<br>m = 1 | $^1$H NMR(300 MHz, CDCl$_3$): δ 7.08(m, 10H), 6.46(m, 3H), 6.38(s, 1H) 3.70(t, 2H, J = 7.23 Hz), 3.42(t, 2H, J = 7.61 Hz), 2.78(t, 2H, J = 7.32 Hz), 1.70(m, 2H); MS (EI) m/e 420 [M$^+$] |
| 150 | 25-9 | $R^M$ = —OH<br>$R^N$ = —OCH$_3$<br>$R^P$ = —(CH$_2$)$_2$Ph<br>m = 2 | $^1$H NMR(300 MHz, CDCl$_3$): δ 7.21(m, 10H), 6.82(d, 1H, J = 8.04 Hz), 6.64(s, 1H) 6.56(d, 1H, J = 7.56 Hz), 5.53(s, 1H), 5.10(m, 1H), 3.87(s, 3H), 3.82(d, 2H, J = 5.13 Hz), 3.63(d, 2H, J = 5.13 Hz), 2.80(m, 6H); MS (EI) m/e 434 [M$^+$] |
| 151 | 25-10 | $R^M$ = —OH<br>$R^N$ = —OCH$_3$<br>$R^P$ = -isopropyl<br>m = 2 | $^1$H NMR(300 MHz, CDCl$_3$): δ 7.28(m, 5H), 6.70(m, 3H), 5.56(m, 2H) 5.20(m, 1H), 3.95(m, 2H), 3.88(s 3H), 3.45(m, 1H), 2.94(t, 2H), 2.69(t, 2H, J = 7.53 Hz), 1.18(d, 2H, J = 6.57 Hz)<br>MS(EI) m/e 372 [M$^+$] |
| 152 | 25-11 | $R^M$ = —OH<br>$R^N$ = —OCH$_3$<br>$R^P$ = -benzyl<br>m = 3 | $^1$H NMR(300 MHz, CDCl$_3$): δ 7.18(m, 10H), 6.66(m, 3H), 5.47(s, 1H) 5.20(m, 1H), 4.77(s, 2H), 3.83(s, 3H), 3.83(m, 2H), 3.54(t, 2H, J = 7.68 Hz), 2.79(t, 2H, J = 6.825 Hz), 2.46(t, 2H, J = 744 Hz), 1.82(m, 2H); MS (EI) m/e 434 [M$^+$] |
| 153 | 25-12 | $R^M$ = —OH<br>$R^N$ = —OCH$_3$<br>$R^P$ = —(CH$_2$)$_2$Ph<br>m = 3 | $^1$H NMR(300 MHz, CDCl$_3$): δ 7.20(m, 10H), 6.69(m, 3H), 5.51(s, 1H) 5.07(t, 2H, J = 7.30 Hz), 3.85(m, 5H), 3.71(t, 2H, J = 7.68 Hz), 3.33(t, 2H, J = 7.80 Hz) 2.84(m, 4H), 2.47(t, 2H, J = 7.30 Hz), 1.79(m, 2H); MS(EI) m/e 448 [M$^+$] |

| Examples | Compounds No. | $R^M, R^N, R^P$, m | Spectral data |
|---|---|---|---|

25-6

25-7

25-8

25-9

25-10

25-11

| Examples | Compounds No. | $R^M, R^N, R^P$, m | Spectral data |
|---|---|---|---|

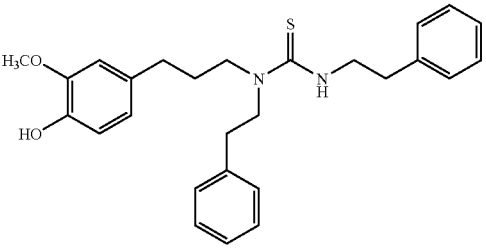

25-12

| Examples | Compounds No. | $R^M, R^N, R^P$, m | Spectral data |
|---|---|---|---|
| 154 | 25-13 | $R^M$ = —OH<br>$R^N$ = —OCH$_3$<br>$R^P$ = —(CH$_2$)$_3$Ph<br>m = 3 | $^1$H NMR(300 MHz, CDCl$_3$): δ 7.22(m, 5H), 6.73(m, 3H), 5.55(s, 1H) 5.04(t, 1H, J = 4.96 Hz), 3.88(s, 3H), 3.83(m, 2H), 3.48(m, 4H), 3.88(t, 2H, J = 6.80 Hz), 2.56(t, 2H, J = 7.58 Hz), 2.51(t, 2H, J = 7.45 Hz), 1.85(m, 4H); MS(EI) m/e 462 [M$^+$] |
| 155 | 25-14 | $R^M$ = —OH<br>$R^N$ = —OCH$_3$<br>$R^P$ = —H<br>m = 3 | $^1$H NMR(300 MHz, CDCl$_3$): δ 7.23(m, 5H), 6.74(m, 3H), 3.84(m, 5H) 3.61(m, 2H), 3.27(m, 2H), 2.87(m, 2H), 2.59(t, 2H, J = 7.94 Hz), 2.83(m, 2H); MS(EI) m/e 344 [M$^+$] |
| 156 | 25-15 | $R^M$ = —OH<br>$R^N$ = —OCH$_3$<br>$R^P$ = —CH$_3$<br>m = 3 | $^1$H NMR(300 MHz, CDCl$_3$): δ 7.23(m, 5H), 6.70(m, 3H), 5.28(s, 2H) 3.86(m, 5H), 3.64(m, 2H), 3.02(s, 3H), 2.92(t, 2H, J = 6.69 Hz), 2.52(t, 2H, J = 7.43 Hz) 1.84(m, 2H); MS(EI) m/e 358 [M$^+$] |
| 157 | 25-16 | $R^M$ = —OH<br>$R^N$ = —OCH$_3$<br>$R^P$ = —C$_8$H$_{17}$<br>m = 3 | $^1$H NMR(300 MHz, CDCl$_3$): δ 7.28(m, 5H), 6.73(m, 3H), 5.50(s, 1H) 5.12(m, 1H), 3.91(m, 5H), 3.55(t, 2H, J = 7.34 Hz), 2.93(m, 2H), 2.53(t, 2H, J = 7.50 Hz), 1.87(m, 2H), 1.44(m, 2H), 1.25(m, 10H), 0.91(m, 3H); MS(EI) m/e 456 [M$^+$] |
| 158 | 25-17 | $R^M$ = —OH<br>$R^N$ = —OCH$_3$<br>$R^P$ = -isobutyl<br>m = 3 | $^1$H NMR(300 MHz, CDCl$_3$): δ 7.21(m, 5H), 6.70(m, 3H), 3.88(m, 5H) 5.59(m, 2H), 5.25(m, 2H), 3.11(m, 4H), 2.75(m, 1H), 2.56(m, 2H), 1.83(m, 2H), 0.86(m, 2H), 0.79(d, 6H)<br>MS(EI) m/e 400 [M$^+$] |
| 159 | 25-18 | $R^M$ = —OH<br>$R^N$ = —OCH$_3$<br>$R^P$ = -isopropyl<br>m = 3 | $^1$H NMR(300 MHz, CDCl$_3$): δ 7.26(m, 5H), 6.67(m, 3H), 5.53(s, m, 2H) 5.02(t, 1H), 3.85(m, 2H), 3.80(m, 2H) 3.09(t, 2H, J = 8.28 Hz), 2.85(t, 2H, J = 6.81 Hz) 2.45(t, 2H, J = 6.95 Hz), 2.72(m, 2H), 1.09(d, 6H); MS (EI) m/e 386 [M$^+$] |
| 160 | 25-19 | $R^M$ = —OH<br>$R^N$ = —OCH$_3$<br>$R^P$ = -cyclo-hexyl<br>m = 3 | $^1$H NMR(300 MHz, CDCl$_3$): δ 7.23(m. 5H), 6.65(m, 3H), 5.50(s, 1H) 4.93(m, 2H), 3.85(s, 3H), 3.83(m 2H), 3.13(t, 2H, J = 7.8 Hz), 2.83(t, 2H, J = 6.82 Hz), 2.42(t, 2H, J = 7.07 Hz), 1.65(m, 9H), 1.18(m, 5H); MS(EI) m/e 426 [M$^+$] |
| 161 | 25-20 | $R^M$ = —OH<br>$R^N$ = —OCH$_3$<br>$R^P$ = —CH(Ph)$_2$<br>m = 3 | $^1$H NMR(300 MHz, CDCl$_3$): δ 7.64(s, 1H), 7.23(m, 15H), 6.52(m, 3H) 5.48(s, 1H), 5.25(t, 1H, J = 5.00 Hz), 3.85(m, 5H), 3.33(t, 2H, J = 8.30 Hz), 2.83(t, 2H, J = 6.823 Hz), 2.07(t, 2H, J = 4.49 Hz), 1.26(m, 2H); MS(EI) m/e 510 [M$^+$] |

-continued

| Examples | Compounds No. | $R^M, R^N, R^P$, m | Spectral data |
|---|---|---|---|

25-13

25-14

25-15

25-16

25-17

25-18

25-19

| Examples | Compounds No. | $R^M$, $R^N$, $R^P$, m | Spectral data |
|---|---|---|---|

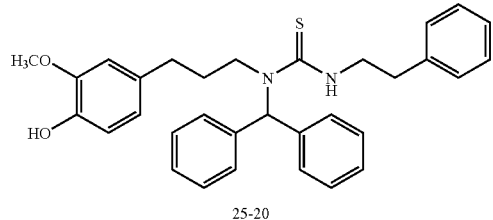

25-20

| Examples | Compounds No. | $R^M$, $R^N$, $R^P$, m | Spectral data |
|---|---|---|---|
| 162 | 25-21 | $R^M$ = —OH<br>$R^N$ = —OCH$_3$<br>$R^P$ = -p-t-butybenzyl<br>m = 3 | $^1$H NMR(300 MHz, CDCl$_3$): δ 7.17(m, 9H), 6.68(m, 3H), 5.49(s, 1H) 5.22(m, 1H), 4.71(s, 2H), 3.85(m, 5H), 3.61(m, 2H), 2.81(t, 2H, J = 6.83 Hz), 2.50(t, 2H, J = 7.44 Hz), 1.88(m, 2H), 1.31(s, 9H); MS(EI) m/e 490 [M$^+$] |
| 163 | 25-22 | $R^M$ = —OH<br>$R^N$ = —OCH$_3$<br>$R^P$ = -isopropyl<br>m = 3 | $^1$H NMR(300 MHz, CDCl$_3$): δ 7.28(m, 5H), 6.73(m, 3H), 6.45(t, 2H, J = 8.04 Hz) 3.80(m, 4H), 3.05(m, 4H), 2.88(m, 2H), 2.54(m, 1H), 2.39(t, 2H, J = 6.83 Hz), 1.71(m, 4H), 1.11(d, 6H)<br>MS(EI) m/e 372 [M$^+$] |
| 164 | 25-23 | $R^M$ = —OCH$_3$<br>$R^N$ = —OCH$_3$<br>$R^P$ = -isopropyl<br>m = 3 | $^1$H NMR(300 MHz, CDCl$_3$): δ 7.23(m, 5H), 6.69(m, 3H), 5.31(s, 1H) 3.85(m, 5H), 3.11(t, 2H, J = 7.32), 2.85(t, 2H, J = 6.71 Hz), 2.46(t, 2H, J = 6.83 Hz) 1.75(m, 2H), 1.90(m, 1H), 1.09(d, 6H, J = 3.32 Hz); MS(EI) m/e 400 [M$^+$] |
| 165 | 25-24 | $R^M$ = —OH<br>$R^N$ = —H<br>$R^P$ = -isopropyl<br>m = 3 | $^1$H NMR(300 MHz, CDCl$_3$): δ 7.14(m, 5H), 6.77(m, 4H), 3.77(m, 7H) 3.10(m, 2H), 2.88(m, 1H), 0.83(m, 10H);<br>MS(EI) m/e 356 [M$^+$] |
| 166 | 25-25 | $R^M$ = —H<br>$R^N$ = —OCH$_3$<br>$R^P$ = -isopropyl<br>m = 3 | $^1$H NMR(300 MHz, CDCl$_3$): δ 7.23(m, 5H), 6.69(m, 3H), 5.32(m, 1H) 3.77(m, 5H), 3.11(t, 2H, J = 7.07 Hz), 2.87(t, 2H, J = 6.60 Hz), 2.49(t, 2H, J = 7.20 Hz), 2.73(m, 2H), 1.91(m, 1H), 1.08(d, 6H, J = 6.84 Hz); MS(EI) m/e 370 [M$^+$] |
| 167 | 25-26 | $R^M$ = —H<br>$R^N$ = —H<br>$R^P$ = -isopropyl<br>m = 3 | $^1$H NMR(300 MHz, CDCl$_3$): δ 7.21(m, 10H), 5.48(m, 1H), 5.038(m, 1H) 3.83(m, 2H), 3.11(t, 2H, J = 8.30 Hz), 2.89(t, 2H, J = 6.83 Hz), 2.54(t, 2H, J = 7.19 Hz), 1.78(m, 2H), 1.11(d, 2H, J = 6.81 Hz);<br>MS(EI) m/e 340 [M$^+$] |

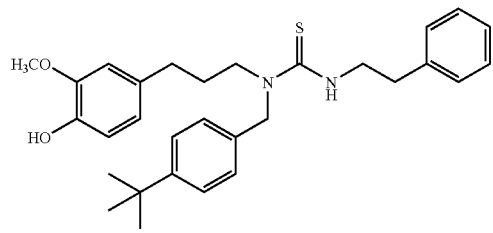

25-21

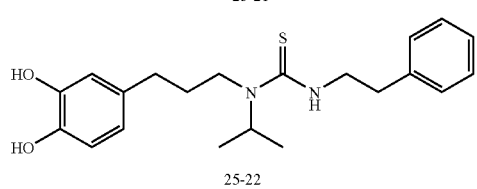

25-22

| Examples | Compounds No. | $R^M, R^N, R^P$, m | Spectral data |
|---|---|---|---|

25-23

25-24

25-25

25-26

EXAMPLE 168

Synthesis of N-(4-t-4-butylbenzyl)-3-(3-fluoro-4-methanesulfonylaminophenyl)propionamide (26-3)

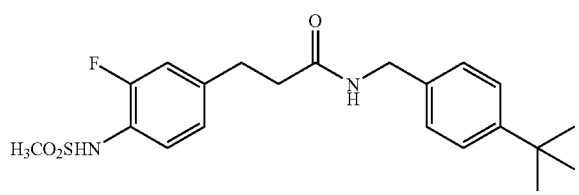

26-3

Step 1: Synthesis of (3-fluoro-4-methanesulfonylamino)cinnamic acid methyl ester (26-1)

2-fluoro-4-iodomethanesulfonylaminobenzene 3-2 (200 mg) was dissolved in dimethylformamide (16 ml) and to the solution were added palladium acetate (7.2 mg), 1,1'-bis(diphenylphosphino)ferrocene (20 mg), triethylamine (200 μl) and methylacrylate (550 mg), followed by stirring at 60° C. for a day. The reaction mixture was cooled to room temperature, diluted with dichloromethane (40 ml) and then washed with water and aqueous hydrochloric acid solution. The obtained mixture was dried over anhydrous magnesium sulfate, concentrated under reduced pressure, and then column-chromatographed (ethyl acetate/hexane=1/1) to yield the compound 26-1 (214 mg, 70%).

$^1$H NMR(300 MHz, CDCl$_3$+CD$_3$OD): δ 7.62(d, 1H, J=16.3 Hz), 7.55(t, 1H, J=8.3 Hz), 7.46(dd, 1H, J=2.0, 11.7 Hz), 7.41(dd, 1H, J=2.0, 8.3 Hz), 6.50(d, 1H, J=15.8 Hz), 3.77(s, 3H), 3.03(s, 3H)

Step 2: Synthesis of methyl 3-(3-fluoro-4-methanesulfonylaminophenyl)propionate (26-2)

The compound 26-1 (78 mg) prepared according to the same procedure as described in Step 1 was dissolved in methanol (10 ml) and to the solution was added a catalytic amount of 10% palladium/carbon, followed by stiring at room temperature under hydrogen atmosphere for 2 hours. The resulting mixture was diluted with ether, filtered through celite, and then concentrated under reduced pressure to yield the compound 26-2 (68 mg, 86%).

$^1$H NMR(300 MHz, CDCl$_3$): δ 7.45(t, 1H, J=8.2 Hz), 6.98 (d, 2H), 6.46(s, 1H), 3.66(s, 3H), 3.00(s, 3H), 2.91(t, 2H, J=7.6 Hz), 2.60(t, 2H, J=7.6 Hz)

Step 3: Synthesis of N-(4-t-butylbenzyl) 3-(3-fluoro-4-methanesulfonylaminophenyl)propionamide (26-3)

The compound 26-2 (30 mg) prepared in Step 2 was dissolved in toluene (4 ml) and to the solution was added 4-t-butylbenzylamine (150 μl), followed by refluxing for 3 hours. The resulting mixture was concentrated under reduced pressure and the obtained residue was chromatographed on silica gel column (ethyl acetate/hexane=1/1) to yield the compound 26-3 (28 mg, 58%).

$^1$H NMR(300 MHz, CDCl$_3$): δ 7.39(t, 1H, J=8.3 Hz) 7.29 (d, 2H), 7.07(d, 2H), 6.95(m, 2H), 6.33(s, 1H), 5.54(s, 1H), 4.31(d, 2H, J=5.6 Hz), 2.93(s, 3H), 2.92(t, 2H, J=7.4 Hz), 2.41(t, 2H, J=7.6 Hz), 1.24(s, 9H)

EXAMPLE 169

Synthesis of N-(3-fluoro-4-methanesulfonylaminobenzyl) 4-t-butylbenzamide (27)

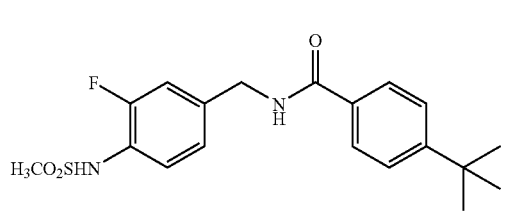

27

Hydrochloride salt 3-4 (100 mg) prepared according to the same procedure as described in Example 13 was dissolved in dichloromethane (6 ml) and to the solution were added 4-t-butylbenzoylchloride (85 mg) and triethylamine (60 µl), followed by stirring at room temperature for 2 hours. The resulting mixture was concentrated under reduced pressure and the obtained residue was column-chromatographed (ethyl acetate/hexane=1/1) to yield the compound 27 (110 mg, 72%).

$^1$H NMR(300 MHz, CDCl$_3$): δ 7.72(d, 2H), 7.49(t, 1H, J=8.0 Hz) 7.43(d, 2H), 7.13(m, 2H), 6.54(s, 1H), 4.59(d, 2H, J=5.9 Hz), 2.93(s, 3H), 2.99(s, 3H), 1.31(s, 9H)

EXAMPLE 170

Synthesis of (3-fluoro-4-methanesulfonylaminobenzyl)dithiocarbamic acid 4-t-butylbenzyl ester (28)

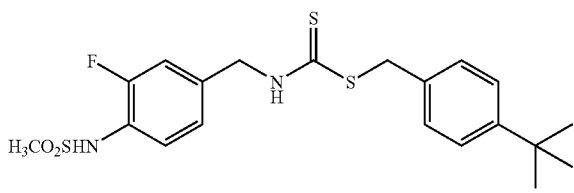

28

The compound 3-4 (15.4 mg) prepared by Example 13 was dissolved in dimethylformamide (1 ml) and to the solution were added tetrabutylammonium iodide (67 mg), cesium (I) carbonate (59 mg) and carbon bisulfide (7 µl), followed by stirring at 0° C. for 1 hour. To the mixture was added 4-t-butylbenzylbromide (34 µl) and stirred at room temperature for 1 hour. After the completion of the reaction, the resulting mixture was concentrated under reduced pressure and the obtained residue was chromatographed on silica gel column eluting with ethyl acetate/hexane (1/3) to yield the compound 28 (12 mg, 52%).

$^1$H NMR(300 MHz, CD$_3$OD): δ 7.43 (t, 1H, J=8.3 Hz), 7.25-7.34 (m, 4H), 7.10-7.16 (t, 2H, J=8.3 Hz), 4.88 (s, 2H), 4.55 (s, 2H), 2.97 (s, 3H), 1.30 (s, 9H)

EXAMPLE 171

Synthesis of 1-(4-t-butylbenzyl)-3-(3-fluorophenethyl)urea (29)

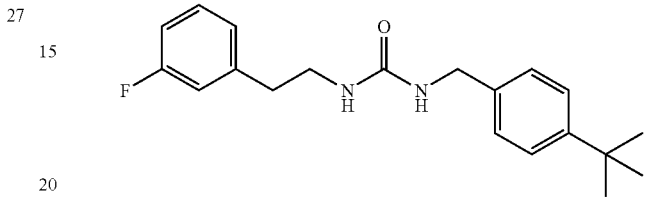

29

4t-butylbenzylamine (3.2 g) was dissolved in dichloromethane (10 ml) and to the solution was added triethylamine (2.79 ml), followed by cooling to 0° C. and slowly adding dropwise a solution of triphosgene (1.98 g) in dichloromethane (5 ml). The mixture was stirred at room temperature for 5 hours and water (10 ml) was added thereto. The resulting mixture was extracted with dichloromethane, dried over anhydrous sodium sulfate, and then concentrated under reduced pressure. The obtained residue was purified by column-chromatography (hexane/ethyl acetate=20/1) to yield 4-t-butylbenzylisocyanate (880 mg) as a solid. The obtained compound (400 mg) and 3-fluorophenethylamine (290 mg) were dissolved in dichloromethane (20 ml) and the solution was stirred at room temperature for 22 hours. The solvent was removed therefrom and the residue was purified by column-chromatography (hexane/ethyl acetate=4/1) to yield the compound 29 (400 mg, 58%) as a solid.

$^1$H NMR(300 MHz, CDCl$_3$) δ 7.35-6.82(m, 8H), 4.91(s, 1H), 4.39(d, 2H, J=5.4 Hz), 3.60-3.48(m, 2H), 2.79(t, 2H, J=6.9 Hz), 1.31(s,9H)

EXAMPLE 172

Synthesis of 1-(4-t-butylbenzyl)-3-(2-fluorobenzoyl) thiourea (30)

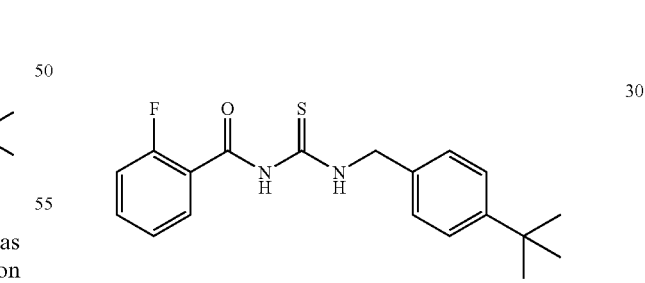

30

Potassium thiocyanate (KSCN) (240 mg) was dissolved in acetone (5 ml) and the solution was allowed to warm up to 50° C. To the solution was added 2-fluorobenzoylchloride (330 mg) and the mixture was stirred at 50° C. for 4 hours. The produced potassium chloride was filtered off and to the obtained solution was 4-t-butylbenzylamine (330 mg), followed by stirring at room temperature for 24 hours. The resulting mixture was concentrated and the residue was purified by column-chromatography (hexane/ethyl acetate=5/1) to yield the compound 30 (156 mg, 23%) as a liquid.

$^1$H NMR(300 MHz, CDCl$_3$): δ 8.18-8.11(m, 1H), 7.50-7.07(m, 8H), 7.02(brs, 1H), 4.70-4.65(m, 2H), 1.31(s, 9H)

EXAMPLE 173

Synthesis of N"-cyano-N-(4t-butylbenzyl)-N'-(2pyridinylethyl)guanidine (31-1)

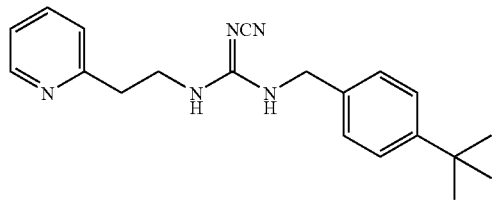

31-1

N-(4-t-butylbenzyl)N'-cyano-S-methylisothiourea (180 mg) was dissolved in xylene (10 ml) and to the solution was added 2-(2-aminoethyl)pyridine (86 mg), followed by refluxing for 7 hours. The resulting mixture was concentrated under reduced pressure and the obtained residue was purified by column-chromatography (acetone/ethyl acetate=1/1) to yield the compound 31-1 (70 mg, 30%) as a liquid.

$^1$H NMR(300 MHz, CDCl$_3$): δ 8.01(brs, 1H), 7.62-7.56(m, 1H), 7.39-7.35(m, 2H), 7.26-7.20(m, 3H), 7.14-7.03(m, 2H), 6.42(brs, 1H), 4.34(d, 2H, J=5.1 Hz), 3.71-3.65(m, 2H), 3.03-2.98(m, 2H), 1.32(s, 9H)

EXAMPLE 174~EXAMPLE 178

Compounds of Example 174~Example 178, which are shown in the Scheme 31, were synthesized according to the similar procedure as described in Example 173, and properties and spectral data thereof are shown in below table

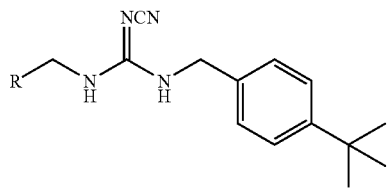

| Examples | Compounds | R = | Spectral data |
|---|---|---|---|
| 174 | 31-2 | 3-fluorobenzyl | $^1$H NMR(300 MHz, CDCl$_3$): δ 7.38-7.35(m, 2H), 7.27-7.20(m, 1H), 7.13-7.10(m, 2H), 6.95-6.78(m, 3H), 5.53(brs, 1H), 4.77(brs, 1H), 4.23(d, 2H, J = 5.4 Hz), 3.49-3.42(m, 2H), 2.79(t, 2H, J = 6.9 Hz), 1.32(s, 9H) |
| 175 | 31-3 | 3,4-difluorobenzyl | $^1$H NMR(300 MHz, CDCl$_3$): δ 7.40-7.35(m, 2H), 7.14-7.10(m, 2H), 7.08-6.99(m, 1H), 6.93-6.86(m, 1H), 6.82-6.77(m, 1H), 5.75(brs, 1H), 4.84(brs, 1H), 4.25(d, 2H, J = 5.4 Hz), 3.46-3.39(m, 2H), 2.76(t, 2H, J = 6.9 Hz), 1.32(s, 9H) |
| 176 | 31-4 | 2-fluorobenzyl | $^1$H NMR(300 MHz, CDCl$_3$): δ 7.39-7.35(m, 2H), 7.32-7.23(m, 2H), 7.19-7.16(m, 2H), 7.12-6.98(m, 2H), 5.65(brs, 1H), 5.35(brs, 1H), 4.42(d, 2H, J = 6.0 Hz), 4.34(d, 2H, J = 5.4 Hz). 1.32(s, 9H) |
| 177 | 31-5 | 2,3,4-trifluorobenzyl | $^1$H NMR(300 MHz, CDCl$_3$): δ 7.39-7.35(m, 2H), 7.23-7.20(m, 2H), 7.12-7.05(m, 1H), 6.95-6.88(m, 1H), 6.16(brs, 1H), 5.88(brs, 1H), 4.79(d, 2H, J = 5.4 Hz), 4.52(d, 2H, J = 4.8 Hz), 1.31(s, 9H) |
| 178 | 31-6 | 4-(H$_3$CO$_2$SHN)phenyl | $^1$H NMR(300 MHz, CDCl$_3$): δ 7.41-7.37(m, 2H), 7.27-7.15(m, 6H), 6.81(brs, 1H), 5.55(brs, 1H), 5.32(brs, 1H), 4.38-4.34(m, 4H), 3.01(s, 3H), 1.31(s, 9H) |

-continued
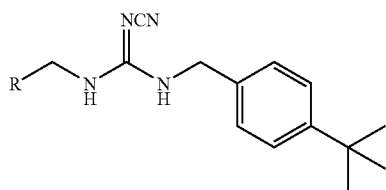
| Examples | Compounds | R = | Spectral data |
|---|---|---|---|
| | 31-2 | 3-F-C6H4-CH2- | |
| | 31-3 | 3,4-F2-C6H3-CH2- | |
| | 31-4 | 2-F-C6H4- | |
| | 31-5 | 2,3,4-F3-C6H2- | |
| | 31-6 | 4-(H3CO2SHN)-C6H4- | |

EXAMPLE 179

Synthesis of N''-cyano-N-(4-t-butylbenzyl)-N'-(2,6-difluoro-3-methanesulfonylaminobenzyl)guanidine (31-7)

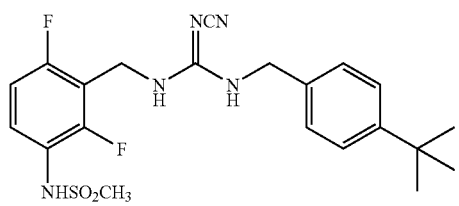

1-(4-t-butylbenzyl)-3-(2,6-difluoro-3-methanesulfonylaminobenzyl)thiourea (44 mg) and lead cyanamide (30 mg) were added to ethyl acetate (10 ml) and the mixture was refluxed for 18 hours. The resulting mixture was purified by column-chromatogrphy (hexane/ethyl acetate=1/1) to yield the compound 31-7 (35 mg, 78%).

$^1$H NMR (CDCl$_3$): δ 7.47(dt, J=5.7, 8.7 Hz, 1H), 7.37(d, J=8.4 Hz, 2H), 7.21(d, J=8.4 Hz, 2H), 6.90(t, J=8.7 Hz, 1H), 6.67(bs, 1H), 6.28(bs, 1H), 6.16(bs, 1H), 4.78(d, J=5.4 Hz, 2H), 4.55(d, J=4.2 Hz, 2H), 3.00(s, 3H), 1.31(s, 9H)

EXAMPLE 180

Synthesis of N''-cyano-N-(4-t-butylbenzyl)-N'-(2-fluoro-5-methanesulfonylaminobenzyl)guanidine (31-8)

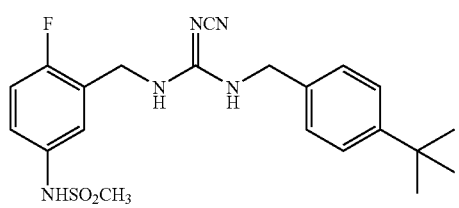

Compound 31-8 was synthesized according to the similar procedure as described in Example 179.

$^1$H NMR(CDCl$_3$): δ 7.34(d, J=8.1 Hz, 2H), 7.28(dd, J=2.4, 6.0 Hz, 1H), 7.20(d, J=8.1 Hz, 2H), 7.18(m, 1H), 6.98(t, J=9.0 Hz, 1H), 6.48(bs, 1H), 6.34(bs, 1H), 4.74(d, J=5.7 Hz, 2H), 4.56(d, J=4.2 Hz, 2H), 2.95(s, 3H), 1.29(s, 9H)

EXAMPLE 181

Synthesis of N''-cyano-N-[2-(1-methyl-1H-pyrrol-2-yl)ethyl]-N'-[1-(4-t-butylbenzyl)]guanidine (31-9)

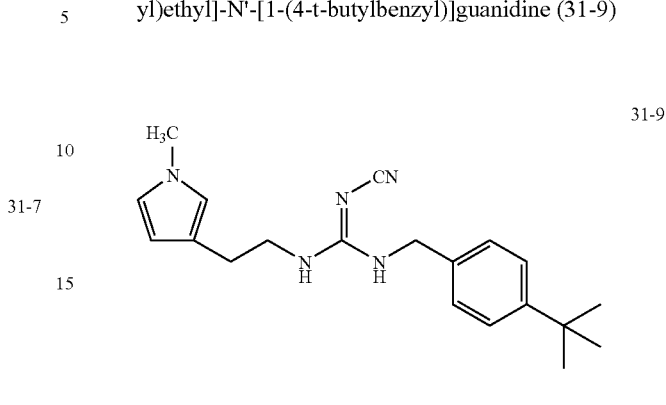

1-(4-t-butylbenzyl)-3-[2-(1-methyl-1H-pyrrol-2-yl)ethyl]thiourea (0.2 g) and lead cyanamide (170 mg) were dissolved in ethyl acetate (20 ml) and the solution was refluxed for 12 hours. After confirming the completion of the reaction, the resulting mixture was filtered to remove the yellow solid, and the obtained residue was concentrated under reduced pressure and purified by column-chromatography (ethyl acetate/hexane=2/3) to yield the compound 31-9 (174 mg, 85%) as a yellow solid.

$^1$H NMR (300 MHz, CDCl$_3$): δ 7.38(d, 2H), 7.21(d, 2H), 7.15(m, 2H), 6.05(d, 1H, J=2.1 Hz), 4.48(m, 2H), 3.86(m, 2H), 2.99(t, 2H, J=6.9 Hz), 1.31(s, 9H)

EXAMPLE 182

Synthesis of 1-(4-chlorobenzyl)-3-(6-methoxy-1,2,3,4-tetrahydronaphthalen-1-yl)thiourea (32-2)

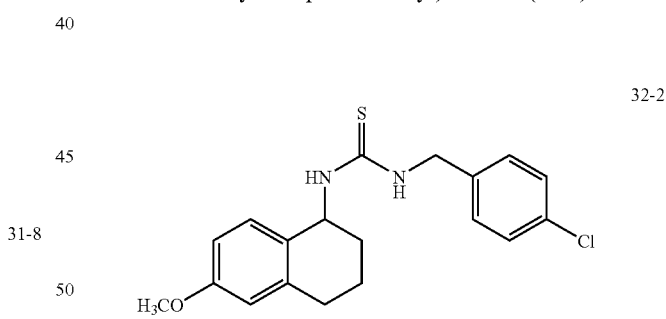

Step 1: Synthesis of 6-methoxy-1,2,3,4-tetrahydro-naphthalen-1-ylamine (32-1)

6-methoxy-1-tetralone (881 mg) and hydroxylamine hydrochloride (1.19 g) were dissolved in methanol (50 ml) and to the solution was slowly added pyridine (645 mg) at room temperature, followed by stirring for 18 hours. The resulting mixture was concentrated under reduced pressure. The concentrate was dissolved in ethyl acetate (30 ml), washed with water (10 ml×2) and aqueous saturated copper sulfate solution (10 ml), dried over magnesium sulfate, and then concentrated under reduced pressure. The residue was purified by column-chromatography (hexane/ethyl acetate=3/1) to yield an intermediate material, oxime (886 mg, 93%).

The obtained oxime (586 mg) was dissolved in methanol (50 ml) and the solution was cooled to −30° C., followed by adding nickel(II) chloride hexahydrate (1.46 g) thereto. After the solid was completely dissolved, to the solution was slowly added sodium borohydride (1.16 g) and the mixture was stirred at −30° C. for 30 minutes. Then, the mixture was stirred at room temperature for 90 minutes and concentrated under reduced pressure. The obtained residue was dissolved in 10% hydrochloric acid (30 ml) and the solution was slowly basified with 1 N aqueous sodium hydroxide solution. The obtained solution was extracted with ethyl acetate (50 ml×3) and the organic layers were collected. The total organic layer was washed with brine, dried over magnesium sulfate, concentrated under reduced pressure, and then purified by column-chromatography (dichloromethane/methanol=10/1) to yield the compound 32-1 (385 mg, 71%).

$^1$H NMR(CDCl$_3$): δ 7.31(d, J=8.7 Hz, 1H), 6.75(dd, J=8.5, 2.4 Hz, 1H), 6.61(d, J=2.4 Hz, 1H), 3.94(t, J=5.4 Hz, 1H), 3.78(s, 3H), 2.75(m, 2H), 1.96(m, 2H), 1.73(bs, 2H), 1.70(m, 2H)

The similar compounds 32-3 and 32-5 were synthesized according to the same procedure as described above.

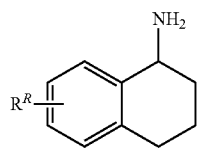

| Examples-step | Compounds No. | $R^R$ = | Spectral data |
|---|---|---|---|
| 183-1 | 32-3 | 5-OMe | $^1$H NMR(CDCl$_3$): δ 7.17(t, J = 7.8 Hz, 1H), 7.02(d, J = 7.8 Hz, 1H), 6.71(d, J = 7.8 Hz, 1H), 3.97(t, J = 5.7 Hz, 1H), 3.81(s, 3H), 2.65(m, 2H), 1.94(m, 2H), 1.76(bs, 2H), 1.73(m, 2H). |
| 184-1 | 32-5 | 7-OMe | $^1$H NMR(CDCl$_3$): δ 7.00(d, J = 8.7 Hz, 1H), 6.97(d, J = 3.0 Hz, 1H), 6.73(dd, J = 8.7, 3.0 Hz, 1H), 3.94(t, J = 5.6 Hz, 1H), 3.80(s, 3H), 2.70(m, 2H), 2.00(m, 1H), 1.90(m, 1H), 1.80(bs, 2H), 1.77(m, 2H). |

Step 2: Synthesis of 1-(4-chlorobenzyl)-3-(6-methoxy-1,2,3,4-tetrahydronaphthalen-1-yl)thiourea (32-2)

The compound 32-1 (100 mg) prepared according to the same procedure as described in Step 1 was dissolved in ethyl acetate (4 ml) and to the solution were added a solution of 4-chlorobenzylisothiocyanate (123 mg) in ethyl acetate (2 ml), followed by stirring at room temperarure for 18 hours. The obtained reaction mixture was concentrated under reduced pressure and purified by column-chromatography (hexane/ethyl acetate=2/1) to yield the compound 32-2 (201 mg, 99%).

$^1$H NMR(DMSO-d$_6$): δ 7.62(d, J=7.5 Hz, 1H), 7.52(bs, 1H), 7.23(d, J=8.4 Hz, 2H), 7.14(d, J=8.4 Hz, 2H), 6.92(bs, 1H), 6.55(d, J=8.7 Hz, 1H), 6.47(s, 1H), 5.30(bs, 1H), 4.50 (bs, 2H), 3.53(s, 3H), 2.52(m, 2H), 1.71(m, 1H), 1.55(m, 3H)

The similar compounds 32-4 and 32-6~32-10 were synthesized according to the same procedure as described above.

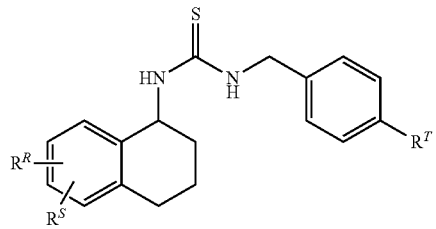

| Examples | Compounds No. | $R^R$ = $R^S$ = $R^T$ = | Spectral data |
|---|---|---|---|
| 183 | 32-4 | $R^R$ = 5-OMe $R^T$ = Cl | $^1$H NMR (DMSO-d$_6$): δ 7.85 (d, J = 8.0 Hz, 1H), 7.69 (bs, 1H), 7.40 (d, J = 8.4 Hz, 2H), 7.32 (d, J = 8.4 Hz, 2H), 7.12 (t, J = 8.0 Hz, 1H), 6.81 (d, J = 8.0 Hz, 1H), 5.54 (bs, 1H), 4.68 (bs, 2H), 3.76 (s, 3H), 2.56 (m, 2H), 1.88 (m, 2H), 1.73 (m, 2H). |
| 184 | 32-6 | $R^R$ = 7-OMe $R^T$ = Cl | $^1$H NMR (CDCl$_3$): δ 7.29 (d, J = 8.7 Hz, 2H), 7.22 (d, J = 8.7 Hz, 2H), 6.99 (d, J = 9.0 Hz, 1H), 6.74 (m, 3H), 6.23 (bs, 1H), 5.92 (bs, 1H), 5.40 (bs, 1H), 4.56 (bs, 2H), 3.72 (s, 3H), 2.67 |

-continued

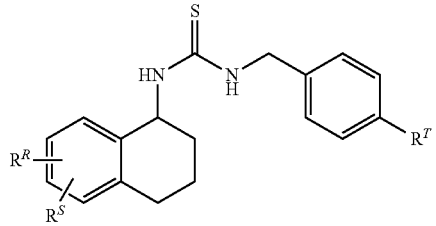

| Examples | Compounds No. | $R^R$ = $R^S$ = $R^T$ = | Spectral data |
|---|---|---|---|
| | | | (m, 2H), 2.05 (m, 1H), 1.77 (m, 3H). |
| 185 | 32-7 | $R^R$ = 5-OMe $R^T$ = t-butyl | $^1$H NMR (acetone-d$_6$): δ 7.38 (d, J = 8.4 Hz, 2H), 7.29 (d, J = 8.4 Hz, 2H), 7.17 (bs, 1H), 7.10 (t, J = 8.0 Hz, 1H), 7.04 (bs, 1H), 6.91 (d, J = 8.0 Hz, 1H), 6.78 (d, J = 8.0 Hz, 1H), 5.71 (bs, 1H), |

-continued

[Structure: thiourea with tetrahydronaphthalen-1-yl (bearing R^R, R^S) and 4-R^T-benzyl groups]

| Examples | Compounds No. | R^R = R^S = R^T = | Spectral data |
|---|---|---|---|
| 186 | 32-8 | R^R = 6-OMe R^T = t-butyl | 4.77 (d, J = 5.1 Hz, 2H), 3.80 (s, 3H), 2.83 (t, J = 6.0 Hz, 2H), 1.89 (m, 1H), 1.80 (m, 3H), 1.30 (s, 9H). $^1$H NMR (acetone-d$_6$): δ 7.38 (d, J = 8.4 Hz, 2H), 7.29 (d, J = 8.4 Hz, 2H), 7.21 (d, J = 8.4 Hz, 1H), 7.14 (bs, 1H), 7.05 (bs, 1H), 6.51 (dd, J = 8.4, 2.4 Hz, 1H), 6.62 (d, J = 2.4 Hz, 1H), 5.65 (bs, 1H), 4.76 (d, J = 5.4 Hz, 2H), 3.76 (s, 3H), 2.73 (m, 2H), 2.02 (m, 1H), 1.81 (m, 3H), 1.31 (s, 9H). |
| 187 | 32-9 | R^R = 7-OMe R^T = t-butyl | $^1$H NMR (acetone-d$_6$): δ 7.37 (d, J = 8.4 Hz, 2H), 7.30 (d, J = 8.4 Hz, 2H), 7.20 (bs, 1H), 7.11 (bs, 1H), 6.98 (d, J = 8.4 Hz, 1H), 6.92 (d, J = 2.7 Hz, 1H), 6.73 (dd, J = 8.4, 2.7 Hz, 1H), 5.71 (bs, 1H), 4.77 (d, J = 4.8 Hz, 2H), 3.71 (s, 3H), 2.67 (m, 2H), 2.06 (m, 1H), 1.81 (m, 3H), 1.30 (s, 9H). |
| 188 | 32-10 | R^R = 6-OMe R^S = 7-OMe R^T = t-butyl | $^1$H NMR (CDCl$_3$): δ 7.34 (d, J = 8.1 Hz, 2H), 7.21 (d, J = 8.1 Hz, 2H), 6.76 (s, 1H), 6.50 (d, 1H), 6.32 (bs, 1H), 5.96 (bs, 1H), 5.40 (bs, 1H), 4.52 (bs, 2H), 3.80 (s, 3H), 3.75 (s, 3H), 2.63 (m, 2H), 1.92 (m, 2H), 1.70 (m, 2H) 1.29 (s, 9H). |

32-4

32-6

32-7

32-8

32-9

32-10

EXAMPLE 189

Synthesis of 1-(4-t-butylbenzyl)-3-(5-hydroxy-1,2,3,4-tetrahyronaphthalen-1-yl)thiourea (32-11)

32-11

The compound 32-3 (570 mg) prepared by Step 1 of Example 183 was dissolved in 48% hydrobromic acid (10 ml) and the mixture was refluxed for 24 hours. The mixture was cooled to room temperature, and then concentrated under reduced pressure to remove the hydrobromic acid (residue: 766 mg, 97%). Part (500 mg) of the residue was dissolved in dimethylformamide (5 ml) and the solution was cooled to 0° C. To the obtained mixture was added 5 M sodium hydroxide (800 µl), followed by stirring for 15 minutes to obtain a solution. To the solution was slowly added a solution of 4-t-butylbenzylisothiocyanate (421 mg) in dimethylformamide (5 ml) and the mixture was stirred at room temperature for 48 hours. Then, to the obtained solution was added water and the resulting mixture was extracted with ether (50 ml×3). The extracted organic layer was collected, washed with 1 N hydrochloric acid, water and saturated aqueous sodium chloride solution, dried over magnesium sulfate, and then concentrated under reduced pressure. The residue was purified by column-chromatography (hexane/ethyl acetate=2/1) to yield the compound 32-11 (550 mg, 73%).

$^1$H NMR(acetone-$d_6$): δ 7.38(d, J=8.4 Hz, 2H), 7.29(d, J=8.4 Hz, 2H), 7.15(bs, 1H), 7.03(bs, 1H), 6.95(t, J=7.8 Hz, 1H), 6.81(d, J=7.8 Hz, 1H), 6.69(d, J=7.8 Hz, 1H), 5.70(bs, 1H), 4.77(d, J=5.1 Hz, 2H), 2.63(t, J=6.0 Hz, 2H), 2.00(m, 1H), 1.81(m, 3H), 1.30(s, 9H)

The similar compound 32-12 was synthesized according to the same procedure as described above.

| Example | Compound No. | $R^R$ = $R^T$ = | Spectral data |
|---|---|---|---|
| 190 | 32-12 | $R^R$ = 7-OH $R^T$ = Cl | $^1$H NMR (CD$_3$OD): δ 7.32 (s, 4H), 6.89 (d, J = 8.4 Hz, 1H), 6.71 (d, J = 2.4 Hz, 1H), 6.59 (dd, J = 8.4, 2.4 Hz, 1H), 5.54 (bs, 1H), 4.75 (bs, 2H), 2.65 (m, 2H), 2.03 (m, 1H), 1.79 (m, 3H). |

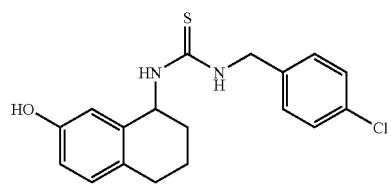

32-12

EXAMPLE 191

Synthesis of 1-(4-t-butylbenzyl)-3-(3-formyl-chromone)thiourea (33-2)

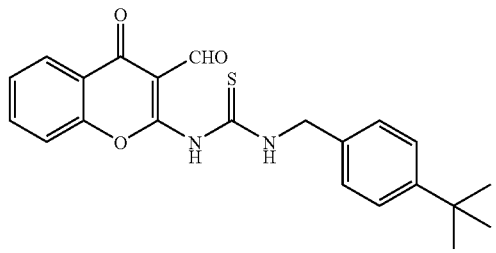

33-2

2-amino-3-formylchromone 33-1 (100 mg) was dissolved in anhydrous tetrahydrofuran (15 ml) and the solution was stirred. To the solution was added sdium hydride (15 mg) at 0° C. and the mixture was stirred for 30 minutes. To the mixture was added 4-t-butylbenzylisothiocyanate (130 mg), followed by stirring for 6 hours. The resulting mixture was neutralized with an iced water and concentrated under reduced pressure. The residue was extracted with ethyl acetate (30 ml×3), dried over magnesium sulfate, and then filtered. The filtrate was purified by column-chromatography (ethyl acetate/hexane=3/2) to yield the compound 33-2 (25 mg, 10%).

$^1$H NMR(300 MHz, CDCl$_3$): δ8.75(s, 1H), 8.14(m, 1H), 7.77(m, 1H), 7.42(m, 6H), 5.73(s, 2H), 1.33(s, 9H)

EXAMPLE 192

Synthesis of (4-t-butylbenzyl)thiocarbamic acid — O-(3,5-dimethylpyrazol-1-ylmethyl)ester (33-4)

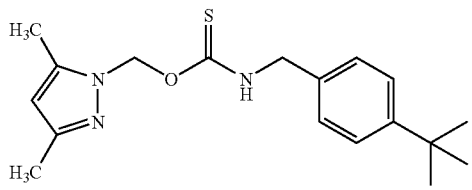

33-4

3,5-dimethylpyrazol-1-methanol 33-3 (200 mg) and sodium hydride (42 mg) were dissolved in anhydrous tetrahydrofuran (20 ml) and the solution was stirred for 1 hour. To the solution was added 4-t-butylbenzylisothiocyanate (330 mg) and the mixture was stirred at room temperature for 12 hours. The resulting mixture was filtered under reduced pressure and the solvent was removed therefrom. The residue was purified by column-chromatography (ethyl acetate/hexane=1/2) to yield the compound 33-4 (253 mg, 48%) as a solid.

$^1$H NMR (300 MHz, acetone-d$_6$) δ 7.29(m, 4H), 7.09(m, 1H), 6.30(s, 2H), 4.68(d, 2H, J=2.85 Hz), 2.33(s, 3H), 2.22(s, 3H), 1.30(s, 9H)

EXAMPLE 193

Synthesis of N-(3-fluoro-4-methanesulfonylaminobenzyl) 3-(4-t-butylphenyl)propionamide (34-5)

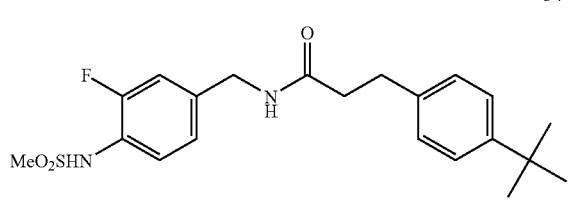

Step 1: Synthesis of 4-t-butylcinnamic acid ethyl ester (34-2)

4-t-butylbenzaldehyde (34-1) (69 mg) was dissolved in acetonitrile (16 ml) and to the solution were added diisopropylethylamine (84 mg) and triethyl phosphonoacetate (117 mg), followed by stirring at room temperature for 1 hours. The resulting mixture was diluted with dichloromethane (20 ml), washed with water and aqueous hydrochloric acid solution, dried over anhydrous magnesium sulfate, and then concentrated under reduced pressure. The residue was column-chromatographed (ethyl acetate/hexane=1/5) to yield the compound 34-2 (64 mg, 65%)
$^1$H NMR(300 MHz, CDCl$_3$): δ 7.65(d, 1H, J=16.1 Hz), 7.46-7.34 (m, 4H), 6.38(d, 1H, J=16.1 Hz), 4.24(q, 2H, J=7.2 Hz), 1.31(m, 12H)

Step 2: Synthesis of ethyl 3-(4-t-butylphenyl)propionate (34-3)

The compound 34-2 (64 mg) according to the same procedure as described in Step 1 was dissolved in methanol (10 ml) and to the solution was added a catalytic amount of 10% palladium/carbon, followed by stirring at room temperature under hydrogen gas atmosphere for 2 hours. The resulting mixture was diluted with ether, filtered through celite, and then concentrated under reduced pressure to yield the compound 34-3 (60 mg, 93%)
$^1$H NMR(300 MHz, CDCl$_3$): δ 7.28(d, 2H, J=8.0 Hz), 7.11(d, 2H, J=8.0 Hz), 4.11(q, 2H, J=7.1 Hz), 2.90(t, 2H, J=7.6 Hz), 2.59(t, 2H, J=7.6 Hz), 1.29(s, 9H), 1.21(t, 3H, J=6.8 Hz)

Step 3: Synthesis of N-(3-fluoro-4-methanesulfonylaminobenzyl) 3-(4-t-butylphenyl)propionamide (34-5)

The compound 34-3 (60 mg) prepared according to the same procedure as described in Step 2 was dissolved in 50% aqueous tetrahydrofuran solution (10 ml) and to the solution was added lithium hydroxide (24 mg). The mixture was stirred at room temperature for 5 hours to hydrolyze the compound 34-3 and the solvent was removed therefrom. The residue was dissolved in ethyl acetate and extracted to the obtain the compound 34-4 (43 mg, 81%). The compound 34-4 was dissolved in benzene (2 ml) and to the solution was added dropwise oxalyl chloride (100 μl), followed by refluxing for 2 hours. The reaction mixture obtained by concentrating the resultant under reduced pressure and hydrochloride compound 3-4 (67 mg) prepared in Example 13 were added to dichloromethane (6 ml), and to the mixture was added triethylamine (60 μl), followed by stirring at room temperature for 2 hours. The resulting mixture was concentrated under reduced pressure and the obtained residue was purified by column-chromatography (ethyl acetate/hexane=1/1) to yield the compound 34-5 (34 mg, 38%).
$^1$H NMR(300 MHz, CDCl$_3$): δ 7.40(t, 1H, J=8.2 Hz) 7.23 (d, 2H, J=8.3 Hz), 7.06(d, 2H, J=8.3 Hz), 6.90(m, 2H), 6.49(s, 1H), 5.68(s, 1H), 4.30(d, 2H, J=5.6 Hz), 2.93(s, 3H), 2.89(t, 2H, J=7.6 Hz), 2.47(t, 2H, J=7.4 Hz), 1.19(s, 9H)

EXAMPLE 194

Synthesis of 1-(4-t-butylbenzyl)-3-(4-methylaminosulfonylaminobenzyl)thiourea (35-2a)

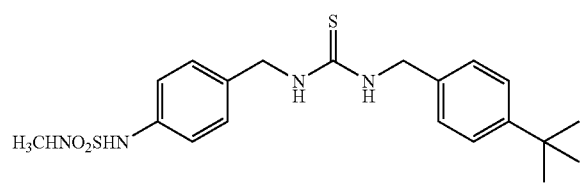

Step 1: Synthesis of N-t-butyloxycarbonyl-4-methylaminosulfonylaminobenzylamine (35-1a)

Sodium hydride (18 mg) was suspended in dimethylformamide, and to the suspension was added a solution of N-t-butyloxycarbonyl-p-aminobenzylamine (150 mg) and methylaminosulfamoylchloride (97 mg) in dimethylformamide while the temperature was controlled to 0° C., followed by stirring at room temperature for 3 hours. The reaction solution was evaporated under reduced pressure, and the residue was diluted with ethyl acetate (70 ml), washed with saturated aqueous sodium bicarbonate solution, water and saturated saline, and then evaporated under reduced pressrure. The obtained residue was purified by column-chromatography (hexane/ethyl acetate=5/1) to yield the compound 35-1a (170 mg, 79%).
$^1$H NMR(300 MHz, DMSO): δ7.27(d, 2H, J=8.5 Hz), 7.10 (m, 2H), 4.18(s, 2H), 3.29(s, 3H), 1.43(s, 9H)

Step 2: Synthesis of 1-(4-t-butylbenzyl)-3-(4-methylaminosulfonylaminobenzyl)thiourea (35-2a)

The compound 35-1a (170 mg) prepared in Step 1 was dissolved in anhydrous dichloromethane (4 ml), and to the solution was added excess trifluoroacetic acid while the temperature was contolled to 0° C., followed by stirring for 30 minutes. The resulting mixture was evaporated under reduced pressure to remove excess trifluoroacetic acid and the residue was dissolved in anhydrous dichloromethane (4 ml). To the solution were added triethylamine (98 μl) and 4-t-butylbenzylisothiocyanate (144 mg) and the mixture was stirred at room temperature for 3 hours. The reaction solution was evaporated under reduced pressure, and the remained was diluted with ethyl acetate (70 ml), washed with water and saturated saline, and then concentrated under reduced pressure. The obtained residue was purified by column-chromatography (hexane/ethyl acetate=10/1) to yield the compound 35-2a (157 mg, 69%).

$^1$H NMR(300 MHz, MeOH-d$_5$): δ7.33(d, 2H, J=8.5 Hz), 7.17(m, 2H), 4.65(s, 4H), 2.55(s, 3H), 1.25(s, 9H)

MS (FAB) m/e 421 [M$^+$+1]

EXAMPLE 195

Synthesis of 1-(4-t-butylbenzyl)-3-(4-N,N-dimethylaminosulfonylaminobenzyl)thiourea (35-2b)

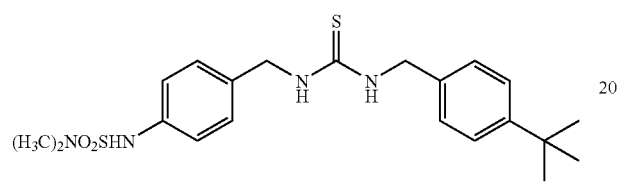

35-2b

Step 1: Synthesis of N-t-butyloxycarbonyl-4-N,N-dimethylaminosulfonylaminobenzylamine (35-1b)

Compound 35-1b (393 mg, 53%) was synthesized by adding dimethylsulfamoylchloride (266 μl) and then by being allowed to warm up to 60° C. according the procedure as described in Example 194.

$^1$H NMR(300 MHz, CDCl$_3$): δ7.18(m, 8H), 4.16(s, 4H), 2.77(s, 3H), 1.45(s, 9H)

Step 2: Synthesis of 1-(4-t-butylbenzyl)-3-(4-N,N-dimethylaminosulfonylaminobenzyl)thiourea (35-2b)

Compound 35-2b (337 mg, 65%) was synthesized according to the similar procedure as described in Example 194.

$^1$H NMR(300 MHz, CDCl$_3$): δ7.18(m, 8H), 4.56(s, 4H), 3.92(s, 3H), 1.27(s, 9H)

MS (FAB) m/e 435[M$^+$+1]

EXAMPLE 196

Synthesis of 1-(4-t-butylbenzyl)-3-(4-aminosulfonylaminobenzyl)thiourea (35-2c)

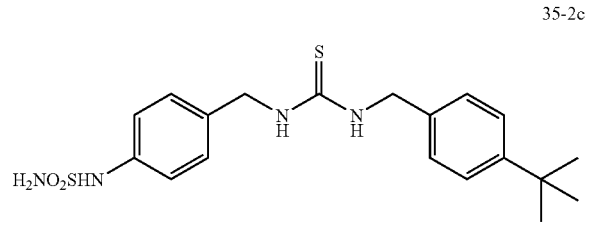

35-2c

Step 1: Synthesis of N-t-butyloxycarbonyl-4-N-(t-butyloxycarbonylaminosulfonyl)aminobenzylamine (35-1c)

Compound 35-1c (333 mg, 54%) was synthesized by adding N-(t-butyloxycarbonyl)-N-[4-(dimethylazanumylidene)-1,4-dihydropyridin-1-ylsulfonyl]azamide (464 mg) and then by being allowed to warm up to 60° C. according the procedure as described in Example 194.

$^1$H NMR(300 MHz, DMSO): δ7.12(m, 4H), 4.06(d, 2H, J=5.9 Hz), 1.37(s, 9H), 1.33(s, 9H)

Step 2: Synthesis of 1-(4-t-butylbenzyl)-3-(4-aminosulfonylaminobenzyl)thiourea (35-2c)

Compound 35-2c (257 mg, 69%) was synthesized according to the similar procedure as described in Example 194.

$^1$H NMR(300 MHz, DMSO): δ7.18(m, 8H), 4.58(s, 4H), 1.25(s, 9H)

MS (FAB) m/e 407[M$^+$+1]

EXAMPLE 197

Synthesis of 1-(4-t-butylbenzyl)-3-(4-methanesulfonylamino-3-nitrobenzyl)thiourea (35-5)

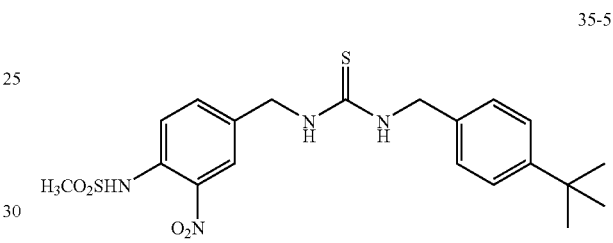

35-5

Step 1: Synthesis of 4-methanesulfonylamino-3-nitrobenzonitrile (35-4)

3-nitro-4-aminobenzonitrile (150 mg) and sodium bistrimethylsilylamide (2 ml) were dissolved in anhydrous tetrahydrofuran (6 ml), and to the solution was added methanesulfonic anhydride (191 mg) at 0° C., followed by stirring for 3 hours. The reaction solution was evaporated under reduced pressure and the residue was diluted with ethyl acetate (70 ml), washed with diluted aqueous hydrochloric acid solution, saturated aqueous sodium bicarbonate solution, water and brine, and then evapoarated under reduced pressure. The obtained residue was purified by column-chromatogaphy (hexane/ethyl acetate=5/1) to yield the compound 354 (120 mg, 54%)

$^1$H NMR(300 MHz, Pyridine-d$_5$): δ8.60(s, 1H), 8.17(d, 1H, J=8.76 Hz), 7.88(dd, 1H, J=1.95, 8.79 Hz), 3.48(s, 3H)

Step 2: Synthesis of 1-(4-t-butylbenzyl)-3-(4-methanesulfonylamino-3-nitrobenzyl)thiourea (35-5)

The compound 35-4 (90 mg) prepared according to the same procedure as described in Step 1 was dissolved in ahydrous tetrahydrofuran and to the solution was added borane (1 M, 1.1 ml), followed by stirring for 6 hours. The resulting mixture was evaporated under reduced pressure, and the residue was diluted with ethyl acetate (50 ml), washed with water and brine, and then evaporated under reduced pressure to obtain amine. The obtained amine, which was not purified, was dissolved in dichloromethane (2 ml) and to the solution were added triethylamine (57 μl) and 4-t-butylbenzylisothiocyanate (8.4 mg) at 0° C., followed by stirring at room temperature for 3 hours. The reaction solution was evaporated under reduced pressure. The residue was diluted with ethyl acetate (70 ml), and washed with water and brine. The solvent was evaporated under reduced pressure, and then the obtained residue was purified by column-chromatography (hexane/ethyl acetate=30/1) to yield the compound 35-5 (56 mg, 33%).

$^1$H NM(300 MHz, CDCl$_3$): δ8.60(s, 1H), 8.17(d, 1H, J=8.76 Hz), 7.88(dd, 1H, J=1.95, 8.79 Hz), 7.40(m, 4H), 4.80(d, 2H, J=5.13 Hz), 4.55(s, 2H), 3.10(s, 3H), 1.27(s, 9H)

MS (FAB) m/e 451[M$^+$+1]

EXAMPLE 198

Synthesis of 1-(4-t-butylbenzyl)-3-(1-(4-methanesulfonylphenyl)ethyl)thiourea (36-4)

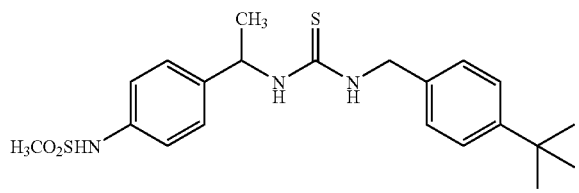

36-4

Step 1: Synthesis of 4-methanesulfonylaminoacetophenone (36-1)

4-aminoacetophenone (300 mg) was dissolved in dichloromethane, and to the solution were added methanesulfonic anhydride (2.44 mmol) and pyridine (53.85 μl) at 0° C., followed by stirring at room temperature for 3 hours. After confirming the completion of the reaction using TLC, the reaction was quenched with saturated sodium bicarbonate solution. The reaction mixture was diluted with dichloromethane, washed with water and saturated aqueous sodium chloride solution, dried over anhydrous sodium sulfate, and then concentrated under reduced pressure to obtain a solid. The solid was recrystallized with ethyl acetate and hexane, to yield a pale yellow crystal (293.2 mg, 61.95%).

mp: 155.1-161.2° C.;

$^1$H NMR(400 MHz, CDCl$_3$): δ 7.98(d, 2H, J=8.8 Hz), 7.27(d, 2H, J=8.8 Hz), 3.11(d, 3H, J=1.6 Hz),2.59(d, 3H, J=1.6 Hz)

IR(KBr pellet, cm$^{-1}$): 3290.93, 3003.59, 2928.38, 1667.16, 1600.63, 1469.49, 1330.64, 1279.54, 1146.47

Step 2: Synthesis of 4-methanesulfonylaminoacetophenonoxime (36-2)

4-methanesulfonylaminoacetophenone (36-1) (360.2 mg) was dissolved in ethanol and to the solution was added a solution of hydroxylamine hydrochloride (129.11 mg) and sodium acetate (249.40 mg) in minimal amount of water. To the mixture was added ethanol until the solution became clear and then the solution was refluxed for 20 hours, thereby to be changed from transparent yellow to transparent colorlessness. After confirming the completion of the reaction using TLC, the ethanol was removed therefrom, and the residue was extracted with ethyl acetate, washed with water and saturated aqueous sodium chloride solution, dried over anhydrous sodium sulfate, and then concentratd under reduced pressure to obain a solid. The solid was recrystallized with ethyl acetate and hexane to yield a pale yellow crystal (289.6 mg, 75.11%).

mp: 181.5-182.1° C.;

$^1$H NMR(400 MHz, CDCl$_3$): δ 7.60(d, 2H, J=7.2 Hz), 7.26(d, 2H, J=7.4 Hz), 2.96(s, 3H), 2.21(s, 3H).

IR(KBr pellet, cm$^{-1}$): 3495.35, 3255.25, 3023.84, 2926.38, 1605.45, 1323.89, 1155.15;

Step 3: Synthesis of 1-(4-methanesulfonylaminophenyl)ethylamine (36-3)

4-methanesulfonylaminoacetophenonoxime (36-2) (279 mg) was dissolved in methanol and to the solution was added palladium/carbon (55.8 mg), followed by stirring under hydrogen atmosphere. After confirming the completion of the reaction using TLC, palladium/carbon was filtered off and the filtrate was concentrated under reduced pressure to remove the methanol, thereby to yield a transparent yellow liquid (251.1 mg, 95.89%).

$^1$H NMR(400 MHz, CDCl$_3$): δ 7.28(d, 2H, J=8.8 Hz), 7.15(d, 2H, J=8.8 Hz), 4.09(q, 1H, J=6.6 Hz), 2.95 (s, 3H), 1.35(d, 3H, J=6.4 Hz)

IR(NaCl neat, cm$^{-1}$): 3350.71, 3270.69, 3136.65, 3023.84, 2965.98, 1610.27, 1512.88, 1325.82, 1153.22;

Step 4: Synthesis of 1-(4-t-butylbenzyl)-3-(1-(4-methanesulfonylphenyl)ethyl)thiourea (36-4)

The compound 36-3 (56.3 mg) prepared in Step 3 was dissolved in dichloromethane and to the solution was added 4-t-butylbenzylisothiocyanate (64.7 mg), followed by stirring at room temperature for 12 hours. After confiming the completion of the reaction using TLC, dichloromethane was evaporated under reduced pressure and the residue was purified by column-chromatography (hexane/ethyl acetate=4/1) to yield a white solid (41.9 mg, 38.01%).

mp: 177.8-178.5° C.

$^1$H NMR(400 MHz, CDCl$_3$): δ 9.33(s, 1H), 7.28(m, 8H), 5.51(s, 1H), 4.68(s, 2H), 4.08(q, 1H, J=4.8 Hz), 2.93(s, 3H), 1.48(d, 3H, J=4.8 Hz),1.31(s, 9H).

IR(KBr pellet, cm$^{-1}$): 3356.50, 3262.97, 3057.58, 3025.76, 2964.05, 2868.59, 1544.70, 1512.88, 1325.82

EXAMPLE 199

Synthesis of 1-(1-(4-methanesulfonylphenyl)ethyl)-3-phenethylthiourea (36-5)

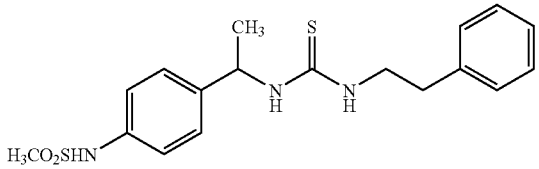

36-5

Solution of compound 36-3 (50 mg) in dichloromethane was mixed with phenethylisothiocyanate (65.7 mg) and the mixture was stirred at room temperature for 12 hours, followed by confirming the completion of the reaction using TLC. Dichloromethane was evaporated and the residue was column-chromatographed (hexane/ethyl acetate=2/1) to yield a white solid (12.8 mg, 14.53%).

mp: 190.8-192.1° C.

$^1$H NMR(400 MHz, DMSO-d$_6$): δ 9.63(s, 1H), 7.78(s, 1H), 7.19(m, 9H), 5.34(s, 1H), 3.56(s, 1H), 2.92(s, 2H), 2.74(t, 2H, J=6.6 Hz), 2.47(s, 3H), 1.33(d, 3H, J=6.6 Hz).IR(NaCl neat, cm$^{-1}$): 3365.17, 3229.22, 3020.94, 1731.76, 1523.49, 1374.03;

EXAMPLE 200

Synthesis of 1-(4-t-butylbenzyl)-3-(1-(4-methanesulfonylphenyl)ethyl)-3-methylthiourea (36-6)

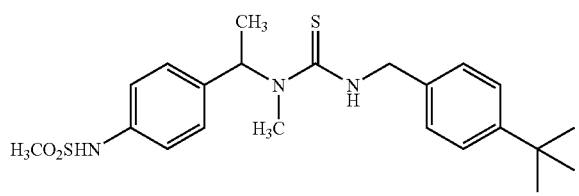

36-6

Compound 36-1 (200 mg) was dissolved in methanol and to the solution was added palladium/carbon (30.0 mg), followed by bringing the atmosphere of the reactor into an atmsphere of hydrogen gas. To the solution was added methylamine solution (2 M) and the mixture was allowed to be reacted for 5 days. After confirming the completion of the reaction using TLC, palladium/carbon was filtered off and the filtrate was purified by column-chromatography eluting with hexane/ethyl acetate (3/1) to remove neural material and subsequently eluting with dichloromethane/methanol (10/1) to obtain a yellow liquid (70 mg, 32.70%). The obtained compound (70 mg) was dissolved in dichloromethane and to the solution was added phenethylisothiocyanate (75.5 mg), followed by stirring at room temperature for 4 hours. After confirming the completion of the reaction using TLC, the resulting mixture was diluted with dichloromethane, washed with water and saturated aqueous sodium chloride solution, dried over anhydrous sodium sulfate, and then concentrated under reduced pressure to obain a solid. The solid was purified by column-chromatography (hexane/ethyl acetate=3/1) to yield a colorless liquid (42.6 mg, 32%).

$^1$H NMR(400 MHz, CDCl$_3$): δ 7.27(m, 8H), 6.90(q, 1H, J=7.2 Hz), 5.53(s, 1H), 4.84(d, 2H, J=4.4 Hz), 2.98(s, 3H), 2.66(s, 3H), 1.58(s, 1H), 1.52(d, 3H, J=7.2 Hz), 1.29(s, 3H).

IR(NaCl neat, cm$^{-1}$): 3386.39, 3267.79, 2963.09, 1512.88, 1326.79;

EXPERIMENTAL EXAMPLE

Biological Potency Test (1) $^{45}$Ca Influx Test

1) Separation of Spinal Dorsal Root Ganglia (DRG) in Newborn Rats and Primary Culture Thereof Neonatal(2-day old or younger than 2-day old) SD rats were put in ice for 5 minutes to anesthetize and disinfected with 70% ethanol. DRG of all part of spinal cord were dissected (Wood et al., 1988, J. Neurosci. 8, pp 3208-3220) and collected in DME/F12 medium to which 1.2 g/l sodium bicarbonate, 50 mg/l gentamycin were added. The DRG were incubated sequentially at 37° C. for 30 min in 200 U/ml collagenase and 2.5 mg/ml trypsin, separately. The ganglia were washed twice with DME/F12 medium supplemented with 10% horse serum, triturated through a fire-polished Pasteur pipette, filtered through Nitex 40 membrane to obtain single cell suspension. This was subjected to centrifugation, then re-suspended in cell culture medium at certain level of cell density. As the cell culture medium, DME/F12 medium supplemented with 10% horse serum, diluted 1:1 with identical medium conditioned by C6 glioma cells (2 days on a confluent monolayer) was used, and NGF(Nerve Growth Factor) was added to final concentration of 200 ng/ml. After the cells were grown 2 days in medium where cytosine arabinoside (Ara-C, 100 μM) was added to kill dividing nonneuronal cells, medium was changed to one without Ara-C. The resuspended cells were plated at a density of 1500-1700 neurons/well onto Terasaki plates previously coated with 10 μg/ml poly-D-ornithine.

2) $^{45}$Ca Influx Experiments

DRG nerve cells from the primary culture of 2-3 days were equilibrated by washing 4 times with HEPES (10 mM, pH 7.4)-buffered Ca$^{2+}$, Mg$^{2+}$-free HBSS (H-HBSS). The solution in each well was removed from the individual well. Medium containing the test compound plus capsaicin (final concentration 0.5 μM) and $^{45}$Ca (final concentration 10 μCi/ml) in H-HBSS was added to each well and incubated at room temperature for 10 min. Terasaki plates were washed six times with H-HBSS and dried in an oven. To each well, 0.3% SDS (10 μl) was added to elute $^{45}$Ca. After the addition of 2 ml of scintillation cocktail into each well, the amount of $^{45}$Ca influx into neuron was measured by counting radioactivity. Antagonistic activities of test compounds against vanilloid receptor were calculated as percent of the inhibition of maximal response of capsaicin at a concentration of 0.5 μM and results are given as IC$_{50}$ (Table 1a, 1b and 1c).

Agonistic activities of the test compounds for vanilloid receptor were determined as a concentration of the test compound showing 50% of the $^{45}$Ca influx, compared to the maximal amount of $^{45}$Ca influx in case of using 3 μM capsaicin and results are given as EC$_{50}$ (Table 1d).

(2) Channel Activity Assay

Antagonistic activities of test compounds were assayed based on electrical change of cation channel connected to vanilloid receptor and experiments were conducted according to reference method (Oh et al., 1996, J. Neuroscience 16, pp 1659-1667) (Table 1a, 1b and 1c).

TABLE 1a

Results of Calcium Influx and Patchclamp Tests

| Examples | Calcium Uptake Test (IC$_{50}$) | Patchclamp Test (antagonistic activities) |
|---|---|---|
| 5 | 1.1 | |
| 9 | 0.23 | |
| 13 | 0.037 | ++ |
| 15 | 1.2 | |
| 17 | 0.0084 | ++ |
| 18 | 0.72 | |
| 19 | 0.0058 | ++ |
| 30 | 1.5 | |
| 32 | 0.031 | + |
| 33 | 0.11 | |
| 36 | 1.1 | |
| 44 | 0.11 | + |
| 51 | 0.7 | |

NR: no response
+: antagonistic potency equal to capsazepine
++: antagonistic potency 10 times higher than capsazepine

TABLE 1b

Results of Calcium Influx and Patchclamp Tests

| Examples | Calcium Uptake Test ($IC_{50}$) | Patchclamp Test (antagonistic activities) |
|---|---|---|
| 60 | 1.14 | + |
| 61 | 0.25 | + |
| 62 | 0.06 | + |
| 64 | 0.35 | + |
| 65 | 0.019 | + |
| 66 | 0.25 | + |
| 67 | 0.5 | + |
| 68 | 0.063 | + |
| 69 | 0.77 | + |
| 70 | 0.58 | + |
| 73 | 1.2 | |
| 83 | 1.1 | |
| 90 | 0.42 | |
| 96 | 0.59 | |

+: antagonistic potency equal to capsazepine

TABLE 1c

Results of Calcium Influx and Patchclamp Tests

| Examples | Calcium Uptake Test ($IC_{50}$) | Patchclamp Test (antagonistic activities) |
|---|---|---|
| 134 | 0.81 | |
| 152 | 0.95 | + |
| 153 | 0.38 | |
| 161 | 0.46 | |
| 178 | 0.11 | |
| 193 | 0.21 | |
| 194 | 0.31 | |
| 196 | 0.15 | |
| Capsazepine | 0.59 | + |

+: antagonistic potency equal to capsazepine

TABLE 1d

Results of Calcium Influx Tests

| Examples | Calcium Uptake Test ($EC_{50}$) |
|---|---|
| 6 | 14.6 |
| 24 | 8.2 |
| 41 | 7.0 |
| 46 | 2.6 |
| 82 | 2.8 |

(3) Analgesic Activity Test: Mouse Writhing Test by Inducing with phenyl-p-quinone Male ICR mice (mean body weight 25 g) were maintained in a controlled lighting environment (12 h on/12 h off) for experiment. Animals received an intraperitoneal injection of 0.3 ml of the chemical irritant phenyl-p-quinone (dissolved in saline containing 5% ethanol to be a dose of 4.5 mg/kg) and 6 min later, the number of abdominal constrictions was counted in the subsequent 6 min period. Animals (10 animals/group) received 0.2 ml of test compounds solution in vehicle of ethanol/Tween 80/saline (10/10/80) intraperitoneally 30 min before the injection of phenyl-p-quinone. A reduction in the number of writhes responding to the test drug compound relative to the number responding in saline control group was considered to be indicative of an analgesic effect Analgesic effect was calculated by % inhibition equation (% inhibition= $(C-T)/C \times 100$), wherein C and T represent the number of writhes in control and compound-treated group, respectively (Table 2).

The test results demonstrated that analgesic effect of the compounds used in this experiment is as potent as indomethacin which is a very potent antiinflmmatory and analgesic agent. In particular, it is significant to clarify that vanilloid receptor antagonist can exhibit such potent analgesic effect, and the results suggests that vanilloid receptor antagonist has potential as an analgesic agent.

TABLE 2

Test result of analgesic activity for writhing by phenyl-p-quinone

| Examples | Dose (mg/kg) | Analgesic effect (% Inhibition) |
|---|---|---|
| 5 | 10 | 53 |
| 13 | 10 | 82 |
| 17 | 10 | 98 |
| 44 | 3 | 92 |
| 52 | 10 | 94 |
| 73 | 10 | 88 |
| 83 | 10 | 85 |
| 96 | 10 | 58 |
| 104 | 10 | 95 |
| 107 | 10 | 44 |
| 153 | 1 | 57 |
| 161 | 1 | 73 |
| Indomethacin | 3 | 94 |

(4) Antiinflammatory Activity Test: TPA(12-O-tetraecanoylphorbol 13-acetate)-induced mouse ear edema test Male ICR mice(body weight 25-30 g), 10 animals/group, were treated topically on the right ear with 30 μl of TPA (2.5 μg) solution in acetone and after 15 min, 30 μl of acetone or test compound solution in acetone was applied topically. After six hours, an identical treatment was applied again. After twenty four hours following the treatment of TPA, the animals were sacrificed and ear tissue was dissected using 6 mm-diameter punch. Ear tissue dissected were weighed to the nearest 0.1 mg on an electrobalance. The increased weight of the tissue compared to control group was considered as an index of inflammation. The percent inhibition is defined by the following equation:

% inhibition=$(C-T)/C \times 100$, wherein C and T represent an increase of ear weight in TPA-treated and TPA+drug-treated group, respectively (Table 3).

The above experiment shows that vanilloid receptor antagonist exhibits anti-inflammatory effects of the same level with indomethacin which is very potent anti-inflammatory and analgesic agent. This phenomenon can be understood by connecting with the action of vanilloid receptor in neurogenic inflammation, and suggests potential applicability of vanilloid receptor antagonist in various inflammatory diseases, in particular, neurogenic inflammatory diseases.

TABLE 3

TPA-induced mice ear edema test

| Examples | Dose (mg/ear) | Anti-inflammtory effect (% Inhibition) |
|---|---|---|
| 13 | 1 | 74 |
| 17 | 1 | 80 |
| 33 | 1 | 66 |
| 44 | 1 | 83 |
| 73 | 1 | 77 |
| 107 | 1 | 75 |
| Indomethacin | 1 | 74 |

(5) Ulcer Test: Ethanol-induced Anti-ulcer Test

Male SD rats (body weight 180-200 g), 5 animals/group, were fasted for 24 hours, and their stomachs were damaged. The rats were administered with 10 ml/kg of test drug suspended in 1% methylceflulose orally and, after 1 hour, 1 ml of 99% ethanol orally. After 1 hour without food and water, the rats were sacrificed by cervical dislocation and stomachs thereof were removed. The removed stomachs were incised along the greater curvature and opened. Then, the degree of gastric damage was scored based on the following ulcer index which is a criterion for evaluation and the percent inhibition of test drug against ulcer was calculated compared to control group (1% methylcellulose) (table 4). % inhibition=[(ulcer index of control group−ulcer index of drug-treated group)/ (ulcer index of control group)]×100

According to the present study using ethanol-induced ulcer model, the vanilloid receptor antagonist was found out to exhibit significant anti-ulcerous activities, contrary to ranitidine, which is a representative antiulcerant but did not show anti-ulcer activity in the present study. This study is the first to demonstrate the anti-ulcerous potential of vanilloid receptor antagonist. Based on the result, possibility that vanilloid receptor antagonist will be developed as an anti-ulcerant is suggested.

| Scoring (grade) | Ulcer Index (UI) |
|---|---|
| 0 | No lesion |
| 1 | One hemorrhagic ulcer of length less than 5 mm & thin |
| 2 | One hemorrhagic ulcer of length not less than 5 mm & thin |
| 3 | More than one ulcer of grade 2 |
| 4 | One ulcer of length not less than 5 mm & width not less than 2 mm |
| 5 | Two or three ulcers of grade 4 |
| 6 | Four or five ulcers of grade 4 |
| 7 | More than six ulcers of grade 4 |
| 8 | Complete lesion of the mucosa |

TABLE 4

Ethanol-induced anti-ulcer test

| Examples | Dose (mg/kg) | Anti-ulcerous effect (% inhibition) |
|---|---|---|
| 13 | 30 | 30 |
| 17 | 30 | 58 |
| 33 | 30 | 31 |
| 44 | 30 | 36 |
| 73 | 30 | 22 |
| 107 | 30 | 18 |
| Ranitidine | 30 | 4 |

INDUSTRIAL APPLICABILITY

The compounds according to the present invention are useful in the prevention or treatment of pain, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma and chronic obstructive pulmonary diseases, irritation in skin, eye or mucous membrane, stomach-duodenal ulcer, inflammatory bowel disease, inflammatory disease, etc.

The invention claimed is:
1. A compound of the following formula (I):

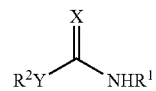

(I)

or a pharmaceutically acceptable salt thereof,
wherein:
X represents S, O or —NCN;
Y represents NH;
$R^1$ represents

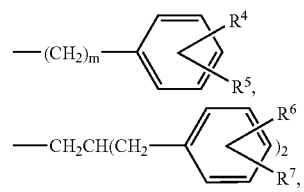

anthracenylmethyl, naphthylmethyl, alkoxycarbonyl or alkylcarbonyloxy (wherein, m is 1, 2, 3 or 4; $R^4$ and $R^5$ are independently hydrogen, lower alkyl having 2 to 5 carbon atoms, methanesulfonylamino, lower alkoxy having 2 to 5 carbon atoms, methoxyalkoxy, methoxyalkoxyalkyl, alkoxycarbonyloxy, benzyloxy, acetoxymethyl, propinoyloxymethyl, butoxyalkyl, trimethylacetoxy, or trimethylacetoxymethyl; and $R^6$ and $R^7$ are independently hydrogen or lower alkyl having 1 to 5 carbon atoms);
$R^2$ represents $R^8$—$(CH_2)_n$—
{wherein, n is 1, 2, 3 or 4; $R^8$ is benzoyl substituted or unsubstituted with lower alkyl having 1 to 5 carbon atoms, nitro, amino, cyano, methanesulfonylamino, formyl or halogen; or

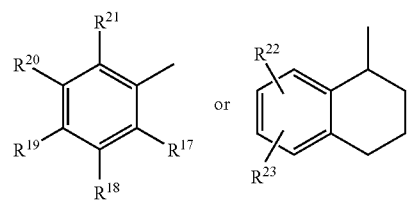

(wherein, $R^{17}$ $R^{18}$, $R^{20}$ and $R^{21}$ are independently hydrogen, halogen, lower alkyl having 1 to 5 carbon atoms, alkoxy, methylenedioxy, methanesulfonylaminomethyl, alkoxycarbonyl, sulfamoyl, alkoxycarbonylamino, —NHCH$_2$CO$_2$H, alkoxyalkylcarbonylamino, alkoxycarbonylalkylamino, nitro, formyl, acetyl, formylamino, acetylamino, cyano, —OSO$_2$CH$_3$, thiocarbamoyl, —C(=O)NHNH$_2$, —PO(=O)(OCH$_3$)$_2$, carboxyl, NHBoc or guanidine; $R^{19}$ is alkylsulfonylamino (wherein, alkyl has 1 to 5 carbon atoms); and $R^{22}$ and $R^{23}$ are independently hydrogen, halogen, alkoxy or hydroxy; or hydroxyphenylalkyl or (methanesulfonylaminophenyl)alkyl},
with the proviso that
if both $R^4$ and $R^5$ are hydrogen, then $R^{17}$ $R^{18}$, $R^{20}$ and $R^{21}$ are not simultaneously alkyl and halogen;
when $R^4$ or $R^5$ is alkoxy, then at least one of $R^{17}$ $R^{18}$, $R^{20}$ and $R^{21}$ is alkylsulfonylamino, sulfamoyl, alkoxyalkylcarbonylamino, alkoxycarbonylamino, alkoxycarbonylalkylamino, —NHCH$_2$CO$_2$H, guanidine, acetylamino, trifluorormethylsulfonylamino or formylamino; and when R$^{17}$ R$^{18}$, R$^{20}$ or R$^{21}$ is alkoxy, then at least one of R$^4$ and R$^5$ is methanesulfonylamino or alkoxycarbonyloxy.

2. The compound or a pharmaceutically acceptable salt thereof of claim 1, wherein, R$^1$ represents

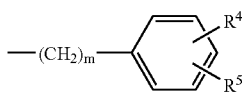

(wherein, m is 1 or 2; and R$^4$ and R$^5$ are independently hydrogen, lower alkyl having 2 to 4 carbon atoms, methanesulfonylamino, lower alkoxy having 2 to 5 carbon atoms, methoxyalkoxy, methoxyalkoxyalkyl, benzyloxy, acetoxymethyl, or trimethylacetoxymethyl);

R$^2$ represents R$^8$—(CH$_2$)$_n$—

{wherein, n is 1, 2 or 3; R$^8$ is benzoyl substituted or unsubstituted with lower alkyl having 1 to 5 carbon atoms, nitro, amino, cyano, methanesulfonylamino, formyl or halogen; or

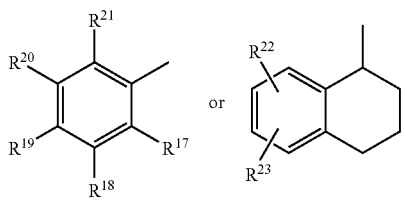

(wherein, R$^{17}$, R$^{18}$, R$^{20}$ and R$^{21}$ are independently hydrogen, halogen, lower alkyl having 1 to 5 carbon atoms, alkoxy, methylenedioxy, methanesulfonylaminomethyl, alkoxycarbonyl, sulfamoyl, alkoxycarbonylamino, —NHCH$_2$CO$_2$H, alkoxyalkylcarbonylamino, alkoxycarbonylalkylamino, nitro, formyl, acetyl, formylamino, acetylamino, cyano, —OSO$_2$CH$_3$, thiocarbamoyl, carboxyl, NHBoc, or guanidine; R$^{19}$ is alkylsulfonylamino (wherein, alkyl has 1 to 4 carbon atoms); and R$^{22}$ and R$^{23}$ are independently hydrogen, alkoxy or hydroxy; or hydroxyphenylalkyl or (methanesulfonylaminophenyl)alkyl}, with the proviso that if both R$^4$ and R$^5$ are hydrogen, then R$^{17}$, R$^{18}$, R$^{20}$ and R$^{21}$ are not simultaneously alkyl and halogen;

when R$^4$ or R$^5$ is alkoxy, then at least one R$^{17}$, R$^{18}$, R$^{20}$ and R$^{21}$ is alkylsulfonylamino, sulfamoyl, alkoxyalkylcarbonylamino, alkoxycarbonylamino, alkoxycarbonylalkylamino, —NHCH$_2$CO$_2$H, guanidine, acetylamino, trifluoromethylsulfonylamino or formylamino; and when R$^{17}$, R$^{18}$, R$^{20}$ or R$^{21}$ is alkoxy, then at least one of R$^4$ and R$^5$ is methanesulfonylamino or alkoxycarbonyloxy.

3. The compound or a pharmaceutically acceptable salt thereof of claim 2, wherein, R$^1$ represents

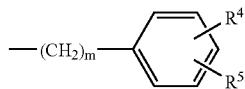

(wherein, m is 1 or 2; and R$^4$ and R$^5$ are independently hydrogen, t-butyl, methanesulfonylamino, lower alkoxy having 2 to 5 carbon atoms, methoxymethoxy, methoxyethoxy, benzyloxy, acetoxymethyl, or trimethylacetoxymethyl);

R$^2$ represents R$^8$—(CH$_2$)$_n$—

{wherein, n is 1, 2 or 3; R$^8$ is benzoyl substituted or unsubstituted with methyl, nitro or halogen; or

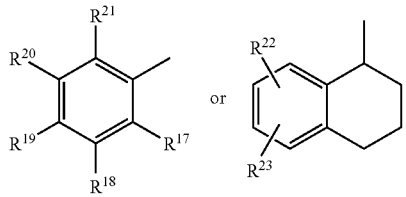

(wherein, R$^{17}$, R$^{18}$, R$^{20}$ and R$^{21}$ are independently hydrogen, halogen, lower alkyl having 1 to 4 carbon atoms, methylenedioxy, methanesulfonylaminomethyl, methoxycarbonyl, sulfamoyl, alkoxycarbonylamino, —NHCH$_2$CO$_2$H, methoxymethylcarbonylamino, alkoxycarbonylalkylamino, nitro, acetyl, formylamino, acetylamino, cyano, —OSO$_2$CH$_3$, thiocarbamoyl, carboxyl, NHBoc, —NHC(=O)SCH$_3$ or guanidine; R$^{19}$ is alkylsulfonylamino (wherein, alkyl has 1 to 4 carbon atoms); and R$^{22}$ and R$^{23}$ are independently hydrogen, methoxy or hydroxy; or hydroxyphenylalkyl or (methanesulfonylaminophenyl)alkyl}, with the proviso that if both R$^4$ and R$^5$ are hydrogen, then R$^{17}$, R$^{18}$, R$^{20}$ and R$^{21}$ are not simultaneously alkyl and halogen;

when R$^4$ or R$^5$ is alkoxy, then at least one of R$^{17}$ R$^{18}$, R$^{20}$ and R$^{21}$ is alkylsulfonylamino, sulfamoyl, methoxymethylcarbonylarnino, alkoxycarbonylamino, alkoxycarbonylalkylamino, —NHCH$_2$CO$_2$H, guanidine, acetylamino, trifluoromethylsulfonylamino or formylamino.

4. A compound of the following formula (I):

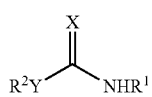

(I)

or a pharmaceutically acceptable salt thereof,
wherein:
X represents S, O or —NCN;
Y represents NH;
R$^1$ represents

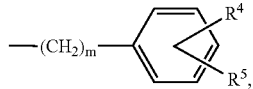

-continued

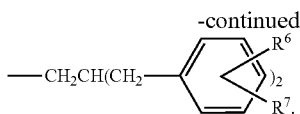

anthracenylmethyl, naphthylmethyl, alkoxycarbonyl or alkylcarbonyloxy (wherein, m is 1, 2, 3 or 4; R and R are independently hydrogen, lower alkyl having 1 to 5 carbon atoms, methanesulfonylamino, lower alkoxy having 1 to 5 carbon atoms, methoxyalkoxy, methoxyalkoxyalkyl, alkoxycarbonyloxy, benzyloxy, acetoxymethyl, propinoyloxymethyl, butoxyalkyl, trimethylacetoxy or trim ethylacetoxymethyl; and $R^6$ and $R^7$ are independently hydrogen, or lower alkyl having 1 to 5 carbon atoms);

$R^2$ represents $R^8$—$(CH_2)_n$—

{wherein, n is 1, 2, 3 or 4; R is benzoyl substituted or unsubstituted with lower alkyl having 1 to 5 carbon atoms, nitro, amino, cyano, methanesulfonylamino, formyl or halogen; or

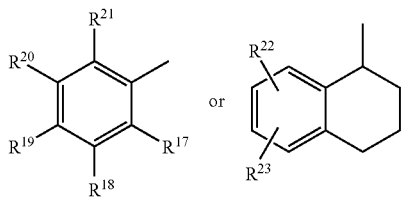

(wherein, $R^{17}$, $R^{18}$, $R^{20}$ and $R^{21}$ are independently hydrogen, halogen, lower alkyl having 1 to 5 carbon atoms, alkoxy, methylenedioxy, methanesulfonylaminomethyl, alkoxycarbonyl, sulfamoyl, alkoxycarbonylamino, —NHCH$_2$CO$_2$H, alkoxyalkylcarbonylamino, alkoxycarbonylalkylamino, nitro, formyl, acetyl, formylamino, acetylamino, cyano, —OSO$_2$CH$_3$, thiocarbamoyl, —PO(=O)(OCH$_3$)$_2$, carboxyl, NHBoc, or guanidine; $R^{19}$ is alkylsulfonylamino (wherein, alkyl has 1 to 5 carbon atoms); and $R^{22}$ and $R^{23}$ are independently hydrogen, halogen, alkoxy or hydroxy; or hydroxyphenylalkyl or (methanesulfonylaminophenyl)alkyl}, with the proviso that if both $R^4$ and $R^5$ are hydrogen, then $R^{17}$, $R^{18}$, $R^{20}$ and $R^{21}$ are not simultaneously alkyl and halogen;

when $R^4$ or $R^5$ is alkoxy, then at least one of $R^{17}$, $R^{18}$, $R^{20}$ and $R^{21}$ is alkylsulfonylamino, sulfamoyl, alkoxyalkylcarbonylamino, alkoxycarbonylamino, alkoxycarbonylalkylamino, —NHCH$_2$CO$_2$H, guanidine, acetylamino, trifluoromethylsulfonylamino or formylamino; and when $R^{17}$, $R^{18}$, $R^{20}$ or $R^{21}$ is alkoxy, then at least one of $R^4$ and $R^5$ is methanesulfonylamino or alkoxycarbonyloxy.

5. The compound or a pharmaceutically acceptable salt thereof of claim 4, wherein $R^1$ represents

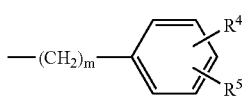

(wherein, m is 1 or 2; and $R^4$ and $R^5$ are independently hydrogen, t-butyl, methanesulfonylamino, lower alkoxy having 1 to 5 carbon atoms, methoxymethoxy, methoxyethoxy, benzyloxy, acetoxymethyl or trimethylacetoxymethyl);

$R^2$ represents $R^8$—$(CH_2)_n$—

{wherein, n is 1, 2 or 3; $R^8$ is benzoyl substituted or unsubstituted with methyl, nitro or halogen; or

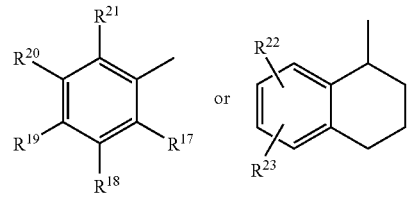

(wherein, $R^{17}$, $R^{18}$, $R^{20}$ and $R^{21}$ are independently hydrogen, halogen, lower alkyl having 1 to 4 carbon atoms, methylenedioxy, methanesulfonylaminomethyl, methoxycarbonyl, sulfamoyl, alkoxycarbonylamino, —NHCH$_2$CO$_2$H, methoxymethylcarbonylamino, alkoxycarbonylalkylamino, nitro, acetyl, formylamino, acetylamino, cyano, —OSO$_2$CH$_3$, thiocarbamoyl, carboxyl, NHBoc, or guanidine; $R^{19}$ is alkylsulfonylamino (wherein, alkyl has 1 to 4 carbon atoms); and $R^{22}$ and $R^{23}$ are independently hydrogen, methoxy or hydroxy; or hydroxyphenylalkyl or (methanesulfonylaminophenyl)alkyl}, with the proviso that if both $R^4$ and $R^5$ are hydrogen, then $R^{17}$, $R^{18}$, $R^{20}$ and $R^{21}$ are not simultaneously alkyl and halogen;

when $R^4$ and $R^5$ is alkoxy, then at least one of $R^{17}$, $R^{18}$, $R^{20}$ and $R^{21}$ is alkylsulfonylamino, sulfamoyl, methoxymethylcarbonylamino, alkoxycarbonylamino, alkoxycarbonylalkylamino, —NHCH$_2$CO$_2$H, guanidine, acetylamino, trifluoromethylsulfonylamino or formylamino.

6. The compound or a pharmaceutically acceptable salt thereof of claim 3 or 5, wherein $R^4$ is t-butyl.

7. The compound or a pharmaceutically acceptable salt thereof of claim 3 or 5, wherein $R^8$ is

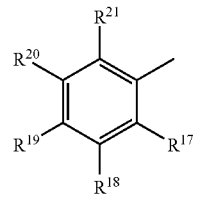

and wherein $R^{19}$ is methanesulfonylamino.

8. The compound or a pharmaceutically acceptable salt thereof of claim 7, wherein X is S and $R^4$ is 4-t-butyl.

9. The compound or a pharmaceutically acceptable salt thereof of claim 1, wherein the formula (I) is:

1-(4-t-butylbenzyl)-3-(3-fluoro-4-methanesulfonylaminobenzyl)thiourea;

1-phenethyl-3-(3-fluoro-4-methanesulfonylaminobenzyl)thiourea;

1-(4-t-butylbenzyl)-3-(3-chloro-4-methanesulfonylaminobenzyl)thiourea:

1-(4-t-butylbenzyl)-3-(3-methoxycarbonyl-4-methanesulfonylaminobenzyl) thiourea;

1-(4-t-butylbenzyl)-3-(3-carboxyl-4-methanesulfonylaminobenzyl)thiourea;

1-(4-t-butylbenzyl)-3-((3-N-hydroxyaminocarbonyl-4-methanesulfonylamino)benzyl)thiourea;
1-(4-t-butylbenzyl)-3-(3-methoxycarbonyl benzyl)thiourea;
1-(4-t-butylbenzyl)-3-(2,3,5,6-tetrafluoro-4-methanesulfonylaminobenzyl)thiourea;
1-(4-t-butylbenzyl)-3-(2,5-difluoro-4-methanesulfonylaminobenzyl)thiourea;
1-(4-t-butylbenzyl)-3-(2,6-dichloro-5-methanesulfonylaminobenzyl)thiourea;
1-(4-t-butylbenzyl)-3-(4-methanesulfonylaminophenethyl)thiourea;
1-(4-t-butylbenzyl)-3-(4-methanesulfonylaminobenzyl)thiourea;
1-(4-t-butylbenzyl)-3-[2,6-difluro-3-(methanesulfonylamino)benzyl]thiourea;
1-(4-t-butylbenzyl)-3-[3-(methanesulfonylamino)benzyl]thiourea;
1-(4-t-butyl-2-methoxybenzyl)-3-(4-methanesulfonylaminobenzyl)thiourea;
1-(4-t-butyl-2-ethoxybenzyl)-3-(4-methanesulfonylaminobenzyl)thiourea;
1-(4-butyl-2-propoxybenzyl)-3-(4-methanesulfonylaminobenzyl)thiourea;
1-(4-t-butyl-2-butoxybenzyl)-3-(4-methanesulfonylaminobenzyl)thiourea;
1-(4-t-butyl-2-isopropoxybenzyl)-3-(4-methanesulfonylaminobenzy)thiourea;
1-(4-t-butyl-2-isobutoxybenzyl)-3-(4-methanesulfonylaminobenzyl)thiourea;
1-(4-t-butyl-2-neopentoxybenzyl)-3-(4-methanesulfonylaminobenzyl)thiourea;
1-(4-t-butyl-2-methoxymethoxybenzyl)-3-(4-methanesulfonylaminobenzyl) thiourea;
1-(4-t-butyl-2-methoxyethoxybenzyl)-3-(4-methanesulfonylaminobenzyl)thiourea;
1-(4-t-butyl-2-benzyloxybenzyl)-3-(4-methanesulfonylaminobenzyl)thiourea;
1-(2-acetoxymethyl-4-t-butylbenzyl)-3-(4-methanesulfonylaminobenzyl)thiourea;
N''-cyano-N-(4-t-butylbenryl)-N'-(4-methanesulfonylaminobenzyl)guanidine.

10. The compound or a pharmaceutically acceptable salt thereof of claim 1, wherein the formula (I) is:
1-(4-t-butylbenzyl)-3-(3-fluoro-4-methanesulfonylaminobenzyl)thiourea;
1-(4-t-butylbenzyl)-3-(3-chloro-4-methanesulfonylaminobenzyl)thiourea;
1-(4-t-butylbenzyl)-3-(3-methoxycarbonyl-4-methanesulfonylaminobenzyl) thiourea;
1-(4-t-butylbenzyl)-3-(4-methanesulfonylaminobenzyl)thiourea; or
1-(4-t-butyl-2-isobutoxybenzyl)-3-(4-methanesulfonylaminobenzypthiourea.

11. A pharmaceutical composition comprising a compound of claim 1, 4 or 9 or a pharmaceutically acceptable salt thereof as an active ingredient and a pharmaceutically acceptable carrier.

12. The pharmaceutical composition of claim 11, wherein said compound or a pharmaceutically acceptable salt thereof as an active ingredient and the pharmaceutically acceptable carrier is present in an amount effective for treating pain, migraine, arthralgia, neuropathies, nerve injury, neurotic skin disorder, urinary bladder hypersensitiveness, irritable bowel syndrome, a respiratory disorder, irritation of skin, eye or mucous membrane, stomach-duodenal ulcer, or inflammatory diseases.

13. A method for treating pain, migraine, arthralgia, neuropathies, nerve injury, neurotic skin disorder, urinary bladder hypersensitiveness, irritable bowel syndrome, a respiratory disorder, irritation of skin, eye or mucous membrane, stomach-duodenal ulcer, or inflammatory diseases, wherein the method comprises administering to a person in need thereof a therapeutically effective amount of a compound of claim 1, 4 or 9 or a pharmaceutically acceptable salt thereof.

14. A compound of the following formula (I):

or a pharmaceutically acceptable salt thereof,
wherein:
X represents S, O or —NCN;
Y represents single bond, $NR^3$, O or S;
$R^1$ represents

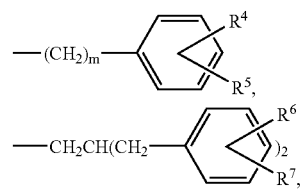

anthracenylmethyl, naphthylmethyl, alkoxycarbonyl or alkylcarbonyloxy (wherein, m is 0, 1, 2, 3 or 4; $R^4$ and $R^5$ are independently hydrogen, lower alkyl having 1 to 5 carbon atoms, hydroxy, methanesulfonylamino, lower alkoxy having 1 to 5 carbon atoms, methoxyalkoxy, methoxyalkoxyalkyl, alkoxycarbonyloxy, benzyloxy, acetoxymethyl, propinoyloxymethyl, butoxyalkyl, trimethylacetoxy, trimethylacetoxymethyl or halogen; and $R^6$ and $R^7$ are independently hydrogen, or lower alkyl having 1 to 5 carbon atoms);
$R^2$ represents $R^8$—$(CH_2)_2$—
{wherein, n is 0, 1, 2, 3 or 4; $R^8$ is benzoyl substituted or unsubstituted with lower alkyl having 1 to 5 carbon atoms, nitro, amino, cyano, methanesulfonylamino, formyl or halogen; or

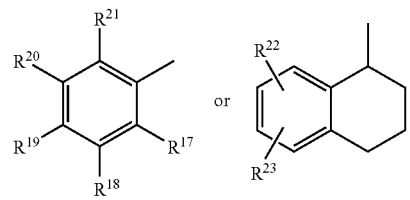

(wherein, $R^{17}$, $R^{18}$, $R^{20}$ and $R^{21}$ are independently hydrogen, halogen, lower alkyl having 1 to 5 carbon atoms, alkoxy, methylenedioxy, methanesulfonylaminomethyl, alkoxycarbonyl, hydroxy, sulfamoyl, aminoalkoxy, alkoxycarbonylamino, —$NHCH_2CO_2H$, alkoxylalkylcarbonylamino, alkoxycarbonylalkylamino, nitro, formyl, acetyl, formylamino, acetylamino, cyano, —$OSO_2CH_3$, —$NHSO_2R^{12}$, —$N(SO_2R^{12})CH_3$, —$N(SO_2R^{12})_2$, —$S(O)_pR^{12}$, —$NR^{13}R^{14}$, thiocarbamoyl, —$C(=O)NHNH_2$, —$C(=O)NHOH$, —$C(=O)$ NHOCH$_3$, —PO(=O)(OCH$_3$)$_2$, carboxyl, NHBoc, —NHC(=O)SCH$_3$ or guanidine; R$^{19}$ is alkylsulfonylamino (wherein, alkyl has 1 to 5 carbon atoms); R$^{22}$ and R$^{23}$ are independently hydrogen, halogen, alkoxy or hydroxy; R$^{12}$ is lower alkyl having 1 to 5 carbon atoms, methylphenyl, NR$^{13}$R$^{14}$, trifluoromethyl or alkenyl; R$^{13}$ and R$^{14}$ are independently hydrogen or lower alkyl having 1 to 5 carbon atoms; and p is 0 or 2); or hydroxyphenylalkyl or (methanesulfonylaminophenyl)alkyl}; and R$^3$ represents cycloalkyl having 3 to 8 carbon atoms, lower alkylphenyl having 1 to 5 carbon atoms, bisphenylmethyl; or phenylalkyl unsubstituted or substituted with lower alkyl having 1 to 5 carbon atoms, halogen or methanesulfonylamino.

15. The compound or a pharmaceutically acceptable salt thereof of claim 14, wherein, Y represents NR$^3$ or O;

R$^1$ represents

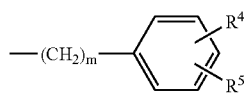

(wherein, m is 0, 1 or 2; and R$^4$ and R$^5$ are independently hydrogen, lower alkyl having 1 to 4 carbon atoms, hydroxy, methanesulfonylamino, lower alkoxy having 1 to 5 carbon atoms, methoxyalkoxy, methoxyalkoxyalkyl, benzyloxy, acetoxymethyl, trimethylacetoxymethyl or halogen);

R$^2$ represents R$^8$—(CH$_2$)$_n$—

{wherein, n is 0, 1, 2 or 3; R$^8$ is benzoyl substituted or unsubstituted with lower alkyl having 1 to 5 carbon atoms, nitro, amino, cyano, methanesulfonylamino, formyl or halogen; or

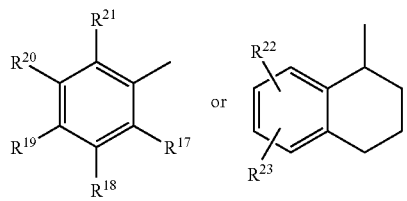

(wherein, R$^{17}$, R$^{18}$, R$^{20}$ and R$^{21}$ are independently hydrogen, halogen, lower alkyl having 1 to 5 carbon atoms, alkoxy, methylenedioxy, methanesulfonylaminomethyl, alkoxycarbonyl, hydroxy, sulfamoyl, alkoxycarbonylamino, —NHCH$_2$CO$_2$H, alkoxyalkylcarbonylamino, alkoxycarbonylalkylamino, nitro, formyl, acetyl, formylamino, acetylamino, cyano, —OSO$_2$CH$_3$, —NHSO$_2$R$^{12}$, —N(SO$_2$R$^{12}$)CH$_3$, —N(SO$_2$R$^{12}$)$_2$, —S(O)$_p$R$^{12}$, NR$^{13}$R$^{14}$, thiocarbamoyl, —C(=O)NHNH$_2$, —C(=O)NHOH, —C(=O)NHOCH$_3$, carboxyl, NHBoc, —NHC(=O)SCH$_3$, guanidine; R$^{19}$ is alkylsulfonylamino (wherein, alkyl has 1 to 4 carbon atoms); R$^{22}$ and R$^{23}$ are independently hydrogen, alkoxy or hydroxy; R$^{12}$ is lower alkyl having 1 to 4 carbon atoms, methylphenyl, NR$^{13}$R$^{14}$ or trifluoromethyl; R$^{13}$ and R$^{14}$ are independently hydrogen or lower alkyl having 1 to 4 carbon atoms; and p is 0 or 2); or hydroxyphenylalkyl or (methanesulfonylaminophenyl)alkyl}; and R$^3$ represents cyclohexyl, lower alkylphenyl having 1 to 3 carbon atoms, bisphenylmethyl; or phenylalkyl unsubstituted or substituted with lower alkyl having 1 to 4 carbon atoms, halogen or methanesulfonylamino.

16. The compound or a pharmaceutically acceptable salt thereof of claim 15, wherein, R$^1$ represents

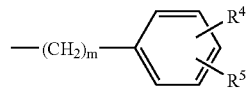

(wherein, m is 1 or 2; and R$^4$ and R$^5$ are independently hydrogen, t-butyl, hydroxy, methanesulfonylamino, lower alkoxy having 1 to 5 carbon atoms, methoxymethoxy, methoxyethoxy, benzyloxy, acetoxymethyl, trimethylacetoxymethyl or halogen);

R$^2$ represents R$^8$—(CH$_2$)$_n$—

{wherein, n is 1, 2 or 3; R$^8$ is benzoyl substituted or unsubstituted with methyl, nitro or halogen; or

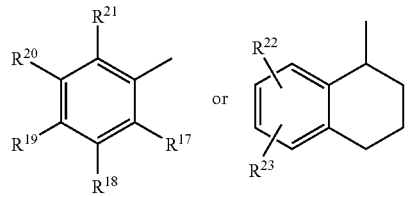

(wherein, R$^{17}$, R$^{18}$, R$^{20}$ and R$^{21}$, and are independently hydrogen, halogen, lower alkyl having 1 to 4 carbon atoms, methoxy, methylenedioxy, methanesulfonylaminomethyl, methoxycarbonyl, hydroxy, sulfamoyl, alkoxycarbonylamino, —NHCH$_2$CO$_2$H, methoxymethylcarbonylamino, alkoxycarbonylalkylamino, nitro, acetyl, formylamino, acetylamino, cyano, —OSO$_2$CH$_3$, —NHSO$_2$R$^{12}$, —N(SO$_2$R$^{12}$)CH$_3$, —N(SO$_2$R12)$_2$, —S(O)$_p$R$^{12}$, R$^{13}$R$^{14}$, thiocarbamoyl, —C(=O)NHNH$_2$, —C(=O)NHOH, —C(=O)NHOCH$_3$, carboxyl, NHBoc, —NHC(=O)SCH$_3$ or guanidine; R$^{19}$ is alkylsulfonylamino (wherein, alkyl has 1 to 4 carbon atoms); R$^{22}$ and R$^{23}$ are independently hydrogen, methoxy or hydroxy; R$^{12}$ is lower alkyl having 1 to 4 carbon atoms, methylphenyl, NR$^{13}$R$^{14}$ or trifluoromethyl; R$^{13}$ and R14$^{14}$ are independently hydrogen or lower alkyl having 1 to 4 carbon atoms; and p is 0 or 2); or hydroxyphenylalkyl or (methanesulfonylaminophenyl)alkyl); and R$^3$ represents cyclohexyl, benzyl, phenethyl or bisphenylmethyl; or phenylalkyl unsubstituted or substituted with t-butyl, halogen or methanesulfonylamino.

17. A pharmaceutical composition comprising a compound of claim 14, or a pharmaceutically acceptable salt thereof as an active ingredient and a pharmaceutically acceptable carrier.

18. A pharmaceutical composition comprising a compound of claim 16, or a pharmaceutically acceptable salt thereof as an active ingredient and a pharmaceutically acceptable carrier.

19. The pharmaceutical composition of claim 17 or 18, wherein said compound or a pharmaceutically acceptable salt thereof as an active ingredient and the pharmaceutically acceptable carrier is present in an amount effective for treating pain, migraine, arthralgia, neuropathies, nerve injury, urinary bladder hypersensitiveness, irritable bowel syndrome, a respiratory disorder, irritation of skin, eye or mucous membrane, stomach-duodenal ulcer, or inflammatory diseases.

20. A method for treating pain, migraine, arthralgia, neuropathies, nerve injury, urinary bladder hypersensitiveness, irritable bowel syndrome, a respiratory disorder, irritation of skin, eye or mucous membrane, stomach-duodenal ulcer, or inflammatory diseases, wherein the method comprises administering to a person in need thereof a therapeutically effective amount of a compound selected from the group consisting of compounds of claim 14 or a pharmaceutically acceptable salt thereof.

21. A method for treating pain, migraine, arthralgia, neuropathies, nerve injury, urinary bladder hypersensitiveness, irritable bowel syndrome, a respiratory disorder, irritation of skin, eye or mucous membrane, stomach-duodenal ulcer, or inflammatory diseases, wherein the method comprises administering to a person in need thereof a therapeutically effective amount of a compound selected from the group consisting of compounds of claim 16 or a pharmaceutically acceptable salt thereof.

22. A method for treating pain wherein the method comprises administering to a person in need thereof a therapeutically effective amount of a compound selected from the group consisting of compounds of claim 1, 8, 9 or 16 or a pharmaceutically acceptable salt thereof.

23. The pharmaceutical composition of claim 11, wherein said compound or a pharmaceutically acceptable salt thereof as an active ingredient together with a pharmaceutically acceptable carrier is present in an effective amount for treating acute pain, chronic pain, neuropathic pain, post-operative pain, diabetic neuropathy, neurodegeneration, stroke, asthma, chronic obstructive pulmonary disease, or inflammatory bowel disease.

24. A method for treating acute pain, chronic pain, neuropathic pain, post-operative pain, diabetic neuropathy, neurodegeneration, stroke, asthma, chronic obstructive pulmonary disease, or inflammatory bowel disease, wherein the method comprises administering to a person in need thereof a therapeutically effective amount of a compound according to claim 1, 4, or 9 or a pharmaceutically acceptable salt thereof.

25. The pharmaceutical composition of claim 17 or 18, wherein said compound or a pharmaceutically acceptable salt thereof as an active ingredient together with a pharmaceutically acceptable carrier is present in an effective amount for treating acute pain, chronic pain, neuropathic pain, post-operative pain, diabetic neuropathy, neurodegeneration, neurotic skin disorder, stroke, asthma, chronic obstructive pulmonary disease, or inflammatory bowel disease.

26. A method for treating acute pain, chronic pain, neuropathic pain, post-operative pain, diabetic neuropathy, neurodegeneration, neurotic skin disorder, stroke, asthma, chronic obstructive pulmonary disease, or inflammatory bowel disease, wherein the method comprises administering to a person in need thereof a therapeutically effective amount of the compound selected from the group consisting of compounds according to claim 14 or a pharmaceutically acceptable salt thereof.

27. A method for treating acute pain, chronic pain, neuropathic pain, post-operative pain, diabetic neuropathy, neurodegeneration, neurotic skin disorder, stroke, asthma, chronic obstructive pulmonary disease, or inflammatory bowel disease, wherein the method comprises administering to a person in need thereof a therapeutically effective amount of the compound selected from the group consisting of compounds according to claim 16 or a pharmaceutically acceptable salt thereof.

\* \* \* \* \*